US007001764B2

(12) United States Patent
Little et al.

(10) Patent No.: US 7,001,764 B2
(45) Date of Patent: Feb. 21, 2006

(54) COMPOSITIONS COMPRISING TISSUE SPECIFIC ADENOVIRAL VECTORS

(75) Inventors: Andrew S. Little, Balboa Island, CA (US); Henry G. Lamparski, San Mateo, CA (US); Daniel R. Henderson, Palo Alto, CA (US); Eric R. Schuur, Palo Alto, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 488 days.

(21) Appl. No.: 10/139,089

(22) Filed: May 2, 2002

(65) Prior Publication Data

US 2003/0152553 A1 Aug. 14, 2003

Related U.S. Application Data

(63) Continuation-in-part of application No. 09/509,591, filed on Jun. 2, 2000, and a continuation-in-part of application No. 09/151,376, filed on Sep. 10, 1998, now Pat. No. 6,676,935, which is a continuation-in-part of application No. 08/669,753, filed on Jun. 26, 1996, now Pat. No. 5,871,726, which is a continuation-in-part of application No. 08/495,034, filed on Jun. 27, 1995, now Pat. No. 5,698,443, application No. 10/139,089, and a continuation-in-part of application No. 09/033,428, filed on Mar. 2, 1998, now Pat. No. 6,254,862, and a continuation-in-part of application No. 09/033,555, filed on Mar. 2, 1998, now abandoned, and a continuation-in-part of application No. 09/033,333, filed on Mar. 2, 1998, now Pat. No. 6,197,293.

(60) Provisional application No. 60/039,763, filed on Mar. 3, 1997, provisional application No. 60/039,762, filed on Mar. 3, 1997, and provisional application No. 60/039,597, filed on Mar. 3, 1997.

(51) Int. Cl.

| | |
|---|---|
| *C12N 7/00* | (2006.01) |
| *C12N 1/00* | (2006.01) |
| *C12N 15/861* | (2006.01) |
| *C12N 21/06* | (2006.01) |
| *A01N 63/00* | (2006.01) |

(52) U.S. Cl. .................. 435/320.1; 424/93.1; 424/93.2; 424/93.6; 435/235.1; 435/69.1; 536/23.1; 536/23.72; 536/24.1

(58) Field of Classification Search .............. 435/235.1, 435/243, 320.1, 471, 69.1; 424/93.1, 93.2, 424/93.6

See application file for complete search history.

(56) References Cited

U.S. PATENT DOCUMENTS

| | | | | |
|---|---|---|---|---|
| 5,698,443 A | * 12/1997 | Henderson et al. | 435/320.1 |
| 5,871,726 A | * 2/1999 | Henderson et al. | 424/93.2 |
| 5,998,205 A | * 12/1999 | Hallenbeck et al. | 435/325 |
| 6,197,293 B1 | * 3/2001 | Henderson et al. | 424/93.2 |
| 6,254,862 B1 | * 7/2001 | Little et al. | 424/93.2 |
| 6,676,935 B1 | * 1/2004 | Henderson et al. | 424/93.2 |

FOREIGN PATENT DOCUMENTS

| | | | |
|---|---|---|---|
| WO | WO 96/14874 | * | 5/1996 |
| WO | WO96/17053 | | 6/1996 |
| WO | WO 96/21036 | * | 7/1996 |
| WO | WO97/01358 | | 1/1997 |

OTHER PUBLICATIONS

Berkner and Sharp, "Generation of adenovirus by transfection of plasmids", (1983), *Nucleic Acid Research*, 11(17): 6003–6020.

Bett et al., "An efficient and flexible system for construction of adenovirus vectors with insertions or deletions in early regions 1 and 3", (1994), *Proc. Natl. Acad. Sci.*, 91:8802–8806.

Bett et al., "Packaging capacity and stability of human adenovirus type 5 vectors", (1993), *J. Virology*, 67(10):5911–5921.

Croyle et al., "Development of a Rapid Method for the PECylation of Adenoviruses with Enhanced Transduction and Improved Stability under Harsh Storage Conditions", (2000), Human Gene Therapy, 11:1713–1722.

Graham, "Growth of 293 cells in suspension culture", (1987), *J. Genetic Virology*, 68:937–940.

Graham, "Covalently closed circles of human adenovirus DNA are infectious", (1984), *EMBO. J.*, 3(12):2917–2922.

Graham et al., "Characteristics of a human cell line transformed by DNA from human adenovirus type 5", (1977), *J. Gen. Virol.*, 38:59–72.

Graham et al., "A new technique for the assay of infectivity of human adenovirus 5 DNA", (1973), *Virology*, 52:456–467.

Hayashi et al., "Expression of a thyroid hormone–responsive recombinant gene introduced into adult mice livers by replication–defective adenovirus can be regulated by endogenous thyroid hormone receptor", (1994), *J. Biol. Chem.*, 269:23872–23875.

Jaffe et al., "Adenovirus–mediated in vivo gene transfer and expression in normal rat liver", (1992), *Nat Gent.*, 1:372–378.

Le Gal La Salle et al., "An adenovirus vector for gene transfer into neurons and glia in the brain", (1993), *Science*, 259:988–990.

Mastrangeli et al., "Diversity of airway epithelial cell targets for in vivo recombination adenovirus–mediated gene transfer", (1993), *J. Clin. Invest.*, 91:225–234.

(Continued)

*Primary Examiner*—David Guzo
*Assistant Examiner*—Michael Burkhart
(74) *Attorney, Agent, or Firm*—DLA Piper Rudnick Gray Cary US LLP

(57) ABSTRACT

Compositions comprising host cell specific adenovirus vehicles are provided for transfecting target host cells. The compositions comprise replication competent adenovirus having an adenovirus gene essential for replication under transcriptional control of a cell type specific transcriptional response element (TRE) and polyethylene glycol (PEG) as a masking agent.

21 Claims, 47 Drawing Sheets

OTHER PUBLICATIONS

Quantin et al., "Adenovirus as an expression vector in muscle cells in vivo", (1992), *Proc Natl. Acad. Sci.*, 89:2581–3584.

Ragot et al., "Efficient adenovirus–mediated transfer of a human minidystrophin gene to skeletal muscle of mdx mice", (1993), *Nature*, 361:647–650.

Rosenfeld, "Adenovirus–mediated transfer of a recombinant alpha 1–antitrypsin gene to the lung epithelium in vivo", (1991), Science, 252:431–434.

Rosenfeld et al., "In vivo transfer of the human cystic fibrosis transmembrane conductance regulator gene to the airway epithelium", (1992), *Cell*, 68:143–155.

Stratford–Perricaudet, "Evaluation of the transfer and expression in mice of an enzyme–encoding gene using a human adenovirus vector", (1990), *Human Gene Therapy*, 1:241–256.

Stratford–Perricaudet et al., "Widespread long term gene transfer to mouse skeletal muscles and heart", (1992), *J. Clin. Invest*. 90:626–630.

Takiff et al., "Propagation and in vitro studies of previously non–cultivable enteral adenoviruses in 293 cells", (1981), *Lancet*, 11:832–834.

Wang et al., "Expression of the APRT gene in an adenovirus vector system as a model for studying gene therapy", (1991), *Adv. Exp. Med. Biol.*, 309:61–66.

* cited by examiner

AFP E1a and E1b Adenovirus Constructs

Error bars = standard error

Animals from groups treated with a single dose of CN733 and buffer were sacrificed at 28 days because of excessive tumor burden CEA E1a and E1b Adenovirus Constructs

-426

5'-AAGCTTCCACAAGTGCATTTAGCCTCTCCAGTATTGCTGATGAATCCACAGT

TCAGGTTCAATGGCGTTCAAAACTTGATCAAAAATGACCAGACTTTATATTCTTA

CACCAACATCTATCTGATTGGAGGAATGGATAATAGTCATCATGTTTAAACATCT

ACCATTCCAGTTAAGAAAATATGATAGCATCTTGTTCTTAGTCTTTTTCTTAATA

ARE-1

GGGACATAAAGCCCACAAATAAAAATATGCCTGAAGAATGGGACAGGCATTGG

GCATTGTCCATGCCTAGTAAAGTACTCCAAGAACCTATTTGTATACTAGATGACA

ARE-2

CAATGTCAATGTCTGTGTACAACTGCCAACTGGGATGCAAGACACTGCCCATG

+1

CCAATCATCCTGAAAAGCAGGTATAAAAAGCAGGAAGCTACTCTGCACGTT

CAAT box TATAA box Transcription site

+26

GTCAGTGAGGTCCAGATACCTACAG-3'

```
aagcttttta gtgctttaga cagtgagctg gtctgtctaa cccaagtgac ctgggctcca     60
tactcagccc cagaagtgaa gggtgaagct gggtggagcc aaaccaggca agcctaccct    120
cagggctccc agtggcctga gaaccattgg acccaggacc cattacttct agggtaagga    180
aggtacaaac accagatcca accatggtct gggggacag ctgtcaaatg cctaaaaata    240
tacctgggag aggagcaggc aaactatcac tgccccaggt tctctgaaca gaaacagagg    300
ggcaacccaa agtccaaatc caggtgagca ggtgcaccaa atgcccagag atatgacgag    360
gcaagaagtg aaggaaccac ccctgcatca aatgttttgc atgggaagga gaagggggtt    420
gctcatgttc ccaatccagg agaatgcatt tgggatctgc cttcttctca ctccttggtt    480
agcaagacta agcaaccagg actctggatt tggggaaaga cgtttatttg tggaggccag    540
tgatgacaat cccacgaggg cctaggtgaa gagggcagga aggctcgaga cactggggac    600
tgagtgaaaa ccacacccat gatctgcacc acccatggat gctccttcat tgctcacctt    660
tctgttgata tcagatggcc ccattttctg taccttcaca gaaggacaca ggctagggtc    720
tgtgcatggc cttcatcccc ggggccatgt gaggacagca ggtgggaaag atcatgggtc    780
ctcctgggtc ctgcagggcc agaacattca tcacccatac tgacctccta gatgggaatg    840
gcttccctgg ggctgggcca acggggcctg ggcaggggag aaaggacgtc aggggacagg    900
gaggaagggt catcgagacc cagcctggaa ggttcttgtc tctgaccatc caggatttac    960
ttccctgcat ctacctttgg tcattttccc tcagcaatga ccagctctgc ttcctgatct   1020
cagcctccca ccctggacac agcaccccag tccctggccc ggctgcatcc acccaatacc   1080
ctgataaccc aggacccatt acttctaggg taaggagggt ccaggagaca gaagctgagg   1140
aaaggtctga agaagtcaca tctgtcctgg ccagagggga aaaaccatca gatgctgaac   1200
caggagaatg ttgacccagg aaagggaccg aggacccaag aaaggagtca gaccaccagg   1260
gtttgcctga gaggaaggat caaggccccg agggaaagca gggctggctg catgtgcagg   1320
acactggtgg ggcatatgtg tcttagattc tccctgaatt cagtgtccct gccatggcca   1380
gactctctac tcaggcctgg acatgctgaa ataggacaat ggccttgtcc tctctcccca   1440
ccatttggca agagacataa aggacattcc aggacatgcc ttcctgggag gtccaggttc   1500
tctgtctcac acctcaggga ctgtagttac tgcatcagcc atggtaggtg ctgatctcac   1560
ccagcctgtc caggcccttc cactctccac tttgtgacca tgtccaggac cacccctcag   1620
atcctgagcc tgcaaatacc cccttgctgg gtgggtggat tcagtaaaca gtgagctcct   1680
```

FIGURE 14B

```
atccagcccc cagagccacc tctgtcacct tcctgctggg catcatccca ccttcacaag 1740
cactaaagag catggggaga cctggctagc tgggtttctg catcacaaag aaaataatcc 1800
cccaggttcg gattcccagg gctctgtatg tggagctgac agacctgagg ccaggagata 1860
gcagaggtca gccctaggga gggtgggtca tccacccagg ggacaggggt gcaccagcct 1920
tgctactgaa agggcctccc caggacagcg ccatcagccc tgcctgagag ctttgctaaa 1980
cagcagtcag aggaggccat ggcagtggct gagctcctgc tccaggcccc aacagaccag 2040
accaacagca caatgcagtc cttccccaac gtcacaggtc accaaaggga aactgaggtg 2100
ctacctaacc ttagagccat caggggagat aacagcccaa tttcccaaac aggccagttt 2160
caatcccatg acaatgacct ctctgctctc attcttccca aaataggacg ctgattctcc 2220
cccaccatgg atttctccct tgtcccggga gccttttctg ccccctatga tctgggcact 2280
cctgacacac acctcctctc tggtgacata tcagggtccc tcactgtcaa gcagtccaga 2340
aaggacagaa ccttggacag cgcccatctc agcttcaccc ttcctccttc acagggttca 2400
gggcaaagaa taaatggcag aggccagtga gcccagagat ggtgacaggc agtgacccag 2460
gggcagatgc ctggagcagg agctggcggg gccacaggga gaaggtgatg caggaaggga 2520
aacccagaaa tgggcaggaa aggaggacac aggctctgtg gggctgcagc ccagggttgg 2580
actatgagtg tgaagccatc tcagcaagta aggccaggtc ccatgaacaa gagtgggagc 2640
acgtggcttc ctgctctgta tatggggtgg gggattccat gccccataga accagatggc 2700
cggggttcag atggagaagg agcaggacag gggatcccca ggataggagg accccagtgt 2760
ccccacccag gcaggtgact gatgaatggg catgcagggt cctcctgggc tgggctctcc 2820
ctttgtccct caggattcct tgaaggaaca tccggaagcc gaccacatct acctggtggg 2880
ttctggggag tccatgtaaa gccaggagct tgtgttgcta ggaggggtca tggcatgtgc 2940
tgggggcacc aaagagagaa acctgagggc aggcaggacc tggtctgagg aggcatggga 3000
gcccagatgg ggagatggat gtcaggaaag gctgccccat cagggagggt gatagcaatg 3060
gggggtctgt gggagtgggc acgtgggatt ccctgggctc tgccaagttc cctcccatag 3120
tcacaacctg ggacactgc ccatgaaggg gcgcctttgc ccagccagat gctgctggtt 3180
ctgcccatcc actaccctct ctgctccagc cactctgggt ctttctccag atgccctgga 3240
cagccctggc ctgggcctgt cccctgagag gtgttgggag aagctgagtc tctggggaca 3300
ctctcatcag agtctgaaag gcacatcagg aaacatccct ggtctccagg actaggcaat 3360
```

FIGURE 14C

```
gaggaaaggg ccccagctcc tccctttgcc actgagaggg tcgaccctgg gtggccacag    3420
tgacttctgc gtctgtccca gtcaccctga aaccacaaca aaaccccagc cccagaccct    3480
gcaggtacaa tacatgtggg gacagtctgt acccagggga agccagttct ctcttcctag    3540
gagaccgggc ctcagggctg tgcccggggc aggcgggggc agcacgtgcc tgtccttgag    3600
aactcgggac cttaagggtc tctgctctgt gaggcacagc aaggatcctt ctgtccagag    3660
atgaaagcag ctcctgcccc tcctctgacc tcttcctcct tcccaaatct caaccaacaa    3720
ataggtgttt caaatctcat catcaaatct tcatccatcc acatgagaaa gcttaaaacc    3780
caatggattg acaacatcaa gagttggaac aagtggacat ggagatgtta cttgtggaaa    3840
tttagatgtg ttcagctatc gggcaggaga atctgtgtca aattccagca tggttcagaa    3900
gaatcaaaaa gtgtcacagt ccaaatgtgc aacagtgcag gggataaaac tgtggtgcat    3960
tcaaactgag ggatattttg gaacatgaga aaggaaggga ttgctgctgc acagaacatg    4020
gatgatctca cacatagagt tgaaagaaag gagtcaatcg cagaatagaa aatgatcact    4080
aattccacct ctataaagtt tccaagagga aaacccaatt ctgctgctag agatcagaat    4140
ggaggtgacc tgtgccttgc aatggctgtg agggtcacgg gagtgtcact tagtgcaggc    4200
aatgtgccgt atcttaatct gggcagggct ttcatgagca cataggaatg cagacattac    4260
tgctgtgttc attttacttc accggaaaag aagaataaaa tcagccgggc gcggtggctc    4320
acgcctgtaa tcccagcact ttagaaggct gaggtgggca gattacttga ggtcaggagt    4380
tcaagaccac cctggccaat atggtgaaac cccggctcta ctaaaaatac aaaaattagc    4440
tgggcatggt ggtgcgcgcc tgtaatccca gctactcggg aggctgaggc tggacaattg    4500
cttggaccca ggaagcagag gttgcagtga gccaagattg tgccactgca ctccagcttg    4560
ggcaacagag ccagactctg taaaaaaaaa aaaaaaaaaa aaaaaaagaa agaaagaaaa    4620
agaaaagaaa gtataaaatc tctttgggtt aacaaaaaaa gatccacaaa acaaacacca    4680
gctcttatca aacttacaca actctgccag agaacaggaa acacaaatac tcattaactc    4740
acttttgtgg caataaaacc ttcatgtcaa aaggagacca ggacacaatg aggaagtaaa    4800
actgcaggcc ctacttgggt gcagagaggg aaaatccaca aataaaacat taccagaagg    4860
agctaagatt tactgcattg agttcattcc ccaggtatgc aaggtgattt taacacctga    4920
aaatcaatca ttgcctttac tacatagaca gattagctag aaaaaaatta caactagcag    4980
aacagaagca atttggcctt cctaaaattc cacatcatat catcatgatg gagacagtgc    5040
agacgccaat gacaataaaa agagggacct ccgtcacccg gtaaacatgt ccacacagct    5100
```

FIGURE 14D

```
ccagcaagca cccgtcttcc cagtgaatca ctgtaacctc ccctttaatc agccccaggc 5160
aaggctgcct gcgatggcca cacaggctcc aaccccgtggg cctcaacctc ccgcagaggc 5220
tctcctttgg ccaccccatg gggagagcat gaggacaggg cagagccctc tgatgcccac 5280
acatggcagg agctgacgcc agagccatgg gggctggaga gcagagctgc tggggtcaga 5340
gcttcctgag gacacccagg cctaagggaa ggcagctccc tggatggggg caaccaggct 5400
ccgggctcca acctcagagc ccgcatggga ggagccagca ctctaggcct ttcctagggt 5460
gactctgagg ggaccctgac acgacaggat cgctgaatgc acccgagatg aaggggccac 5520
cacgggaccc tgctctcgtg gcagatcagg agagagtggg acaccatgcc aggcccccat 5580
ggcatggctg cgactgaccc aggccactcc cctgcatgca tcagcctcgg taagtcacat 5640
gaccaagccc aggaccaatg tggaaggaag gaaacagcat cccctttagt gatggaaccc 5700
aaggtcagtg caaagagagg ccatgagcag ttaggaaggg tggtccaacc tacagcacaa 5760
accatcatct atcataagta gaagccctgc tccatgaccc ctgcatttaa ataaacgttt 5820
gttaaatgag tcaaattccc tcaccatgag agctcacctg tgtgtaggcc catcacacac 5880
acaaacacac acacacacac acacacacac acacacacac acagggaaag tgcaggatcc 5940
tggacagcac caggcaggct tcacaggcag agcaaacagc gtgaatgacc catgcagtgc 6000
cctgggcccc atcagctcag agaccctgtg agggctgaga tggggctagg caggggagag 6060
acttagagag ggtggggcct ccagggaggg ggctgcaggg agctgggtac tgccctccag 6120
ggagggggct gcagggagct gggtactgcc ctccagggag ggggctgcag ggagctgggt 6180
actgccctcc agggaggggg ctgcagggag ctgggtactg ccctccaggg agggggctgc 6240
agggagctgg gtactgccct ccagggaggc aggagcactg ttcccaacag agagcacatc 6300
ttcctgcagc agctgcacag acacaggagc ccccatgact gccctgggcc agggtgtgga 6360
ttccaaattt cgtgccccat tgggtgggac ggaggttgac cgtgacatcc aaggggcatc 6420
tgtgattcca aacttaaact actgtgccta caaaatagga aataacccta ctttttctac 6480
tatctcaaat tccctaagca caagctagca ccctttaaat caggaagttc agtcactcct 6540
ggggtcctcc catgcccccca gtctgacttg caggtgcaca gggtggctga catctgtcct 6600
tgctcctcct cttggctcaa ctgccgcccc tcctgggggt gactgatggt caggacaagg 6660
gatcctagag ctggccccat gattgacagg aaggcaggac ttggcctcca ttctgaagac 6720
taggggtgtc aagagagctg ggcatcccac agagctgcac aagatgacgc ggacagaggg 6780
```

FIGURE 14E tgacacaggg ctcagggctt cagacgggtc gggaggctca gctgagagtt cagggacaga 6840
cctgaggagc ctcagtggga aaagaagcac tgaagtggga agttctggaa tgttctggac 6900
aagcctgagt gctctaagga aatgctccca ccccgatgta gcctgcagca ctggacggtc 6960
tgtgtacctc cccgctgccc atcctctcac agccccccgcc tctagggaca caactcctgc 7020
cctaacatgc atctttcctg tctcattcca cacaaaaggg cctctggggt ccctgttctg 7080
cattgcaagg agtggaggtc acgttcccac agaccaccca gcaacagggt cctatggagg 7140
tgcggtcagg aggatcacac gtcccccccat gcccagggga ctgactctgg gggtgatgga 7200
ttggcctgga ggccactggt cccctctgtc cctgagggga atctgcaccc tggaggctgc 7260
cacatccctc ctgattcttt cagctgaggg cccttcttga aatcccaggg aggactcaac 7320
ccccactggg aaaggcccag tgtggacggt tccacagcag cccagctaag gcccttggac 7380
acagatcctg agtgagagaa cctttaggga cacaggtgca cggccatgtc cccagtgccc 7440
acacagagca ggggcatctg gaccctgagt gtgtagctcc cgcgactgaa cccagcccctt 7500
ccccaatgac gtgacccctg gggtggctcc aggtctccag tccatgccac caaaatctcc 7560
agattgaggg tcctcccttg agtccctgat gcctgtccag gagctgcccc ctgagcaaat 7620
ctagagtgca gagggctggg attgtggcag taaaagcagc cacatttgtc tcaggaagga 7680
aagggaggac atgagctcca ggaagggcga tggcgtcctc tagtgggcgc ctcctgttaa 7740
tgagcaaaaa ggggccagga gagttgagag atcagggctg gccttggact aaggctcaga 7800
tggagaggac tgaggtgcaa agagggggct gaagtagggg agtggtcggg agagatggga 7860
ggagcaggta aggggaagcc ccagggaggc cgggggaggg tacagcagag ctctccactc 7920
ctcagcattg acatttgggg tggtcgtgct agtggggttc tgtaagttgt agggtgttca 7980
gcaccatctg ggactctac ccactaaatg ccagcaggac tccctcccca agctctaaca 8040
accaacaatg tctccagact ttccaaatgt cccctggaga gcaaaattgc ttctggcaga 8100
atcactgatc tacgtcagtc tctaaaagtg actcatcagc gaaatccttc acctcttggg 8160
agaagaatca caagtgtgag aggggtagaa actgcagact tcaaaatctt tccaaaagag 8220
ttttacttaa tcagcagttt gatgtcccag gagaagatac atttagagtg tttagagttg 8280
atgccacatg gctgcctgta cctcacagca ggagcagagt gggttttcca agggcctgta 8340
accacaactg gaatgacact cactgggtta cattacaaag tggaatgtgg ggaattctgt 8400
agactttggg aagggaaatg tatgacgtga gcccacagcc taaggcagtg gacagtccac 8460
tttgaggctc tcaccatcta ggagacatct cagccatgaa catagccaca tctgtcatta 8520

FIGURE 14F

```
gaaaacatgt tttattaaga ggaaaaatct aggctagaag tgctttatgc tctttttct    8580
ctttatgttc aaattcatat acttttagat cattccttaa agaagaatct atccccctaa   8640
gtaaatgtta tcactgactg gatagtgttg gtgtctcact cccaacccct gtgtggtgac   8700
agtgccctgc ttccccagcc ctgggccctc tctgattcct gagagctttg ggtgctcctt   8760
cattaggagg aagagaggaa gggtgttttt aatattctca ccattcaccc atccacctct   8820
tagacactgg gaagaatcag ttgcccactc ttggatttga tcctcgaatt aatgacctct   8880
atttctgtcc cttgtccatt tcaacaatgt gacaggccta agaggtgcct tctccatgtg   8940
atttttgagg agaaggttct caagataagt tttctcacac ctctttgaat tacctccacc   9000
tgtgtcccca tcaccattac cagcagcatt tggacccttt ttctgttagt cagatgcttt   9060
ccacctcttg agggtgtata ctgtatgctc tctacacagg aatatgcaga ggaaatagaa   9120
aaagggaaat cgcattacta ttcagagaga agaagacctt tatgtgaatg aatgagagtc   9180
taaaatccta agagagccca tataaaatta ttaccagtgc taaaactaca aaagttacac   9240
taacagtaaa ctagaataat aaaacatgca tcacagttgc tggtaaagct aaatcagata   9300
tttttttctt agaaaaagca ttccatgtgt gttgcagtga tgacaggagt gcccttcagt   9360
caatatgctg cctgtaattt ttgttccctg gcagaatgta ttgtcttttc tccctttaaa   9420
tcttaaatgc aaaactaaag gcagctcctg ggccccctcc ccaaagtcag ctgcctgcaa   9480
ccagccccac gaagagcaga ggcctgagct tccctggtca aaataggggg ctagggagct   9540
taaccttgct cgataaagct gtgttcccag aatgtcgctc ctgttcccag gggcaccagc   9600
ctggagggtg gtgagcctca ctggtggcct gatgcttacc ttgtgccctc acaccagtgg   9660
tcactggaac cttgaacact tggctgtcgc ccggatctgc agatgtcaag aacttctgga   9720
agtcaaatta ctgcccactt ctccagggca gatacctgtg aacatccaaa accatgccac   9780
agaaccctgc ctggggtcta caacacatat ggactgtgag caccaagtcc agccctgaat   9840
ctgtgaccac ctgccaagat gcccctaact gggatccacc aatcactgca catggcaggc   9900
agcgaggctt ggaggtgctt cgccacaagg cagccccaat ttgctgggag tttcttggca   9960
cctggtagtg gtgaggagcc ttgggaccct caggattact ccccttaagc atagtgggga   10020
cccttctgca tccccagcag gtgccccgct cttcagagcc tctctctctg aggtttaccc   10080
agacccctgc accaatgaga ccatgctgaa gcctcagaga gagagatgga gctttgacca   10140
ggagccgctc ttccttgagg gccagggcag ggaaagcagg aggcagcacc aggagtggga   10200
```

FIGURE 14G acaccagtgt ctaagcccct gatgagaaca gggtggtctc tcccatatgc ccataccagg 10260
cctgtgaaca gaatcctcct tctgcagtga caatgtctga gaggacgaca tgtttcccag 10320
cctaacgtgc agccatgccc atctacccac tgcctactgc aggacagcac caacccagga 10380
gctgggaagc tgggagaaga catggaatac ccatggcttc tcaccttcct ccagtccagt 10440
gggcaccatt tatgcctagg acacccacct gccggcccca ggctcttaag agttaggtca 10500
cctaggtgcc tctgggaggc cgaggcagga gaattgcttg aacccgggag gcagaggttg 10560
cagtgagccg agatcacacc actgcactcc agcctgggtg acagaatgag actctgtctc 10620
aaaaaaaaag agaaagatag catcagtggc taccaagggc taggggcagg ggaaggtgga 10680
gagttaatga ttaatagtat gaagtttcta tgtgagatga tgaaaatgtt ctggaaaaaa 10740
aaatatagtg gtgaggatgt agaatattgt gaatataatt aacggcattt aattgtacac 10800
ttaacatgat taatgtggca tattttatct tatgtatttg actacatcca agaaacactg 10860
ggagagggaa agcccaccat gtaaaataca cccaccctaa tcagatagtc ctcattgtac 10920
ccaggtacag gcccctcatg acctgcacag gaataactaa ggatttaagg acatgaggct 10980
tcccagccaa ctgcaggtgc acaacataaa tgtatctgca aacagactga gagtaaagct 11040
gggggcacaa acctcagcac tgccaggaca cacacccttc tcgtggattc tgactttatc 11100
tgacccggcc cactgtccag atcttgttgt gggattggga caagggaggt cataaagcct 11160
gtccccaggg cactctgtgt gagcacacga gacctcccca cccccccacc gttaggtctc 11220
cacacataga tctgaccatt aggcattgtg aggaggactc tagcgcgggc tcagggatca 11280
caccagagaa tcaggtacag agaggaagac ggggctcgag gagctgatgg atgacacaga 11340
gcaggcttcc tgcagtccac aggtccagct caccctggtg taggtgcccc atccccctga 11400
tccaggcatc cctgacacag ctccctcccg gagcctcctc ccaggtgaca catcagggtc 11460
cctcactcaa gctgtccaga gagggcagca ccttggacag cgcccacccc acttcactct 11520
tcctccctca cagggctcag ggctcagggc tcaagtctca gaacaaatgg cagaggccag 11580
tgagcccaga gatggtgaca gggcaatgat ccaggggcag ctgcctgaaa cgggagcagg 11640
tgaagccaca gatgggagaa gatggttcag gaagaaaaat ccaggaatgg gcaggagagg 11700
agaggaggac acaggctctg tggggctgca gcccaggatg ggactaagtg tgaagacatc 11760
tcagcaggtg aggccaggtc ccatgaacag agaagcagct cccacctccc ctgatgcacg 11820
gacacacaga gtgtgtggtg ctgtgccccc agagtcgggc tctcctgttc tggtccccag 11880
ggagtgagaa gtgaggttga cttgtccctg ctcctctctg ctaccccaac attcaccttc 11940

FIGURE 14H tcctcatgcc cctctctctc aaatatgatt tggatctatg tccccgccca aatctcatgt 12000
caaattgtaa accccaatgt tggaggtggg gccttgtgag aagtgattgg ataatgcggg 12060
tggattttct gctttgatgc tgtttctgtg atagagatct cacatgatct ggttgtttaa 12120
aagtgtgtag cacctctccc ctctctctct ctctctctta ctcatgctct gccatgtaag 12180
acgttcctgt ttccccttca ccgtccagaa tgattgtaag ttttctgagg cctccccagg 12240
agcagaagcc actatgcttc ctgtacaact gcagaatgat gagcgaatta aacctctttt 12300
ctttataaat tacccagtct caggtatttc tttatagcaa tgcgaggaca gactaataca 12360
atcttctact cccagatccc cgcacacgct tagccccaga catcactgcc cctgggagca 12420
tgcacagcgc agcctcctgc cgacaaaagc aaagtcacaa aaggtgacaa aaatctgcat 12480
ttggggacat ctgattgtga aagagggagg acagtacact tgtagccaca gagactgggg 12540
ctcaccgagc tgaaacctgg tagcactttg gcataacatg tgcatgaccc gtgttcaatg 12600
tctagagatc agtgttgagt aaaacagcct ggtctggggc cgctgctgtc cccacttccc 12660
tcctgtccac cagagggcgg cagagttcct cccaccctgg agcctcccca ggggctgctg 12720
acctccctca gccgggccca cagcccagca gggtccaccc tcacccgggt cacctcggcc 12780
cacgtcctcc tcgccctccg agctcctcac acggactctg tcagctcctc cctgcagcct 12840
atcggccgcc cacctgaggc ttgtcggccg cccacttgag gcctgtcggc tgccctctgc 12900
aggcagctcc tgtcccctac accccctcct tccccgggct cagctgaaag ggcgtctccc 12960
agggcagctc cctgtgatct ccaggacagc tcagtctctc acaggctccg acgcccccta 13020
tgctgtcacc tcacagccct gtcattacca ttaactcctc agtcccatga agttcactga 13080
gcgcctgtct cccggttaca ggaaaactct gtgacaggga ccacgtctgt cctgctctct 13140
gtggaatccc agggcccagc ccagtgcctg acacggaaca gatgctccat aaatactggt 13200
taaatgtgtg ggagatctct aaaaagaagc atatcacctc cgtgtggccc ccagcagtca 13260
gagtctgttc catgtggaca caggggcact ggcaccagca tgggaggagg ccagcaagtg 13320
cccgcggctg ccccaggaat gaggcctcaa cccccagagc ttcagaaggg aggacagagg 13380
cctgcaggga atagatcctc cggcctgacc ctgcagccta atccagagtt cagggtcagc 13440
tcacaccacg tcgaccctgg tcagcatccc tagggcagtt ccagacaagg ccggaggtct 13500
cctcttgccc tccagggggt gacattgcac acagacatca ctcaggaaac ggattcccct 13560
ggacaggaac ctggctttgc taaggaagtg gaggtggagc ctggtttcca tcccttgctc 13620

FIGURE 14I

```
caacagaccc ttctgatctc tcccacatac ctgctctgtt cctttctggg tcctatgagg   13680
accctgttct gccaggggtc cctgtgcaac tccagactcc ctcctggtac caccatgggg   13740
aaggtggggt gatcacagga cagtcagcct cgcagagaca gagaccaccc aggactgtca   13800
gggagaacat ggacaggccc tgagccgcag ctcagccaac agacacggag agggagggtc   13860
cccctggagc cttccccaag gacagcagag cccagagtca cccacctccc tccaccacag   13920
tcctctcttt ccaggacaca caagacacct ccccctccac atgcaggatc tggggactcc   13980
tgagacctct gggcctgggt ctccatccct gggtcagtgg cggggttggt ggtactggag   14040
acagagggct ggtccctccc cagccaccac ccagtgagcc tttttctagc ccccagagcc   14100
acctctgtca ccttcctgtt gggcatcatc ccaccttccc agagccctgg agagcatggg   14160
gagacccggg accctgctgg gtttctctgt cacaaaggaa aataatcccc ctggtgtgac   14220
agacccaagg acagaacaca gcagaggtca gcactgggga agacaggttg tcctcccagg   14280
ggatgggggt ccatccacct tgccgaaaag atttgtctga ggaactgaaa atagaaggga   14340
aaaaagagga gggacaaaag aggcagaaat gagaggggag gggacagagg acacctgaat   14400
aaagaccaca cccatgaccc acgtgatgct gagaagtact cctgccctag gaagagactc   14460
agggcagagg gaggaaggac agcagaccag acagtcacag cagccttgac aaaacgttcc   14520
tggaactcaa gctcttctcc acagaggagg acagagcaga cagcagagac catggagtct   14580
ccctcggccc ctcccccacag atggtgcatc ccctggcaga ggctcctgct cacaggtgaa   14640
gggaggacaa cctgggagag ggtgggagga gggagctggg gtctcctggg taggacaggg   14700
ctgtgagacg gacagagggc tcctgttgga gcctgaatag ggaagaggac atcagagagg   14760
gacaggagtc acaccagaaa aatcaaattg aactggaatt ggaaaggggc aggaaaacct   14820
caagagttct attttcctag ttaattgtca ctggccacta cgtttttaaa aatcataata   14880
actgcatcag atgacacttt aaataaaaac ataaccaggg catgaaacac tgtcctcatc   14940
cgcctaccgc ggacattgga aaataagccc caggctgtgg agggccctgg gaaccctcat   15000
gaactcatcc acaggaatct gcagcctgtc ccaggcactg gggtgcaacc aagatc        15056
```

FIGURE 15A aagcttctag ttttcttttc ccggtgacat cgtggaaagc actagcatct ctaagcaatg 60
atctgtgaca atattcacag tgtaatgcca tccagggaac tcaactgagc cttgatgtcc 120
agagattttt gtgttttttt ctgagactga gtctcgctct gtgccaggct ggagtgcagt 180
ggtgcaacct tggctcactg caagctccgc ctcctgggtt cacgccattc tcctgcctca 240
gcctcctgag tagctgggac tacaggcacc cgccaccacg cctggctaat ttttttgtat 300
ttttagtaga gatggggttt cactgtgtta gccaggatgg tctcagtctc ctgacctcgt 360
gatctgccca ccttggcctc ccaaagtgct gggatgacag gcgtgagcca ccgcgcctgg 420
ccgatatcca gagatttttt ggggggctcc atcacacaga catgttgact gtcttcatgg 480
ttgactttta gtatccagcc cctctagaaa tctagctgat atagtgtggc tcaaaacctt 540
cagcacaaat cacaccgtta gactatctgg tgtggcccaa accttcaggt gaacaaaggg 600
actctaatct ggcaggatat tccaaagcat tagagatgac ctcttgcaaa gaaaaagaaa 660
tggaaaagaa aaagaaagaa aggaaaaaaa aaaaaaaaaa gagatgacct ctcaggctct 720
gaggggaaac gcctgaggtc tttgagcaag gtcagtcctc tgttgcacag tctccctcac 780
agggtcattg tgacgatcaa atgtggtcac gtgtatgagg caccagcaca tgcctggctc 840
tggggagtgc cgtgtaagtg tatgcttgca ctgctgaatg cttgggatgt gtcagggatt 900
atcttcagca cttacagatg ctcatctcat cctcacagca tcactatggg atgggtatta 960
ctggcctcat ttgatggaga aagtggctgt ggctcagaaa gggggaccca ctagaccagg 1020
gacactctgg atgctgggga ctccagagac catgaccact caccaactgc agagaaatta 1080
attgtggcct gatgtccctg tcctggagag ggtggaggtg gaccttcact aacctcctac 1140
cttgaccctc tcttttaggg ctctttctga cctccaccat ggtactagga ccccattgta 1200
ttctgtaccc tcttgactct atgaccccca ctgcccactg catccagctg ggtcccctcc 1260
tatctctatt cccagctggc cagtgcagtc tcagtgccca cctgtttgtc agtaactctg 1320
aaggggctga cattttactg acttgcaaac aaataagcta actttccaga gttttgtgaa 1380
tgctggcaga gtccatgaga ctcctgagtc agaggcaaag gcttttactg ctcacagctt 1440
agcagacagc atgaggttca tgttcacatt agtacacctt gcccccccca aatcttgtag 1500
ggtgaccaga gcagtctagg tggatgctgt gcagaagggg tttgtgccac tggtgagaaa 1560
cctgagatta ggaatcctca atcttatact gggacaactt gcaaacctgc tcagcctttg 1620
tctctgatga agatattatc ttcatgatct tggattgaaa acagacctac tctggaggaa 1680

FIGURE 15B catattgtat cgattgtcct tgacagtaaa caaatctgtt gtaagagaca ttatctttat 1740
tatctaggac agtaagcaag cctggatctg agagagatat catcttgcaa ggatgcctgc 1800
tttacaaaca tccttgaaac aacaatccag aaaaaaaaag gtgttgctgt ctttgctcag 1860
aagacacaca gatacgtgac agaaccatgg agaattgcct cccaacgctg ttcagccaga 1920
gccttccacc cttgtctgca ggacagtctc aacgttccac cattaaatac ttcttctatc 1980
acatcctgct tctttatgcc taaccaaggt tctaggtccc gatcgactgt gtctggcagc 2040
actccactgc caaacccaga ataaggcagc gctcaggatc ccgaaggggc atggctgggg 2100
atcagaactt ctgggtttga gtgaggagtg ggtccaccct cttgaatttc aaaggaggaa 2160
gaggctggat gtgaaggtac tgggggaggg aaagtgtcag ttccgaactc ttaggtcaat 2220
gagggaggag actggtaagg tcccagctcc cgaggtactg atgtgggaat ggcctaagaa 2280
tctcatatcc tcaggaagaa ggtgctggaa tcctgagggg tagagttctg ggtatatttg 2340
tggcttaagg ctctttggcc cctgaaggca gaggctggaa ccattaggtc cagggtttgg 2400
ggtgatagta atgggatctc ttgattcctc aagagtctga ggatcgaggg ttgcccattc 2460
ttccatcttg ccacctaatc cttactccac ttgagggtat caccagccct tctagctcca 2520
tgaaggtccc ctgggcaagc acaatctgag catgaaagat gccccagagg ccttgggtgt 2580
catccactca tcatccagca tcacactctg agggtgtggc cagcaccatg acgtcatgtt 2640
gctgtgacta tccctgcagc gtgcctctcc agccacctgc caaccgtaga gctgcccatc 2700
ctcctctggt gggagtggcc tgcatggtgc caggctgagg cctagtgtca gacagggagc 2760
ctggaatcat agggatccag gactcaaaag tgctagagaa tggccatatg tcaccatcca 2820
tgaaatctca agggcttctg ggtggagggc acagggacct gaacttatgg tttcccaagt 2880
ctattgctct cccaagtgag tctcccagat acgaggcact gtgccagcat cagccttatc 2940
tccaccacat cttgtaaaag gactacccag ggccctgatg aacaccatgg tgtgtacagg 3000
agtagggggt ggaggcacgg actcctgtga ggtcacagcc aagggagcat catcatgggt 3060
ggggaggagg caatggacag gcttgagaac ggggatgtgg ttgtatttgg ttttctttgg 3120
ttagataaag tgctgggtat aggattgaga gtggagtatg aagaccagtt aggatggagg 3180
atcagattgg agttgggtta gataaagtgc tgggtatagg attgagagtg gagtatgaag 3240
accagttagg atggaggatc agattggagt tgggttagag atggggtaaa attgtgctcc 3300
ggatgagttt gggattgaca ctgtggaggt ggtttgggat ggcatggctt tgggatggaa 3360

FIGURE 15C atagatttgt tttgatgttg gctcagacat ccttggggat tgaactgggg atgaagctgg 3420
gtttgatttt ggaggtagaa gacgtggaag tagctgtcag atttgacagt ggccatgagt 3480
tttgtttgat ggggaatcaa acaatggggg aagacataag ggttggcttg ttaggttaag 3540
ttgcgttggg ttgatggggt cggggctgtg tataatgcag ttggattggt ttgtattaaa 3600
ttgggttggg tcaggttttg gttgaggatg agttgaggat atgcttgggg acaccggatc 3660
catgaggttc tcactggagt ggagacaaac ttcctttcca ggatgaatcc agggaagcct 3720
taattcacgt gtaggggagg tcaggccact ggctaagtat atccttccac tccagctcta 3780
agatggtctt aaattgtgat tatctatatc cacttctgtc tccctcactg tgcttggagt 3840
ttacctgatc actcaactag aaacagggga agattttatc aaattctttt ttttttttt 3900
ttttttttga gacagagtct cactctgttg cccaggctgg agtgcagtgg cgcagtctcg 3960
gctcactgca acctctgcct cccaggttca agtgattctc ctgcctcagc ctcctgagtt 4020
gctgggatta caggcatgca gcaccatgcc cagctaattt ttgtattttt agtagagatg 4080
gggtttcacc aatgtttgcc aggctggcct cgaactcctg acctggtgat ccacctgcct 4140
cagcctccca aagtgctggg attacaggcg tcagccaccg cgcccagcca cttttgtcaa 4200
attcttgaga cacagctcgg gctggatcaa gtgagctact ctggttttat tgaacagctg 4260
aaataaccaa ctttttggaa attgatgaaa tcttacggag ttaacagtgg aggtaccagg 4320
gctcttaaga gttcccgatt ctcttctgag actacaaatt gtgattttgc atgccacctt 4380
aatctttttt ttttttttt taaatcgagg tttcagtctc attctatttc ccaggctgga 4440
gttcaatagc gtgatcacag ctcactgtag ccttgaactc ctggccttaa gagattctcc 4500
tgcttcggtc tcccaatagc taagactaca gtagtccacc accatatcca gataattttt 4560
aaattttttg gggggccggg cacagtggct cacgcctgta atcccaacac catgggaggc 4620
tgagatgggt ggatcacgag gtcaggagtt tgagaccagc ctgaccaaca tggtgaaact 4680
ctgtctctac taaaaaaaaa aaaaatagaa aaattagccg ggcgtggtgg cacacggcac 4740
ctgtaatccc agctactgag gaggctgagg caggagaatc acttgaaccc agaaggcaga 4800
ggttgcaatg agccgagatt gcgccactgc actccagcct gggtgacaga gtgagactct 4860
gtctcaaaaa aaaaaaattt tttttttttt tttgtagaga tggatcttgc tttgtttctc 4920
tggttggcct tgaactcctg gcttcaagtg atcctcctac cttggcctcg gaaagtgttg 4980
ggattacagg cgtgagccac catgactgac ctgtcgttaa tcttgaggta cataaacctg 5040
gctcctaaag gctaaaggct aaatatttgt tggagaaggc gcattggatt ttgcatgagg 5100

FIGURE 15D

```
atgattctga cctgggaggg caggtcagca ggcatctctg ttgcacagat agagtgtaca 5160
ggtctggaga acaaggagtg gggggttatt ggaattccac attgtttgct gcacgttgga 5220
ttttgaaatg ctagggaact ttgggagact catatttctg ggctagagga tctgtggacc 5280
acaagatctt tttatgatga cagtagcaat gtatctgtgg agctggattc tgggttggga 5340
gtgcaaggaa aagaatgtac taaatgccaa gacatctatt tcaggagcat gaggaataaa 5400
agttctagtt tctggtctca gagtggtgca gggatcaggg agtctcacaa tctcctgagt 5460
gctggtgtct tagggcacac tgggtcttgg agtgcaaagg atctaggcac gtgaggcttt 5520
gtatgaagaa tcggggatcg tacccacccc ctgtttctgt ttcatcctgg gcatgtctcc 5580
tctgcctttg tcccctagat gaagtctcca tgagctacaa gggcctggtg catccagggt 5640
gatctagtaa ttgcagaaca gcaagtgcta gctctccctc cccttccaca gctctgggtg 5700
tgggaggggg ttgtccagcc tccagcagca tggggagggc cttggtcagc ctctgggtgc 5760
cagcagggca ggggcggagt cctggggaat gaaggtttta tagggctcct gggggaggct 5820
ccccagcccc aagctt                                                 5836
```

FIGURE 16A

```
gaattcagaa ataggggaag gttgaggaag gacactgaac tcaaagggga tacagtgatt 60
ggtttatttg tcttctcttc acaacattgg tgctggagga attcccaccc tgaggttatg 120
aagatgtctg aacacccaac acatagcact ggagatatga gctcgacaag agtttctcag 180
ccacagagat tcacagccta gggcaggagg acactgtacg ccaggcagaa tgacatggga 240
attgcgctca cgattggctt gaagaagcaa ggactgtggg aggtgggctt tgtagtaaca 300
agagggcagg gtgaactctg attcccatgg gggaatgtga tggtcctgtt acaaattttt 360
caagctggca gggaataaaa cccattacgg tgaggacctg tggagggcgg ctgccccaac 420
tgataaagga aatagccagg tggggccttt tcccattgta gggggacat atctggcaat 480
agaagccttt gagacccttt agggtacaag tactgaggca gcaaataaaa tgaaatctta 540
tttttcaact ttatactgca tgggtgtgaa gatatatttg tttctgtaca gggggtgagg 600
gaaaggaggg gaggaggaaa gttcctgcag gtctggtttg gtcttgtgat ccagggggtc 660
ttggaactat ttaaattaaa ttaaattaaa acaagcgact gttttaaatt aaattaaatt 720
aaattaaatt ttactttatt ttatcttaag ttctgggcta catgtgcagg acgtgcagct 780
ttgttacata ggtaaacgtg tgccatggtg gtttgctgta cctatcaacc catcacctag 840
gtattaagcc cagcatgcat tagctgtttt tcctgacgct ctccctctcc ctgactccca 900
caacaggccc cagtgtgtgt tgttcccctc cctgtgtcca tgtgttctca ttgttcagct 960
cccacttata agtgagaaca tgtggtgttt ggttttctgt ttctgtgtta gtttgctgag 1020
gataatggct tccacctcca tccatgttcc tgcaaaggac gtgatcttat tctttttat 1080
ggttgcatag aaattgtttt tacaaatcca attgatattg tatttaatta caagttaatc 1140
taattagcat actagaagag attacagaag atattaggta cattgaatga ggaaatatat 1200
aaaataggac gaaggtgaaa tattaggtag gaaaagtata atagttgaaa gaagtaaaaa 1260
aaaatatgca tgagtagcag aatgtaaaag aggtgaagaa cgtaatagtg actttttaga 1320
ccagattgaa ggacagagac agaaaaattt taaggaattg ctaaaccatg tgagtgttag 1380
aagtacagtc aataacatta aagcctcagg aggagaaaag aataggaaag gaggaaatat 1440
gtgaataaat agtagagaca tgtttgatgg attttaaaat atttgaaaga cctcacatca 1500
aaggattcat accgtgccat tgaagaggaa gatggaaaag ccaagaagcc agatgaaagt 1560
tagaaatatt attggcaaag cttaaatgtt aaaagtccta gagacaaagg atggcagaaa 1620
tattggcggg aaagaatgca gaacctagaa tataaattca tcccaacagt ttggtagtgt 1680
```

FIGURE 16B

```
gcagctgtag cctttttctag ataatacact attgtcatac atcgcttaag cgagtgtaaa 1740
atggtctcct cactttattt atttatatat ttatttagtt ttgagatgga gcctcgctct 1800
gtctcctagg ctggagtgca atagtgcgat accactcact gcaacctctg cctcctctgt 1860
tcaagtgatt ttcttacctc agcctcccga gtagctggga ttacaggtgc gtgccaccac 1920
acccggctaa tttttgtatt ttttgtagag acggggtttt gccatgttgg ccaggctggt 1980
cttgaactcc tgacatcagg tgatccacct gccttggcct cctaaagtgc tgggattaca 2040
ggcatgagcc accgtgccca accactttat ttattttta tttttatttt taaatttcag 2100
cttctatttg aaatacaggg ggcacatata taggattgtt acatgggtat attgaactca 2160
ggtagtgatc atactaccca acaggtaggt tttcaaccca ctccccctct tttcctcccc 2220
attctagtag tgtgcagtgt ctattgttct catgtttatg tctatgtgtg ctccaggttt 2280
agctcccacc tgtaagtgag aacgtgtggt atttgatttt ctgtccctgt gttaattcac 2340
ttaggattat ggcttccagc tccattcata ttgctgtaaa ggatatgatt catttttcat 2400
ggccatgcag tattccatat tgcgtataga tcacattttc tttcttttt tttttgaga 2460
cggagtcttg ctttgctgcc taggctggag tgcagtagca cgatctcggc tcactgcaag 2520
cttcacctcc ggggttcacg tcattcttct gtctcagctt cccaagtagc tgggactaca 2580
ggcgcccgcc accacgtccg gctaattttt ttgtgtgttt ttagtagaga tgggggtttc 2640
actgtgttag ccaggatggt cttgatctcc tgaccttgtg gtccacctgc ctcggtctcc 2700
caaagtgctg ggattacagg ggtgagccac tgcgcccggc ccatatatac cacattttct 2760
ttaaccaatc caccattgat gggcaactag gtagattcca tggattccac agttttgcta 2820
ttgtgtgcag tgtggcagta gacatatgaa tgaatgtgtc tttttggtat aatgatttgc 2880
attcctttgg gtatacagtc attaatagga gtgctgggtt gaacggtggc tctgtttaaa 2940
attctttgag aattttccaa actgtttgcc atagagagca aactaattta catttccacg 3000
aacagtatat aagcattccc ttttctccac agctttgtca tcatggtttt tttttttctt 3060
tattttaaaa aagaatatgt tgttgttttc ccagggtaca tgtgcaggat gtgcaggttt 3120
gttacatagg tagtaaacgt gagccatggt ggtttgctgc acctgtcaac ccattacctg 3180
ggtatgaagc cctgcctgca ttagctcttt tccctaatgc tctcactact gcccccaccct 3240
caccctgaca gggcaaacag acaacctaca gaatgggagg aaatttttgc aatctattca 3300
tctgacaaag gtcaagaata tccagaatct acaaggaact taagcaaatt tttactttttt 3360
```

FIGURE 16C

```
aataatagcc actctgactg gcgtgaaatg gtatctcatt gtggttttca tttgaatttc 3420
tctgatgatc agtgacgatg agcatttttt catatttgtt ggctgcttgt acgtcttttg 3480
agaagtgtct cttcatgcct tttggccact ttaatgggat tattttttgc tttttagttt 3540
aagttcctta tagattctgg atattagact tcttattgga tgcatagttt gtgaatactc 3600
tcttccattc tgtaggttgt ctgtttactc tattgatggc ttcttttgct gtgccgaagc 3660
atcttagttt aattagaaac cacctgccaa tttttgtttt tgttgcaatt gcttttgggg 3720
acttagtcat aaactctttg ccaaggtctg ggtcaagaag agtatttcct aggttttctt 3780
ctagaatttt gaaagtctga atgtaaacat ttgcattttt aatgcatctt gagttagttt 3840
ttgtatatgt gaaaggtcta ctctcatttt ctttccctct ttctttcttt ctttctttc 3900
tttctttctt tctttctttc tttctttctt tctttctttc tttcttttg tccttctttc 3960
tttctttctt tctctttctt tctctctttc tttttttttt ttgatggagt attgctctgt 4020
tgcccaggct gcagtgcagc ggcacgatct cggctcactg caacctctgc ctcctgggtt 4080
caactgattc tcctgcatca gccttccaag tagctgggat tataggcgcc cgccaccacg 4140
cccgactaat ttttgtattt ttagtagaga cggggttgtg ccatgttggc caggctggtt 4200
tgaaactcct gacctcaaac gatctgcctg ccttggcctc ccaaagtgct gggattacag 4260
gtgtgagcca ctgtgcccag ccaagaatgt cattttctaa gaggtccaag aacctcaaga 4320
tattttggga ccttgagaag agaggaattc atacaggtat tacaagcaca gcctaatggc 4380
aaatctttgg catggcttgg cttcaagact ttaggctctt aaaagtcgaa tccaaaaatt 4440
tttataaaag ctccagctaa gctaccttaa aaggggcctg tatggctgat cactcttctt 4500
gctatacttt acacaaataa acaggccaaa tataatgagg ccaaaattta ttttgcaaat 4560
aaattggtcc tgctatgatt tactcttggt aagaacaggg aaaatagaga aaaatttaga 4620
ttgcatctga cctttttttc tgaattttta tatgtgccta caatttgagc taaatcctga 4680
attattttct ggttgcaaaa actctctaaa gaagaacttg gttttcattg tcttcgtgac 4740
acatttatct ggctctttac tagaacagct ttcttgtttt tggtgttcta gcttgtgtgc 4800
cttacagttc tactcttcaa attattgtta tgtgtatctc atagtttcc ttcttttgag 4860
aaaactgaag ccatggtatt ctgaggacta gagatgactc aacagagctg gtgaatctcc 4920
tcatatgcaa tccactgggc tcgatctgct tcaaattgct gatgcactgc tgctaaagct 4980
atacatttaa aaccctcact aaaggatcag ggaccatcat ggaagagcag gaaacatgaa 5040
attgtaagag ccagattcgg ggggtagagt gtggaggtca gagcaactcc accttgaata 5100
```

FIGURE 16D

```
agaaggtaaa gcaacctatc ctgaaagcta acctgccatg gtggcttctg attaacctct 5160
gttctaggaa gactgacagt ttgggtctgt gtcattgccc aaatctcatg ttaaattgta 5220
atccccagtg ttcggaggtg ggacttggtg gtaggtgatt cggtcatggg agtagatttt 5280
cttctttgtg gtgttacagt gatagtgagt gagttctcgt gagatctggt catttaaaag 5340
tgtgtggccc ctcccctccc tctcttggtc ctcctactgc catgtaagat acctgctcct 5400
gctttgcctt ctaccataag taaaagcccc ctgaggcctc cccagaagca gatgccacca 5460
tgcttcctgt acagcctgca gaaccatcag ccaattaaac ctcttttctg tataaattac 5520
cagtcttgag tatctcttta cagcagtgtg agaacggact aatacaaggg tctccaaaat 5580
tccaagttta tgtattcttt cttgccaaat agcaggtatt taccataaat cctgtcctta 5640
ggtcaaacaa ccttgatggc atcgtacttc aattgtctta cacattcctt ctgaatgact 5700
cctcccctat ggcatataag ccctgggtct tgggggataa tggcagaggg gtccaccatc 5760
ttgtctggct gccacctgag acacggacat ggcttctgtt ggtaagtctc tattaaatgt 5820
ttctttctaa gaaactggat ttgtcagctt gtttctttgg cctctcagct tcctcagact 5880
ttggggtagg ttgcacaacc ctgcccacca cgaaacaaat gtttaatatg ataaatatgg 5940
atagatataa tccacataaa taaaagctct tggagggccc tcaataattg ttaagagtgt 6000
aaatgtgtcc aaagatggaa aatgtttgag aactactgtc ccagagattt tcctgagttc 6060
tagagtgtgg gaatatagaa cctggagctt ggcttcttca gcctagaatc aggagtatgg 6120
ggctgaagtc tgaagcttgg cttcagcagt ttggggttgg cttccggagc acatatttga 6180
catgttgcga ctgtgatttg gggtttggta tttgctctga atcctaatgt ctgtccttga 6240
ggcatctaga atctgaaatc tgtggtcaga attctattat cttgagtagg acatctccag 6300
tcctggttct gccttctagg gctggagtct gtagtcagtg acccggtctg gcatttcaac 6360
ttcatataca gtgggctatc ttttggtcca tgtttcaacc aaacaaccga ataaaccatt 6420
agaacctttc cccacttccc tagctgcaat gttaaaccta ggatttctgt ttaataggtt 6480
catatgaata atttcagcct gatccaactt tacattcctt ctaccgttat tctacaccca 6540
ccttaaaaat gcattcccaa tatattccct ggattctacc tatatatggt aatcctggct 6600
ttgccagttt ctagtgcatt aacatacctg atttacattc ttttacttta aagtggaaat 6660
aagagtccct ctgcagagtt caggagttct caagatggcc cttacttctg acatcaattg 6720
agatttcaag ggagtcgcca agatcatcct caggttcagt gattgctggt agccctcata 6780
```

FIGURE 16E taactcaatg aaagctgtta tgctcatggc tatggtttat tacagcaaaa gaatagagat 6840
gaaaatctag caagggaaga gttgcatggg gcaaagacaa ggagagctcc aagtgcagag 6900
attcctgttg ttttctccca gtggtgtcat ggaaagcagt atcttctcca tacaatgatg 6960
tgtgataata ttcagtgtat tgccaatcag ggaactcaac tgagccttga ttatattgga 7020
gcttggttgc acagacatgt cgaccacctt catggctgaa ctttagtact tagcccctcc 7080
agacgtctac agctgatagg ctgtaaccca acattgtcac cataaatcac attgttagac 7140
tatccagtgt ggcccaagct cccgtgtaaa cacaggcact ctaaacaggc aggatatttc 7200
aaaagcttag agatgacctc ccaggagctg aatgcaaaga cctggcctct ttgggcaagg 7260
agaatccttt accgcacact ctccttcaca gggttattgt gaggatcaaa tgtggtcatg 7320
tgtgtgagac accagcacat gtctggctgt ggagagtgac ttctatgtgt gctaacattg 7380
ctgagtgcta agaaagtatt aggcatggct ttcagcactc acagatgctc atctaatcct 7440
cacaacatgg ctacagggtg ggcactacta gcctcatttg acagaggaaa ggactgtgga 7500
taagaagggg gtgaccaata ggtcagagtc attctggatg caaggggctc cagaggacca 7560
tgattagaca ttgtctgcag agaaattatg gctggatgtc tctgccccgg aaaggggat 7620
gcactttcct tgacccccta tctcagatct tgactttgag gttatctcag acttcctcta 7680
tgataccagg agcccatcat aatctctctg tgtcctctcc ccttcctcag tcttactgcc 7740
cactcttccc agctccatct ccagctggcc aggtgtagcc acagtaccta actctttgca 7800
gagaactata aatgtgtatc ctacagggga gaaaaaaaaa aagaactctg aaagagctga 7860
cattttaccg acttgcaaac acataagcta acctgccagt tttgtgctgg tagaactcat 7920
gagactcctg ggtcagaggc aaaagatttt attacccaca gctaaggagg cagcatgaac 7980
tttgtgttca catttgttca ctttgccccc caattcatat gggatgatca gagcagttca 8040
ggtggatgga cacaggggtt tgtggcaaag gtgagcaacc taggcttaga aatcctcaat 8100
cttataagaa ggtactagca aacttgtcca gtctttgtat ctgacggaga tattatcttt 8160
ataattgggt tgaaagcaga cctactctgg aggaacatat tgtatttatt gtcctgaaca 8220
gtaaacaaat ctgctgtaaa atagacgtta actttattat ctaaggcagt aagcaaacct 8280
agatctgaag gcgataccat cttgcaaggc tatctgctgt acaaatatgc ttgaaaagat 8340
ggtccagaaa agaaaacggt attattgcct ttgctcagaa gacacacaga aacataagag 8400
aaccatggaa aattgtctcc caacactgtt cacccagagc cttccactct tgtctgcagg 8460
acagtcttaa catcccatca ttagtgtgtc taccacatct ggcttcaccg tgcctaacca 8520

FIGURE 16F agatttctag gtccagttcc ccaccatgtt tggcagtgcc ccactgccaa ccccagaata 8580
agggagtgct cagaattccg aggggacatg ggtggggatc agaacttctg ggcttgagtg 8640
cagaggggc ccatactcct tggttccgaa ggaggaagag gctggaggtg aatgtccttg 8700
gaggggagga atgtgggttc tgaactctta aatccccaag ggaggagact ggtaaggtcc 8760
cagcttccga ggtactgacg tgggaatggc ctgagaggtc taagaatccc gtatcctcgg 8820
gaaggagggg ctgaaattgt gaggggttga gttgcagggg tttgttagct tgagactcct 8880
tggtgggtcc ctgggaagca aggactggaa ccattggctc cagggtttgg tgtgaaggta 8940
atgggatctc ctgattctca aagggtcaga ggactgagag ttgcccatgc tttgatcttt 9000
ccatctactc cttactccac ttgagggtaa tcacctactc ttctagttcc acaagagtgc 9060
gcctgcgcga gtataatctg cacatgtgcc atgtcccgag gcctggggca tcatccactc 9120
atcattcagc atctgcgcta tgcgggcgag gccggcgcca tgacgtcatg tagctgcgac 9180
tatccctgca gcgcgcctct cccgtcacgt cccaaccatg gagctgtgga cgtgcgtccc 9240
ctggtggatg tggcctgcgt ggtgccaggc cggggcctgg tgtccgataa agatcctaga 9300
accacaggaa accaggactg aaaggtgcta gagaatggcc atatgtcgct gtccatgaaa 9360
tctcaaggac ttctgggtgg agggcacagg agcctgaact tacgggtttg ccccagtcca 9420
ctgtcctccc aagtgagtct cccagatacg aggcactgtg ccagcatcag cttcatctgt 9480
accacatctt gtaacaggga ctacccagga ccctgatgaa caccatggtg tgtgcaggaa 9540
gaggggtga aggcatggac tcctgtgtgg tcagagccca gaggggcca tgacgggtgg 9600
ggaggaggct gtggactggc tcgagaagtg ggatgtggtt gtgtttgatt tcctttggcc 9660
agataaagtg ctggatatag cattgaaaac ggagtatgaa gaccagttag aatggagggt 9720
caggttggag ttgagttaca gatggggtaa aattctgctt cggatgagtt tggggattgg 9780
caatctaaag gtggtttggg atggcatggc tttgggatgg aaataggttt gtttttatgt 9840
tggctgggaa gggtgtgggg attgaattgg ggatgaagta ggtttagttt tggagataga 9900
atacatggag ctggctattg catgcgagga tgtgcattag tttggtttga tctttaaata 9960
aaggaggcta ttagggttgt cttgaattag attaagttgt gttgggttga tgggttgggc 10020
ttgtgggtga tgtggttgga ttgggctgtg ttaaattggt ttgggtcagg ttttggttga 10080
ggttatcatg gggatgagga tatgcttggg acatggattc aggtggttct cattcaagct 10140
gaggcaaatt tcctttcaga cggtcattcc agggaacgag tggttgtgtg ggggaaatca 10200

FIGURE 16G ggccactggc tgtgaatatc cctctatcct ggtcttgaat tgtgattatc tatgtccatt 10260
ctgtctcctt cactgtactt ggaattgatc tggtcattca gctggaaatg ggggaagatt 10320
ttgtcaaatt cttgagacac agctgggtct ggatcagcgt aagccttcct tctggtttta 10380
ttgaacagat gaaatcacat tttttttttc aaaatcacag aaatcttata gagttaacag 10440
tggactctta taataagagt taacaccagg actcttattc ttgattcttt tctgagacac 10500
caaaatgaga tttctcaatg ccaccctaat tctttttttt tttttttttt tttttgagac 10560
acagtctggg tcttttgctc tgtcactcag gctggagcgc agtggtgtga tcatagctca 10620
ctgaaccctt gacctcctgg acttaaggga tcctcctgct tcagcctcct gagtagatgg 10680
ggctacaggt gcttgccacc acacctggct aattaaattt tttttttttt tttgtagaga 10740
aagggtctca ctttgttgcc ctggctgatc ttgaacttct gacttcaagt gattcttcag 10800
ccttggactc ccaaagcact gggattgctg gcatgagcca ctcaccgtgc ctggcttgca 10860
gcttaatctt ggagtgtata aacctggctc ctgatagcta gacatttcag tgagaaggag 10920
gcattggatt ttgcatgagg acaattctga cctaggaggg caggtcaaca ggaatccccg 10980
ctgtacctgt acgttgtaca ggcatggaga atgaggagtg aggaggccgt accggaaccc 11040
catattgttt agtggacatt ggattttgaa ataataggga acttggtctg ggagagtcat 11100
atttctggat tggacaatat gtggtatcac aaggttttat gatgagggag aaatgtatgt 11160
ggggaaccat tttctgagtg tggaagtgca agaatcagag agtagctgaa tgccaacgct 11220
tctatttcag gaacatggta agttggaggt ccagctctcg ggctcagacg ggtataggga 11280
ccaggaagtc tcacaatccg atcattctga tatttcaggg catattaggt ttggggtgca 11340
aaggaagtac ttgggactta ggcacatgag actttgtatt gaaaatcaat gattggggct 11400
ggccgtggtg ctcacgcctg taatctcatc actttgggag accgaagtgg gaggatggct 11460
tgatctcaag agttggacac cagcctaggc aacatggcca gaccctctct ctacaaaaaa 11520
attaaaaatt agctggatgt ggtggtgcat gcttgtggtc tcagctatcc tggaggctga 11580
gacaggagaa tcggttgagt ctgggagttc aaggctacag ggagctgcga tcacgccgct 11640
gcactccagc ctgggaaaca gagtgagact gtctcagaat ttttttaaaa aagaatcagt 11700
gatcatccca acccctgttg ctgttcatcc tgagcctgcc ttctctggct ttgttcccta 11760
gatcacatct ccatgatcca taggccctgc ccaatctgac ctcacaccgt gggaatgcct 11820
ccagactgat ctagtatgtg tggaacagca agtgctggct ctccctcccc ttccacagct 11880
ctgggtgtgg gaggggggttg tccagcctcc agcagcatgg ggagggcctt ggtcagcatc 11940

FIGURE 16H

```
taggtgccaa cagggcaagg gcggggtcct ggagaatgaa ggctttatag ggctcctcag 12000
ggaggccccc cagccccaaa ctgcaccacc tggccgtgga caccggt              12047
```

FIGURE 17

```
cgagcggccc ctcagcttcg gcgcccagcc ccgcaaggct cccggtgacc actagagggc 60
gggaggagct cctggccagt ggtggagagt ggcaaggaag gaccctaggg ttcatcggag 120
cccaggttta ctcccttaag tggaaatttc ttcccccact cctccttggc tttctccaag 180
gagggaaccc aggctgctgg aaagtccggc tggggcgggg actgtgggtt caggggagaa 240
cggggtgtgg aacgggacag ggagcggtta gaagggtggg gctattccgg gaagtggtgg 300
ggggagggag cccaaaacta gcacctagtc cactcattat ccagccctct tatttctcgg 360
ccgctctgct tcagtggacc cggggagggc ggggaagtgg agtgggagac ctaggggtgg 420
gcttcccgac cttgctgtac aggacctcga cctagctggc tttgttcccc atccccacgt 480
tagttgttgc cctgaggcta aaactagagc ccagggggccc caagttccag actgcccctc 540
cccccctcccc cggagccagg gagtggttgg tgaaaggggg aggccagctg gagaacaaac 600
gggtagtcag ggggttgagc gattagagcc cttgtaccct acccaggaat ggttggggag 660
gaggaggaag aggtaggagg taggggaggg ggcggggttt tgtcacctgt cacctgctcg 720
ctgtgcctag ggcgggcggg cggggagtgg ggggaccggt ataaagcggt aggcgcctgt 780
gcccgctcca cctctcaagc agccagcgcc tgcctgaatc tgttctgccc cctccccacc 840
catttcacca ccaccatg                                               858
```

FIGURE 18

```
aagcttccac aagtgcattt agcctctcca gtattgctga tgaatccaca gttcaggttc 60
aatggcgttc aaaacttgat caaaaatgac cagactttat attcttacac caacatctat 120
ctgattggag gaatggataa tagtcatcat gtttaaacat ctaccattcc agttaagaaa 180
atatgatagc atcttgttct tagtcttttt cttaataggg acataaagcc cacaaataaa 240
aatatgcctg aagaatggga caggcattgg gcattgtcca tgcctagtaa agtactccaa 300
gaacctattt gtatactaga tgacacaatg tcaatgtctg tgtacaactg ccaactggga 360
tgcaagacac tgcccatgcc aatcatcctg aaaagcagct ataaaaagca ggaagctact 420
ctgcaccttg tcagtgaggt ccagatacct acag                            454
```

```
g atg acc ggc tca acc atc gcg ccc aca acg gac tat cgc aac acc act  49
  Met Thr Gly Ser Thr Ile Ala Pro Thr Thr Asp Tyr Arg Asn Thr Thr
   1               5                  10                  15

gct acc gga cta aca tct gcc cta aat tta ccc caa gtt cat gcc ttt    97
Ala Thr Gly Leu Thr Ser Ala Leu Asn Leu Pro Gln Val His Ala Phe
            20                  25                  30

gtc aat gac tgg gcg agc ttg gac atg tgg tgg ttt tcc ata gcg ctt   145
Val Asn Asp Trp Ala Ser Leu Asp Met Trp Trp Phe Ser Ile Ala Leu
        35                  40                  45

atg ttt gtt tgc ctt att att atg tgg ctt att tgt tgc cta aag cgc   193
Met Phe Val Cys Leu Ile Ile Met Trp Leu Ile Cys Cys Leu Lys Arg
    50                  55                  60

aga cgc gcc aga ccc ccc atc tat agg cct atc att gtg ctc aac cca   241
Arg Arg Ala Arg Pro Pro Ile Tyr Arg Pro Ile Ile Val Leu Asn Pro
65                  70                  75                  80

cac aat gaa aaa att cat aga ttg gac ggt ctg aaa cca tgt tct ctt   289
His Asn Glu Lys Ile His Arg Leu Asp Gly Leu Lys Pro Cys Ser Leu
                85                  90                  95

ctt tta cag tat gat taa                                           307
Leu Leu Gln Tyr Asp
            100
```

FIGURE 19

SEQUENCE LISTING

<160> NUMBER OF SEQ ID NOS: 77

<210> SEQ ID NO 1
<211> LENGTH: 5836
<212> TYPE: DNA
<213> ORGANISM: Homo sapiens

<400> SEQUENCE: 1
aagcttctag ttttcttttc ccggtgacat cgtggaaagc actagcatct ctaagcaatg 60
atctgtgaca atattcacag tgtaatgcca tccagggaac tcaactgagc cttgatgtcc 120
agagattttt gtgtttttttt ctgagactga gtctcgctct gtgccaggct ggagtgcagt 180
ggtgcaacct tggctcactg caagctccgc ctcctgggtt cacgccattc tcctgcctca 240
gcctcctgag tagctgggac tacaggcacc cgccaccacg cctggctaat ttttttgtat 300
ttttagtaga gatggggttt cactgtgtta gccaggatgg tctcagtctc ctgacctcgt 360
gatctgccca ccttggcctc ccaaagtgct gggatgacag gcgtgagcca ccgcgcctgg 420
ccgatatcca gagatttttt ggggggctcc atcacacaga catgttgact gtcttcatgg 480
ttgactttta gtatccagcc cctctagaaa tctagctgat atagtgtggc tcaaaacctt 540
cagcacaaat cacaccgtta gactatctgg tgtggcccaa accttcaggt gaacaaaggg 600
actctaatct ggcaggatat tccaaagcat tagagatgac ctcttgcaaa gaaaaagaaa 660
tggaaaagaa aaagaaagaa aggaaaaaaa aaaaaaaaaa gagatgacct ctcaggctct 720
gaggggaaac gcctgaggtc tttgagcaag gtcagtcctc tgttgcacag tctccctcac 780
agggtcattg tgacgatcaa atgtggtcac gtgtatgagg caccagcaca tgcctggctc 840
tggggagtgc cgtgtaagtg tatgcttgca ctgctgaatg cttgggatgt gtcagggatt 900

-continued

```
atcttcagca cttacagatg ctcatctcat cctcacagca tcactatggg atgggtatta    960
ctggcctcat ttgatggaga aagtggctgt ggctcagaaa gggggggacca ctagaccagg   1020
gacactctgg atgctggggga ctccagagac catgaccact caccaactgc agagaaatta   1080
attgtggcct gatgtccctg tcctggagag ggtggaggtg gaccttcact aacctcctac   1140
cttgaccctc tcttttaggg ctctttctga cctccaccat ggtactagga ccccattgta   1200
ttctgtaccc tcttgactct atgaccccca ctgcccactg catccagctg ggtcccctcc   1260
tatctctatt cccagctggc cagtgcagtc tcagtgccca cctgtttgtc agtaactctg   1320
aaggggctga cattttactg acttgcaaac aaataagcta actttccaga gttttgtgaa   1380
tgctggcaga gtccatgaga ctcctgagtc agaggcaaag gcttttactg ctcacagctt   1440
agcagacagc atgaggttca tgttcacatt agtacacctt gcccccccca aatcttgtag   1500
ggtgaccaga gcagtctagg tggatgctgt gcagaagggg tttgtgccac tggtgagaaa   1560
cctgagatta ggaatcctca atcttatact gggacaactt gcaaacctgc tcagcctttg   1620
tctctgatga agatattatc ttcatgatct tggattgaaa acagacctac tctggaggaa   1680
catattgtat cgattgtcct tgacagtaaa caaatctgtt gtaagagaca ttatctttat   1740
tatctaggac agtaagcaag cctggatctg agagagatat catcttgcaa ggatgcctgc   1800
tttacaaaca tccttgaaac aacaatccag aaaaaaaaag gtgttgctgt ctttgctcag   1860
aagacacaca gatacgtgac agaaccatgg agaattgcct cccaacgctg ttcagccaga   1920
gccttccacc cttgtctgca ggacagtctc aacgttccac cattaaatac ttcttctatc   1980
acatcctgct tctttatgcc taaccaaggt tctaggtccc gatcgactgt gtctggcagc   2040
actccactgc caaacccaga ataaggcagc gctcaggatc ccgaaggggc atggctgggg   2100
atcagaactt ctgggtttga gtgaggagtg ggtccaccct cttgaatttc aaaggaggaa   2160
gaggctggat gtgaaggtac tgggggaggg aaagtgtcag ttccgaactc ttaggtcaat   2220
gagggaggag actggtaagg tcccagctcc cgaggtactg atgtgggaat ggcctaagaa   2280
tctcatatcc tcaggaagaa ggtgctggaa tcctgagggg tagagttctg ggtatatttg   2340
tggcttaagg ctctttggcc cctgaaggca gaggctggaa ccattaggtc cagggtttgg   2400
ggtgatagta atgggatctc ttgattcctc aagagtctga ggatcgaggg ttgcccattc   2460
ttccatcttg ccacctaatc cttactccac ttgagggtat caccagccct tctagctcca   2520
tgaaggtccc ctgggcaagc acaatctgag catgaaagat gccccagagg ccttgggtgt   2580
catccactca tcatccagca tcacactctg agggtgtggc cagcaccatg acgtcatgtt   2640
gctgtgacta tccctgcagc gtgcctctcc agccacctgc caaccgtaga gctgcccatc   2700
ctcctctggt gggagtggcc tgcatggtgc caggctgagg cctagtgtca gacagggagc   2760
ctggaatcat agggatccag gactcaaaag tgctagagaa tggccatatg tcaccatcca   2820
tgaaatctca agggcttctg ggtggagggc acagggacct gaacttatgg tttcccaagt   2880
ctattgctct cccaagtgag tctcccagat acgaggcact gtgccagcat cagccttatc   2940
tccaccacat cttgtaaaag gactacccag ggccctgatg aacaccatgg tgtgtacagg   3000
agtagggggt ggaggcacgg actcctgtga ggtcacagcc aagggagcat catcatgggt   3060
ggggaggagg caatggacag gcttgagaac ggggatgtgg ttgtatttgg ttttctttgg   3120
ttagataaag tgctgggtat aggattgaga gtggagtatg aagaccagtt aggatggagg   3180
atcagattgg agttgggtta gataaagtgc tgggtatagg attgagagtg gagtatgaag   3240
accagttagg atggaggatc agattggagt tgggttagag atggggtaaa attgtgctcc   3300
```

-continued

```
ggatgagttt gggattgaca ctgtggaggt ggtttgggat ggcatggctt tgggatggaa   3360
atagatttgt tttgatgttg gctcagacat ccttggggat tgaactgggg atgaagctgg   3420
gtttgatttt ggaggtagaa gacgtggaag tagctgtcag atttgacagt ggccatgagt   3480
tttgtttgat ggggaatcaa acaatggggg aagacataag ggttggcttg ttaggttaag   3540
ttgcgttggg ttgatggggt cggggctgtg tataatgcag ttggattggt ttgtattaaa   3600
ttgggttggg tcaggttttg gttgaggatg agttgaggat atgcttgggg acaccggatc   3660
catgaggttc tcactggagt ggagacaaac ttcctttcca ggatgaatcc agggaagcct   3720
taattcacgt gtaggggagg tcaggccact ggctaagtat atccttccac tccagctcta   3780
agatggtctt aaattgtgat tatctatatc cacttctgtc tccctcactg tgcttggagt   3840
ttacctgatc actcaactag aaacagggga agattttatc aaattctttt tttttttttt   3900
ttttttttga gacagagtct cactctgttg cccaggctgg agtgcagtgg cgcagtctcg   3960
gctcactgca acctctgcct cccaggttca agtgattctc ctgcctcagc ctcctgagtt   4020
gctgggatta caggcatgca gcaccatgcc cagctaattt ttgtattttt agtagagatg   4080
gggtttcacc aatgtttgcc aggctggcct cgaactcctg acctggtgat ccacctgcct   4140
cagcctccca aagtgctggg attacaggcg tcagccaccg cgcccagcca cttttgtcaa   4200
attcttgaga cacagctcgg gctggatcaa gtgagctact ctggttttat tgaacagctg   4260
aaataaccaa ctttttggaa attgatgaaa tcttacggag ttaacagtgg aggtaccagg   4320
gctcttaaga gttcccgatt ctcttctgag actacaaatt gtgattttgc atgccacctt   4380
aatctttttt tttttttttt taaatcgagg tttcagtctc attctatttc ccaggctgga   4440
gttcaatagc gtgatcacag ctcactgtag ccttgaactc ctggccttaa gagattctcc   4500
tgcttcggtc tcccaatagc taagactaca gtagtccacc accatatcca gataattttt   4560
aaattttttg gggggccggg cacagtggct cacgcctgta atcccaacac catgggaggc   4620
tgagatgggt ggatcacgag gtcaggagtt tgagaccagc ctgaccaaca tggtgaaact   4680
ctgtctctac taaaaaaaaa aaaaatagaa aaattagccg ggcgtggtgg cacacggcac   4740
ctgtaatccc agctactgag gaggctgagg caggagaatc acttgaaccc agaaggcaga   4800
ggttgcaatg agccgagatt gcgccactgc actccagcct gggtgacaga gtgagactct   4860
gtctcaaaaa aaaaaaattt tttttttttt tttgtagaga tggatcttgc tttgtttctc   4920
tggttggcct tgaactcctg gcttcaagtg atcctcctac cttggcctcg gaaagtgttg   4980
ggattacagg cgtgagccac catgactgac ctgtcgttaa tcttgaggta cataaacctg   5040
gctcctaaag gctaaaggct aaatatttgt tggagaaggg gcattggatt ttgcatgagg   5100
atgattctga cctgggaggg caggtcagca ggcatctctg ttgcacagat agagtgtaca   5160
ggtctggaga acaaggagtg gggggttatt ggaattccac attgtttgct gcacgttgga   5220
ttttgaaatg ctagggaact ttgggagact catatttctg ggctagagga tctgtggacc   5280
acaagatctt tttatgatga cagtagcaat gtatctgtgg agctggattc tgggttggga   5340
gtgcaaggaa aagaatgtac taaatgccaa gacatctatt tcaggagcat gaggaataaa   5400
agttctagtt tctggtctca gagtggtgca gggatcaggg agtctcacaa tctcctgagt   5460
gctggtgtct tagggcacac tgggtcttgg agtgcaaagg atctaggcac gtgaggcttt   5520
gtatgaagaa tcggggatcg tacccacccc ctgtttctgt ttcatcctgg gcatgtctcc   5580
tctgcctttg tcccctagat gaagtctcca tgagctacaa gggcctggtg catccagggt   5640
```

-continued

```
gatctagtaa ttgcagaaca gcaagtgcta gctctccctc cccttccaca gctctgggtg   5700

tgggaggggg ttgtccagcc tccagcagca tggggagggc cttggtcagc ctctgggtgc   5760

cagcagggca ggggcggagt cctggggaat gaaggtttta tagggctcct gggggaggct   5820

ccccagcccc aagctt                                                   5836
```

<210> SEQ ID NO 2
<211> LENGTH: 5835
<212> TYPE: DNA
<213> ORGANISM: Homo sapiens

<400> SEQUENCE: 2

```
aagcttctag ttttcttttc ccggtgacat cgtggaaagc actagcatct ctaagcaatg     60

atctgtgaca atattcacag tgtaatgcca tccagggaac tcaactgagc cttgatgtcc    120

agagattttt gtgttttttt ctgagactga gtctcgctct gtgccaggct ggagtgcagt    180

ggtgcaacct tggctcactg caagctccgc ctcctgggtt cacgccattc tcctgcctca    240

gcctcctgag tagctgggac tacaggcacc cgccaccacg cctggctaat ttttttgtat    300

ttttagtaga gatggggttt cactgtgtta gccaggatgg tctcagtctc ctgacctcgt    360

gatctgccca ccttggcctc ccaaagtgct gggatgacag gcgtgagcca ccgcgcctgg    420

ccgatatcca gagatttttt ggggggctcc atcacacaga catgttgact gtcttcatgg    480

ttgactttta gtatccagcc cctctagaaa tctagctgat atagtgtggc tcaaaacctt    540

cagcacaaat cacaccgtta gactatctgg tgtggcccaa accttcaggt gaacaaaggg    600

actctaatct ggcaggatac tccaaagcat tagagatgac ctcttgcaaa gaaaaagaaa    660

tggaaaagaa aaagaaagaa aggaaaaaaa aaaaaaaaaa gagatgacct ctcaggctct    720

gaggggaaac gcctgaggtc tttgagcaag gtcagtcctc tgttgcacag tctccctcac    780

agggtcattg tgacgatcaa atgtggtcac gtgtatgagg caccagcaca tgcctggctc    840

tggggagtgc cgtgtaagtg tatgcttgca ctgctgaatg gctgggatgt gtcagggatt    900

atcttcagca cttacagatg ctcatctcat cctcacagca tcactatggg atgggtatta    960

ctggcctcat ttgatggaga aagtggctgt ggctcagaaa gggggaccca ctagaccagg   1020

gacactctgg atgctgggga ctccagagac catgaccact caccaactgc agagaaatta   1080

attgtggcct gatgtccctg tcctggagag ggtggaggtg gaccttcact aacctcctac   1140

cttgaccctc tcttttaggg ctctttctga cctccaccat ggtactagga ccccattgta   1200

ttctgtaccc tcttgactct atgaccccca ccgcccactg catccagctg ggtcccctcc   1260

tatctctatt cccagctggc cagtgcagtc tcagtgccca cctgtttgtc agtaactctg   1320

aaggggctga cattttactg acttgcaaac aaataagcta actttccaga gttttgtgaa   1380

tgctggcaga gtccatgaga ctcctgagtc agaggcaaag gcttttactg ctcacagctt   1440

agcagacagc atgaggttca tgttcacatt agtacacctt gcccccccca aatcttgtag   1500

ggtgaccaga gcagtctagg tggatgctgt gcagaagggg tttgtgccac tggtgagaaa   1560

cctgagatta ggaatcctca atcttatact gggacaactt gcaaacctgc tcagcctttg   1620

tctctgatga agatattatc ttcatgatct tggattgaaa acagacctac tctggaggaa   1680

catattgtat cgattgtcct tgacagtaaa caaatctgtt gtaagagaca ttatctttat   1740

tatctaggac agtaagcaag cctggatctg agagagatat catcttgcaa ggatgcctgc   1800

tttacaaaca tccttgaaac aacaatccag aaaaaaaaag gtgttactgt ctttgctcag   1860

aagacacaca gatacgtgac agaaccatgg agaattgcct cccaacgctg ttcagccaga   1920
```

-continued

```
gccttccacc ctttctgcag gacagtctca acgttccacc attaaatact tcttctatca   1980
catcccgctt ctttatgcct aaccaaggtt ctaggtcccg atcgactgtg tctggcagca   2040
ctccactgcc aaacccagaa taaggcagcg ctcaggatcc cgaaggggca tggctgggga   2100
tcagaacttc tgggtttgag tgaggagtgg gtccaccctc ttgaatttca aaggaggaag   2160
aggctggatg tgaaggtact gggggaggga aagtgtcagt tccgaactct taggtcaatg   2220
agggaggaga ctggtaaggt cccagctccc gaggtactga tgtgggaatg gcctaagaat   2280
ctcatatcct caggaagaag gtgctggaat cctgaggggt agagttctgg gtatatttgt   2340
ggcttaaggc tctttggccc ctgaaggcag aggctggaac cattaggtcc agggtttggg   2400
gtgatagtaa tgggatctct tgattcctca agagtctgag gatcgagggt tgcccattct   2460
tccatcttgc cacctaatcc ttactccact tgagggtatc accagccctt ctagctccat   2520
gaaggtcccc tgggcaagca caatctgagc atgaaagatg ccccagaggc cttgggtgtc   2580
atccactcat catccagcat cacactctga gggtgtggcc agcaccatga cgtcatgttg   2640
ctgtgactat ccctgcagcg tgcctctcca gccacctgcc aaccgtagag ctgcccatcc   2700
tcctctggtg ggagtggcct gcatggtgcc aggctgaggc ctagtgtcag acagggagcc   2760
tggaatcata gggatccagg actcaaaagt gctagagaat ggccatatgt caccatccat   2820
gaaatctcaa gggcttctgg gtggagggca cagggacctg aacttatggt ttcccaagtc   2880
tattgctctc ccaagtgagt ctcccagata cgaggcactg tgccagcatc agccttatct   2940
ccaccacatc ttgtaaaagg actacccagg gccctgatga acaccatggt gtgtacagga   3000
gtagggggtg gaggcacgga ctcctgtgag gtcacagcca agggagcatc atcatgggtg   3060
gggaggaggc aatggacagg cttgagaacg gggatgtggt tgtatttggt tttctttggt   3120
tagataaagt gctgggtata ggattgagag tggagtatga agaccagtta ggatggagga   3180
tcagattgga gttgggttag ataaagtgct gggtatagga ttgagagtgg agtatgaaga   3240
ccagttagga tggaggatca gattggagtt gggttagaga tggggtaaaa ttgtgctccg   3300
gatgagtttg ggattgacac tgtggaggtg gtttgggatg gcatggcttt gggatggaaa   3360
tagatttgtt ttgatgttgg ctcagacatc cttggggatt gaactgggga tgaagctggg   3420
tttgattttg gaggtagaag acgtggaagt agctgtcaga tttgacagtg gccatgagtt   3480
ttgtttgatg gggaatcaaa caatggggga agacataagg gttggcttgt taggttaagt   3540
tgcgttgggt tgatggggtc ggggctgtgt ataatgcagt tggattggtt tgtattaaat   3600
tgggttgggt caggttttgg ttgaggatga gttgaggata tgcttgggga caccggatcc   3660
atgaggttct cactggagtg gagacaaact tcctttccag gatgaatcca gggaagcctt   3720
aattcacgtg taggggaggt caggccactg gctaagtata tccttccact ccagctctaa   3780
gatggtctta aattgtgatt atctatatcc acttctgtct ccctcactgt gcttggagtt   3840
tacctgatca ctcaactaga aacaggggaa gattttatca aattcttttt tttttttttt   3900
tttttttgag acagagtctc actctgttgc ccaggctgga gtgcagtggc gcagtctcgg   3960
ctcactgcaa cctctgcctc ccaggttcaa gtgattctcc tgcctcagcc tcctgagttg   4020
ctgggattac aggcatgcag caccatgccc agctaatttt tgtattttta gtagagatgg   4080
ggtttcacca atgtttgcca ggctggcctc gaactcctga cctggtgatc cacctgcctc   4140
agcctcccaa agtgctggga ttacaggcgt cagccaccgc gcccagccac ttttgtcaaa   4200
ttcttgagac acagctcggg ctggatcaag tgagctactc tggttttatt gaacagctga   4260
```

-continued

```
aataaccaac tttttggaaa ttgatgaaat cttacggagt taacagtgga ggtaccaggg   4320
ctcttaagag ttcccgattc tcttctgaga ctacaaattg tgattttgca tgccacctta   4380
atcttttttt tttttttttt aaatcgaggt ttcagtctca ttctatttcc caggctggag   4440
ttcaatagcg tgatcacagc tcactgtagc cttgaactcc tggccttaag agattctcct   4500
gcttcggtct cccaatagct aagactacag tagtccacca ccatatccag ataattttta   4560
aattttttgg ggggccgggc acagtggctc acgcctgtaa tcccaacacc atgggaggct   4620
gagatgggtg gatcacgagg tcaggagttt gagaccagcc tgaccaacat ggtgaaactc   4680
tgtctctact aaaaaaaaaa aaaatagaaa aattagccgg gcgtggtggc acacggcacc   4740
tgtaatccca gctactgagg aggctgaggc aggagaatca cttgaaccca gaaggcagag   4800
gttgcaatga gccgagattg cgccactgca ctccagcctg ggtgacagag tgagactctg   4860
tctcaaaaaa aaaaaatttt tttttttttt ttgtagagat ggatcttgct ttgtttctct   4920
ggttggcctt gaactcctgg cttcaagtga tcctcctacc ttggcctcgg aaagtgttgg   4980
gattacaggc gtgagccacc atgactgacc tgtcgttaat cttgaggtac ataaacctgg   5040
ctcctaaagg ctaaaggcta aatatttgtt ggagaagggg cattggattt tgcatgagga   5100
tgattctgac ctgggagggc aggtcagcag gcatctctgt tgcacagata gagtgtacag   5160
gtctggagaa caaggagtgg ggggttattg gaattccaca ttgtttgctg cacgttggat   5220
tttgaaatgc tagggaactt tgggagactc atatttctgg gctagaggat ctgtggacca   5280
caagatcttt ttatgatgac agtagcaatg tatctgtgga gctggattct gggttgggag   5340
tgcaaggaaa agaatgtact aaatgccaag acatctattt caggagcatg aggaataaaa   5400
gttctagttt ctggtctcag agtggtgcat ggatcaggga gtctcacaat ctcctgagtg   5460
ctggtgtctt agggcacact gggtcttgga gtgcaaagga tctaggcacg tgaggctttg   5520
tatgaagaat cggggatcgt acccaccccc tgtttctgtt tcatcctggg catgtctcct   5580
ctgcctttgt cccctagatg aagtctccat gagctacaag ggcctggtgc atccagggtg   5640
atctagtaat tgcagaacag caagtgctag ctctccctcc ccttccacag ctctgggtgt   5700
gggagggggt tgtccagcct ccagcagcat ggggagggcc ttggtcagcc tctgggtgcc   5760
agcagggcag gggcggagtc ctggggaatg aaggttttat agggctcctg ggggaggctc   5820
cccagcccca agctt                                                    5835
```

<210> SEQ ID NO 3
<211> LENGTH: 12047
<212> TYPE: DNA
<213> ORGANISM: Homo sapiens

<400> SEQUENCE: 3

```
gaattcagaa ataggggaag gttgaggaag gacactgaac tcaaagggga tacagtgatt     60
ggtttatttg tcttctcttc acaacattgg tgctggagga attcccaccc tgaggttatg    120
aagatgtctg aacacccaac acatagcact ggagatatga gctcgacaag agtttctcag    180
ccacagagat tcacagccta gggcaggagg acactgtacg ccaggcagaa tgacatggga    240
attgcgctca cgattggctt gaagaagcaa ggactgtggg aggtgggctt tgtagtaaca    300
agagggcagg gtgaactctg attcccatgg gggaatgtga tggtcctgtt acaaattttt    360
caagctggca gggaataaaa cccattacgg tgaggacctg tggagggcgg ctgccccaac    420
tgataaagga aatagccagg tgggggcctt tcccattgta ggggggacat atctggcaat    480
agaagccttt gagacccttt agggtacaag tactgaggca gcaaataaaa tgaaatctta    540
```

-continued

```
tttttcaact ttatactgca tgggtgtgaa gatatatttg tttctgtaca gggggtgagg    600
gaaaggaggg gaggaggaaa gttcctgcag gtctggtttg gtcttgtgat ccagggggtc    660
ttggaactat ttaaattaaa ttaaattaaa acaagcgact gttttaaatt aaattaaatt    720
aaattaaatt ttactttatt ttatcttaag ttctgggcta catgtgcagg acgtgcagct    780
ttgttacata ggtaaacgtg tgccatggtg gtttgctgta cctatcaacc catcacctag    840
gtattaagcc cagcatgcat tagctgtttt tcctgacgct ctccctctcc ctgactccca    900
caacaggccc cagtgtgtgt tgttcccctc cctgtgtcca tgtgttctca ttgttcagct    960
cccacttata agtgagaaca tgtggtgttt ggttttctgt ttctgtgtta gtttgctgag   1020
gataatggct tccacctcca tccatgttcc tgcaaaggac gtgatcttat tcttttttat   1080
ggttgcatag aaattgtttt tacaaatcca attgatattg tatttaatta caagttaatc   1140
taattagcat actagaagag attacagaag atattaggta cattgaatga ggaaatatat   1200
aaaataggac gaaggtgaaa tattaggtag gaaaagtata atagttgaaa gaagtaaaaa   1260
aaaatatgca tgagtagcag aatgtaaaag aggtgaagaa cgtaatagtg actttttaga   1320
ccagattgaa ggacagagac agaaaaattt taaggaattg ctaaaccatg tgagtgttag   1380
aagtacagtc aataacatta aagcctcagg aggagaaaag aataggaaag gaggaaatat   1440
gtgaataaat agtagagaca tgtttgatgg attttaaaat atttgaaaga cctcacatca   1500
aaggattcat accgtgccat tgaagaggaa gatggaaaag ccaagaagcc agatgaaagt   1560
tagaaatatt attggcaaag cttaaatgtt aaaagtccta gagagaaagg atggcagaaa   1620
tattggcggg aaagaatgca gaacctagaa tataaattca tcccaacagt ttggtagtgt   1680
gcagctgtag ccttttctag ataatacact attgtcatac atcgcttaag cgagtgtaaa   1740
atggtctcct cactttattt atttatatat ttatttagtt ttgagatgga gcctcgctct   1800
gtctcctagg ctggagtgca atagtgcgat accactcact gcaacctctg cctcctctgt   1860
tcaagtgatt ttcttacctc agcctcccga gtagctggga ttacaggtgc gtgccaccac   1920
acccggctaa tttttgtatt ttttgtagag acggggtttt gccatgttgg ccaggctggt   1980
cttgaactcc tgacatcagg tgatccacct gccttggcct cctaaagtgc tgggattaca   2040
ggcatgagcc accgtgccca accactttat ttattttttta tttttatttt taaatttcag   2100
cttctatttg aaatacaggg ggcacatata taggattgtt acatgggtat attgaactca   2160
ggtagtgatc atactaccca acaggtaggt tttcaaccca ctccccctct tttcctcccc   2220
attctagtag tgtgcagtgt ctattgttct catgtttatg tctatgtgtg ctccaggttt   2280
agctcccacc tgtaagtgag aacgtgtggt atttgatttt ctgtccctgt gttaattcac   2340
ttaggattat ggcttccagc tccattcata ttgctgtaaa ggatatgatt catttttcat   2400
ggccatgcag tattccatat tgcgtataga tcacattttc tttctttttt ttttttgaga   2460
cggagtcttg ctttgctgcc taggctggag tgcagtagca cgatctcggc tcactgcaag   2520
cttcacctcc ggggttcacg tcattcttct gtctcagctt cccaagtagc tgggactaca   2580
ggcgcccgcc accacgtccg gctaattttt ttgtgtgttt ttagtagaga tgggggtttc   2640
actgtgttag ccaggatggt cttgatctcc tgaccttgtg gtccacctgc ctcggtctcc   2700
caaagtgctg ggattacagg ggtgagccac tgcgcccggc ccatatatac cacattttct   2760
ttaaccaatc caccattgat gggcaactag gtagattcca tggattccac agttttgcta   2820
ttgtgtgcag tgtggcagta gacatatgaa tgaatgtgtc tttttggtat aatgatttgc   2880
```

-continued

```
attcctttgg gtatacagtc attaatagga gtgctgggtt gaacggtggc tctgtttaaa   2940
attctttgag aattttccaa actgtttgcc atagagagca aactaattta catttccacg   3000
aacagtatat aagcattccc ttttctccac agctttgtca tcatggtttt tttttttctt   3060
tattttaaaa aagaatatgt tgttgttttc ccagggtaca tgtgcaggat gtgcaggttt   3120
gttacatagg tagtaaacgt gagccatggt ggtttgctgc acctgtcaac ccattacctg   3180
ggtatgaagc cctgcctgca ttagctcttt tccctaatgc tctcactact gccccaccct   3240
caccctgaca gggcaaacag acaacctaca gaatgggagg aaatttttgc aatctattca   3300
tctgacaaag gtcaagaata tccagaatct acaaggaact taagcaaatt tttacttttt   3360
aataatagcc actctgactg gcgtgaaatg gtatctcatt gtggttttca tttgaatttc   3420
tctgatgatc agtgacgatg agcatttttt catatttgtt ggctgcttgt acgtcttttg   3480
agaagtgtct cttcatgcct tttggccact ttaatgggat tattttttgc tttttagttt   3540
aagttcctta tagattctgg atattagact tcttattgga tgcatagttt gtgaatactc   3600
tcttccattc tgtaggttgt ctgtttactc tattgatggc ttcttttgct gtgccgaagc   3660
atcttagttt aattagaaac cacctgccaa tttttgtttt tgttgcaatt gcttttgggg   3720
acttagtcat aaactctttg ccaaggtctg ggtcaagaag agtatttcct aggttttctt   3780
ctagaatttt gaaagtctga atgtaaacat ttgcattttt aatgcatctt gagttagttt   3840
ttgtatatgt gaaaggtcta ctctcatttt ctttccctct ttctttcttt ctttcttttc   3900
tttctttctt tctttctttc tttctttctt tctttctttc tttctttttg tccttctttc   3960
tttctttctt tctctttctt tctctctttc tttttttttt ttgatggagt attgctctgt   4020
tgcccaggct gcagtgcagc ggcacgatct cggctcactg caacctctgc ctcctgggtt   4080
caactgattc tcctgcatca gccttccaag tagctgggat tataggcgcc cgccaccacg   4140
cccgactaat ttttgtattt ttagtagaga cggggttgtg ccatgttggc caggctggtt   4200
tgaaactcct gacctcaaac gatctgcctg ccttggcctc ccaaagtgct gggattacag   4260
gtgtgagcca ctgtgcccag ccaagaatgt cattttctaa gaggtccaag aacctcaaga   4320
tattttggga ccttgagaag agaggaattc atacaggtat tacaagcaca gcctaatggc   4380
aaatctttgg catggcttgg cttcaagact ttaggctctt aaaagtcgaa tccaaaaatt   4440
tttataaaag ctccagctaa gctaccttaa aaggggcctg tatggctgat cactcttctt   4500
gctatacttt acacaaataa acaggccaaa tataatgagg ccaaaattta ttttgcaaat   4560
aaattggtcc tgctatgatt tactcttggt aagaacaggg aaaatagaga aaaatttaga   4620
ttgcatctga cctttttttc tgaattttta tatgtgccta caatttgagc taaatcctga   4680
attattttct ggttgcaaaa actctctaaa gaagaacttg gttttcattg tcttcgtgac   4740
acatttatct ggctctttac tagaacagct ttcttgtttt tggtgttcta gcttgtgtgc   4800
cttacagttc tactcttcaa attattgtta tgtgtatctc atagttttcc ttcttttgag   4860
aaaactgaag ccatggtatt ctgaggacta gagatgactc aacagagctg gtgaatctcc   4920
tcatatgcaa tccactgggc tcgatctgct tcaaattgct gatgcactgc tgctaaagct   4980
atacatttaa aaccctcact aaaggatcag ggaccatcat ggaagaggag gaaacatgaa   5040
attgtaagag ccagattcgg ggggtagagt gtggaggtca gagcaactcc accttgaata   5100
agaaggtaaa gcaacctatc ctgaaagcta acctgccatg gtggcttctg attaacctct   5160
gttctaggaa gactgacagt ttgggtctgt gtcattgccc aaatctcatg ttaaattgta   5220
atccccagtg ttcggaggtg ggacttggtg gtaggtgatt cggtcatggg agtagatttt   5280
```

-continued

```
cttctttgtg gtgttacagt gatagtgagt gagttctcgt gagatctggt catttaaaag   5340
tgtgtggccc ctcccctccc tctcttggtc ctcctactgc catgtaagat acctgctcct   5400
gctttgcctt ctaccataag taaaagcccc ctgaggcctc cccagaagca gatgccacca   5460
tgcttcctgt acagcctgca gaaccatcag ccaattaaac ctcttttctg tataaattac   5520
cagtcttgag tatctcttta cagcagtgtg agaacggact aatacaaggg tctccaaaat   5580
tccaagttta tgtattcttt cttgccaaat agcaggtatt taccataaat cctgtcctta   5640
ggtcaaacaa ccttgatggc atcgtacttc aattgtctta cacattcctt ctgaatgact   5700
cctcccctat ggcatataag ccctgggtct tgggggataa tggcagaggg gtccaccatc   5760
ttgtctggct gccacctgag acacggacat ggcttctgtt ggtaagtctc tattaaatgt   5820
ttctttctaa gaaactggat ttgtcagctt gtttctttgg cctctcagct tcctcagact   5880
ttggggtagg ttgcacaacc ctgcccacca cgaaacaaat gtttaatatg ataaatatgg   5940
atagatataa tccacataaa taaaagctct tggagggccc tcaataattg ttaagagtgt   6000
aaatgtgtcc aaagatggaa aatgtttgag aactactgtc ccagagattt tcctgagttc   6060
tagagtgtgg gaatatagaa cctggagctt ggcttcttca gcctagaatc aggagtatgg   6120
ggctgaagtc tgaagcttgg cttcagcagt ttggggttgg cttccggagc acatatttga   6180
catgttgcga ctgtgatttg gggtttggta tttgctctga atcctaatgt ctgtccttga   6240
ggcatctaga atctgaaatc tgtggtcaga attctattat cttgagtagg acatctccag   6300
tcctggttct gccttctagg gctggagtct gtagtcagtg acccggtctg gcatttcaac   6360
ttcatataca gtgggctatc ttttggtcca tgtttcaacc aaacaaccga ataaaccatt   6420
agaacctttc cccacttccc tagctgcaat gttaaaccta ggatttctgt ttaataggtt   6480
catatgaata atttcagcct gatccaactt tacattcctt ctaccgttat tctacaccca   6540
ccttaaaaat gcattcccaa tatattccct ggattctacc tatatatggt aatcctggct   6600
ttgccagttt ctagtgcatt aacatacctg atttacattc ttttacttta aagtggaaat   6660
aagagtccct ctgcagagtt caggagttct caagatggcc cttacttctg acatcaattg   6720
agatttcaag ggagtcgcca agatcatcct caggttcagt gattgctggt agccctcata   6780
taactcaatg aaagctgtta tgctcatggc tatggtttat tacagcaaaa gaatagagat   6840
gaaaatctag caagggaaga gttgcatggg gcaaagacaa ggagagctcc aagtgcagag   6900
attcctgttg ttttctccca gtggtgtcat ggaaagcagt atcttctcca tacaatgatg   6960
tgtgataata ttcagtgtat tgccaatcag ggaactcaac tgagccttga ttatattgga   7020
gcttggttgc acagacatgt cgaccacctt catggctgaa ctttagtact tagcccctcc   7080
agacgtctac agctgatagg ctgtaaccca acattgtcac cataaatcac attgttagac   7140
tatccagtgt ggcccaagct cccgtgtaaa cacaggcact ctaaacaggc aggatatttc   7200
aaaagcttag agatgacctc ccaggagctg aatgcaaaga cctggcctct ttgggcaagg   7260
agaatccttt accgcacact ctccttcaca gggttattgt gaggatcaaa tgtggtcatg   7320
tgtgtgagac accagcacat gtctggctgt ggagagtgac ttctatgtgt gctaacattg   7380
ctgagtgcta agaaagtatt aggcatggct ttcagcactc acagatgctc atctaatcct   7440
cacaacatgg ctacagggtg ggcactacta gcctcatttg acagaggaaa ggactgtgga   7500
taagaagggg gtgaccaata ggtcagagtc attctggatg caaggggctc cagaggacca   7560
tgattagaca ttgtctgcag agaaattatg gctggatgtc tctgccccgg aaagggggat   7620
```

-continued

```
gcactttcct tgacccccta tctcagatct tgactttgag gttatctcag acttcctcta   7680
tgataccagg agcccatcat aatctctctg tgtcctctcc ccttcctcag tcttactgcc   7740
cactcttccc agctccatct ccagctggcc aggtgtagcc acagtaccta actctttgca   7800
gagaactata aatgtgtatc ctacagggga gaaaaaaaaa aagaactctg aaagagctga   7860
cattttaccg acttgcaaac acataagcta acctgccagt tttgtgctgg tagaactcat   7920
gagactcctg ggtcagaggc aaaagatttt attacccaca gctaaggagg cagcatgaac   7980
tttgtgttca catttgttca ctttgccccc caattcatat gggatgatca gagcagttca   8040
ggtggatgga cacaggggtt tgtggcaaag gtgagcaacc taggcttaga aatcctcaat   8100
cttataagaa ggtactagca aacttgtcca gtctttgtat ctgacggaga tattatcttt   8160
ataattgggt tgaaagcaga cctactctgg aggaacatat tgtatttatt gtcctgaaca   8220
gtaaacaaat ctgctgtaaa atagacgtta actttattat ctaaggcagt aagcaaacct   8280
agatctgaag gcgataccat cttgcaaggc tatctgctgt acaaatatgc ttgaaaagat   8340
ggtccagaaa agaaaacggt attattgcct ttgctcagaa gacacacaga aacataagag   8400
aaccatggaa aattgtctcc caacactgtt cacccagagc cttccactct tgtctgcagg   8460
acagtcttaa catcccatca ttagtgtgtc taccacatct ggcttcaccg tgcctaacca   8520
agatttctag gtccagttcc ccaccatgtt tggcagtgcc ccactgccaa ccccagaata   8580
agggagtgct cagaattccg aggggacatg ggtggggatc agaacttctg ggcttgagtg   8640
cagagggggc ccatactcct tggttccgaa ggaggaagag gctggaggtg aatgtccttg   8700
gaggggagga atgtgggttc tgaactctta aatccccaag ggaggagact ggtaaggtcc   8760
cagcttccga ggtactgacg tgggaatggc ctgagaggtc taagaatccc gtatcctcgg   8820
gaaggagggg ctgaaattgt gaggggttga gttgcagggg tttgttagct tgagactcct   8880
tggtgggtcc ctgggaagca aggactggaa ccattggctc cagggtttgg tgtgaaggta   8940
atgggatctc ctgattctca aagggtcaga ggactgagag ttgcccatgc tttgatcttt   9000
ccatctactc cttactccac ttgagggtaa tcacctactc ttctagttcc acaagagtgc   9060
gcctgcgcga gtataatctg cacatgtgcc atgtcccgag gcctggggca tcatccactc   9120
atcattcagc atctgcgcta tgcgggcgag gccggcgcca tgacgtcatg tagctgcgac   9180
tatccctgca gcgcgcctct cccgtcacgt cccaaccatg gagctgtgga cgtgcgtccc   9240
ctggtggatg tggcctgcgt ggtgccaggc cggggcctgg tgtccgataa agatcctaga   9300
accacaggaa accaggactg aaaggtgcta gagaatggcc atatgtcgct gtccatgaaa   9360
tctcaaggac ttctgggtgg agggcacagg agcctgaact tacgggtttg ccccagtcca   9420
ctgtcctccc aagtgagtct cccagatacg aggcactgtg ccagcatcag cttcatctgt   9480
accacatctt gtaacaggga ctacccagga ccctgatgaa caccatggtg tgtgcaggaa   9540
gagggggtga aggcatggac tcctgtgtgg tcagagccca gaggggccca tgacgggtgg   9600
ggaggaggct gtggactggc tcgagaagtg ggatgtggtt gtgtttgatt tcctttggcc   9660
agataaagtg ctggatatag cattgaaaac ggagtatgaa gaccagttag aatggagggt   9720
caggttggag ttgagttaca gatggggtaa aattctgctt cggatgagtt tggggattgg   9780
caatctaaag gtggtttggg atggcatggc tttgggatgg aaataggttt gtttttatgt   9840
tggctgggaa gggtgtgggg attgaattgg ggatgaagta ggtttagttt tggagataga   9900
atacatggag ctggctattg catgcgagga tgtgcattag tttggtttga tctttaaata   9960
aaggaggcta ttagggttgt cttgaattag attaagttgt gttgggttga tgggttgggc  10020
```

-continued

```
ttgtgggtga tgtggttgga ttgggctgtg ttaaattggt ttgggtcagg ttttggttga  10080
ggttatcatg gggatgagga tatgcttggg acatggattc aggtggttct cattcaagct  10140
gaggcaaatt tcctttcaga cggtcattcc agggaacgag tggttgtgtg ggggaaatca  10200
ggccactggc tgtgaatatc cctctatcct ggtcttgaat tgtgattatc tatgtccatt  10260
ctgtctcctt cactgtactt ggaattgatc tggtcattca gctggaaatg ggggaagatt  10320
ttgtcaaatt cttgagacac agctgggtct ggatcagcgt aagccttcct tctggtttta  10380
ttgaacagat gaaatcacat ttttttttc aaaatcacag aaatcttata gagttaacag  10440
tggactctta taataagagt taacaccagg actcttattc ttgattcttt tctgagacac  10500
caaaatgaga tttctcaatg ccaccctaat tcttttttt tttttttttt tttttgagac  10560
acagtctggg tcttttgctc tgtcactcag gctggagcgc agtggtgtga tcatagctca  10620
ctgaaccctt gacctcctgg acttaaggga tcctcctgct tcagcctcct gagtagatgg  10680
ggctacaggt gcttgccacc acacctggct aattaaattt tttttttttt tttgtagaga  10740
aagggtctca ctttgttgcc ctggctgatc ttgaacttct gacttcaagt gattcttcag  10800
ccttggactc ccaaagcact gggattgctg gcatgagcca ctcaccgtgc ctggcttgca  10860
gcttaatctt ggagtgtata aacctggctc ctgatagcta gacatttcag tgagaaggag  10920
gcattggatt ttgcatgagg acaattctga cctaggaggg caggtcaaca ggaatccccg  10980
ctgtacctgt acgttgtaca ggcatggaga atgaggagtg aggaggccgt accggaaccc  11040
catattgttt agtggacatt ggattttgaa ataataggga acttggtctg ggagagtcat  11100
atttctggat tggacaatat gtggtatcac aaggttttat gatgagggag aaatgtatgt  11160
ggggaaccat tttctgagtg tggaagtgca agaatcagag agtagctgaa tgccaacgct  11220
tctatttcag gaacatggta agttggaggt ccagctctcg ggctcagacg ggtataggga  11280
ccaggaagtc tcacaatccg atcattctga tatttcaggg catattaggt ttggggtgca  11340
aaggaagtac ttgggactta ggcacatgag actttgtatt gaaaatcaat gattggggct  11400
ggccgtggtg ctcacgcctg taatctcatc actttgggag accgaagtgg gaggatggct  11460
tgatctcaag agttggacac cagcctaggc aacatggcca gaccctctct ctacaaaaaa  11520
attaaaaatt agctggatgt ggtggtgcat gcttgtggtc tcagctatcc tggaggctga  11580
gacaggagaa tcggttgagt ctgggagttc aaggctacag ggagctgcga tcacgccgct  11640
gcactccagc ctgggaaaca gagtgagact gtctcagaat tttttaaaa aagaatcagt  11700
gatcatccca acccctgttg ctgttcatcc tgagcctgcc ttctctggct ttgttcccta  11760
gatcacatct ccatgatcca taggccctgc ccaatctgac ctcacaccgt gggaatgcct  11820
ccagactgat ctagtatgtg tggaacagca agtgctggct ctccctcccc ttccacagct  11880
ctgggtgtgg gagggggttg tccagcctcc agcagcatgg ggagggcctt ggtcagcatc  11940
taggtgccaa cagggcaagg gcggggtcct ggagaatgaa ggctttatag ggctcctcag  12000
ggaggccccc cagccccaaa ctgcaccacc tggccgtgga caccggt               12047
```

<210> SEQ ID NO 4
<211> LENGTH: 454
<212> TYPE: DNA
<213> ORGANISM: Homo sapiens

<400> SEQUENCE: 4

```
aagcttccac aagtgcattt agcctctcca gtattgctga tgaatccaca gttcaggttc     60
```

-continued

```
aatggcgttc aaaacttgat caaaaatgac cagactttat attcttacac caacatctat    120

ctgattggag gaatggataa tagtcatcat gtttaaacat ctaccattcc agttaagaaa    180

atatgatagc atcttgttct tagtcttttt cttaataggg acataaagcc cacaaataaa    240

aatatgcctg aagaatggga caggcattgg gcattgtcca tgcctagtaa agtactccaa    300

gaacctattt gtatactaga tgacacaatg tcaatgtctg tgtacaactg ccaactggga    360

tgcaagacac tgcccatgcc aatcatcctg aaaagcagct ataaaaagca ggaagctact    420

ctgcaccttg tcagtgaggt ccagatacct acag                                454
```

<210> SEQ ID NO 5
<211> LENGTH: 5224
<212> TYPE: DNA
<213> ORGANISM: Homo sapiens

<400> SEQUENCE: 5

```
gaattcttag aaatatgggg gtaggggtgg tggtggtaat tctgttttca ccccataggt     60

gagataagca ttgggttaaa tgtgctttca cacacacatc acatttcata agaattaagg    120

aacagactat gggctggagg actttgagga tgtctgtctc ataacacttg ggttgtatct    180

gttctatggg gcttgtttta agcttggcaa cttgcaacag ggttcactga ctttctcccc    240

aagcccaagg tactgtcctc ttttcatatc tgttttgggg cctctggggc ttgaatatct    300

gagaaaatat aaacatttca ataatgttct gtggtgagat gagtatgaga gatgtgtcat    360

tcatttgtat caatgaatga atgaggacaa ttagtgtata aatccttagt acaacaatct    420

gagggtaggg gtggtactat tcaatttcta tttataaaga tacttatttc tatttattta    480

tgcttgtgac aaatgttttg ttcgggacca caggaatcac aaagatgagt ctttgaattt    540

aagaagttaa tggtccagga ataattacat agcttacaaa tgactatgat ataccatcaa    600

acaagaggtt ccatgagaaa ataatctgaa aggtttaata agttgtcaaa ggtgagaggg    660

ctcttctcta gctagagact aatcagaaat acattcaggg ataattattt gaatagacct    720

taagggttgg gtacattttg ttcaagcatt gatggagaag gagagtgaat atttgaaaac    780

attttcaact aaccaaccac ccaatccaac aaacaaaaaa tgaaaagaat ctcagaaaca    840

gtgagataag agaaggaatt ttctcacaac ccacacgtat agctcaactg ctctgaagaa    900

gtatatatct aatatttaac actaacatca tgctaataat gataataatt actgtcattt    960

tttaatgtct ataagtacca ggcatttaga agatattatt ccatttatat atcaaaataa   1020

acttgagggg atagatcatt ttcatgatat atgagaaaaa ttaaaaacag attgaattat   1080

ttgcctgtca tacagctaat aattgaccat aagacaatta gatttaaatt agttttgaat   1140

ctttctaata ccaaagttca gtttactgtt ccatgttgct tctgagtggc ttcacagact   1200

tatgaaaaag taaacggaat cagaattaca tcaatgcaaa agcattgctg tgaactctgt   1260

acttaggact aaactttgag caataacaca catagattga ggattgtttg ctgttagcat   1320

acaaactctg gttcaaagct cctctttatt gcttgtcttg gaaaatttgc tgttcttcat   1380

ggtttctctt ttcactgcta tctatttttc tcaaccactc acatggctac aataactgtc   1440

tgcaagctta tgattcccaa atatctatct ctagcctcaa tcttgttcca gaagataaaa   1500

agtagtattc aaatgcacat caacgtctcc acttggaggg cttaaagacg tttcaacata   1560

caaaccgggg agttttgcct ggaatgtttc ctaaaatgtg tcctgtagca catagggtcc   1620

tcttgttcct taaaatctaa ttacttttag cccagtgctc atcccaccta tggggagatg   1680

agagtgaaaa gggagcctga ttaataatta cactaagtca ataggcatag agccaggact   1740
```

-continued

```
gtttgggtaa actggtcact ttatcttaaa ctaaatatat ccaaaactga acatgtactt   1800
agttactaag tctttgactt tatctcattc ataccactca gctttatcca ggccacttat   1860
ttgacagtat tattgcgaaa acttcctaac tggtctcctt atcatagtct tatccccttt   1920
tgaaacaaaa gagacagttt caaaatacaa atatgatttt tattagctcc cttttgttgt   1980
ctataatagt cccagaagga gttataaact ccatttaaaa agtctttgag atgtggccct   2040
tgccaacttt gccaggaatt cccaatatct agtattttct actattaaac tttgtgcctc   2100
ttcaaaactg cattttctct cattccctaa gtgtgcattg ttttccctta ccggttggtt   2160
tttccaccac cttttacatt ttcctggaac actataccct ccctcttcat ttggcccacc   2220
tctaatttc tttcagatct ccatgaagat gttacttcct ccaggaagcc ttatctgacc    2280
cctccaaaga tgtcatgagt tcctcttttc attctactaa tcacagcatc catcacacca   2340
tgttgtgatt actgatacta ttgtctgttt ctctgattag gcagtaagct caacaagagc   2400
tacatggtgc ctgtctcttg ttgctgatta ttcccatcca aaaacagtgc ctggaatgca   2460
gacttaacat tttattgaat gaataaataa aaccccatct atcgagtgct actttgtgca   2520
agacccggtt ctgaggcatt tatatttatt gatttattta attctcattt aaccatgaag   2580
gaggtactat cactatcctt attttatagt tgataaagat aaagcccaga gaaatgaatt   2640
aactcaccca aagtcatgta gctaagtgac agggcaaaaa ttcaaaccag ttccccaact   2700
ttacgtgatt aatactgtgc tatactgcct ctctgatcat atggcatgga atgcagacat   2760
ctgctccgta aggcagaata tggaaggaga ttggaggatg acacaaaacc agcataatat   2820
cagaggaaaa gtccaaacag gacctgaact gatagaaaag ttgttactcc tggtgtagtc   2880
gcatcgacat cttgatgaac tggtggctga cacaacatac attggcttga tgtgtacata   2940
ttatttgtag ttgtgtgtgt atttttatat atatatttgt aatattgaaa tagtcataat   3000
ttactaaagg cctaccattt gccaggcatt tttacatttg tcccctctaa tcttttgatg   3060
agatgatcag attggattac ttggccttga agatgatata tctacatcta tatctatatc   3120
tatatctata tctatatcta tatctatatc tatatctata tatgtatatc agaaaagctg   3180
aaatatgttt tgtaaagtta taaagatttc agactttata gaatctggga tttgccaaat   3240
gtaacccctt tctctacatt aaacccatgt tggaacaaat acatttatta ttcattcatc   3300
aaatgttgct gagtcctggc tatgaaccag acactgtgaa agcctttggg atattttgcc   3360
catgcttggg caagcttata tagtttgctt cataaaactc tatttcagtt cttcataact   3420
aatacttcat gactattgct tttcaggtat tccttcataa caaatacttt ggctttcata   3480
tatttgagta aagtccccct tgaggaagag tagaagaact gcactttgta aatactatcc   3540
tggaatccaa acggatagac aaggatggtg ctacctcttt ctggagagta cgtgagcaag   3600
gcctgttttg ttaacatgtt ccttaggaga caaaacttag gagagacacg catagcagaa   3660
aatggacaaa aactaacaaa tgaatgggaa ttgtacttga ttagcattga agaccttgtt   3720
tatactatga taaatgtttg tatttgctgg aagtgctact gacggtaaac ccttttttgtt   3780
taaatgtgtg ccctagtagc ttgcagtatg atctattttt taagtactgt acttagctta   3840
tttaaaaatt ttatgtttaa aattgcatag tgctctttca ttgaagaagt tttgagagag   3900
agatagaatt aaattcactt atcttaccat ctagagaaac ccaatgttaa aactttgttg   3960
tccattattt ctgtctttta ttcaacattt tttttagagg gtgggaggaa tacagaggag   4020
gtacaatgat acacaaatga gagcactctc catgtattgt tttgtcctgt ttttcagtta   4080
```

-continued

```
acaatatatt atgagcatat ttccatttca ttaaatattc ttccacaaag ttattttgat   4140
ggctgtatat caccctactt tatgaatgta ccatattaat ttatttcctg gtgtgggtta   4200
tttgatttta taatcttacc tttagaataa tgaaacacct gtgaagcttt agaaaatact   4260
ggtgcctggg tctcaactcc acagattctg atttaactgg tctgggttac agactaggca   4320
ttgggaattc aaaaagttcc cccagtgatt ctaatgtgta gccaagatcg ggaacccttg   4380
tagacaggga tgataggagg tgagccactc ttagcatcca tcatttagta ttaacatcat   4440
catcttgagt tgctaagtga atgatgcacc tgacccactt tataaagaca catgtgcaaa   4500
taaaattatt ataggacttg gtttattagg gcttgtgctc taagttttct atgttaagcc   4560
atacatcgca tactaaatac tttaaaatgt accttattga catacatatt aagtgaaaag   4620
tgtttctgag ctaaacaatg acagcataat tatcaagcaa tgataatttg aaatgaattt   4680
attattctgc aacttaggga caagtcatct ctctgaattt tttgtacttt gagagtattt   4740
gttatatttg caagatgaag agtctgaatt ggtcagacaa tgtcttgtgt gcctggcata   4800
tgataggcat ttaatagttt taaagaatta atgtatttag atgaattgca taccaaatct   4860
gctgtctttt ctttatggct tcattaactt aatttgagag aaattaatta ttctgcaact   4920
tagggacaag tcatgtcttt gaatattctg tagtttgagg agaatatttg ttatatttgc   4980
aaaataaaat aagtttgcaa gttttttttt tctgccccaa agagctctgt gtccttgaac   5040
ataaaataca aataaccgct atgctgttaa ttattggcaa atgtcccatt ttcaacctaa   5100
ggaaatacca taaagtaaca gatataccaa caaaaggtta ctagttaaca ggcattgcct   5160
gaaaagagta taaaagaatt tcagcatgat tttccatatt gtgcttccac cactgccaat   5220
aaca                                                                5224
```

<210> SEQ ID NO 6
<211> LENGTH: 822
<212> TYPE: DNA
<213> ORGANISM: Homo sapiens

<400> SEQUENCE: 6

```
gcattgctgt gaactctgta cttaggacta aactttgagc aataacacac atagattgag     60
gattgtttgc tgttagcata caaactctgg ttcaaagctc ctctttattg cttgtcttgg    120
aaaatttgct gttcttcatg gtttctcttt tcactgctat ctatttttct caaccactca    180
catggctaca ataactgtct gcaagcttat gattcccaaa tatctatctc tagcctcaat    240
cttgttccag aagataaaaa gtagtattca aatgcacatc aacgtctcca cttggagggc    300
ttaaagacgt ttcaacatac aaaccgggga gttttgcctg gaatgtttcc taaaatgtgt    360
cctgtagcac atagggtcct cttgttcctt aaaatctaat tacttttagc ccagtgctca    420
tcccacctat ggggagatga gagtgaaaag ggagcctgat taataattac actaagtcaa    480
taggcataga gccaggactg tttgggtaaa ctggtcactt tatcttaaac taaatatatc    540
caaaactgaa catgtactta gttactaagt ctttgacttt atctcattca taccactcag    600
ctttatccag gccacttatg agctctgtgt ccttgaacat aaaatacaaa taaccgctat    660
gctgttaatt attggcaaat gtcccatttt caacctaagg aaataccata aagtaacaga    720
tataccaaca aaaggttact agttaacagg cattgcctga aaagagtata aaagaatttc    780
agcatgattt tccatattgt gcttccacca ctgccaataa ca                       822
```

<210> SEQ ID NO 7
<211> LENGTH: 472

-continued

<212> TYPE: DNA
<213> ORGANISM: Homo sapiens

<400> SEQUENCE: 7
agccaccacc cagtgagcct ttttctagcc cccagagcca cctctgtcac cttcctgttg 60
ggcatcatcc caccttccca gagccctgga gagcatgggg agacccggga ccctgctggg 120
tttctctgtc acaaaggaaa ataatccccc tggtgtgaca gacccaagga cagaacacag 180
cagaggtcag cactggggaa gacaggttgt cctcccaggg gatgggggtc catccacctt 240
gccgaaaaga tttgtctgag gaactgaaaa tagaagggaa aaaagaggag ggacaaaaga 300
ggcagaaatg agaggggagg ggacagagga cacctgaata aagaccacac ccatgaccca 360
cgtgatgctg agaagtactc ctgccctagg aagagactca gggcagaggg aggaaggaca 420
gcagaccaga cagtcacagc agccttgaca aaacgttcct ggaactcaag ca 472

<210> SEQ ID NO 8
<211> LENGTH: 858
<212> TYPE: DNA
<213> ORGANISM: Homo sapiens

<400> SEQUENCE: 8
cgagcggccc ctcagcttcg gcgcccagcc ccgcaaggct cccggtgacc actagagggc 60
gggaggagct cctggccagt ggtggagagt ggcaaggaag gaccctaggg ttcatcggag 120
cccaggttta ctcccttaag tggaaatttc ttcccccact cctccttggc tttctccaag 180
gagggaaccc aggctgctgg aaagtccggc tggggcgggg actgtgggtt caggggagaa 240
cggggtgtgg aacgggacag ggagcggtta gaagggtggg gctattccgg gaagtggtgg 300
ggggagggag cccaaaacta gcacctagtc cactcattat ccagccctct tatttctcgg 360
ccgctctgct tcagtggacc cggggagggc ggggaagtgg agtgggagac ctaggggtgg 420
gcttcccgac cttgctgtac aggacctcga cctagctggc tttgttcccc atccccacgt 480
tagttgttgc cctgaggcta aaactagagc ccaggggccc caagttccag actgcccctc 540
ccccctcccc cggagccagg gagtggttgg tgaaaggggg aggccagctg gagaacaaac 600
gggtagtcag ggggttgagc gattagagcc cttgtaccct acccaggaat ggttggggag 660
gaggaggaag aggtaggagg taggggaggg ggcggggttt tgtcacctgt cacctgctcg 720
ctgtgcctag ggcgggcggg cggggagtgg ggggaccggt ataaagcggt aggcgcctgt 780
gcccgctcca cctctcaagc agccagcgcc tgcctgaatc tgttctgccc cctccccacc 840
catttcacca ccaccatg 858

<210> SEQ ID NO 9
<211> LENGTH: 454
<212> TYPE: DNA
<213> ORGANISM: Homo sapiens

<400> SEQUENCE: 9
aagcttccac aagtgcattt agcctctcca gtattgctga tgaatccaca gttcaggttc 60
aatggcgttc aaaacttgat caaaaatgac cagactttat attcttacac caacatctat 120
ctgattggag gaatggataa tagtcatcat gtttaaacat ctaccattcc agttaagaaa 180
atatgatagc atcttgttct tagtcttttt cttaataggg acataaagcc cacaaataaa 240
aatatgcctg aagaatggga caggcattgg gcattgtcca tgcctagtaa agtactccaa 300
gaacctattt gtatactaga tgacacaatg tcaatgtctg tgtacaactg ccaactggga 360

-continued

```
tgcaagacac tgcccatgcc aatcatcctg aaaagcagct ataaaaagca ggaagctact    420

ctgcaccttg tcagtgaggt ccagatacct acag                                454


<210> SEQ ID NO 10
<211> LENGTH: 307
<212> TYPE: DNA
<213> ORGANISM: Homo sapiens
<220> FEATURE:
<221> NAME/KEY: CDS
<222> LOCATION: (2)..(304)

<400> SEQUENCE: 10

g atg acc ggc tca acc atc gcg ccc aca acg gac tat cgc aac acc act     49
  Met Thr Gly Ser Thr Ile Ala Pro Thr Thr Asp Tyr Arg Asn Thr Thr
    1               5                  10                  15

gct acc gga cta aca tct gcc cta aat tta ccc caa gtt cat gcc ttt       97
Ala Thr Gly Leu Thr Ser Ala Leu Asn Leu Pro Gln Val His Ala Phe
             20                  25                  30

gtc aat gac tgg gcg agc ttg gac atg tgg tgg ttt tcc ata gcg ctt      145
Val Asn Asp Trp Ala Ser Leu Asp Met Trp Trp Phe Ser Ile Ala Leu
         35                  40                  45

atg ttt gtt tgc ctt att att atg tgg ctt att tgt tgc cta aag cgc      193
Met Phe Val Cys Leu Ile Ile Met Trp Leu Ile Cys Cys Leu Lys Arg
     50                  55                  60

aga cgc gcc aga ccc ccc atc tat agg cct atc att gtg ctc aac cca      241
Arg Arg Ala Arg Pro Pro Ile Tyr Arg Pro Ile Ile Val Leu Asn Pro
 65                  70                  75                  80

cac aat gaa aaa att cat aga ttg gac ggt ctg aaa cca tgt tct ctt      289
His Asn Glu Lys Ile His Arg Leu Asp Gly Leu Lys Pro Cys Ser Leu
                 85                  90                  95

ctt tta cag tat gat taa                                              307
Leu Leu Gln Tyr Asp
            100


<210> SEQ ID NO 11
<211> LENGTH: 101
<212> TYPE: PRT
<213> ORGANISM: Homo sapiens

<400> SEQUENCE: 11

Met Thr Gly Ser Thr Ile Ala Pro Thr Thr Asp Tyr Arg Asn Thr Thr
  1               5                  10                  15

Ala Thr Gly Leu Thr Ser Ala Leu Asn Leu Pro Gln Val His Ala Phe
             20                  25                  30

Val Asn Asp Trp Ala Ser Leu Asp Met Trp Trp Phe Ser Ile Ala Leu
         35                  40                  45

Met Phe Val Cys Leu Ile Ile Met Trp Leu Ile Cys Cys Leu Lys Arg
     50                  55                  60

Arg Arg Ala Arg Pro Pro Ile Tyr Arg Pro Ile Ile Val Leu Asn Pro
 65                  70                  75                  80

His Asn Glu Lys Ile His Arg Leu Asp Gly Leu Lys Pro Cys Ser Leu
                 85                  90                  95

Leu Leu Gln Tyr Asp
            100


<210> SEQ ID NO 12
<211> LENGTH: 25
<212> TYPE: DNA
<213> ORGANISM: Unknown
<220> FEATURE:
<223> OTHER INFORMATION: Description of Unknown Organism: unknown
```

-continued

<400> SEQUENCE: 12
ggacctcgag gtctccatga gctac 25

<210> SEQ ID NO 13
<211> LENGTH: 23
<212> TYPE: DNA
<213> ORGANISM: Unknown
<220> FEATURE:
<223> OTHER INFORMATION: Description of Unknown Organism: unknown

<400> SEQUENCE: 13
agctcgagct tcgggatcct gag 23

<210> SEQ ID NO 14
<211> LENGTH: 19
<212> TYPE: DNA
<213> ORGANISM: Unknown
<220> FEATURE:
<223> OTHER INFORMATION: Description of Unknown Organism: unknown

<400> SEQUENCE: 14
tcgtcttcaa gaattctca 19

<210> SEQ ID NO 15
<211> LENGTH: 20
<212> TYPE: DNA
<213> ORGANISM: Unknown
<220> FEATURE:
<223> OTHER INFORMATION: Description of Unknown Organism: unknown

<400> SEQUENCE: 15
tttcagtcac cggtgtcgga 20

<210> SEQ ID NO 16
<211> LENGTH: 20
<212> TYPE: DNA
<213> ORGANISM: Unknown
<220> FEATURE:
<223> OTHER INFORMATION: Description of Unknown Organism: unknown

<400> SEQUENCE: 16
gcattctcta gacacaggtg 20

<210> SEQ ID NO 17
<211> LENGTH: 22
<212> TYPE: DNA
<213> ORGANISM: Unknown
<220> FEATURE:
<223> OTHER INFORMATION: Description of Unknown Organism: unknown

<400> SEQUENCE: 17
tccgacaccg ggtgacctga aa 22

<210> SEQ ID NO 18
<211> LENGTH: 29
<212> TYPE: DNA
<213> ORGANISM: Unknown
<220> FEATURE:
<223> OTHER INFORMATION: Description of Unknown Organism: unknown

<400> SEQUENCE: 18
cattaaccgg tacctctaga aaatctagc 29

<210> SEQ ID NO 19

-continued

<211> LENGTH: 27
<212> TYPE: DNA
<213> ORGANISM: Unknown
<220> FEATURE:
<223> OTHER INFORMATION: Description of Unknown Organism: unknown

<400> SEQUENCE: 19
cattaaccgg taagcttggg gctgggg 27

<210> SEQ ID NO 20
<211> LENGTH: 26
<212> TYPE: DNA
<213> ORGANISM: Unknown
<220> FEATURE:
<223> OTHER INFORMATION: Description of Unknown Organism: unknown

<400> SEQUENCE: 20
ccgctcgaga tcacactccg ccacac 26

<210> SEQ ID NO 21
<211> LENGTH: 24
<212> TYPE: DNA
<213> ORGANISM: Unknown
<220> FEATURE:
<223> OTHER INFORMATION: Description of Unknown Organism: unknown

<400> SEQUENCE: 21
ccgctcgagc actcttgagt gcca 24

<210> SEQ ID NO 22
<211> LENGTH: 156
<212> TYPE: DNA
<213> ORGANISM: Unknown
<220> FEATURE:
<223> OTHER INFORMATION: Description of Unknown Organism: unknown

<400> SEQUENCE: 22
tcgagggatg ttgtagtaaa tttgggcgta accgagtaag atttggccat tttcgcggga 60
aaactgaata agactcttcg aaatctgaat aattttgtgt tactcatagc gcgtaatatt 120
tgtctagggc cgcggggact ttgaccgttt acgtgg 156

<210> SEQ ID NO 23
<211> LENGTH: 156
<212> TYPE: DNA
<213> ORGANISM: Unknown
<220> FEATURE:
<223> OTHER INFORMATION: Description of Unknown Organism: unknown

<400> SEQUENCE: 23
gatcccacgt aaacggtcaa agtccccgcg gccctagaca aatattacgc gctatgagta 60
acacaaaatt attcagattt cgaagagtct tattcagttt tcccgcgaaa atggccaaat 120
cttactcggt tacgcccaaa tttactacaa catccc 156

<210> SEQ ID NO 24
<211> LENGTH: 27
<212> TYPE: DNA
<213> ORGANISM: Unknown
<220> FEATURE:
<223> OTHER INFORMATION: Description of Unknown Organism: unknown

<400> SEQUENCE: 24
ggaagatctg aaatctagct gatatag 27

-continued

<210> SEQ ID NO 25
<211> LENGTH: 24
<212> TYPE: DNA
<213> ORGANISM: Unknown
<220> FEATURE:
<223> OTHER INFORMATION: Description of Unknown Organism: unknown

<400> SEQUENCE: 25
ttctcgagaa gcttggggct gggg 24

<210> SEQ ID NO 26
<211> LENGTH: 39
<212> TYPE: DNA
<213> ORGANISM: Unknown
<220> FEATURE:
<223> OTHER INFORMATION: Description of Unknown Organism: unknown

<400> SEQUENCE: 26
gtcgacgtga aatctgaata attttgtgtt actcatagc 39

<210> SEQ ID NO 27
<211> LENGTH: 23
<212> TYPE: DNA
<213> ORGANISM: Unknown
<220> FEATURE:
<223> OTHER INFORMATION: Description of Unknown Organism: unknown

<400> SEQUENCE: 27
caccggcgca caccaaaaac gtc 23

<210> SEQ ID NO 28
<211> LENGTH: 21
<212> TYPE: DNA
<213> ORGANISM: Unknown
<220> FEATURE:
<223> OTHER INFORMATION: Description of Unknown Organism: unknown

<400> SEQUENCE: 28
gcccacggcc gcattatata c 21

<210> SEQ ID NO 29
<211> LENGTH: 21
<212> TYPE: DNA
<213> ORGANISM: Unknown
<220> FEATURE:
<223> OTHER INFORMATION: Description of Unknown Organism: unknown

<400> SEQUENCE: 29
gtatataatg cggccgtggg c 21

<210> SEQ ID NO 30
<211> LENGTH: 21
<212> TYPE: DNA
<213> ORGANISM: Unknown
<220> FEATURE:
<223> OTHER INFORMATION: Description of Unknown Organism: unknown

<400> SEQUENCE: 30
ccagaaaatc cagcaggtac c 21

<210> SEQ ID NO 31
<211> LENGTH: 26
<212> TYPE: DNA
<213> ORGANISM: Unknown
<220> FEATURE:
<223> OTHER INFORMATION: Description of Unknown Organism: unknown -continued

<400> SEQUENCE: 31
taacggccgt ctagaaatct agctga 26

<210> SEQ ID NO 32
<211> LENGTH: 23
<212> TYPE: DNA
<213> ORGANISM: Unknown
<220> FEATURE:
<223> OTHER INFORMATION: Description of Unknown Organism: unknown

<400> SEQUENCE: 32
taacggccga agcttgggct ggg 23

<210> SEQ ID NO 33
<211> LENGTH: 20
<212> TYPE: DNA
<213> ORGANISM: Unknown
<220> FEATURE:
<223> OTHER INFORMATION: Description of Unknown Organism: unknown

<400> SEQUENCE: 33
taactcacgt tgtgcattgt 20

<210> SEQ ID NO 34
<211> LENGTH: 21
<212> TYPE: DNA
<213> ORGANISM: Unknown
<220> FEATURE:
<223> OTHER INFORMATION: Description of Unknown Organism: unknown

<400> SEQUENCE: 34
ggtgccgtgc tcgagtggtg t 21

<210> SEQ ID NO 35
<211> LENGTH: 21
<212> TYPE: DNA
<213> ORGANISM: Unknown
<220> FEATURE:
<223> OTHER INFORMATION: Description of Unknown Organism: unknown

<400> SEQUENCE: 35
acaccactcg agcacggcac c 21

<210> SEQ ID NO 36
<211> LENGTH: 24
<212> TYPE: DNA
<213> ORGANISM: Unknown
<220> FEATURE:
<223> OTHER INFORMATION: Description of Unknown Organism: unknown

<400> SEQUENCE: 36
gctactattc gacagtttgt actg 24

<210> SEQ ID NO 37
<211> LENGTH: 27
<212> TYPE: DNA
<213> ORGANISM: Unknown
<220> FEATURE:
<223> OTHER INFORMATION: Description of Unknown Organism: unknown

<400> SEQUENCE: 37
gggtcgacgt acctctagaa atctagc 27

<210> SEQ ID NO 38
<211> LENGTH: 30

-continued

<212> TYPE: DNA
<213> ORGANISM: Unknown
<220> FEATURE:
<223> OTHER INFORMATION: Description of Unknown Organism: unknown

<400> SEQUENCE: 38
gtttgtgtat tttagatcaa agatgctgca 30

<210> SEQ ID NO 39
<211> LENGTH: 26
<212> TYPE: DNA
<213> ORGANISM: Unknown
<220> FEATURE:
<223> OTHER INFORMATION: Description of Unknown Organism: unknown

<400> SEQUENCE: 39
gcatctttga tctaaaatac acaaac 26

<210> SEQ ID NO 40
<211> LENGTH: 30
<212> TYPE: DNA
<213> ORGANISM: Unknown
<220> FEATURE:
<223> OTHER INFORMATION: Description of Unknown Organism: unknown

<400> SEQUENCE: 40
taaaggagga gatctgccta aaacactgca 30

<210> SEQ ID NO 41
<211> LENGTH: 25
<212> TYPE: DNA
<213> ORGANISM: Unknown
<220> FEATURE:
<223> OTHER INFORMATION: Description of Unknown Organism: unknown

<400> SEQUENCE: 41
gtgttttagg cagatctcct ccttt 25

<210> SEQ ID NO 42
<211> LENGTH: 43
<212> TYPE: DNA
<213> ORGANISM: Unknown
<220> FEATURE:
<223> OTHER INFORMATION: Description of Unknown Organism: unknown

<400> SEQUENCE: 42
gcaacccacc ggtgctaatc aagtatggca aaggagtaag cgc 43

<210> SEQ ID NO 43
<211> LENGTH: 26
<212> TYPE: DNA
<213> ORGANISM: Unknown
<220> FEATURE:
<223> OTHER INFORMATION: Description of Unknown Organism: unknown

<400> SEQUENCE: 43
tggccttgct agactgctcc ttcagc 26

<210> SEQ ID NO 44
<211> LENGTH: 822
<212> TYPE: DNA
<213> ORGANISM: Unknown
<220> FEATURE:
<223> OTHER INFORMATION: Description of Unknown Organism: unknown

<400> SEQUENCE: 44

-continued

```
gcattgctgt gaactctgta cttaggacta aactttgagc aataacacac atagattgag     60

gattgtttgc tgttagcata caaactctgg ttcaaagctc ctctttattg cttgtcttgg    120

aaaatttgct gttcttcatg gtttctcttt tcactgctat ctatttttct caaccactca    180

catggctaca ataactgtct gcaagcttat gattcccaaa tatctatctc tagcctcaat    240

cttgttccag aagataaaaa gtagtattca aatgcacatc aacgtctcca cttggagggc    300

ttaaagacgt ttcaacatac aaaccgggga gttttgcctg gaatgtttcc taaaatgtgt    360

cctgtagcac atagggtcct cttgttcctt aaaatctaat tacttttagc ccagtgctca    420

tcccacctat ggggagatga gagtgaaaag ggagcctgat taataattac actaagtcaa    480

taggcataga gccaggactg tttgggtaaa ctggtcactt tatcttaaac taaatatatc    540

caaaactgaa catgtactta gttactaagt ctttgacttt atctcattca taccactcag    600

ctttatccag gccacttatg agctctgtgt ccttgaacat aaaatacaaa taaccgctat    660

gctgttaatt attggcaaat gtcccatttt caacctaagg aaataccata aagtaacaga    720

tataccaaca aaaggttact agttaacagg cattgcctga aaagagtata aaagaatttc    780

agcatgattt tccatattgt gcttccacca ctgccaataa ca                       822
```

```
<210> SEQ ID NO 45
<211> LENGTH: 5224
<212> TYPE: DNA
<213> ORGANISM: Unknown
<220> FEATURE:
<223> OTHER INFORMATION: Description of Unknown Organism: unknown

<400> SEQUENCE: 45

gaattcttag aaatatgggg gtaggggtgg tggtggtaat tctgttttca ccccataggt     60

gagataagca ttgggttaaa tgtgctttca cacacacatc acatttcata agaattaagg    120

aacagactat gggctggagg actttgagga tgtctgtctc ataacacttg ggttgtatct    180

gttctatggg gcttgtttta agcttggcaa cttgcaacag ggttcactga ctttctcccc    240

aagcccaagg tactgtcctc ttttcatatc tgttttgggg cctctggggc ttgaatatct    300

gagaaaatat aaacatttca ataatgttct gtggtgagat gagtatgaga gatgtgtcat    360

tcatttgtat caatgaatga atgaggacaa ttagtgtata aatccttagt acaacaatct    420

gagggtaggg gtggtactat tcaatttcta tttataaaga tacttatttc tatttattta    480

tgcttgtgac aaatgttttg ttcgggacca caggaatcac aaagatgagt ctttgaattt    540

aagaagttaa tggtccagga ataattacat agcttacaaa tgactatgat ataccatcaa    600

acaagaggtt ccatgagaaa ataatctgaa aggtttaata agttgtcaaa ggtgagaggg    660

ctcttctcta gctagagact aatcagaaat acattcaggg ataattattt gaatagacct    720

taagggttgg gtacattttg ttcaagcatt gatggagaag gagagtgaat atttgaaaac    780

attttcaact aaccaaccac ccaatccaac aaacaaaaaa tgaaaagaat ctcagaaaca    840

gtgagataag agaaggaatt ttctcacaac ccacacgtat agctcaactg ctctgaagaa    900

gtatatatct aatatttaac actaacatca tgctaataat gataataatt actgtcattt    960

tttaatgtct ataagtacca ggcatttaga agatattatt ccatttatat atcaaaataa   1020

acttgagggg atagatcatt ttcatgatat atgagaaaaa ttaaaaacag attgaattat   1080

ttgcctgtca tacagctaat aattgaccat aagacaatta gatttaaatt agttttgaat   1140

ctttctaata ccaaagttca gtttactgtt ccatgttgct tctgagtggc ttcacagact   1200

tatgaaaaag taaacggaat cagaattaca tcaatgcaaa agcattgctg tgaactctgt   1260
```

-continued

```
actaggact aaactttgag caataacaca catagattga ggattgtttg ctgttagcat   1320
acaaactctg gttcaaagct cctctttatt gcttgtcttg gaaaatttgc tgttcttcat   1380
ggtttctctt ttcactgcta tctatttttc tcaaccactc acatggctac aataactgtc   1440
tgcaagctta tgattcccaa atatctatct ctagcctcaa tcttgttcca gaagataaaa   1500
agtagtattc aaatgcacat caacgtctcc acttggaggg cttaaagacg tttcaacata   1560
caaaccgggg agttttgcct ggaatgtttc ctaaaatgtg tcctgtagca catagggtcc   1620
tcttgttcct taaaatctaa ttacttttag cccagtgctc atcccaccta tggggagatg   1680
agagtgaaaa gggagcctga ttaataatta cactaagtca ataggcatag agccaggact   1740
gtttgggtaa actggtcact ttatcttaaa ctaaatatat ccaaaactga acatgtactt   1800
agttactaag tctttgactt tatctcattc ataccactca gctttatcca ggccacttat   1860
ttgacagtat tattgcgaaa acttcctaac tggtctcctt atcatagtct tatccccttt   1920
tgaaacaaaa gagacagttt caaaatacaa atatgatttt tattagctcc cttttgttgt   1980
ctataatagt cccagaagga gttataaact ccatttaaaa agtctttgag atgtggccct   2040
tgccaacttt gccaggaatt cccaatatct agtattttct actattaaac tttgtgcctc   2100
ttcaaaactg cattttctct cattccctaa gtgtgcattg ttttccctta ccggttggtt   2160
tttccaccac cttttacatt ttcctggaac actataccct ccctcttcat ttggcccacc   2220
tctaattttc tttcagatct ccatgaagat gttacttcct ccaggaagcc ttatctgacc   2280
cctccaaaga tgtcatgagt tcctcttttc attctactaa tcacagcatc catcacacca   2340
tgttgtgatt actgatacta ttgtctgttt ctctgattag gcagtaagct caacaagagc   2400
tacatggtgc ctgtctcttg ttgctgatta ttcccatcca aaaacagtgc ctggaatgca   2460
gacttaacat tttattgaat gaataaataa aaccccatct atcgagtgct actttgtgca   2520
agacccggtt ctgaggcatt tatatttatt gatttattta attctcattt aaccatgaag   2580
gaggtactat cactatcctt attttatagt tgataaagat aaagcccaga gaaatgaatt   2640
aactcaccca aagtcatgta gctaagtgac agggcaaaaa ttcaaaccag ttccccaact   2700
ttacgtgatt aatactgtgc tatactgcct ctctgatcat atggcatgga atgcagacat   2760
ctgctccgta aggcagaata tggaaggaga ttggaggatg acacaaaacc agcataatat   2820
cagaggaaaa gtccaaacag gacctgaact gatagaaaag ttgttactcc tggtgtagtc   2880
gcatcgacat cttgatgaac tggtggctga cacaacatac attggcttga tgtgtacata   2940
ttatttgtag ttgtgtgtgt atttttatat atatatttgt aatattgaaa tagtcataat   3000
ttactaaagg cctaccattt gccaggcatt tttacatttg tcccctctaa tcttttgatg   3060
agatgatcag attggattac ttggccttga agatgatata tctacatcta tatctatatc   3120
tatatctata tctatatcta tatctatatc tatatctata tatgtatatc agaaaagctg   3180
aaatatgttt tgtaaagtta taaagatttc agactttata gaatctggga tttgccaaat   3240
gtaacccctt tctctacatt aaacccatgt tggaacaaat acatttatta ttcattcatc   3300
aaatgttgct gagtcctggc tatgaaccag acactgtgaa agcctttggg atattttgcc   3360
catgcttggg caagcttata tagtttgctt cataaaactc tatttcagtt cttcataact   3420
aatacttcat gactattgct tttcaggtat tccttcataa caaatacttt ggctttcata   3480
tatttgagta aagtcccccct tgaggaagag tagaagaact gcactttgta aatactatcc   3540
tggaatccaa acggatagac aaggatggtg ctacctcttt ctggagagta cgtgagcaag   3600
```

-continued

```
gcctgttttg ttaacatgtt ccttaggaga caaaacttag gagagacacg catagcagaa   3660

aatggacaaa aactaacaaa tgaatgggaa ttgtacttga ttagcattga agaccttgtt   3720

tatactatga taaatgtttg tatttgctgg aagtgctact gacggtaaac cctttttgtt   3780

taaatgtgtg ccctagtagc ttgcagtatg atctattttt taagtactgt acttagctta   3840

tttaaaaatt ttatgtttaa aattgcatag tgctctttca ttgaagaagt tttgagagag   3900

agatagaatt aaattcactt atcttaccat ctagagaaac ccaatgttaa aactttgttg   3960

tccattattt ctgtctttta ttcaacattt tttttagagg gtgggaggaa tacagaggag   4020

gtacaatgat acacaaatga gagcactctc catgtattgt tttgtcctgt ttttcagtta   4080

acaatatatt atgagcatat ttccatttca ttaaatattc ttccacaaag ttattttgat   4140

ggctgtatat caccctactt tatgaatgta ccatattaat ttatttcctg gtgtgggtta   4200

tttgatttta taatcttacc tttagaataa tgaaacacct gtgaagcttt agaaaatact   4260

ggtgcctggg tctcaactcc acagattctg atttaactgg tctgggttac agactaggca   4320

ttgggaattc aaaaagttcc cccagtgatt ctaatgtgta gccaagatcg ggaacccttg   4380

tagacaggga tgataggagg tgagccactc ttagcatcca tcatttagta ttaacatcat   4440

catcttgagt tgctaagtga atgatgcacc tgacccactt tataaagaca catgtgcaaa   4500

taaaattatt ataggacttg gtttattagg gcttgtgctc taagttttct atgttaagcc   4560

atacatcgca tactaaatac tttaaaatgt accttattga catacatatt aagtgaaaag   4620

tgtttctgag ctaaacaatg acagcataat tatcaagcaa tgataatttg aaatgaattt   4680

attattctgc aacttaggga caagtcatct ctctgaattt tttgtacttt gagagtattt   4740

gttatatttg caagatgaag agtctgaatt ggtcagacaa tgtcttgtgt gcctggcata   4800

tgataggcat ttaatagttt taaagaatta atgtatttag atgaattgca taccaaatct   4860

gctgtctttt ctttatggct tcattaactt aatttgagag aaattaatta ttctgcaact   4920

tagggacaag tcatgtcttt gaatattctg tagtttgagg agaatatttg ttatatttgc   4980

aaaataaaat aagtttgcaa gttttttttt tctgccccaa agagctctgt gtccttgaac   5040

ataaaataca aataaccgct atgctgttaa ttattggcaa atgtcccatt ttcaacctaa   5100

ggaaatacca taaagtaaca gatataccaa caaaaggtta ctagttaaca ggcattgcct   5160

gaaaagagta taaaagaatt tcagcatgat tttccatatt gtgcttccac cactgccaat   5220

aaca                                                                5224
```

<210> SEQ ID NO 46
<211> LENGTH: 21
<212> TYPE: DNA
<213> ORGANISM: Unknown
<220> FEATURE:
<223> OTHER INFORMATION: Description of Unknown Organism: Unknown

<400> SEQUENCE: 46

```
gcccacggcc gcattatata c                                               21
```

<210> SEQ ID NO 47
<211> LENGTH: 21
<212> TYPE: DNA
<213> ORGANISM: Unknown
<220> FEATURE:
<223> OTHER INFORMATION: Description of Unknown Organism: Unknown

<400> SEQUENCE: 47

```
gtatataatg cggccgtggg c                                               21
```

-continued

<210> SEQ ID NO 48
<211> LENGTH: 29
<212> TYPE: DNA
<213> ORGANISM: Unknown
<220> FEATURE:
<223> OTHER INFORMATION: Description of Unknown Organism: Unknown

<400> SEQUENCE: 48
gtgaccggtg cattgctgtg aactctgta 29

<210> SEQ ID NO 49
<211> LENGTH: 27
<212> TYPE: DNA
<213> ORGANISM: Unknown
<220> FEATURE:
<223> OTHER INFORMATION: Description of Unknown Organism: Unknown

<400> SEQUENCE: 49
ataagtggcc tggataaagc tgagtgg 27

<210> SEQ ID NO 50
<211> LENGTH: 28
<212> TYPE: DNA
<213> ORGANISM: Unknown
<220> FEATURE:
<223> OTHER INFORMATION: Description of Unknown Organism: Unknown

<400> SEQUENCE: 50
gtcaccggtc tttgttattg gcagtggt 28

<210> SEQ ID NO 51
<211> LENGTH: 30
<212> TYPE: DNA
<213> ORGANISM: Unknown
<220> FEATURE:
<223> OTHER INFORMATION: Description of Unknown Organism: Unknown

<400> SEQUENCE: 51
atccaggcca cttatgagct ctgtgtcctt 30

<210> SEQ ID NO 52
<211> LENGTH: 26
<212> TYPE: DNA
<213> ORGANISM: Unknown
<220> FEATURE:
<223> OTHER INFORMATION: Description of Unknown Organism: Unknown

<400> SEQUENCE: 52
tatcggccgg cattgctgtg aactct 26

<210> SEQ ID NO 53
<211> LENGTH: 26
<212> TYPE: DNA
<213> ORGANISM: Unknown
<220> FEATURE:
<223> OTHER INFORMATION: Description of Unknown Organism: Unknown

<400> SEQUENCE: 53
ttacggccgc tttgttattg gcagtg 26

<210> SEQ ID NO 54
<211> LENGTH: 472
<212> TYPE: DNA
<213> ORGANISM: Unknown
<220> FEATURE:

-continued

<223> OTHER INFORMATION: Description of Unknown Organism: Unknown

<400> SEQUENCE: 54
agccaccacc cagtgagcct ttttctagcc cccagagcca cctctgtcac cttcctgttg 60
ggcatcatcc caccttccca gagccctgga gagcatgggg agacccggga ccctgctggg 120
tttctctgtc acaaaggaaa ataatccccc tggtgtgaca gacccaagga cagaacacag 180
cagaggtcag cactggggaa gacaggttgt cctcccaggg gatgggggtc catccacctt 240
gccgaaaaga tttgtctgag gaactgaaaa tagaagggaa aaaagaggag ggacaaaaga 300
ggcagaaatg agaggggagg ggacagagga cacctgaata aagaccacac ccatgaccca 360
cgtgatgctg agaagtactc ctgccctagg aagagactca gggcagaggg aggaaggaca 420
gcagaccaga cagtcacagc agccttgaca aaacgttcct ggaactcaag ca 472

<210> SEQ ID NO 55
<211> LENGTH: 26
<212> TYPE: DNA
<213> ORGANISM: Unknown
<220> FEATURE:
<223> OTHER INFORMATION: Description of Unknown Organism: Unknown

<400> SEQUENCE: 55
attaccggta gccaccaccc agtgag 26

<210> SEQ ID NO 56
<211> LENGTH: 26
<212> TYPE: DNA
<213> ORGANISM: Unknown
<220> FEATURE:
<223> OTHER INFORMATION: Description of Unknown Organism: Unknown

<400> SEQUENCE: 56
tagaccggtg cttgagttcc aggaac 26

<210> SEQ ID NO 57
<211> LENGTH: 21
<212> TYPE: DNA
<213> ORGANISM: Unknown
<220> FEATURE:
<223> OTHER INFORMATION: Description of Unknown Organism: Unknown

<400> SEQUENCE: 57
atttgtctag ggccgggact t 21

<210> SEQ ID NO 58
<211> LENGTH: 24
<212> TYPE: DNA
<213> ORGANISM: Unknown
<220> FEATURE:
<223> OTHER INFORMATION: Description of Unknown Organism: Unknown

<400> SEQUENCE: 58
cgcgcgcaaa acccctaaat aaag 24

<210> SEQ ID NO 59
<211> LENGTH: 21
<212> TYPE: DNA
<213> ORGANISM: Unknown
<220> FEATURE:
<223> OTHER INFORMATION: Description of Unknown Organism: Unknown

<400> SEQUENCE: 59
taacggccga gccaccaccc a 21

-continued

<210> SEQ ID NO 60
<211> LENGTH: 23
<212> TYPE: DNA
<213> ORGANISM: Unknown
<220> FEATURE:
<223> OTHER INFORMATION: Description of Unknown Organism: Unknown

<400> SEQUENCE: 60
tatcggccgg cttgagttcc agg 23

<210> SEQ ID NO 61
<211> LENGTH: 307
<212> TYPE: DNA
<213> ORGANISM: Unknown
<220> FEATURE:
<223> OTHER INFORMATION: Description of Unknown Organism: Unknown

<400> SEQUENCE: 61
gatgaccggc tcaaccatcg cgcccacaac ggactatcgc aacaccactg ctaccggact 60
aacatctgcc ctaaatttac cccaagttca tgcctttgtc aatgactggg cgagcttgga 120
catgtggtgg ttttccatag cgcttatgtt tgtttgcctt attattatgt ggcttatttg 180
ttgcctaaag cgcagacgcg ccagaccccc catctatagg cctatcattg tgctcaaccc 240
acacaatgaa aaaattcata gattggacgg tctgaaacca tgttctcttc ttttacagta 300
tgattaa 307

<210> SEQ ID NO 62
<211> LENGTH: 26
<212> TYPE: DNA
<213> ORGANISM: Unknown
<220> FEATURE:
<223> OTHER INFORMATION: Description of Unknown Organism: Unknown

<400> SEQUENCE: 62
taatccggac ggtgaccact agaggg 26

<210> SEQ ID NO 63
<211> LENGTH: 26
<212> TYPE: DNA
<213> ORGANISM: Unknown
<220> FEATURE:
<223> OTHER INFORMATION: Description of Unknown Organism: Unknown

<400> SEQUENCE: 63
tattccggat cacttaggca gcgctg 26

<210> SEQ ID NO 64
<211> LENGTH: 24
<212> TYPE: DNA
<213> ORGANISM: Unknown
<220> FEATURE:
<223> OTHER INFORMATION: Description of Unknown Organism: Unknown

<400> SEQUENCE: 64
taacggccgc ggtgaccact agag 24

<210> SEQ ID NO 65
<211> LENGTH: 24
<212> TYPE: DNA
<213> ORGANISM: Unknown
<220> FEATURE:
<223> OTHER INFORMATION: Description of Unknown Organism: Unknown -continued

<400> SEQUENCE: 65
tatcggccgg cagaacagat tcag 24

<210> SEQ ID NO 66
<211> LENGTH: 34
<212> TYPE: DNA
<213> ORGANISM: Unknown
<220> FEATURE:
<223> OTHER INFORMATION: Description of Unknown Organism: Unknown

<400> SEQUENCE: 66
gatcaccggt aagcttccac aagtgcattt agcc 34

<210> SEQ ID NO 67
<211> LENGTH: 33
<212> TYPE: DNA
<213> ORGANISM: Unknown
<220> FEATURE:
<223> OTHER INFORMATION: Description of Unknown Organism: Unknown

<400> SEQUENCE: 67
gatcaccggt ctgtaggtat ctggacctca ctg 33

<210> SEQ ID NO 68
<211> LENGTH: 34
<212> TYPE: DNA
<213> ORGANISM: Unknown
<220> FEATURE:
<223> OTHER INFORMATION: Description of Unknown Organism: Unknown

<400> SEQUENCE: 68
gatccggccg aagcttccac aagtgcattt agcc 34

<210> SEQ ID NO 69
<211> LENGTH: 33
<212> TYPE: DNA
<213> ORGANISM: Unknown
<220> FEATURE:
<223> OTHER INFORMATION: Description of Unknown Organism: Unknown

<400> SEQUENCE: 69
gatccggccg ctgtaggtat ctggacctca ctg 33

<210> SEQ ID NO 70
<211> LENGTH: 32
<212> TYPE: DNA
<213> ORGANISM: Unknown
<220> FEATURE:
<223> OTHER INFORMATION: Description of Unknown Organism: Unknown

<400> SEQUENCE: 70
gatcggtacc aaaagcttag agatgacctc cc 32

<210> SEQ ID NO 71
<211> LENGTH: 35
<212> TYPE: DNA
<213> ORGANISM: Unknown
<220> FEATURE:
<223> OTHER INFORMATION: Description of Unknown Organism: Unknown

<400> SEQUENCE: 71
gatcctcgag gcaataatac cgttttcttt tctgg 35

<210> SEQ ID NO 72
<211> LENGTH: 15056

-continued

<212> TYPE: DNA
<213> ORGANISM: H. sapiens

<400> SEQUENCE: 72
aagcttttta gtgctttaga cagtgagctg gtctgtctaa cccaagtgac ctgggctcca 60
tactcagccc cagaagtgaa gggtgaagct gggtggagcc aaaccaggca agcctaccct 120
cagggctccc agtggcctga gaaccattgg acccaggacc cattacttct agggtaagga 180
aggtacaaac accagatcca accatggtct ggggggacag ctgtcaaatg cctaaaaata 240
tacctgggag aggagcaggc aaactatcac tgccccaggt tctctgaaca gaaacagagg 300
ggcaacccaa agtccaaatc caggtgagca ggtgcaccaa atgcccagag atatgacgag 360
gcaagaagtg aaggaaccac ccctgcatca aatgttttgc atgggaagga gaagggggtt 420
gctcatgttc ccaatccagg agaatgcatt tgggatctgc cttcttctca ctccttggtt 480
agcaagacta agcaaccagg actctggatt tggggaaaga cgtttatttg tggaggccag 540
tgatgacaat cccacgaggg cctaggtgaa gagggcagga aggctcgaga cactggggac 600
tgagtgaaaa ccacacccat gatctgcacc acccatggat gctccttcat tgctcacctt 660
tctgttgata tcagatggcc ccattttctg taccttcaca gaaggacaca ggctagggtc 720
tgtgcatggc cttcatcccc ggggccatgt gaggacagca ggtgggaaag atcatgggtc 780
ctcctgggtc ctgcagggcc agaacattca tcacccatac tgacctccta gatgggaatg 840
gcttccctgg ggctgggcca acggggcctg ggcaggggag aaaggacgtc aggggacagg 900
gaggaagggt catcgagacc cagcctggaa ggttcttgtc tctgaccatc caggatttac 960
ttccctgcat ctacctttgg tcattttccc tcagcaatga ccagctctgc ttcctgatct 1020
cagcctccca ccctggacac agcaccccag tccctggccc ggctgcatcc acccaatacc 1080
ctgataaccc aggacccatt acttctaggg taaggagggt ccaggagaca gaagctgagg 1140
aaaggtctga agaagtcaca tctgtcctgg ccagagggga aaaaccatca gatgctgaac 1200
caggagaatg ttgacccagg aaagggaccg aggacccaag aaaggagtca gaccaccagg 1260
gtttgcctga gaggaaggat caaggccccg agggaaagca gggctggctg catgtgcagg 1320
acactggtgg ggcatatgtg tcttagattc tccctgaatt cagtgtccct gccatggcca 1380
gactctctac tcaggcctgg acatgctgaa ataggacaat ggccttgtcc tctctcccca 1440
ccatttggca agagacataa aggacattcc aggacatgcc ttcctgggag gtccaggttc 1500
tctgtctcac acctcaggga ctgtagttac tgcatcagcc atggtaggtg ctgatctcac 1560
ccagcctgtc caggcccttc cactctccac tttgtgacca tgtccaggac cacccctcag 1620
atcctgagcc tgcaaatacc cccttgctgg gtgggtggat tcagtaaaca gtgagctcct 1680
atccagcccc cagagccacc tctgtcacct tcctgctggg catcatccca ccttcacaag 1740
cactaaagag catggggaga cctggctagc tgggtttctg catcacaaag aaaataatcc 1800
cccaggttcg gattcccagg gctctgtatg tggagctgac agacctgagg ccaggagata 1860
gcagaggtca gccctaggga gggtgggtca tccacccagg ggacaggggt gcaccagcct 1920
tgctactgaa agggcctccc caggacagcg ccatcagccc tgcctgagag ctttgctaaa 1980
cagcagtcag aggaggccat ggcagtggct gagctcctgc tccaggcccc aacagaccag 2040
accaacagca caatgcagtc cttccccaac gtcacaggtc accaaaggga aactgaggtg 2100
ctacctaacc ttagagccat caggggagat aacagcccaa tttcccaaac aggccagttt 2160
caatcccatg acaatgacct ctctgctctc attcttccca aaataggacg ctgattctcc 2220

-continued

```
cccaccatgg atttctccct tgtcccggga gccttttctg cccccctatga tctgggcact   2280
cctgacacac acctcctctc tggtgacata tcagggtccc tcactgtcaa gcagtccaga   2340
aaggacagaa ccttggacag cgcccatctc agcttcaccc ttcctccttc acagggttca   2400
gggcaaagaa taaatggcag aggccagtga gcccagagat ggtgacaggc agtgacccag   2460
gggcagatgc ctggagcagg agctggcggg gccacaggga gaaggtgatg caggaaggga   2520
aacccagaaa tgggcaggaa aggaggacac aggctctgtg gggctgcagc ccagggttgg   2580
actatgagtg tgaagccatc tcagcaagta aggccaggtc ccatgaacaa gagtgggagc   2640
acgtggcttc ctgctctgta tatggggtgg gggattccat gccccataga accagatggc   2700
cggggttcag atggagaagg agcaggacag gggatcccca ggataggagg accccagtgt   2760
ccccacccag gcaggtgact gatgaatggg catgcagggt cctcctgggc tgggctctcc   2820
ctttgtccct caggattcct tgaaggaaca tccggaagcc gaccacatct acctggtggg   2880
ttctggggag tccatgtaaa gccaggagct tgtgttgcta ggaggggtca tggcatgtgc   2940
tgggggcacc aaagagagaa acctgagggc aggcaggacc tggtctgagg aggcatggga   3000
gcccagatgg ggagatggat gtcaggaaag gctgccccat cagggagggt gatagcaatg   3060
gggggtctgt gggagtgggc acgtgggatt ccctgggctc tgccaagttc cctcccatag   3120
tcacaacctg gggacactgc ccatgaaggg gcgcctttgc ccagccagat gctgctggtt   3180
ctgcccatcc actaccctct ctgctccagc cactctgggt ctttctccag atgccctgga   3240
cagccctggc ctgggcctgt cccctgagag gtgttgggag aagctgagtc tctggggaca   3300
ctctcatcag agtctgaaag gcacatcagg aaacatccct ggtctccagg actaggcaat   3360
gaggaaaggg ccccagctcc tccctttgcc actgagaggg tcgaccctgg gtggccacag   3420
tgacttctgc gtctgtccca gtcaccctga aaccacaaca aaaccccagc cccagaccct   3480
gcaggtacaa tacatgtggg gacagtctgt acccagggga agccagttct ctcttcctag   3540
gagaccgggc ctcagggctg tgcccggggc aggcgggggc agcacgtgcc tgtccttgag   3600
aactcgggac cttaagggtc tctgctctgt gaggcacagc aaggatcctt ctgtccagag   3660
atgaaagcag ctcctgcccc tcctctgacc tcttcctcct tcccaaatct caaccaacaa   3720
ataggtgttt caaatctcat catcaaatct tcatccatcc acatgagaaa gcttaaaacc   3780
caatggattg acaacatcaa gagttggaac aagtggacat ggagatgtta cttgtggaaa   3840
tttagatgtg ttcagctatc gggcaggaga atctgtgtca aattccagca tggttcagaa   3900
gaatcaaaaa gtgtcacagt ccaaatgtgc aacagtgcag gggataaaac tgtggtgcat   3960
tcaaactgag ggatattttg gaacatgaga aaggaaggga ttgctgctgc acagaacatg   4020
gatgatctca cacatagagt tgaaagaaag gagtcaatcg cagaatagaa aatgatcact   4080
aattccacct ctataaagtt tccaagagga aaacccaatt ctgctgctag agatcagaat   4140
ggaggtgacc tgtgccttgc aatggctgtg agggtcacgg gagtgtcact tagtgcaggc   4200
aatgtgccgt atcttaatct gggcagggct ttcatgagca cataggaatg cagacattac   4260
tgctgtgttc attttacttc accggaaaag aagaataaaa tcagccgggc gcggtggctc   4320
acgcctgtaa tcccagcact ttagaaggct gaggtgggca gattacttga ggtcaggagt   4380
tcaagaccac cctggccaat atggtgaaac cccggctcta ctaaaaatac aaaaattagc   4440
tgggcatggt ggtgcgcgcc tgtaatccca gctactcggg aggctgaggc tggacaattg   4500
cttggaccca ggaagcagag gttgcagtga gccaagattg tgccactgca ctccagcttg   4560
ggcaacagag ccagactctg taaaaaaaaa aaaaaaaaaa aaaaaaagaa agaaagaaaa   4620
```

-continued

```
agaaaagaaa gtataaaatc tctttgggtt aacaaaaaaa gatccacaaa acaaacacca   4680
gctcttatca aacttacaca actctgccag agaacaggaa acacaaatac tcattaactc   4740
acttttgtgg caataaaacc ttcatgtcaa aaggagacca ggacacaatg aggaagtaaa   4800
actgcaggcc ctacttgggt gcagagaggg aaaatccaca aataaaacat taccagaagg   4860
agctaagatt tactgcattg agttcattcc ccaggtatgc aaggtgattt taacacctga   4920
aaatcaatca ttgcctttac tacatagaca gattagctag aaaaaaatta caactagcag   4980
aacagaagca atttggcctt cctaaaattc cacatcatat catcatgatg gagacagtgc   5040
agacgccaat gacaataaaa agagggacct ccgtcacccg gtaaacatgt ccacacagct   5100
ccagcaagca cccgtcttcc cagtgaatca ctgtaacctc ccctttaatc agccccaggc   5160
aaggctgcct gcgatggcca cacaggctcc aacccgtggg cctcaacctc ccgcagaggc   5220
tctcctttgg ccaccccatg ggagagcat gaggacaggg cagagccctc tgatgcccac    5280
acatggcagg agctgacgcc agagccatgg gggctggaga gcagagctgc tggggtcaga   5340
gcttcctgag gacacccagg cctaagggaa ggcagctccc tggatggggg caaccaggct   5400
ccgggctcca acctcagagc ccgcatggga ggagccagca ctctaggcct ttcctagggt   5460
gactctgagg ggaccctgac acgacaggat cgctgaatgc acccgagatg aaggggccac   5520
cacgggaccc tgctctcgtg gcagatcagg agagagtggg acaccatgcc aggcccccat   5580
ggcatggctg cgactgaccc aggccactcc cctgcatgca tcagcctcgg taagtcacat   5640
gaccaagccc aggaccaatg tggaaggaag gaaacagcat ccccctttagt gatggaaccc  5700
aaggtcagtg caaagagagg ccatgagcag ttaggaaggg tggtccaacc tacagcacaa   5760
accatcatct atcataagta gaagccctgc tccatgaccc ctgcatttaa ataaacgttt   5820
gttaaatgag tcaaattccc tcaccatgag agctcacctg tgtgtaggcc catcacacac   5880
acaaacacac acacacacac acacacacac acacacacac acagggaaag tgcaggatcc   5940
tggacagcac caggcaggct tcacaggcag agcaaacagc gtgaatgacc catgcagtgc   6000
cctgggcccc atcagctcag agaccctgtg agggctgaga tggggctagg caggggagag   6060
acttagagag ggtggggcct ccagggaggg ggctgcaggg agctgggtac tgccctccag   6120
ggaggggggct gcagggagct gggtactgcc ctccagggag ggggctgcag ggagctgggt  6180
actgccctcc agggaggggg ctgcagggag ctgggtactg ccctccaggg agggggctgc   6240
agggagctgg gtactgccct ccagggaggc aggagcactg ttcccaacag agagcacatc   6300
ttcctgcagc agctgcacag acacaggagc ccccatgact gccctgggcc agggtgtgga   6360
ttccaaattt cgtgccccat tgggtgggac ggaggttgac cgtgacatcc aaggggcatc   6420
tgtgattcca aacttaaact actgtgccta caaaatagga aataacccta ctttttctac   6480
tatctcaaat tccctaagca caagctagca ccctttaaat caggaagttc agtcactcct   6540
ggggtcctcc catgccccca gtctgacttg caggtgcaca gggtggctga catctgtcct   6600
tgctcctcct cttggctcaa ctgccgcccc tcctgggggt gactgatggt caggacaagg   6660
gatcctagag ctggccccat gattgacagg aaggcaggac ttggcctcca ttctgaagac   6720
taggggtgtc aagagagctg ggcatcccac agagctgcac aagatgacgc ggacagaggg   6780
tgacacaggg ctcagggctt cagacgggtc gggaggctca gctgagagtt cagggacaga   6840
cctgaggagc ctcagtggga aaagaagcac tgaagtggga agttctggaa tgttctggac   6900
aagcctgagt gctctaagga aatgctccca ccccgatgta gcctgcagca ctggacggtc   6960
```

-continued

```
tgtgtacctc cccgctgccc atcctctcac agccccccgcc tctagggaca caactcctgc   7020
cctaacatgc atctttcctg tctcattcca cacaaaaggg cctctggggt ccctgttctg   7080
cattgcaagg agtggaggtc acgttcccac agaccaccca gcaacagggt cctatggagg   7140
tgcggtcagg aggatcacac gtccccccat gcccagggga ctgactctgg gggtgatgga   7200
ttggcctgga ggccactggt cccctctgtc cctgagggga atctgcaccc tggaggctgc   7260
cacatccctc ctgattcttt cagctgaggg cccttcttga aatcccaggg aggactcaac   7320
ccccactggg aaaggcccag tgtggacggt tccacagcag cccagctaag gcccttggac   7380
acagatcctg agtgagagaa cctttaggga cacaggtgca cggccatgtc cccagtgccc   7440
acacagagca ggggcatctg gaccctgagt gtgtagctcc cgcgactgaa cccagccctt   7500
ccccaatgac gtgaccccctg gggtggctcc aggtctccag tccatgccac caaaatctcc   7560
agattgaggg tcctcccttg agtccctgat gcctgtccag gagctgcccc ctgagcaaat   7620
ctagagtgca gagggctggg attgtggcag taaaagcagc cacatttgtc tcaggaagga   7680
aagggaggac atgagctcca ggaagggcga tggcgtcctc tagtgggcgc ctcctgttaa   7740
tgagcaaaaa ggggccagga gagttgagag atcagggctg gccttggact aaggctcaga   7800
tggagaggac tgaggtgcaa agagggggct gaagtagggg agtggtcggg agagatggga   7860
ggagcaggta aggggaagcc ccagggaggc cgggggaggg tacagcagag ctctccactc   7920
ctcagcattg acatttgggg tggtcgtgct agtggggttc tgtaagttgt agggtgttca   7980
gcaccatctg ggactctac ccactaaatg ccagcaggac tccctcccca agctctaaca   8040
accaacaatg tctccagact ttccaaatgt cccctggaga gcaaaattgc ttctggcaga   8100
atcactgatc tacgtcagtc tctaaaagtg actcatcagc gaaatccttc acctcttggg   8160
agaagaatca caagtgtgag aggggtagaa actgcagact tcaaaatctt tccaaaagag   8220
ttttacttaa tcagcagttt gatgtcccag gagaagatac atttagagtg tttagagttg   8280
atgccacatg gctgcctgta cctcacagca ggagcagagt gggttttcca agggcctgta   8340
accacaactg gaatgacact cactgggtta cattacaaag tggaatgtgg ggaattctgt   8400
agactttggg aagggaaatg tatgacgtga gcccacagcc taaggcagtg gacagtccac   8460
tttgaggctc tcaccatcta ggagacatct cagccatgaa catagccaca tctgtcatta   8520
gaaaacatgt tttattaaga ggaaaaatct aggctagaag tgctttatgc tctttttttct   8580
ctttatgttc aaattcatat acttttagat cattccttaa agaagaatct atccccctaa   8640
gtaaatgtta tcactgactg gatagtgttg gtgtctcact cccaacccct gtgtggtgac   8700
agtgccctgc ttccccagcc ctgggccctc tctgattcct gagagctttg ggtgctcctt   8760
cattaggagg aagagaggaa gggtgttttt aatattctca ccattcaccc atccacctct   8820
tagacactgg gaagaatcag ttgcccactc ttggatttga tcctcgaatt aatgacctct   8880
atttctgtcc cttgtccatt tcaacaatgt gacaggccta agaggtgcct tctccatgtg   8940
atttttgagg agaaggttct caagataagt tttctcacac ctctttgaat tacctccacc   9000
tgtgtcccca tcaccattac cagcagcatt tggacccttt ttctgttagt cagatgcttt   9060
ccacctcttg agggtgtata ctgtatgctc tctacacagg aatatgcaga ggaaatagaa   9120
aaagggaaat cgcattacta ttcagagaga agaagacctt tatgtgaatg aatgagagtc   9180
taaaatccta agagagccca tataaaatta ttaccagtgc taaaactaca aaagttacac   9240
taacagtaaa ctagaataat aaaacatgca tcacagttgc tggtaaagct aaatcagata   9300
tttttttctt agaaaaagca ttccatgtgt gttgcagtga tgacaggagt gcccttcagt   9360
```

-continued

```
caatatgctg cctgtaattt ttgttccctg gcagaatgta ttgtcttttc tccctttaaa   9420
tcttaaatgc aaaactaaag gcagctcctg ggccccctcc ccaaactcag ctgcctgcaa   9480
ccagccccac gaagagcaga ggcctgagct tccctggtca aaatacgggg ctagggagct   9540
taaccttgct cgataaagct gtgttcccag aatgtcgctc ctgttcccag gggcaccagc   9600
ctggagggtg gtgagcctca ctggtggcct gatgcttacc ttgtgccctc acaccagtgg   9660
tcactggaac cttgaacact tggctgtcgc ccggatctgc agatgtcaag aacttctgga   9720
agtcaaatta ctgcccactt ctccagggca gatacctgtg aacatccaaa accatgccac   9780
agaaccctgc ctggggtcta caacacatat ggactgtgag caccaagtcc agccctgaat   9840
ctgtgaccac ctgccaagat gcccctaact gggatccacc aatcactgca catggcaggc   9900
agcgaggctt ggaggtgctt cgccacaagg cagccccaat ttgctgggag tttcttggca   9960
cctggtagtg gtgaggagcc ttgggaccct caggattact ccccttaagc atagtgggga  10020
cccttctgca tccccagcag gtgccccgct cttcagagcc tctctctctg aggtttaccc  10080
agacccctgc accaatgaga ccatgctgaa gcctcagaga gagagatgga gctttgacca  10140
ggagccgctc ttccttgagg gccagggcag ggaaagcagg aggcaccacc aggagtggga  10200
acaccagtgt ctaacgccct gatgagaaca gggtggtctc tcccatatgc ccataccagg  10260
cctgtgaaca gaatcctcct tctgcagtga caatgtctga gaggacgaca tgtttcccag  10320
cctaacgtgc agccatgccc atctacccac tgcctactgc aggacagcac caacccagga  10380
gctgggaagc tgggagaaga catggaatac ccatggcttc tcaccttcct ccagtccagt  10440
gggcaccatt tatgcctagg acacccacct gccggcccca ggctcttaag agttaggtca  10500
cctaggtgcc tctgggaggc cgaggcagga gaattgcttg aacccgggag gcagaggttg  10560
cagtgagccg agatcacacc actgcactcc agcctgggtg acagaatgag actctgtctc  10620
aaaaaaaaag agaaagatag catcagtggc taccaagggc taggggcagg ggaaggtgga  10680
gagttaatga ttaatagtat gaagtttcta tgtgagatga tgaaaatgtt ctggaaaaaa  10740
aaatatagtg gtgaggatgt agaatattgt gaatataatt aacggcattt aattgtacac  10800
ttaacatgat taatgtggca tattttatct tatgtatttg actacatcca agaaacactg  10860
ggagagggaa agcccaccat gtaaaataca cccaccctaa tcagatagtc ctcattgtac  10920
ccaggtacag gcccctcatg acctgcacag gaataactaa ggatttaagg acatgaggct  10980
tcccagccaa ctgcaggtgc acaacataaa tgtatctgca aacagactga gagtaaagct  11040
gggggcacaa acctcagcac tgccaggaca cacacccttc tcgtggattc tgactttatc  11100
tgacccggcc cactgtccag atcttgttgt gggattggga caagggaggt cataaagcct  11160
gtccccaggg cactctgtgt gagcacacga gacctcccca cccccccacc gttaggtctc  11220
cacacataga tctgaccatt aggcattgtg aggaggactc tagcgcgggc tcagggatca  11280
caccagagaa tcaggtacag agaggaagac ggggctcgag gagctgatgg atgacacaga  11340
gcagggttcc tgcagtccac aggtccagct caccctggtg taggtgcccc atccccctga  11400
tccaggcatc cctgacacag ctccctcccg gagcctcctc ccaggtgaca catcagggtc  11460
cctcactcaa gctgtccaga gagggcagca ccttggacag cgcccacccc acttcactct  11520
tcctccctca cagggctcag ggctcagggc tcaagtctca gaacaaatgg cagaggccag  11580
tgagcccaga gatggtgaca gggcaatgat ccaggggcag ctgcctgaaa cgggagcagg  11640
tgaagccaca gatgggagaa gatggttcag gaagaaaaat ccaggaatgg gcaggagagg  11700
```

-continued

```
agaggaggac acaggctctg tggggctgca gcccaggatg ggactaagtg tgaagacatc  11760
tcagcaggtg aggccaggtc ccatgaacag agaagcagct cccacctccc ctgatgcacg  11820
gacacacaga gtgtgtggtg ctgtgccccc agagtcgggc tctcctgttc tggtccccag  11880
ggagtgagaa gtgaggttga cttgtccctg ctcctctctg ctaccccaac attcaccttc  11940
tcctcatgcc cctctctctc aaatatgatt tggatctatg tccccgccca aatctcatgt  12000
caaattgtaa accccaatgt tggaggtggg gccttgtgag aagtgattgg ataatgcggg  12060
tggattttct gctttgatgc tgtttctgtg atagagatct cacatgatct ggttgtttaa  12120
aagtgtgtag cacctctccc ctctctctct ctctctctta ctcatgctct gccatgtaag  12180
acgttcctgt ttccccttca ccgtccagaa tgattgtaag ttttctgagg cctccccagg  12240
agcagaagcc actatgcttc ctgtacaact gcagaatgat gagcgaatta aacctctttt  12300
ctttataaat tacccagtct caggtatttc tttatagcaa tgcgaggaca gactaataca  12360
atcttctact cccagatccc cgcacacgct tagccccaga catcactgcc cctgggagca  12420
tgcacagcgc agcctcctgc cgacaaaagc aaagtcacaa aaggtgacaa aaatctgcat  12480
ttggggacat ctgattgtga aagagggagg acagtacact tgtagccaca gagactgggg  12540
ctcaccgagc tgaaacctgg tagcactttg gcataacatg tgcatgaccc gtgttcaatg  12600
tctacagatc agtgttgagt aaaacagcct ggtctggggc cgctgctgtc cccacttccc  12660
tcctgtccac cagagggcgg cagagttcct cccaccctgg agcctcccca ggggctgctg  12720
acctccctca gccgggccca cagcccagca gggtccaccc tcacccgggt cacctcggcc  12780
cacgtcctcc tcgccctccg agctcctcac acggactctg tcagctcctc cctgcagcct  12840
atcggccgcc cacctgaggc ttgtcggccg cccacttgag gcctgtcggc tgccctctgc  12900
aggcagctcc tgtcccctac accccctcct tccccgggct cagctgaaag ggcgtctccc  12960
agggcagctc cctgtgatct ccaggacagc tcagtctctc acaggctccg acgcccccta  13020
tgctgtcacc tcacagccct gtcattacca ttaactcctc agtcccatga agttcactga  13080
gcgcctgtct cccggttaca ggaaaactct gtgacaggga ccacgtctgt cctgctctct  13140
gtggaatccc agggcccagc ccagtgcctg acacggaaca gatgctccat aaatactggt  13200
taaatatgtg ggagatctct aaaaagaagc atatcacctc cgtgtggccc ccagcagtca  13260
gagtctgttc catgtggaca caggggcact ggcaccagca tgggaggagg ccagcaagtg  13320
cccgcagctg ccccaggaat gaggcctcaa cccccagagc ttcagaaggg aggacagagg  13380
cctgcaggga atagatcctc cggcctgacc ctgcagccta atccagagtt cagggtcagc  13440
tcacaccacg tcgaccctgg tcagcatccc tagggcagtt ccagacaagg ccggaggtct  13500
cctcttgccc tccaggggggt gacattgcac acagacatca ctcaggaaac ggattcccct  13560
ggacaggaac ctggctttgc taaggaagtg gaggtggagc ctggtttcca tcccttgctc  13620
caacagaccc ttctgatctc tcccacatac ctgctctgtt cctttctcgg tcctatgagg  13680
accctgttct gccaggggtc cctgtgcaac tccagactcc ctcctggtac caccatgggg  13740
aaggtggggt gatcacagga cagtcagcct cgcagagaca gagaccaccc aggactgtca  13800
gggagaacat ggacaggccc tgagccgcag ctcagccaac agacacggag agggagggtc  13860
cccctggagc cttccccaag gacagcagag cccagagtca cccacctccc tccaccacag  13920
tcctctcttt ccaggacaca caagacacct ccccctccac atgcaggatc tggggactcc  13980
tgagacctct gggcctgggt ctccatccct gggtcagtgg cggggttggt ggtactggag  14040
acagaggggct ggtccctccc cagccaccac ccagtgagcc tttttctagc ccccagagcc  14100
```

-continued

```
acctctgtca ccttcctgtt gggcatcatc ccaccttccc agagccctgg agagcatggg  14160
gagacccggg accctgctgg gtttctctgt cacaaaggaa aataatcccc ctggtgtgac  14220
agacccaagg acagaacaca gcagaggtca gcactgggga agacaggttg tcctcccagg  14280
ggatgggggt ccatccacct tgccgaaaag atttgtctga ggaactgaaa atagaaggga  14340
aaaaagagga gggacaaaag aggcagaaat gagaggggag gggacagagg acacctgaat  14400
aaagaccaca cccatgaccc acgtgatgct gagaagtact cctgccctag gaagagactc  14460
agggcagagg gaggaaggac agcagaccag acagtcacag cagccttgac aaaacgttcc  14520
tggaactcaa gctcttctcc acagaggagg acagagcaga cagcagagac catggagtct  14580
ccctcggccc ctccccacag atggtgcatc ccctggcaga ggctcctgct cacaggtgaa  14640
gggaggacaa cctgggagag ggtgggagga gggagctggg gtctcctggg taggacaggg  14700
ctgtgagacg gacagagggc tcctgttgga gcctgaatag ggaagaggac atcagagagg  14760
gacaggagtc acaccagaaa aatcaaattg aactggaatt ggaaaggggc aggaaaacct  14820
caacagttct attttcctag ttaattgtca ctggccacta cgtttttaaa aatcataata  14880
actgcatcag atgacacttt aaataaaaac ataaccaggg catgaaacac tgtcctcatc  14940
cgcctaccgc ggacattgga aaataagccc caggctgtgg agggccctgg gaaccctcat  15000
gaactcatcc acaggaatct gcagcctgtc ccaggcactg ggtgcaaccc aagatc      15056
```

<210> SEQ ID NO 73
<211> LENGTH: 5836
<212> TYPE: DNA
<213> ORGANISM: H. sapiens

<400> SEQUENCE: 73

```
aagcttctag ttttcttttc ccggtgacat cgtggaaagc actagcatct ctaagcaatg     60
atctgtgaca atattcacag tgtaatgcca tccagggaac tcaactgagc cttgatgtcc    120
agagattttt gtgttttttt ctgagactga gtctcgctct gtgccaggct ggagtgcagt    180
ggtgcaacct tggctcactg caagctccgc ctcctgggtt cacgccattc tcctgcctca    240
gcctcctgag tagctgggac tacaggcacc cgccaccacg cctggctaat ttttttgtat    300
ttttagtaga gatggggttt cactgtgtta gccaggatgg tctcagtctc ctgacctcgt    360
gatctgccca ccttggcctc ccaaagtgct gggatgacag gcgtgagcca ccgcgcctgg    420
ccgatatcca gagatttttt ggggggctcc atcacacaga catgttgact gtcttcatgg    480
ttgactttta gtatccagcc cctctagaaa tctagctgat atagtgtggc tcaaaacctt    540
cagcacaaat cacaccgtta gactatctgg tgtggcccaa accttcaggt gaacaaaggg    600
actctaatct ggcaggatat tccaaagcat tagagatgac ctcttgcaaa gaaaaagaaa    660
tggaaaagaa aaagaaagaa aggaaaaaaa aaaaaaaaaa gagatgacct ctcaggctct    720
gaggggaaac gcctgaggtc tttgagcaag gtcagtcctc tgttgcacag tctccctcac    780
agggtcattg tgacgatcaa atgtggtcac gtgtatgagg caccagcaca tgcctggctc    840
tggggagtgc cgtgtaagtg tatgcttgca ctgctgaatg cttgggatgt gtcagggatt    900
atcttcagca cttacagatg ctcatctcat cctcacagca tcactatggg atgggtatta    960
ctggcctcat ttgatggaga aagtggctgt ggctcagaaa gggggaccca ctagaccagg   1020
gacactctgg atgctgggga ctccagagac catgaccact caccaactgc agagaaatta   1080
attgtggcct gatgtccctg tcctggagag ggtggaggtg gaccttcact aacctcctac   1140
```

-continued

```
cttgaccctc tcttttaggg ctctttctga cctccaccat ggtactagga ccccattgta   1200
ttctgtaccc tcttgactct atgaccccca ctgcccactg catccagctg ggtcccctcc   1260
tatctctatt cccagctggc cagtgcagtc tcagtgccca cctgtttgtc agtaactctg   1320
aaggggctga cattttactg acttgcaaac aaataagcta actttccaga gttttgtgaa   1380
tgctggcaga gtccatgaga ctcctgagtc agaggcaaag gcttttactg ctcacagctt   1440
agcagacagc atgaggttca tgttcacatt agtacacctt gcccccccca aatcttgtag   1500
ggtgaccaga gcagtctagg tggatgctgt gcagaagggg tttgtgccac tggtgagaaa   1560
cctgagatta ggaatcctca atcttatact gggacaactt gcaaacctgc tcagcctttg   1620
tctctgatga agatattatc ttcatgatct tggattgaaa acagacctac tctggaggaa   1680
catattgtat cgattgtcct tgacagtaaa caaatctgtt gtaagagaca ttatctttat   1740
tatctaggac agtaagcaag cctggatctg agagagatat catcttgcaa ggatgcctgc   1800
tttacaaaca tccttgaaac aacaatccag aaaaaaaaag gtgttgctgt ctttgctcag   1860
aagacacaca gatacgtgac agaaccatgg agaattgcct cccaacgctg ttcagccaga   1920
gccttccacc cttgtctgca ggacagtctc aacgttccac cattaaatac ttcttctatc   1980
acatcctgct tctttatgcc taaccaaggt tctaggtccc gatcgactgt gtctggcagc   2040
actccactgc caaacccaga ataaggcagc gctcaggatc ccgaaggggc atggctgggg   2100
atcagaactt ctgggtttga gtgaggagtg ggtccaccct cttgaatttc aaaggaggaa   2160
gaggctggat gtgaaggtac tgggggaggg aaagtgtcag ttccgaactc ttaggtcaat   2220
gagggaggag actggtaagg tcccagctcc cgaggtactg atgtgggaat ggcctaagaa   2280
tctcatatcc tcaggaagaa ggtgctggaa ttctgagggg tagagttctg ggtatatttg   2340
tggcttaagg ctctttggcc cctgaaggca gaggctggaa ccattaggtc cagggtttgg   2400
ggtgatagta atgggatctc ttgattcctc aagagtctga ggatcgaggg ttgcccattc   2460
ttccatcttg ccacctaatc cttactccac ttgagggtat caccagccct tctagctcca   2520
tgaaggtccc ctgggcaagc acaatctgag catgaaagat gccccagagg ccttgggtgt   2580
catccactca tcatccagca tcacactctg agggtgtggc cagcaccatg acgtcatgtt   2640
gctgtgacta tccctgcacc gtgcctctcc agccacctgc caaccgtaga gctgcccatc   2700
ctcctctggt gggagtggcc tgcatggtgc caggctgagg cctagtgtca gacagggagc   2760
ctggaatcat agggatccag gactcaaaag tgctagagaa tggccatatg tcaccatcca   2820
tgaaatctca aaggcttctg ggtggagggc acagggacct gaacttatgg tttcccaagt   2880
ctattgctct cccaagtgag tctcccagat acgaggcact gtgccagcat cagccttatc   2940
tccaccacat cttgtaaaag gactacccag ggccctgatg aacaccatgg tgtgtacagg   3000
agtagggggt ggaggcacgg actcctgtga ggtcacagcc aagggagcat catcatgggt   3060
ggggaggagg caatggacag gcttgagaac ggggatgtgg ttgtatttgg ttttctttgg   3120
ttagataaag tactgggtat aggattgaga gtggagtatg aagaccagtt aggatggagg   3180
atcagattgg agttgggtta gataaagtgc tgggtatagg attgagagtg gagtatgaag   3240
accagttagg atagaggatc agattggagt tgggttagag atggggtaaa attgtgctcc   3300
ggatgagttt gggattgaca ctgtggaggt ggtttgggat ggcatggctt tgggatggaa   3360
atagatttgt tttgatgttg gctcagacat ccttggggar tgaactgggg atgaagctgg   3420
gtttgatttt ggaggtagaa gacgtggaag tagctgtcag atttgacagt ggccatgagt   3480
tttgtttgat ggggaatcaa acaatggggg aagacataag ggttggcttg ttaggttaag   3540
```

-continued

```
ttgcgttggg ttgatggggt cggggctgtg tataatgcag ttggattggt ttgtattaaa   3600
ttgggttggg tcaggttttg gttgaggatg agttgaggat atgcttgggg acaccggatc   3660
catgaggttc tcactggagt ggagacaaac ttcctttcca ggatgaatcc agggaagcct   3720
taattcacgt gtaggggagg tcaggccact ggctaagtat atccttccac tccagctcta   3780
agatggtctt aaattgtgat tatctatatc cacttctgtc tccctcactg tgcttggagt   3840
ttacctgatc actcaactag aaacagggga agattttatc aaattctttt tttttttttt   3900
tttttttga gacagagtct cactctgttg cccaggctgg agtgcagtgg cgcagtctcg   3960
gctcactgca acctctgcct cccaggttca agtgattctc ctgcctcagc ctcctgagtt   4020
gctgggatta caggcatgca gcaccatgcc cagctaattt ttgtattttt agtagagatg   4080
gggtttcacc aatgtttgcc aggctggcct cgaactcctg acctggtgat ccacctgcct   4140
cagcctccca aagtgctggg attacaggcg tcagccaccg cgcccagcca cttttgtcaa   4200
attcttgaga cacagctcgg gctggatcaa gtgagctact ctggttttat tgaacagctg   4260
aaataaccaa ctttttggaa attgatgaaa tcttacggag ttaacagtgg aggtaccagg   4320
gctcttaaga gttcccgatt ctcttctgag actacaaatt gtgattttgc atgccacctt   4380
aatctttttt tttttttttt taaatcgagg tttcagtctc attctatttc ccaggctgga   4440
gttcaatagc gtgatcacag ctcactgtag ccttgaactc ctggccttaa gagattctcc   4500
tgcttcggtc tcccaatagc taagactaca gtagtccacc accatatcca gataattttt   4560
aaatttttg gggggccggg cacagtggct cacgcctgta atcccaacac catgggaggc   4620
tgagatgggt ggatcacgag gtcaggagtt tgagaccagc ctgaccaaca tggtgaaact   4680
ctgtctctac taaaaaaaa aaaaatagaa aaattagccg ggcgtggtgg cacacggcac   4740
ctgtaatccc agctactgag gaggctgagg caggagaatc acttgaaccc agaaggcaga   4800
ggttgcaatg agccgagatt gcgccactgc actccagcct gggtgacaga gtgagactct   4860
gtctcaaaaa aaaaaaattt tttttttttt tttgtagaga tggatcttgc tttgtttctc   4920
tggttggcct tgaactcctg gcttcaagtg atcctcctac cttggcctcg gaaagtgttg   4980
ggattacagg cgtgagccac catgactgac ctgtcgttaa tcttgaggta cataaacctg   5040
gctcctaaag gctaaaggct aaatatttgt tggagaaggg gcattggatt ttgcatgagg   5100
atgattctga cctgggaggg caggtcagca ggcatctctg ttgcacagat agagtgtaca   5160
ggtctggaga acaaggagtg gggggttatt ggaattccac attgtttgct gcacgttgga   5220
ttttgaaatg ctagggaact ttgggagact catatttctg ggctagagga tctgtggacc   5280
acaagatctt tttatgatga cagtagcaat gtatctgtgg agctggattc tgggttggga   5340
gtgcaaggaa aagaatgtac taaatgccaa gacatctatt tcaggagcat gaggaataaa   5400
agttctagtt tctggtctca gagtggtgca gggatcaggg agtctcacaa tctcctgagt   5460
gctggtctct tagggcacac tgggtcttgg agtgcaaagg atctaggcac gtgaggcttt   5520
gtatgaagaa tcggggatcg tacccacccc ctgtttctgt ttcatcctgg gcatgtctcc   5580
tctgcctttg tcccctagat gaagtctcca tgagctacaa gggcctggtg catccagggt   5640
gatctagtaa ttgcagaaca gcaagtgcta gctctccctc cccttccaca gctctgggtg   5700
tgggaggggg ttgtccagcc tccagcagca tggggagggc cttggtcagc ctctgggtgc   5760
cagcagggca ggggcggagt cctggggaat gaaggtttta tagggctcct gggggaggct   5820
ccccagcccc aagctt                                                     5836
```

-continued

<210> SEQ ID NO 74
<211> LENGTH: 12047
<212> TYPE: DNA
<213> ORGANISM: H. sapiens

<400> SEQUENCE: 74
gaattcagaa ataggggaag gttgaggaag gacactgaac tcaaagggga tacagtgatt 60
ggtttatttg tcttctcttc acaacattgg tgctggagga attcccaccc tgaggttatg 120
aagatgtctg aacacccaac acatagcact ggagatatga gctcgacaag agtttctcag 180
ccacagagat tcacagccta gggcaggagg acactgtacg ccaggcagaa tgacatggga 240
attgcgctca cgattggctt gaagaagcaa ggactgtggg aggtgggctt tgtagtaaca 300
agagggcagg gtgaactctg attcccatgg gggaatgtga tggtcctgtt acaaattttt 360
caagctggca gggaataaaa cccattacgg tgaggacctg tggagggcgg ctgccccaac 420
tgataaagga aatagccagg tgggggcctt tcccattgta ggggggacat atctggcaat 480
agaagccttt gagacccttt agggtacaag tactgaggca gcaaataaaa tgaaatctta 540
tttttcaact ttatactgca tgggtgtgaa gatatatttg tttctgtaca gggggtgagg 600
gaaaggaggg gaggaggaaa gttcctgcag gtctggtttg gtcttgtgat ccagggggtc 660
ttggaactat ttaaattaaa ttaaattaaa acaagcgact gttttaaatt aaattaaatt 720
aaattaaatt ttactttatt ttatcttaag ttctgggcta catgtgcagg acgtgcagct 780
ttgttacata ggtaaacgtg tgccatggtg gtttgctgta cctatcaacc catcacctag 840
gtattaagcc cagcatgcat tagctgtttt tcctgacgct ctccctctcc ctgactccca 900
caacaggccc cagtgtgtgt tgttcccctc cctgtgtcca tgtgttctca ttgttcagct 960
cccacttata agtgagaaca tgtggtgttt ggttttctgt ttctgtgtta gtttgctgag 1020
gataatggct tccacctcca tccatgttcc tgcaaaggac gtgatcttat tcttttttat 1080
ggttgcatag aaattgtttt tacaaatcca attgatattg tatttaatta caagttaatc 1140
taattagcat actagaagag attacagaag atattaggta cattgaatga ggaaatatat 1200
aaaataggac gaaggtgaaa tattaggtag gaaaagtata atagttgaaa gaagtaaaaa 1260
aaaatatgca tgagtagcag aatgtaaaag aggtgaagaa cgtaatagtg actttttaga 1320
ccagattgaa ggacagagac agaaaaattt taaggaattg ctaaaccatg tgagtgttag 1380
aagtacagtc aataacatta aagcctcagg aggagaaaag aataggaaag gaggaaatat 1440
gtgaataaat agtagagaca tgtttgatgg attttaaaat atttgaaaga cctcacatca 1500
aaggattcat accgtgccat tgaagaggaa gatggaaaag ccaagaagcc agatgaaagt 1560
tagaaatatt attggcaaag cttaaatgtt aaaagtccta gagagaaagg atggcagaaa 1620
tattggcggg aaagaatgca gaacctagaa tataaattca tcccaacagt ttggtagtgt 1680
gcagctgtag ccttttctag ataatacact attgtcatac atcgcttaag cgagtgtaaa 1740
atggtctcct cactttattt atttatatat ttatttagtt ttgagatgga gcctcgctct 1800
gtctcctagg ctggagtgca atagtgcgat accactcact gcaacctctg cctcctctgt 1860
tcaagtgatt ttcttacctc agcctcccga gtagctggga ttacaggtgc gtgccaccac 1920
acccggctaa tttttgtatt ttttgtagag acggggtttt gccatgttgg ccaggctggt 1980
cttgaactcc tgacatcagg tgatccacct gccttggcct cctaaagtgc tgggattaca 2040
ggcatgagcc accgtgccca accactttat ttattttta tttttatttt taaatttcag 2100
cttctatttg aaatacaggg ggcacatata taggattgtt acatgggtat attgaactca 2160

-continued

```
ggtagtgatc atactaccca acaggtaggt tttcaaccca ctccccctct tttcctcccc   2220
attctagtag tgtgcagtgt ctattgttct catgtttatg tctatgtgtg ctccaggttt   2280
agctcccacc tgtaagtgag aacgtgtggt atttgatttt ctgtccctgt gttaattcac   2340
ttaggattat ggcttccagc tccattcata ttgctgtaaa ggatatgatt catttttcat   2400
ggccatgcag tattccatat tgcgtataga tcacattttc tttctttttt ttttttgaga   2460
cggagtcttg ctttgctgcc taggctggag tgcagtagca cgatctcggc tcactgcaag   2520
cttcacctcc ggggttcacg tcattcttct gtctcagctt cccaagtagc tgggactaca   2580
ggcgcccgcc accacgtccg gctaattttt ttgtgtgttt ttagtagaga tggggggtttc   2640
actgtgttag ccaggatggt cttgatctcc tgaccttgtg gtccacctgc ctcggtctcc   2700
caaagtgctg ggattacagg ggtgagccac tgcgcccggc ccatatatac cacattttct   2760
ttaaccaatc caccattgat gggcaactag gtagattcca tggattccac agttttgcta   2820
ttgtgtgcag tgtggcagta gacatatgaa tgaatgtgtc tttttggtat aatgatttgc   2880
attcctttgg gtatacagtc attaatagga gtgctgggtt gaacggtggc tctgtttaaa   2940
attctttgag aattttccaa actgtttgcc atagagagca aactaattta catttccacg   3000
aacagtatat aagcattccc ttttctccac agctttgtca tcatggtttt tttttttctt   3060
tattttaaaa aagaatatgt tgttgttttc ccagggtaca tgtgcaggat gtgcaggttt   3120
gttacatagg tagtaaacgt gagccatggt ggtttgctgc acctgtcaac ccattacctg   3180
ggtatgaagc cctgcctgca ttagctcttt tccctaatgc tctcactact gccccaccct   3240
caccctgaca gggcaaacag acaacctaca gaatgggagg aaatttttgc aatctattca   3300
tctgacaaag gtcaagaata tccagaatct acaaggaact taagcaaatt tttacttttt   3360
aataatagcc actctgactg gcgtgaaatg gtatctcatt gtggttttca tttgaatttc   3420
tctgatgatc agtgacgatg agcatttttt catatttgtt ggctgcttgt acgtcttttg   3480
agaagtgtct cttcatgcct tttggccact ttaatgggat tattttttgc tttttagttt   3540
aagttcctta tagattctgg atattagact tcttattgga tgcatagttt gtgaatactc   3600
tcttccattc tgtaggttgt ctgtttactc tattgatggc ttcttttgct gtgccgaagc   3660
atcttagttt aattagaaac cacctgccaa tttttgtttt tgttgcaatt gcttttgggg   3720
acttagtcat aaactctttg ccaaggtctg ggtcaagaag agtatttcct aggttttctt   3780
ctagaatttt gaaagtctga atgtaaacat ttgcattttt aatgcatctt gagttagttt   3840
ttgtatatgt gaaaggtcta ctctcatttt ctttccctct ttctttcttt ctttcttttc   3900
tttctttctt tctttctttc tttctttctt tctttctttc tttctttttg tccttctttc   3960
tttctttctt tctctttctt tctctctttc tttttttttt ttgatggagt attgctctgt   4020
tgcccaggct gcagtgcagc ggcacgatct cggctcactg caacctctgc ctcctgggtt   4080
caactgattc tcctgcatca gccttccaag tagctgggat tataggcgcc cgccaccacg   4140
cccgactaat ttttgtattt ttagtagaga cggggttgtg ccatgttggc caggctggtt   4200
tgaaactcct gacctcaaac gatctgcctg ccttggcctc ccaaagtgct gggattacag   4260
gtgtgagcca ctgtgcccag ccaagaatgt cattttctaa gaggtccaag aacctcaaga   4320
tattttggga ccttgagaag agaggaattc atacaggtat tacaagcaca gcctaatggc   4380
aaatctttgg catggcttgg cttcaagact ttaggctctt aaaagtcgaa tccaaaaatt   4440
tttataaaag ctccagctaa gctaccttaa aaggggcctg tatggctgat cactcttctt   4500
```

-continued

```
gctatacttt acacaaataa acaggccaaa tataatgagg ccaaaattta ttttgcaaat   4560
aaattggtcc tgctatgatt tactcttggt aagaacaggg aaaatagaga aaaatttaga   4620
ttgcatctga ccttttttttc tgaattttta tatgtgccta caatttgagc taaatcctga   4680
attattttct ggttgcaaaa actctctaaa gaagaacttg gttttcattg tcttcgtgac   4740
acatttatct ggctctttac tagaacagct ttcttgtttt tggtgttcta gcttgtgtgc   4800
cttacagttc tactcttcaa attattgtta tgtgtatctc atagttttcc ttcttttgag   4860
aaaactgaag ccatggtatt ctgaggacta gagatgactc aacagagctg gtgaatctcc   4920
tcatatgcaa tccactgggc tcgatctgct tcaaattgct gatgcactgc tgctaaagct   4980
atacatttaa aaccctcact aaaggatcag ggaccatcat ggaagaggag gaaacatgaa   5040
attgtaagag ccagattcgg ggggtagagt gtggaggtca gagcaactcc accttgaata   5100
agaaggtaaa gcaacctatc ctgaaagcta acctgccatg gtggcttctg attaacctct   5160
gttctaggaa gactgacagt ttgggtctgt gtcattgccc aaatctcatg ttaaattgta   5220
atccccagtg ttcggaggtg ggacttggtg gtaggtgatt cggtcatggg agtagatttt   5280
cttctttgtg gtgttacagt gatagtgagt gagttctcgt gagatctggt catttaaaag   5340
tgtgtggccc ctcccctccc tctcttggtc ctcctactgc catgtaagat acctgctcct   5400
gctttgcctt ctaccataag taaaagcccc ctgaggcctc cccagaagca gatgccacca   5460
tgcttcctgt acagcctgca gaaccatcag ccaattaaac ctcttttctg tataaattac   5520
cagtcttgag tatctcttta cagcagtgtg agaacggact aatacaaggg tctccaaaat   5580
tccaagttta tgtattcttt cttgccaaat agcaggtatt taccataaat cctgtcctta   5640
ggtcaaacaa ccttgatggc atcgtacttc aattgtctta cacattcctt ctgaatgact   5700
cctcccctat ggcatataag ccctgggtct tgggggataa tggcagaggg gtccaccatc   5760
ttgtctggct gccacctgag acacggacat ggcttctgtt ggtaagtctc tattaaatgt   5820
ttctttctaa gaaactggat ttgtcagctt gtttctttgg cctctcagct tcctcagact   5880
ttggggtagg ttgcacaacc ctgcccacca cgaaacaaat gtttaatatg ataaatatgg   5940
atagatataa tccacataaa taaaagctct tggagggccc tcaataattg ttaagagtgt   6000
aaatgtgtcc aaagatggaa aatgtttgag aactactgtc ccagagattt tcctgagttc   6060
tagagtgtgg gaatatagaa cctggagctt ggcttcttca gcctagaatc aggagtatgg   6120
ggctgaagtc tgaagcttgg cttcagcagt ttggggttgg cttccggagc acatatttga   6180
catgttgcga ctgtgatttg gggtttggta tttgctctga atcctaatgt ctgtccttga   6240
ggcatctaga atctgaaatc tgtggtcaga attctattat cttgagtagg acatctccag   6300
tcctggttct gccttctagg gctggagtct gtagtcagtg acccggtctg gcatttcaac   6360
ttcatataca gtgggctatc ttttggtcca tgtttcaacc aaacaaccga ataaaccatt   6420
agaacctttc cccacttccc tagctgcaat gttaaaccta ggatttctgt ttaataggtt   6480
catatgaata atttcagcct gatccaactt tacattcctt ctaccgttat tctacaccca   6540
ccttaaaaat gcattcccaa tatattccct ggattctacc tatatatggt aatcctggct   6600
ttgccagttt ctagtgcatt aacatacctg atttacattc ttttacttta aagtggaaat   6660
aagagtccct ctgcagagtt caggagttct caagatggcc cttacttctg acatcaattg   6720
agatttcaag ggagtcgcca agatcatcct caggttcagt gattgctggt agccctcata   6780
taactcaatg aaagctgtta tgctcatggc tatggtttat tacagcaaaa gaatagagat   6840
gaaaatctag caagggaaga gttgcatggg gcaaagacaa ggagagctcc aagtgcagag   6900
```

-continued

```
attcctgttg ttttctccca gtggtgtcat ggaaagcagt atcttctcca tacaatgatg   6960
tgtgataata ttcagtgtat tgccaatcag ggaactcaac tgagccttga ttatattgga   7020
gcttggttgc acagacatgt cgaccacctt catggctgaa ctttagtact tagcccctcc   7080
agacgtctac agctgatagg ctgtaaccca acattgtcac cataaatcac attgttagac   7140
tatccagtgt ggcccaagct cccgtgtaaa cacaggcact ctaaacaggc aggatatttc   7200
aaaagcttag agatgacctc ccaggagctg aatgcaaaga cctggcctct ttgggcaagg   7260
agaatccttt accgcacact ctccttcaca gggttattgt gaggatcaaa tgtggtcatg   7320
tgtgtgagac accagcacat gtctggctgt ggagagtgac ttctatgtgt gctaacattg   7380
ctgagtgcta agaaagtatt aggcatggct ttcagcactc acagatgctc atctaatcct   7440
cacaacatgg ctacagggtg ggcactacta gcctcatttg acagaggaaa ggactgtgga   7500
taagaagggg gtgaccaata ggtcagagtc attctggatg caaggggctc cagaggacca   7560
tgattagaca ttgtctgcag agaaattatg gctggatgtc tctgccccgg aaagggggat   7620
gcactttcct tgacccccta tctcagatct tgactttgag gttatctcag acttcctcta   7680
tgataccagg agcccatcat aatctctctg tgtcctctcc ccttcctcag tcttactgcc   7740
cactcttccc agctccatct ccagctggcc aggtgtagcc acagtaccta actctttgca   7800
gagaactata aatgtgtatc ctacagggga gaaaaaaaaa aagaactctg aaagagctga   7860
cattttaccg acttgcaaac acataagcta acctgccagt tttgtgctgg tagaactcat   7920
gagactcctg ggtcagaggc aaaagatttt attacccaca gctaaggagg cagcatgaac   7980
tttgtgttca catttgttca ctttgccccc caattcatat gggatgatca gagcagttca   8040
ggtggatgga cacaggggtt tgtggcaaag gtgagcaacc taggcttaga aatcctcaat   8100
cttataagaa ggtactagca aacttgtcca gtctttgtat ctgacggaga tattatcttt   8160
ataattgggt tgaaagcaga cctactctgg aggaacatat tgtatttatt gtcctgaaca   8220
gtaaacaaat ctgctgtaaa atagacgtta actttattat ctaaggcagt aagcaaacct   8280
agatctgaag gcgataccat cttgcaaggc tatctgctgt acaaatatgc ttgaaaagat   8340
ggtccagaaa agaaaacggt attattgcct ttgctcagaa gacacacaga aacataagag   8400
aaccatggaa aattgtctcc caacactgtt cacccagagc cttccactct tgtctgcagg   8460
acagtcttaa catcccatca ttagtgtgtc taccacatct ggcttcaccg tgcctaacca   8520
agatttctag gtccagttcc ccaccatgtt tggcagtgcc ccactgccaa ccccagaata   8580
agggagtgct cagaattccg aggggacatg ggtggggatc agaacttctg ggcttgagtg   8640
cagaggggc ccatactcct tggttccgaa ggaggaagag gctggaggtg aatgtccttg   8700
gaggggagga atgtgggttc tgaactctta aatccccaag ggaggagact ggtaaggtcc   8760
cagcttccga ggtactgacg tgggaatggc ctgagaggtc taagaatccc gtatcctcgg   8820
gaaggagggg ctgaaattgt gaggggttga gttgcagggg tttgttagct tgagactcct   8880
tggtgggtcc ctgggaagca aggactggaa ccattggctc cagggtttgg tgtgaaggta   8940
atgggatctc ctgattctca aagggtcaga ggactgagag ttgcccatgc tttgatcttt   9000
ccatctactc cttactccac ttgagggtaa tcacctactc ttctagttcc acaagagtgc   9060
gcctgcgcga gtataatctg cacatgtgcc atgtcccgag gcctggggca tcatccactc   9120
atcattcagc atctgcgcta tgcgggcgag gccggcgcca tgacgtcatg tagctgcgac   9180
tatccctgca gcgcgcctct cccgtcacgt cccaaccatg gagctgtgga cgtgcgtccc   9240
```

-continued

```
ctggtggatg tggcctgcgt ggtgccaggc cggggcctgg tgtccgataa agatcctaga   9300
accacaggaa accaggactg aaaggtgcta gagaatggcc atatgtcgct gtccatgaaa   9360
tctcaaggac ttctgggtgg agggcacagg agcctgaact tacgggtttg ccccagtcca   9420
ctgtcctccc aagtgagtct cccagatacg aggcactgtg ccagcatcag cttcatctgt   9480
accacatctt gtaacaggga ctacccagga ccctgatgaa caccatggtg tgtgcaggaa   9540
gagggggtga aggcatggac tcctgtgtgg tcagagccca gagggggcca tgacgggtgg   9600
ggaggaggct gtggactggc tcgagaagtg ggatgtggtt gtgtttgatt tcctttggcc   9660
agataaagtg ctggatatag cattgaaaac ggagtatgaa gaccagttag aatggagggt   9720
caggttggag ttgagttaca gatggggtaa aattctgctt cggatgagtt tggggattgg   9780
caatctaaag gtggtttggg atggcatggc tttgggatgg aaataggttt gtttttatgt   9840
tggctgggaa gggtgtgggg attgaattgg ggatgaagta ggtttagttt tggagataga   9900
atacatggag ctggctattg catgcgagga tgtgcattag tttggtttga tctttaaata   9960
aaggaggcta ttagggttgt cttgaattag attaagttgt gttgggttga tgggttgggc  10020
ttgtgggtga tgtggttgga ttgggctgtg ttaaattggt ttgggtcagg ttttggttga  10080
ggttatcatg gggatgagga tatgcttggg acatggattc aggtggttct cattcaagct  10140
gaggcaaatt tcctttcaga cggtcattcc agggaacgag tggttgtgtg ggggaaatca  10200
ggccactggc tgtgaatatc cctctatcct ggtcttgaat tgtgattatc tatgtccatt  10260
ctgtctcctt cactgtactt ggaattgatc tggtcattca gctggaaatg ggggaagatt  10320
ttgtcaaatt cttgagacac agctgggtct ggatcagcgt aagccttcct tctggtttta  10380
ttgaacagat gaaatcacat tttttttttc aaaatcacag aaatcttata gagttaacag  10440
tggactctta taataagagt taacaccagg actcttattc ttgattcttt tctgagacac  10500
caaaatgaga tttctcaatg ccaccctaat tctttttttt tttttttttt tttttgagac  10560
acagtctggg tcttttgctc tgtcactcag gctggagcgc agtggtgtga tcatagctca  10620
ctgaaccctt gacctcctgg acttaaggga tcctcctgct tcagcctcct gagtagatgg  10680
ggctacaggt gcttgccacc acacctggct aattaaattt tttttttttt tttgtagaga  10740
aagggtctca ctttgttgcc ctggctgatc ttgaacttct gacttcaagt gattcttcag  10800
ccttggactc ccaaagcact gggattgctg gcatgagcca ctcaccgtgc ctggcttgca  10860
gcttaatctt ggagtgtata aacctggctc ctgatagcta gacatttcag tgagaaggag  10920
gcattggatt ttgcatgagg acaattctga cctaggaggg caggtcaaca ggaatccccg  10980
ctgtacctgt acgttgtaca ggcatggaga atgaggagtg aggaggccgt accggaaccc  11040
catattgttt agtggacatt ggattttgaa ataataggga acttggtctg ggagagtcat  11100
atttctggat tggacaatat gtggtatcac aaggttttat gatgagggag aaatgtatgt  11160
ggggaaccat tttctgagtg tggaagtgca agaatcagag agtagctgaa tgccaacgct  11220
tctatttcag gaacatggta agttggaggt ccagctctcg ggctcagacg ggtataggga  11280
ccaggaagtc tcacaatccg atcattctga tatttcaggg catattaggt ttggggtgca  11340
aaggaagtac ttgggactta ggcacatgag actttgtatt gaaaatcaat gattggggct  11400
ggccgtggtg ctcacgcctg taatctcatc actttgggag accgaagtgg gaggatggct  11460
tgatctcaag agttggacac cagcctaggc aacatggcca gaccctctct ctacaaaaaa  11520
attaaaaatt agctggatgt ggtggtgcat gcttgtggtc tcagctatcc tggaggctga  11580
gacaggagaa tcggttgagt ctgggagttc aaggctacag ggagctgcga tcacgccgct  11640
```

-continued

```
gcactccagc ctgggaaaca gagtgagact gtctcagaat ttttttaaaa aagaatcagt  11700

gatcatccca acccctgttg ctgttcatcc tgagcctgcc ttctctggct ttgttcccta  11760

gatcacatct ccatgatcca taggccctgc ccaatctgac ctcacaccgt gggaatgcct  11820

ccagactgat ctagtatgtg tggaacagca agtgctggct ctccctcccc ttccacagct  11880

ctgggtgtgg gagggggttg tccagcctcc agcagcatgg ggagggcctt ggtcagcatc  11940

taggtgccaa cagggcaagg gcggggtcct ggagaatgaa ggctttatag ggctcctcag  12000

ggaggccccc cagccccaaa ctgcaccacc tggccgtgga caccggt                12047
```

<210> SEQ ID NO 75
<211> LENGTH: 858
<212> TYPE: DNA
<213> ORGANISM: H. sapiens

<400> SEQUENCE: 75

```
cgagcggccc ctcagcttcg gcgcccagcc ccgcaaggct cccggtgacc actagagggc     60

gggaggagct cctggccagt ggtggagagt ggcaaggaag gaccctaggg ttcatcggag    120

cccaggttta ctcccttaag tggaaatttc ttcccccact cctccttggc tttctccaag    180

gagggaaccc aggctgctgg aaagtccggc tggggcgggg actgtgggtt caggggagaa    240

cggggtgtgg aacgggacag ggagcggtta gaagggtggg gctattccgg gaagtggtgg    300

ggggagggag cccaaaacta gcacctagtc cactcattat ccagccctct tatttctcgg    360

ccgctctgct tcagtggacc cggggagggc ggggaagtgg agtgggagac ctaggggtgg    420

gcttcccgac cttgctgtac aggacctcga cctagctggc tttgttcccc atccccacgt    480

tagttgttgc cctgaggcta aaactagagc ccaggggccc caagttccag actgcccctc    540

ccccctcccc cggagccagg gagtggttgg tgaaaggggg aggccagctg gagaacaaac    600

gggtagtcag gggg ttgagc gattagagcc cttgtaccct acccaggaat ggttggggag    660

gaggaggaag aggtaggagg taggggaggg ggcggggttt tgtcacctgt cacctgctcg    720

ctgtgcctag ggcgggcggg cggggagtgg ggggaccggt ataaagcggt aggcgcctgt    780

gcccgctcca cctctcaagc agccagcgcc tgcctgaatc tgttctgccc cctccccacc    840

catttcacca ccaccatg                                                  858
```

<210> SEQ ID NO 76
<211> LENGTH: 454
<212> TYPE: DNA
<213> ORGANISM: H. sapiens

<400> SEQUENCE: 76

```
aagcttccac aagtgcattt agcctctcca gtattgctga tgaatccaca gttcaggttc     60

aatggcgttc aaaacttgat caaaaatgac cagactttat attcttacac caacatctat    120

ctgattggag gaatggataa tagtcatcat gtttaaacat ctaccattcc agttaagaaa    180

atatgatagc atcttgttct tagtcttttt cttaataggg acataaagcc cacaaataaa    240

aatatgcctg aagaatggga caggcattgg gcattgtcca tgcctagtaa agtactccaa    300

gaacctattt gtatactaga tgacacaatg tcaatgtctg tgtacaactg ccaactggga    360

tgcaagacac tgcccatgcc aatcatcctg aaaagcagct ataaaaagca ggaagctact    420

ctgcaccttg tcagtgaggt ccagatacct acag                                454
```

<210> SEQ ID NO 77

-continued

```
<211> LENGTH: 306
<212> TYPE: DNA
<213> ORGANISM: adenovirus
<220> FEATURE:
<221> NAME/KEY: CDS
<222> LOCATION: (1)...(306)

<400> SEQUENCE: 77

atg acc ggc tca acc atc gcg ccc aca acg gac tat cgc aac acc act       48
Met Thr Gly Ser Thr Ile Ala Pro Thr Thr Asp Tyr Arg Asn Thr Thr
 1               5                  10                  15

gct acc gga cta aca tct gcc cta aat tta ccc caa gtt cat gcc ttt       96
Ala Thr Gly Leu Thr Ser Ala Leu Asn Leu Pro Gln Val His Ala Phe
            20                  25                  30

gtc aat gac tgg gcg agc ttg gac atg tgg tgg ttt tcc ata gcg ctt      144
Val Asn Asp Trp Ala Ser Leu Asp Met Trp Trp Phe Ser Ile Ala Leu
        35                  40                  45

atg ttt gtt tgc ctt att att atg tgg ctt att tgt tgc cta aag cgc      192
Met Phe Val Cys Leu Ile Ile Met Trp Leu Ile Cys Cys Leu Lys Arg
    50                  55                  60

aga cgc gcc aga ccc ccc atc tat agg cct atc att gtg ctc aac cca      240
Arg Arg Ala Arg Pro Pro Ile Tyr Arg Pro Ile Ile Val Leu Asn Pro
65                  70                  75                  80

cac aat gaa aaa att cat aga ttg gac ggt ctg aaa cca tgt tct ctt      288
His Asn Glu Lys Ile His Arg Leu Asp Gly Leu Lys Pro Cys Ser Leu
                85                  90                  95

ctt tta cag tat gat taa                                              306
Leu Leu Gln Tyr Asp  *
            100
```

COMPOSITIONS COMPRISING TISSUE SPECIFIC ADENOVIRAL VECTORS

CROSS REFERENCE TO RELATED APPLICATIONS

This application is a continuation-in-part of application Ser. No. 09/509,591, filed Jun. 2, 2000; and a continuation-in part of application Ser. No. 09/151,376, filed Sep. 10, 1998, now U.S. Pat. No. 6,676,935 which is a continuation-in-part of application Ser. No. 08/669,753, filed Jun. 26, 1996, U.S. Pat. No. 5,871,726, which is a continuation-in-part of application Ser. No. 08/495,034, filed Jun. 27, 1995, now U.S. Pat. No. 5,698,443 the disclosure of which is herein incorporated by reference. This application is also a continuation-in part of application Ser. No. 09/033,428, filed Mar. 2, 1998, now U.S. Pat. No. 6,254,862 which claims the benefit of provisional application Ser. No. 60/039,597, filed Mar. 3, 1997; and a continuation-in-part of application Ser. No. 09/033,555, filed Mar. 2, 1998, now abandoned which claims the benefit of provisional application Ser. No. 60/039,763 filed Mar. 3, 1997; and a continuation-in-part of application Ser. No. 09/033,333, filed Mar. 2, 1998, now U.S. Pat. No. 6,197,293 which claims the benefit of provisional application Ser. No. 60/039,762, filed Mar. 3, 1997. All of the above patent applications are incorporated by reference herein.

TECHNICAL FIELD

The field of this invention is cell transfection, particularly by adenoviral vectors.

BACKGROUND

The ability to change the genotype and phenotype of cells in vitro and in vivo has many applications. For studying physiologic processes, particularly with dedicated cells, there is substantial interest in being able to modify the phenotype to affect a particular process. By enhancing or depressing the amount of a member of the physiological pathway, by inhibiting the activity of a member of the pathway, by providing an allele or mutated analog of the naturally occurring member, one may be able to unravel the role of the various members in the pathway, the order in which the members participate, the presence of alternative pathways and the like. Also, one can use the cells for producing proteins.

Adenovirus does not require cell proliferation for efficient transduction of cells. Adenovirus modified by introduction of a transgene provides for transient expression of proteins. Adenovirus can be rendered incompetent by inactivating one or more essential genes and then be packaged in a helper cell line for use in transfection. Thus, adenovirus affords a convenient vehicle for modifying cellular traits or killing cells, as appropriate.

For many medical applications, there is an interest in being able to specifically modify target cells in vivo or ex vivo. The modification can be associated with random DNA integration, whereby a genetic capability is introduced that complements a genetic defect intracellularly, provides for secretion of a product from the modified cells, which is otherwise undetectably produced or not produced by the host, provide protection from disease, particularly viral disease, and the like. In many situations, in order to be effective, one must have a high efficiency of transfection of the target cells. This is particularly true for in vivo modification. In addition, one would wish to have a high specificity for the target cells, as compared to other cells that may be present ex vivo or in vivo.

Gene therapy involves the transfer of cloned genes to target cells. A variety of viral and non-viral vehicles have been developed to transfer these genes. Of the viruses, retroviruses, herpes virus, adeno-associated virus, Sindbis virus, poxvirus and adenoviruses have been used for gene transfer. These vehicles all have different properties. For example, retroviruses transduce genes in vitro with high efficiency by integrating the transduced gene into the chromosome following division of infected cells. Adeno-associated viruses can stably integrate into and express transduced genes in both dividing and quiescent cells. In contrast, liposomes and adenovirus allow only transient gene expression, and transduce both dividing and quiescent target cells.

Of the viruses, adenoviruses are among the most easily produced and purified, whereas retroviruses are unstable, difficult to produce and impossible to purify. Both classes of virus transduce cells with high efficiency. Liposomes hold the promise of allowing repeat doses of genes for, unlike viruses, they are not immunogenic. However, liposomes completed with DNA are difficult to produce in commercial quantities, and are inefficient gene transfer vehicles, most often transducing fewer than one percent of target cells.

Publications describing various aspects of adenovirus biology and/or techniques relating to adenovirus include the following. Graham and Van de Eb (1973) Virology 52:456–467; Takiff et al. (1981) Lancet ii:832–834; Berkner and Sharp (1983) *Nucleic Acid Research* 6003–6020; Graham (1984) *EMBO J* 3:2917–2922; Bett et al. (1993) *J. Virology* 67:5911–5921; and Bett et al. (1994) *Proc. Natl. Acad. Sci. USA* 91:8802–8806 describe adenoviruses that have been genetically modified to produce replication-defective gene transfer vehicles. In these vehicles, the early adenovirus gene products EIA and EIB are deleted and provided in trans by the packaging cell line 293 developed by Frank Graham (Graham et al. (1987) *J. Gen. Birol.* 36:59–72 and Graham (1977) *J. Genetic Virology* 68:937–940). The gene to be transduced is commonly inserted into adenovirus in the deleted EIA and EIB region of the virus genome Bett et al. (1994), supra. Adenovirus vectors as vehicles for efficient transduction of genes have been described by Stratford-Perricaudet (1990) *Human Gene Therapy* 1:2–256; Rosenfeld (1991) Science 252:431–434; Wang et al. (1991) *Adv. Exp. Med. Biol.* 309:61–66; Jaffe et al. (1992) *Nat Gent.* 1:372–378; Quantin et al. (1992) *Proc Natl. Acad. Sci. USA* 89:2581–2584; Rosenfeld et al. (1992) *Cell* 68:143–155; Stratford-Perricaudet et al. (1992) *J. Clin. Invest.* 90:626–630; Le Gal La Salle et al. (1993) *Science* 259:988–990; Mastrangeli et al. (1993) *J. Clin. Invest.* 91:225–234; Ragot et al. (1993) *Nature* 361:647–650; Hayaski et al. (1994) *J. Biol. Chem.* 269:23872–23875.

There are two major divisions of gene therapy protocols: in vivo and ex vivo. In vivo refers to administration of the therapeutic directly to the patient, usually by inhalation or injection, although oral administration has been suggested in some instances. Ex vivo gene therapy refers to the process of removing cells from a patient, for example in a biopsy, placing the cells into tissue culture, transferring genes to the cells in tissue culture, characterizing the newly genetically engineered cells, and finally returning the cells to the patient by intravenous infusion. Therapeutically, retroviruses are most often used for ex vivo transfer, whereas adenoviruses and liposomes are most often used for in vivo gene transfer.

In the treatment of cancer by replication-defective adenoviruses, the host immune response limits the duration of repeat doses of the therapeutic at two levels. First, the adenovirus delivery vehicle itself is immunogenic. Second, late virus genes are frequently expressed in transduced cells, eliciting cellular immunity. Thus, the ability to repeatedly administer cytokines, tumor suppressor genes, ribozymes or suicide genes is limited by the transient nature of gene expression, and the immunogenicity of both the gene transfer vehicle and the viral gene products of the transfer vehicle.

There is, therefore, substantial interest in being able to develop viral vectors which substantially reduce the present limitations and restrictions on the use of such vectors in vivo.

SUMMARY OF THE INVENTION

Replication-competent adenovirus vectors, and methods for their use as vehicles for the transduction of restricted cell types, are provided. The invention provides compositions comprising replication competent adenovirus having an adenovirus gene essential for replication under transcriptional control of a cell type specific transcriptional response element (TRE), and polyethylene glycol (PEG) as a masking agent.

In one aspect, this adenoviral gene is an early gene. Additionally, one or more late genes and/or one or more transgenes may be under the control of a transcriptional initiation region that is transcriptionally active only in the target cells of interest. In some embodiments, the replication competent adenovirus comprises a transgene.

The cell type specific TRE may be prostate cell specific and may include the promoter sequence found at nucleotides −540 to +8 relative to transcription start site of prostate specific antigen gene and/or the enhancer sequence in the region −5322 to −3739 relative to the transcription start site of the prostate specific antigen gene.

In other embodiments, the prostate cell specific response element is a probasin TRE or a hKLK2-TRE.

In still other embodiments, an adenovirus gene essential for replication is under transcriptional control of an α-fetoprotein transcriptional regulatory element (AFP-TRE), a MUC1-TRE or a CEA-TRE.

The composition may include PEG of a molecular weight between about 2500 to about 30,000, 3000 to about 20,000, or 5000 to about 10,000 and the PEG may be covalently or non-covalently attached to the adenovirus.

In embodiments where the PEG is covalently attached to the adenovirus, the attachment may be by way of an N-hydroxysuccinimidyl (NHS) active ester such as succinimidyl succinate, succinimidyl succinamide or succinimidyl propionate.

BRIEF DESCRIPTION OF THE DRAWINGS

In FIG. 2(A), the left panel shows Huh-7 (AFP+) cells; the right panel shows Dld-1 (AFP−) cells.

FIG. 3(A)) and non-AFP producing (Sk-Hep-1, FIG. 3(B); Dld-1, FIG. 3(C)) cells.

FIG. 6(A) depicts measuring tumor volume over a period of 43 days (six weeks). In FIG. 6(B), single intratumoral administration of CN733 ("B") was compared to five consecutive daily doses of CN733 ("J").

FIG. 10 (SEQ ID NO:9) depicts the sequence of the 5'-flanking region of the rat probasin (PB) gene, including the PB-TRE region. Numbers above the nucleotides indicate position relative to the transcription start site. The locations of androgen response elements (ARE) are indicated.

FIG. 14 depicts a nucleotide sequence (SEQ ID NO:72) of a carcinoembryonic antigen TRE.

FIG. 15 depicts a nucleotide sequence (SEQ ID NO:73) of a prostate-specific antigen TRE.

FIG. 16 depicts a nucleotide sequence (SEQ ID NO:74) of a human glandular kallikrein TRE.

FIG. 17 depicts a nucleotide sequence (SEQ ID NO:75) of a mucin TRE.

FIG. 18 depicts a nucleotide sequence (SEQ ID NO:76) of a rat probasin TRE.

FIG. 19 depicts a nucleotide sequence and translated amino acid sequence (SEQ ID NO:77) of an adenovirus death protein.

MODES FOR CARRYING OUT THE INVENTION

Figure 1:
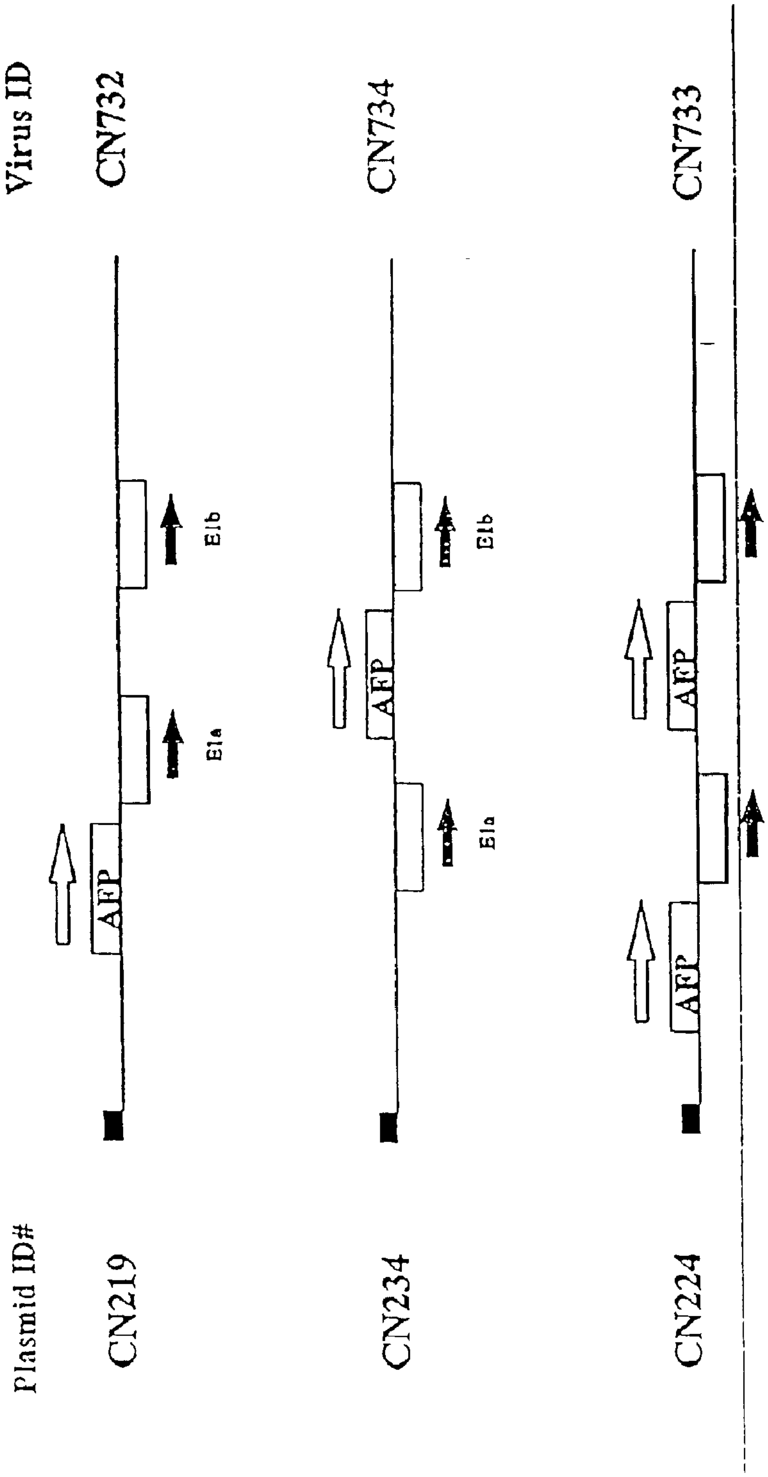
FIG. 1 is a schematic representation of various adenoviral vector constructs comprising AFP-TRE controlling expression of E1A, E1B or both, as described in Example 3.

The present invention is based on the discovery and construction of replication-competent adenovirus vectors containing cell type-specific transcriptional regulatory elements (TREs) which can preferentially replicate in cells that allow function of said TREs, and methods of using these adenovirus vectors. The adenovirus vectors of this invention comprise an adenovirus gene under the transcriptional control of a cell type-specific TRE. Preferably, the adenovirus gene is one that enhances, i.e. promotes, cell death, more preferably one that is essential for adenovirus replication. Preferably, the adenovirus gene necessary for cell replication is an early gene. In some embodiments, the adenovirus vectors of this invention comprise an adenovirus gene under the transcriptional control of a cell type-specific TRE, and at least one other gene, such as an adenoviral gene or a transgene, under control of a second cell type-specific TRE which is substantially identical to the first TRE. Preferably, the first and second genes under transcriptional control of the cell type-specific TREs are both adenovirus genes necessary for replication. By providing for cell-specific transcription through the use of one or more cell type-specific TREs, the invention provides adenovirus vectors that can be used for cell-specific cytotoxic effects due to selective replication.

The adenovirus vectors of the invention replicate preferentially in TRE functional cells (i.e., at a higher yield than in TRE non-functional cells), referred to herein as target cells. This replication preference is indicated by comparing the level of replication (i.e., titer) in cells in which the TRE is active to the level of replication in cells in which the TRE is not active (i.e., a non-target cell). The replication preference is even more significant, as the adenovirus vectors of the invention actually replicate at a significantly lower rate in TRE non-functional cells than wild type virus. Comparison of the adenovirus titer of a target cell to the titer of a TRE inactive cell type provides a key indication that the overall replication preference is enhanced due to the replication in target cells as well as depressed replication in non-target cells. This is especially useful in the cancer context, in which targeted cell killing is desirable.

Runaway infection is prevented due to the cell-specific requirements for viral replication and to this instability, which may be mediated by recombination between TREs. Without wishing to be bound by any particular theory, the inventors note that production of adenovirus proteins can serve to activate and/or stimulate the immune system, either generally or specifically toward target cells producing adenoviral proteins which can be an important consideration in the cancer context, where patients are often moderately to severely immunocompromised.

Adenovirus vectors have been constructed in which each of the E1A and E1B genes have been placed under transcriptional control of cell type-specific TREs, for example, TREs from the PSA gene (PSE-TRE), the probasin gene (PB-TRE), the hKLK2 gene (hKLK2-TRE), the a-fetoprotein gene (AFP-TRE), the carcinoembryonic antigen gene (CEA-TRE), and the mucin gene (MUC-TRE).

The adenovirus vectors, in which cell type-specific TREs are used to control replication, achieve a high level of target cell specificity.

General Techniques

The practice of the present invention will employ, unless otherwise, indicated, conventional techniques of molecular biology (including recombinant techniques), microbiology, cell biology, biochemistry and immunology, which are within the skill of the art. Such techniques are explained fully in the, literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

An "adenovirus vector" or "adenoviral vector" (used interchangeably) is a term well understood in the art and generally comprises a polynucleotide (defined herein) comprising all or a portion of an adenovirus genome. As used herein, "adenovirus" refers to the virus itself or derivatives thereof. The term covers all serotypes and subtypes and both naturally occurring and recombinant forms, except where otherwise indicated. For the purposes of the present invention, an adenovirus vector contains a cell type-specific TRE operably linked to an adenovirus gene, and may optionally contain a second adenoviral gene or a transgene operably linked to a cell type-specific TRE or another type of TRE, which is non-cell type-specific. An adenoviral vector of the present invention can be in any of several forms, including, but not limited to, naked DNA; an adenoviral vector encapsulated in an adenovirus coat; packaged in another viral or viral-like form (such as herpes simplex virus and AAV); encapsulated in a liposome; complexed with polylysine or other biocompatible polymer; complexed with synthetic polycationic molecules; conjugated with transferrin; complexed with compounds such as PEG to immunologically "mask" the molecule and/or increase half-life, or conjugated to a non-viral protein. An adenoviral vector of this invention maybe in the form of any of the delivery-vehicles described herein. Such vectors are one embodiment of the invention. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

As used herein, a "transcriptional regulatory element", or "TRE" is a polynucleotide sequence, preferably a DNA sequence, that regulates (i.e., controls) transcription of an operably-linked polynucleotide sequence by an RNA polymerase to form RNA. As used herein, a TRE increases transcription of an operably linked polynucleotide sequence in a host cell that allows the TRE to function. The TRE comprises an enhancer element and/or promoter element, which may or may not be derived from the same gene. The promoter and enhancer components of a TRE may be in any orientation and/or distance from the coding sequence of interest, and comprise multimers of the foregoing, as long as the desired transcriptional activity is obtained. As discussed herein, a TRE may or may not lack a silencer element.

An "enhancer" is a term well understood in the art and is a polynucleotide sequence derived from a gene which increases transcription of a gene which is operably-linked to a promoter to an extent which is greater than the transcription activation effected by the promoter itself when operably-linked to the gene, i.e. it increases transcription from the promoter. Having "enhancer activity" is a term well understood in the art and means what has been stated, i.e., it increases transcription of a gene which is operably linked to a promoter to an extent which is greater than the increase in transcription effected by the promoter itself when operably linked to the gene, i.e., it increases transcription from the promoter.

"Under transcriptional control" is a term well-understood in the art and indicates that transcription of a polynucleotide sequence, usually a DNA sequence, depends on its being operably (operatively) linked to an element which contributes to the regulation of, either promotes or inhibits, transcription.

The term "operably linked" relates to the orientation of polynucleotide elements in a functional relationship. A TRE is operably linked to a coding segment if the TRE promotes transcription of the coding sequence. Operably linked means that the DNA sequences being linked are generally contiguous and, where necessary to join two protein coding regions, contiguous and in the same reading frame. However, since enhancers generally function when separated from the promoter, by several kilobases and intronic sequences may be of variable length, some polynucleotide elements may be operably linked but not contiguous.

A "cell type-specific TRE" is preferentially functional in a specific type of cell relative to other types of cells of different functionality. "Cell type" is a reflection of a differentiation state of a cell which is, under normal physiological conditions, an irreversible, end-stage state. For example, a prostate-specific antigen TRE is functional in prostate cells, but is not substantially functional in other cell types such as hepatocytes, astrocytes, cardiocytes, lymphocytes, etc. Generally, a cell type-specific TRE is active in only one cell type. When a cell type-specific TRE is active in more than one cell type, its activity is restricted to a limited number of cell types, i.e., it is not active in all cell types. A cell type-specific TRE may or may not be tumor cell specific.

As used herein, the term "cell type-specific" is intended to mean that the TRE sequences to which a gene, which may be a gene essential for replication of an adenoviral vector, is operably linked, or to which a transgene is operably linked, functions specifically in that target cell so that transcription (and replication, if the operably linked gene is one essential for adenovirus replication) proceeds in that target cell, or so that a transgene polynucleotide is expressed in that target cell. This can occur by virtue of the presence in that target cell, and not in non-target cells, of transcription factors that activate transcription driven by the operably linked transcriptional control sequences. It can also occur by virtue of the absence of transcription inhibiting factors that normally occur in non-target cells and prevent transcription driven by the operably linked transcriptional control sequences. The term "cell type-specific", as used herein, is intended to include cell type specificity, tissue specificity, as well as specificity for a cancerous state of a given target cell. In the latter case, specificity for a cancerous state of a normal cell is in comparison to a normal, non-cancerous counterpart.

As used herein, a TRE derived from a specific gene is referred to by the gene from which it was derived and is a polynucleotide sequence which regulates transcription of an operably linked polynucleotide sequence in a host cell that expresses said gene. For example, as used herein, a "human glandular kallikrein transcriptional regulatory element", or "hKLK2-TRE" is a polynucleotide sequence, preferably a DNA sequence, which increases transcription of an operably linked polynucleotide sequence in a host cell that allows an hKLK2-TRE to function, such as a cell (preferably a mammalian cell, even more preferably a human cell) that expresses androgen receptor. An hKLK2-TRE is thus responsive to the binding of androgen receptor and comprises at least a portion of an hKLK2 promoter and/or an hKLK2 enhancer (i.e., the ARE or androgen receptor binding site).

As used herein, a."probasin (PB),transcriptional regulatory element", or"PB-TRE" is a polynucleotide sequence, preferably a DNA sequence, which selectively increases transcription of an operably-linked polynucleotide sequence in a host cell that allows a PB-TRE to function, such as a cell (preferably a mammalian cell, even more preferably a human cell) that expresses androgen receptor. A PB-TRE is thus responsive to the binding of androgen receptor and comprises at least a portion of a PB promoter and/or a PB enhancer (i.e., the ARE or androgen receptor binding site).

As used herein, a "prostate-specific antigen (PSA) transcriptional regulatory element", or "PSA-TRE", or "PSE-TRE" is a polynucleotide sequence, preferably a DNA sequence, which selectively increases transcription of an operably linked polynucleotide sequence in a host cell that allows a PSA-TRE to function, such as a cell (preferably a mammalian cell, even more preferably a human cell) that expresses androgen receptor. A PSE-TRE is thus responsive to the binding of androgen receptor and comprises at least a portion of a PSA promoter and/or a PSA enhancer (i.e., the ARE or androgen receptor binding site).

As used herein, a "carcinoembryonic antigen (CEA) transcriptional regulatory element", or "CEA-TRE" is polynucleotide sequence, preferably a DNA sequence, which selectively increases transcription of an operably linked polynucleotide sequence in a host cell that allows a CEA-TRE to function, such as a cell (preferably a mammalian cell, even more preferably a human cell) that expresses CEA. The CEA-TRE is responsive to transcription factors and/or co-factor(s) associated with CEA-producing cells and comprises at least a portion of the CEA promoter and/or enhancer.

As used herein, an "α-fetoprotein (AFP) transcriptional regulatory element", or "AFP-TRE" is polynucleotide sequence, preferably a DNA sequence, which selectively increases transcription (of an operably linked polynucleotide sequence) in a host cell that allows an AFP-TRE to function, such as a cell (preferably a mammalian cell, even more preferably a human cell) that expresses AFP. The AFP-TRE is responsive to transcription factors and/or co-factor(s) associated with AFP-producing cells and comprises at least a portion of the AFP promoter and/or enhancer.

As used herein, an "a mucin gene (MUC) transcriptional regulatory element", or "MUC1-TRE" is a polynucleotide sequence, preferably a DNA sequence, which selectively increases transcription (of an operably-linked polynucleotide sequence) in a host cell that allows an MUC1-TRE to function, such as a cell (preferably a mammalian cell, even more preferably a human cell) that expresses MUC1. The MUC1-TRE is responsive to transcription factors and/or co-factor(s) associated with MUC1-producing cells and comprises at least a portion of the MUC1 promoter and/or enhancer.

As used herein, a "target cell" is one which allows (i.e., permits or induces) a cell type-specific TRE to function. Preferably, a target cell is a mammalian cell, preferably a human cell.

As used herein, "a cell which allows a TRE to function" or a cell in which the function of a TRE is "sufficiently preserved" or "functionally preserved", or "a cell in which a TRE is functional" is a cell in which the TRE, when operably linked to a promoter (if not included in the TRE) and a reporter gene, increases expression of the reporter gene at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400-to about 500-fold, even more preferably at least about 1000-fold, when compared to the expression of the same promoter and reporter gene when not operably linked to said TRE. Methods for measuring levels (whether relative or absolute) of expression are known in the art and are described herein.

The activity of a TRE generally depends upon the presence of transcriptional regulatory factors and/or the absence of transcriptional regulatory inhibitors. Transcriptional activation can be measured in a number of ways known in the art (and described in more detail below), but is generally measured by detection and/or quantitation of mRNA or the protein product of the coding sequence under control of (i.e., operatively linked to) the TRE. As discussed herein, a TRE can be of varying lengths, and of varying sequence composition. By transcriptional activation, it is intended that transcription will be increased above basal levels in the target cell by at least about 2-fold, preferably at least about 5-fold, preferably at least about 10-fold, more preferably at least about 20-fold. More preferably at least about 50-fold, more preferably at least about 100-fold, even more preferably at least about 200-fold, even more preferably at least about 400- to about 500-fold, even more preferably, at least about 1000-fold. Basal levels are generally the level of activity, if any, in a non-target cells, or the level of activity (if any) of a reporter construct lacking the TRE of interest as tested in a target cell type.

A "functionally-preserved" variant of a TRE is a TRE which differs from another TRE, but still retains ability to increase transcription of an operably linked polynucleotide, especially cell type-specific transcription activity. The difference in a TRE can be due to differences in linear sequence, arising from, for example, single or multiple base mutation(s), addition(s), deletion(s), and/or modification(s) of the bases. The difference can also arise from changes in the sugar(s), and/or linkage(s) between the bases of a TRE.

Certain point mutations within sequences of TREs have been shown to decrease transcription factor binding and gene activation. One of skill in the art would recognize that some alterations of bases in and around known the transcription factor binding sites are more likely to negatively affect gene activation and cell-specificity, while alterations in bases which are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

A "host cell" includes an individual cell or cell culture which can be or has been a recipient of any polynucleotide(s) and/or vector(s) of this invention. Host cells include progeny of a single host cell, and the progeny may not necessarily be completely identical (in morphology or of total DNA complement) to the original parent cell due to natural, accidental, or deliberate mutation and/or change. A host cell includes cells transfected or infected in vivo with a polynucleotide and/or a vector of this invention.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

In the context of a viral vector, e.g., adenovirus vector(s), of the invention, a "heterologous" promoter or enhancer is one which is not present in wild-type virus. Examples of a heterologous promoter or enhancer are the albumin promoter or enhancer and other viral promoters and enhancers, such as SV40.

In the context of adenovirus vector(s), an "endogenous" promoter, enhancer, or TRE is native to or derived from adenovirus.

The term "gene" is well understood in the art and is a polynucleotide encoding a polypeptide. In addition to the polypeptide coding regions, a gene includes non-coding regions including, but not limited to, introns, transcribed but untranslated segments, and regulatory elements upstream and downstream of the coding segments.

In the context of adenovirus vector(s), a "heterologous polynucleotide" or "transgene" is any gene that is not present in wild-type adenovirus. Preferably, the transgene will also not be expressed or present in the target cell prior to introduction by the adenovirus vector. Examples of preferred transgenes are provided below.

A sequence, whether polynucleotide or polypeptide, "depicted in" a SEQ ID NO, means that the sequence is present as an identical contiguous sequence in the sequence of the SEQ ID NO.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. A preferred alignment program is ALIGN Plus (Scientific and Educational Software, Pennsylvania), preferably using default parameters.

"Androgen receptor", or AR as used herein refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In normal cells the AR is activated by androgen, but in non-normal cells (including malignant cells) the AR may be activated by non-androgenic agents, including hormones other than androgens. Encompassed in the term "androgen receptor" are mutant forms of an androgen receptor, as long as the function is sufficiently preserved. Mutants include androgen receptors with amino acid additions, insertions, truncations and deletions, as long as the function is sufficiently preserved. In this context, a functional androgen receptor is one that binds both androgen and, upon androgen binding, an ARE.

"Replication" and "propagation" are used interchangeably and refer to the ability of an adenovirus vector of the invention to reproduce or proliferate. This term is well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression, production of viral proteins, nucleic acids or other components, packaging of viral components into complete viruses, and cell lysis.

A "gene essential for replication" is a gene whose transcription is required for the vector to replicate in a cell.

The terms "polypeptide", "peptide" and "protein" are used interchangeably to refer to polymers of amino acids of any length. These terms also include proteins that are post-translationally modified through reactions that include glycosylation, acetylation and phosphorylation.

As used herein, "cytotoxicity" is a term well understood in the art and refers to a state in which one or more of a cell's usual biochemical or biological functions are perturbed (i.e., inhibited or elevated). These activities include, but are not limited to, metabolism, cellular replication, DNA replication, transcription, translation, and uptake of molecules. "Cytotoxicity" includes cell death and/or cytolysis. Assays are known in the art which indicate cytotoxicity, such as dye exclusion, $^3$H-thymidine uptake, and plaque assays. The term "selective cytotoxicity", as used herein, refers to the cytotoxicity conferred by an adenoviral vector of the present invention on a cell which allows a cell type-specific TRE to function when compared to the cytotoxicity conferred by an adenoviral vector of the present invention on,a cell which does not allow, or is less permissive for, the same TRE to function. Such cytotoxicity may be measured, for example, by plaque assays, reduction or stabilization in size of a tumor comprising target cells, or the reduction or stabilization of serum levels of a marker characteristic of the tumor cells or a tissue-specific marker, e.g., a cancer marker such as prostate specific antigen.

As used herein, a "cytotoxic" gene is a gene whose expression in a cell, either alone or in conjunction with adenovirus replication, enhances the degree and/or rate of cytotoxic and/or cytolytic activity in the cell.

A "therapeutic" gene is a gene whose expression in a cell is associated with a desirable result. In the cancer context, this desirable result may be, for example, cytotoxicity, repression or slowing of cell growth, and/or cell death.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, rodents, primates, farm animals, sport animals, and pets.

An "effective amount" is an amount sufficient to effect beneficial or desired clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering adenoviral vectors of the present invention.

A "masked adenovirus" is an adenovirus which has been complexed with a hydrophilic polymer ("masking agent"). The adenovirus may be any adenovirus, including naturally occurring isolates of adenovirus or engineered adenovirus vectors such as those disclosed in the instant application. Masking agents are preferably of low immunogenicity. Examples of acceptable hydrophilic polymers include polyethylene/polypropylene copolymers, polyacrylic acid analogues, sugar polymers such as cellulose, polyformaldehyde, poly (N-vinylpyrolidone), polyethylene glycol (PEG), and the like. The hydrophilic polymer may be complexed by covalent or non-covalent attachment to the capsid proteins of the virus, particularly the hexon and fiber capsid proteins. A preferred hydrophilic polymer is PEG, and a preferred masked adenovirus is PEG covalently linked to adenovirus ("covalently pegylated adenovirus").

Adenoviral Vectors of the Invention

Replication-competent adenovirus vehicles are provided. The viruses comprise at least one gene under the transcriptional control of a transcriptional initiation region (transcriptional regulatory, or response element, TRE) specifically regulated by target host cells. The genes that are regulated by the specifically regulated transcriptional initiation region may be early or late adenovirus genes and/or transgenes. By providing for regulated transcription restricted to specific host cell targets, one can provide for adenoviruses that can be used as vehicles for introducing genetic capability into host target cells, as distinct from other host cell types. The transgenes serve to modify the genotype or phenotype of the target cell, in addition to any modification of the genotype or phenotype resulting from the presence of the adenovirus. With competent adenoviruses, proliferation of the adenovirus may be used for its cytotoxic effect.

There are a number of different types of adenovirus, such as Ad2, Ad5, and Ad40, which may differ to minor or significant degrees. Particularly, Ad5 and Ad40 differ as to their host cell tropism, as well as the nature of the disease induced by the virus. For the purpose of the subject invention, Ad5 will be exemplified.

The genes of the adenovirus that are of interest for the subject invention may be divided into two groups, the early genes and the late genes, the expression of the latter being controlled by the major late promoter. Of the early genes, there are EIA, EIB, E2, E3 and E4. The EIA gene is expressed immediately after viral infection (0–2 h) and before any other viral genes. EIA protein acts as a trans-acting positive-acting transcriptional regulatory factor, and is required for the expression of the other early viral genes and the promoter proximal major late genes. Despite the nomenclature, the promoter proximal genes driven by the major late promoter are expressed during early times after Ad5 infection. In the absence of a functional EIA gene, viral infection does not proceed, because the gene products necessary for viral DNA replication are not produced.

The EIB protein functions in trans and is necessary for transport of late mRNA from the nucleus to the cytoplasm. Defects in EIB expression result in poor expression of late viral proteins and an inability to shut off host cell protein synthesis.

The E4 gene has a number of transcription products. Open reading frames (ORF) 3 and ORF 6 of the E4 transcription unit increase the accumulation of major late transcription unit mRNAs by binding the 55-kDa protein from EIB and heterodimers of E2F-1 and DP-1. In the absence of functional protein from ORF3 and ORF6, plaques are produced with an efficiency less than $10^{-6}$ of that of wild type virus.

The major late genes relevant to the subject invention are genes such as L1, L2 and L3, which encode proteins of the AD5 virus virion.

Regions of the adenovirus which may be deleted, usually at least 500 nt, more usually at least about 1 knt, include in the AD5 genome nucleotides 300 to 3600 in E1, particularly 342 to 3523; 27000 to 31000, particularly 28133 to 30818 or 27865 to 30995 in E3. The deletion will be at least sufficient for insertion of the desired construct and allow for packaging.

The subject vectors can be used for a wide variety of purposes. The purpose will vary with the target cell. Suitable target cells are characterized by the transcriptional activation of the cell specific transcriptional response element in the adenovirus vehicle. The transcription initiation region will usually be activated in less than about 5%, more usually less than about 1%, and desirably by less than about 0.1% of the cells in the host.

Regulation of transcriptional activation is the result of interaction between transcriptional activators bound to cis-regulatory elements, factors bound to basal transcriptional elements and the activity of transcriptional mediators, or coactivators. The absence or presence of any of these factors may affect the level of transcription. Additionally, factors may be present in an inactive form, where the factors are activated through chemical modification, particularly as the result of a cellular signaling mechanism. In some cases, signaling molecules are able to act directly to activate transcription. Any of these mechanisms may operate to limit the types of cells in which the vehicle transcription initiation region is active.

It will be understood by one of skill in the art that very low basal levels of transcription may be present in non-targeted cell types. By transcriptional activation, it is intended that transcription will be increased above basal levels in the target cell by at least about 100 fold, more usually by at least about 1000 fold.

The cell specific response element, also referred to herein as a cell type-specific transcriptional response element (TRE), may be used with an adenovirus gene that is essential for propagation, so that replication competence is only achievable in the target cell, and/or with a transgene for changing the phenotype of the target cell. By transgene it is intended any gene that is not present in wild-type adenovirus, frequently the transgene will also not be expressed in the target cell, prior to introduction by the adenovirus.

As exemplified by employing a cell specific response element comprising a promoter and enhancer construct specific for prostate cells, various genetic capabilities may be introduced into prostate cells expressing prostate specific antigen. Of particular interest is the opportunity to introduce cytotoxic effects that are controlled by a transcriptional initiation region specifically active in prostate cells. Other cell types that have specific active transcription factors associated with a state for which modulation is desirable include leukocytes, particularly lymphocytes, epithelial cells, endothelial cells, hepatic cells, pancreatic cells, neuronal cells, and keratinocytes. Since the adenovirus results in transient expression (approximately 6 to 8 weeks), one can provide transient capability to cells, where the desired result only requires a limited period for response.

Accordingly, the invention provides an adenovirus vector comprising an adenovirus gene under transcriptional control of a cell type-specific TRE. In some embodiments, a first cell type-specific transcriptional response element controls expression of a first adenovirus gene, and a second cell type-specific transcriptional response element controls expression of a second gene. The genes to be controlled under these TREs are preferably adenoviral genes essential for propagation, more preferably early genes. Alternatively, the genes to be controlled under these TREs may be a gene essential for propagation and a transgene.

Accordingly, the invention includes adenovirus vectors comprising a first adenovirus gene under transcriptional control of a first transcriptional regulatory element (TRE) and at least a second gene under transcriptional control of a second TRE, wherein the first TRE and second TRE are cell (i.e., cell or tissue) specific. It is understood that there may or may not be additional TREs in these adenoviral vectors, and that these additional TREs may or may not be substantially identical to the first and/or second TREs. Accordingly, the invention includes use of three or more, four or more, TREs.

A cell type-specific TRE can also comprise multimers. For example, a cell type-specific TRE can comprise a tandem series of at least two, at least three, at least four, or at least five TREs. These multimers may also contain heterologous promoter and/or enhancer sequences.

A cell type-specific TRE may or may not lack a silencer. The presence of a silencer (i.e., a negative regulatory element) may assist in shutting off transcription (and thus replication) in non-permissive cells (i.e., cells in a normal cell state). Thus, the presence of a silencer may confer enhanced cell status-specific replication by more effectively preventing adenoviral vector replication in non-target cells. Alternatively, the lack of a silencer may assist in effecting replication in target cells, thus conferring enhanced cell type-specific replication due to more effective replication in target cells.

In one embodiment, two substantially identical TREs control transcription of adenovirus early genes, preferably E1A and E1B. It is understood, however, that any of a number of combinations of genes may be used with these at least two TREs. Other preferred embodiments include those which contain substantially identical TREs that drive expression of E1A, E1B, and E4. Such constructs may or may not additionally contain a transgene, which may or may not be under control of a substantially identical TRE. Preparation of these and other embodiments are provided below and in the examples.

In embodiments in which two substantially identical cell type-specific TREs are used, the invention does not require that the TREs be derived from the same gene. As long as the TRE sequences are substantially identical, and the requisite functionality is displayed, the TREs may be derived from different genes.

In another embodiment, the adenovirus vectors of the invention comprise a first adenovirus gene under the transcriptional control of a cell-specific heterologous TRE and at least one other gene, such as an adenoviral gene or a transgene, under control of another heterologous TRE which is different from the first TRE, where the heterologous TREs are functional in the same cell but are not the same in polynucleotide sequence (i.e., have different polynucleotide sequences). Preferably, at least two of the heterologous TREs in an adenovirus vector are cell specific for the same cell. Preferably, the adenovirus gene is one that enhances cell death, more preferably one that is essential for adenovirus replication. Preferably, at least one of the adenovirus genes necessary for cell replication is an early gene and the genes under transcriptional control of the heterologous TREs are necessary for replication. By providing for cell-specific transcription through the use of multiple heterologous TREs, the invention provides adenovirus vectors that can be used for cell-specific cytotoxic effects due to selective replication. It has been demonstrated that adenovirus vectors which include at least two different heterologous TREs are more stable and provide greater cell specificity with regard to replication than previously described adenovirus vectors. Accordingly, adenovirus vectors have been constructed in which each of the E1A and E1B genes are under transcriptional control of two different heterologous. It is understood, however, that any of a number of combinations of genes may be used with any combination of at least two TREs (as further described below). Further preferred embodiments include those which contain at least two different heterologous TREs that drive expression of E1A, E1B, and E4. Such constructs may or may not additionally contain a transgene, which may or may not be under control of a TRE. See, e.g., International Patent Application Nos. WO 98/39466 and WO 98/39464.

Cell Type-specific Transcriptional Response Elements

Depending upon the target cell type, various enhancers may be used to provide for target cell specific transcription. With lymphocytes, for B cells one may use the Ig enhancer, for T cells one may use the T cell antigen receptor promoter. For the different muscle cells, one may use the promoters for the different myosins. For endothelial cells, one may use the different promoters for the different selectins. For each type of cell, there will be specific proteins associated with the cell, which allows for target cell specific transcription.

In one embodiment, the invention includes adenovirus vectors wherein the substantially identical TREs are prostate cell specific. For example, TREs that function preferentially in prostate cells and can be used in the present invention to target adenovirus replication to prostate neoplasia, include, but are not limited to, TREs derived from the prostate-specific antigen gene (PSA-TRE), the glandular kallikrein-1 gene (from the human gene, hKLK2-TRE), and the probasin gene (PB-TRE). All three of these genes are preferentially expressed in prostate cells and the expression is androgen-inducible. Generally, expression of genes responsive to androgen induction requires the presence of an androgen receptor (AR).

The region of the PSA gene that is used to provide cell specificity dependent upon androgens, particular in prostate cells, involves approximately 6.0 kilobases. Schuur et al. (1996) *J. Biol. Chem.* 271:7043–7051. An enhancer region of approximately 1.5 kb in humans is located between nt −5322 and nt −3739, relative to the transcription start site of the PSA gene. The PSA promoter consists of the sequence from about nt −540 to nt +8 relative to the transcription start site. Juxtapositioning of these two genetic elements yields a fully functional, minimal prostate-specific enhancer/promoter (PSE) TRE. Other portions of the approximately 6.0 kb region of the PSA gene can be used in the present invention, as long as requisite functionality is maintained.

The PSE and PSA TRE depicted in (SEQ ID NO:1) is the same as that given in GenBank Accession No. U37672, and published. Schuur et al. (1996). A variant PSA-TRE nucleotide sequence is depicted in (SEQ ID NO:2). This is the PSA-TRE contained within CN706 clone 35.190.13. CN706 is an adenoviral vector in which the E1A gene in Ad5 is under transcriptional control of a PSA-TRE. CN706 demonstrates selective cytotoxicity toward PSA-expressing cells in vitro and in vivo. Rodriguez et al. (1997). CN706 was passaged through 293 and LNCaP cells. A clone, designated 35.190.13 was isolated. The structure of this clone was confirmed by PCR, restriction endonuclease digestion and Southern blotting. Both DNA strands of the CN706 clone 35.190.13 were sequenced between positions 1 and 3537. Seven single base pair changes were found in the PSE, compared to the sequence reported by Schuur et al. (1996). These point mutations are not in the ARE and are thus not likely to affect the function of the enhancer. One mutation was found in the PSA promoter region, but is not likely to affect gene expression from this promoter. In addition to these mutations, a missense mutation was found in the first exon of E1A. This C to G transition at position 3032 results in a Glu to Arg change in the E1A protein sequence. This mutation does not appear to diminish E1A function.

The region that is employed to provide cell specificity dependent upon androgens, particularly in prostate cells, involves an approximately 1.5 kb enhancer region and a 0.5 kb promoter region. The enhancer region in humans is located between nt −5322 and nt −3739, relative to the transcription start site of the prostate specific antigen (PSA) gene. The promoter consists of nt −540 to nt +8. Juxtaposition of the two genetic elements yields a fully functional, minimal prostate-specific enhancer promoter (PSE). The enhancer contains three regions that bind prostate-specific DNA binding proteins, one of which contains a putative androgen response element. The promoter region contains typical TATA and CAAT boxes as well as a second putative androgen response element.

Human glandular kallikrein (hKLK2, encoding the hK2 protein) is expressed exclusively in the prostate and its expression is up-regulated by androgens primarily by transcriptional activation. Wolf et al. (1992) *Molec. Endocrinol.* 6:753–762. Morris (1989) *Clin. Exp. Pharm. Physiol.* 16:345–351; Qui et al. (1990) *J. Urol.* 144:1550–1556; Young et al. (1992) *Biochem.* 31:818–824. The levels of hK2 found in various tumors and in the serum of patients with prostate cancer differ substantially from those of PSA and indicate that hK2 antigen may be a significant marker for prostate cancer. Circulating hK2 in different relative proportions to PSA has been detected in the serum of patients with prostate cancer. Charlesworth et al. (1997) *Urology* 49:487–493. Expression of hK2 has been detected in each of 257 radical prostatectomy specimens analyzed. Darson et al. (1997) *Urology* 49:857–862. The intensity and extent of hK2 expression, detected using specific antibodies, increased from benign epithelium to high-grade prostatic intraepithelial neoplasia (PIN) and adenocarcinoma, whereas PSA and prostate acid phosphatase displayed an inverse pattern of immunoreactivity. Darson et al. (1997). Indeed, it has been reported that a certain percentage of PSA-negative tumors have detectable hK2. Tremblay et al. (1997) *Am. J. Pathol.* 150:455–459.

The activity of the hKLK2 5' promoter has been previously described and a region up to −2256 relative to the transcription start site was previously disclosed. Schedlich et al. (1987) *DNA* 6:429–437. The hKLK2 promoter is androgen responsive and, in plasmid constructs wherein the promoter alone controls the expression of a reporter gene, expression of the reporter gene is increased approximately 10-fold in the presence of androgen. Murtha et al. (1993) *Biochem.* 32:6459–6464. hKLK2 enhancer activity is found within a polynucleotide sequence approximately nt −12,014 to nt −2257 relative to the start of transcription (depicted in SEQ ID NO:3) and, when this sequence is operably linked to an hKLK2 promoter and a reporter gene, transcription of operably-linked sequences in prostate cells increases in the presence of androgen at levels approximately 30- to approximately 100-fold over the level of transcription in the absence of androgen. This induction is generally orientation independent and position independent. Enhancer activity has also been demonstrated in the following regions (all relative to the transcription start site): about nt −3993 to about nt −3643 (nt 8021 to 8371 of SEQ ID NO:3), about nt −4814 to about nt −3643 (nt 7200 to 8371 of SEQ ID NO:3), about nt −5155 to about nt −3387 (nt 6859 to 8627 of SEQ ID NO:3), about nt −6038 to about nt −2394 (nt 5976 to 9620 of SEQ ID NO:3).

Thus, an hKLK2 enhancer can be operably linked to an hKLK2 promoter or a heterologous promoter to form an hKLK2 transcriptional regulatory element (hKLK2-TRE). An hKLK2-TRE can then be operably linked to a heterologous polynucleotide to confer hKLK2-TRE-specific transcriptional regulation on the linked gene, thus increasing its expression.

The rat probasin (PB) gene encodes a nuclear and secreted protein, probasin, that is only expressed in the dorsolateral prostate. Dodd et al. (1983) *J. Biol. Chem.* 258:10731–10737; Matusik et al. (1986) *Biochem. Cell. Biol.* 64: 601–607; and Sweetland et al. (1988) *Mol. Cell. Biochem.* 84: 3–15. The dorsolateral lobes of the murine prostate are considered the most homologous to the peripheral zone of the human prostate, where approximately 68% of human prostate cancers are thought to originate.

A PB-TRE has been shown in an approximately 0.5 kb fragment of sequence upstream of the probasin coding sequence, from about nt −426 to about nt +28 relative to the transcription start site, as depicted in (SEQ ID NO:4). This minimal promoter sequence from the PB gene appears to provide sufficient information to direct development and hormone-regulated expression of an operably linked heterologous gene specifically to the prostate in transgenic mice. Greenberg et al. (1994) *Mol. Endocrinol.* 8:230–239.

In the present invention, replication-competent adenovirus vectors directed at specific target cells may also be generated with the use of TREs that are preferentially functional in the target tumor cells. Non-limiting examples of tumor cell-specific TREs, and non-limiting examples of respective potential target cells, include TREs from the following genes: α-fetoprotein (AFP) (liver cancer); mucin-like glycoprotein DF3 (MUC1) (breast carcinoma); carcinoembryonic antigen (CEA) (colorectal, gastric, pancreatic, breast, and lung cancers); plasminogen activator urokinase (uPA) and its receptor gene (breast, colon, and liver cancers); and HER-2/neu (c-erbB2/neu) (breast, ovarian, stomach, and lung cancers).

AFP is an oncofetal protein, the expression of which is primarily restricted to developing tissues of endodermal origin (yolk sac, fetal liver, and gut), although the level of its expression varies greatly depending on the tissue and the developmental stage. AFP is of clinical interest because the serum concentration of AFP is elevated in a majority of hepatoma patients, with high levels of AFP found in patients with advanced disease. The serum AFP levels in patients appear to be regulated by AFP expression in hepatocellular carcinoma but not in surrounding normal liver. Thus, the AFP gene appears to be regulated to hepatoma cell-specific expression.

Cell-specific TREs from the AFP gene have been identified. For example, the cloning and characterization of human AFP-specific enhancer activity is described in Watanabe et al. (1987) *J. Biol. Chem.* 262:4812–4818. The entire 5' AFP flanking region (containing the promoter, putative silencer, and enhancer elements) is contained within approximately 5 kb upstream from the transcription start site (SEQ ID NO:5).

The AFP enhancer region in human is located between about nt −3954 and about nt −3335, relative to the transcription start site of the AFP gene. The human AFP promoter encompasses a region from about nt −174 to about nt +29. Juxtapositioning of these two genetic elements, as depicted in SEQ ID NO:6, yields a fully functional AFP-TRE. Ido et al. (1995) describe a 259 bp promoter fragment (nt −230 to nt +29) that is, specific for HCC. *Cancer Res.* 55:3105–3109. The AFP enhancer contains two regions, denoted A and B, located between nt −3954 and nt −3335 relative to the transcription start site. The promoter region contains typical TATA and CAAT boxes. Preferably, the AFP-TRE contains at least one enhancer region. More preferably, the AFP-TRE contains both enhancer regions.

Suitable target cells for adenoviral vectors containing AFP-TREs are any cell type that allow an AFP-TRE to function. Preferred are cells that express, or produce, AFP, including, but not limited to, tumor cells expressing AFP. Examples of such cells are hepatocellular carcinoma cells, gonadal and other germ cell tumors (especially endodermal sinus tumors), brain tumor cells, ovarian tumor cells, acinar cell carcinoma of the pancreas (Kawamoto et al. (1992) *Hepatogastroenterology* 39:282–286), primary gall bladder tumor (Katsuragi et al. (1989) *Rinsko Hoshasen* 34:371–374), uterine endometrial adenocarcinoma cells (Koyama et al. (1996) *Jpn. J. Cancer Res.* 87:612–617), and any metastases of the foregoing (which can occur in lung, adrenal gland, bone marrow, and/or spleen). In some cases, metastatic disease to the liver from certain pancreatic and stomach cancers produce AFP. Especially preferred are hepatocellular carcinoma cells and any of their metastases. AFP production can be measured using assays standard in the art, such as RIA, ELISA or Western blots (immunoassays) to determine levels of AFP protein production or Northern blots to determine levels of AFP mRNA production. Alternatively, such cells can be identified and/or characterized by their ability to activate transcriptionally an AFP-TRE (i.e., allow an AFP-TRE to function).

The protein urokinase plasminogen activator (uPA) and its cell surface receptor, urokinase plasminogen activator receptor (uPAR), are expressed in many of the most frequently occurring neoplasia and appear to represent important proteins in cancer metastasis. Both proteins are implicated in breast, colon, prostate, liver, renal, lung and ovarian cancer. Transcriptional regulatory elements that regulate uPA and uPAR transcription have been extensively studied. Riccio et al. (1985) *Nucleic Acids Res.* 13:2759–2771; Cannio et al., (1991) *Nucleic Acids Res.* 19:2303–2308.

CEA is a 180,000-Dalton glycoprotein tumor-associated antigen present on endodermally-derived neoplasia of the gastrointestinal tract, such as colorectal, gastric (stomach) and pancreatic cancer, as well as other adenocarcinomas such as breast and lung cancers. CEA is of clinical interest because circulating CEA can be detected in the great majority of patients with CEA-positive tumors. In lung cancer, about 50% of total cases have circulating CEA, with high concentrations of CEA (greater than 20 ng/ml) often detected in adenocarcinomas. Approximately 50% of patients with gastric carcinoma are serologically positive for CEA.

The 5' upstream flanking sequence of the CEA gene has been shown to confer cell-specific activity. The CEA promoter region, approximately the first 424 nucleotides upstream of the translational start site in the 5' flanking region of the gene, was shown to confer cell-specific activity when the region provided higher promoter activity in CEA-producing cells than in non-producing HeLa cells. Schrewe et al. (1990) *Mol. Cell. Biol.* 10:2738–2748. In addition, cell-specific enhancer regions have been found. WO/95/14100. The entire 5' CEA flanking region (containing the promoter, putative silencer, and enhancer elements) appears to be contained within approximately 14.5 kb upstream from the transcription start site. Richards et al. (1995); WO 95/14100. Further characterization of the 5' flanking region of the CEA gene by Richards et al. (1995) indicated two upstream regions, −13.6 to −10.7 kb or −6.1 to −4.0 kb, when linked to the multimerized promoter resulted in high-level and selective expression of a reporter construct in CEA-producing LoVo and SW1463 cells. Richards et al. (1995) also localized the promoter region to nt −90 and nt +69 relative to the transcriptional start site, with region nt −41 to nt −18 as essential for expression. WO95/14100 describes a series of 5' flanking CEA fragments which confer cell-specific activity, such as about nt −299 to about nt +69; about nt −90 to about nt +69; nt −14,500 to nt −10,600; nt −13,600 to nt −10,600, nt −6100 to nt −3800. In addition, cell specific transcription activity is conferred on an operably linked gene by the CEA fragment from nt −402 to nt +69, depicted in (SEQ ID NO:7). Any CEA-TREs used in the present invention are derived from mammalian cells, including but not limited to, human cells. Thus, any of the CEA-TREs may be used in the invention as long as requisite desired functionality is displayed in the adenovirus vector. The cloning and characterization of CEA sequences have been described in the literature and are thus made available for practice of this invention and need not be described in detail herein.

The protein product of the MUC1 gene (known as mucin or MUC1 protein; episialin; polymorphic epithelial mucin or PEM; EMA; DF3 antigen; NPGP; PAS-O; or CA15.3 antigen) is normally expressed mainly at the apical surface of epithelial cells lining the glands or ducts of the stomach, pancreas, lungs, trachea, kidney, uterus, salivary glands, and mammary glands. Zotter et al. (1988) *Cancer Rev.* 11–12: 55–101; and Girling et al. (1989) *Int. J. Cancer* 43: 1072–1076. However, mucin is overexpressed in 75–90% of human breast carcinomas. Kufe et al. (1984) *Hybridoma* 3: 223–232. For reviews, see Hilkens (1988) *Cancer Rev.* 11–12: 25–54; and Taylor-Papadimitriou, et al. (1990) *J. Nucl. Med. Allied Sci.* 34: 144–150. Mucin protein expression correlates with the degree of breast tumor differentiation. Lundy et al. (1985) *Breast Cancer Res. Treat.* 5: 269–276. This overexpression appears to be controlled at the transcriptional level.

Overexpression of the MUC1 gene in human breast carcinoma cells MCF-7 and ZR-75-1 appears to be regulated at the transcriptional level. Kufe et al. (1984); Kovarik (1993) *J. Biol. Chem.* 268:9917–9926; and Abe et al. (1990) *J. Cell. Physiol.* 143: 226–231. The regulatory sequences of the MUC1 gene have been cloned, including the approximately 0.9 kb upstream of the transcription start site which contains a TRE that appears to be involved in cell-specific transcription, depicted in SEQ ID NO:8. Abe et al. (1993) *Proc. Natl. Acad. Sci. USA* 90: 282–286; Kovarik et al. (1993); and Kovarik et al. (1996) *J. Biol. Chem.* 271:18140–18147.

Any MUC1-TREs used in the present invention are derived from mammalian cells, including but not limited to, human cells. Preferably, the MUC1-TRE is human. In one embodiment, the MUC1-TRE may contain the entire 0.9 kb 5' flanking sequence of the MUC1 gene. In other embodiments, the MUC1-TREs comprise the following sequences (relative to the transcription start site of the MUC1 gene): about nt −725 to about nt +31, nt −743 to about nt +33, nt −750 to about nt +33, and nt −598 to about nt +485 (operably-linked to a promoter).

The c-erbB2/neu gene (HER-2/neu or HER) is a transforming gene that encodes a 185 kD epidermal growth factor receptor-related transmembrane glycoprotein. In humans, the c-erbB2/neu protein is expressed during fetal development, however, in adults, the protein is weakly detectable (by immunohistochemistry) in the epithelium of many normal tissues. Amplification and/or over-expression of the c-erbB2/neu gene has been associated with many human cancers, including breast, ovarian, uterine, prostate, stomach and lung cancers. The clinical consequences of the c-erbB2/neu protein over-expression have been best studied in breast and ovarian cancer. c-erbB2/neu protein over-expression occurs in 20 to 40% of intraductal carcinomas of the breast and 30% of ovarian cancers, and is associated with a poor prognosis in subcategories of both diseases. Human, rat and mouse c-erbB2/neu TREs have been identified and shown to confer c-erbB2/neu expressing cell specific activity. Tal et al. (1987) *Mol. Cell. Biol.* 7:2597–2601; Hudson et al. (1990) *J. Biol. Chem.* 265:4389–4393; Grooteclaes et al. (1994) *Cancer Res.* 54:4193–4199; Ishii et al. (1987) *Proc. Nati. Acad. Sci. USA* 84:4374–4378; Scott et al. (1994) *J. Biol. Chem.* 269:19848–19858.

In the present invention, cell type-specific TREs which are tumor-specific may be used in conjunction with other, non-tumor-specific cell type-specific TREs from the following exemplary genes (tissue in which the TREs are specifically functional are in parentheses): vascular endothelial growth factor receptor,(endothelium); albumin (liver); factor VII (liver); fatty acid synthase (liver); von Willebrand factor and fit-1 (endothelium); alpha-actin and myosin heavy chain (both in smooth muscle); synthetase I (small intestine); Na—K—Cl transporter (kidney). Additional cell type-specific TREs are known in the art.

Additional tumor- and/or cell type-specific TREs known in the art include the following: aromatase, mammary gland-specific promoter, mammaglobin, urokinase, and human alpha-lactalbumin (breast tissue); BCSG1, BRCA1, and BRCA2 (breast cancer); human papilloma virus (HPV) cell type dependent regulatory element (cervical cancer); BLCA4 (bladder cancer); uroplakin (bladder); NCA (gastric cancer); hypoxanthine phosphoribosyltransferase (HPRT) (glioma); AVP, human pulmonary surfactant protein B gene, and puromycin N-acetyltransferase (lung cancer); tyrosinase, gp100, tyrosinase related proteins 1 and 2; MART-1, and melanocyte specific factory (MSF) (melanoma); HER2/neu, urokinase, and CA125 (ovarian cancer); SL3-3 and T cell antigen receptor (T cell lymphoma); and prostatic acid phosphatase (prostate). Descriptions of these cell-specific TREs can be found in various publications, including the following: Zhou et al. (1996) J. Biol. Chem. 271:15164–15202 (aromatase); International Patent Application No. WO 98/15634 (mammary gland-specific promoter); Watson et al. (1996) *Cancer Res.* 56:860–865 (mammaglobin); Ji et al. (1997) *Cancer Res.* 57:759–764 (breast cancer-specific gene BCSG1); (1995) *Gene* 159:65–71 (HER-2/neu); Cannio et al. (1991) *Nucl. Acids Res.* 19:2303–2308 (urokinase); (1993) *Virol.* 195:500–510 (HPV cell type dependent regulatory element); Rincon-Limas et al. (1994) J. Neurosci. Res. 38:259–267 (HPRT); (1992) *Gene* 117:255–258 (puromycin N-acetyltransferase); Bohinski et al. (1993) *J. Biol. Chem.* 268:11160–11166 (human pulmonary surfactant protein B gene); Vile et al. (1993) *Cancer Res.* 53:3860–3864 (tyrosinase); Butterfield et al. (1997) *Gene* 191:129–134 (MART-1); Yavuzer et al. (1994) *Mol. Cell. Biol.* 14:3494–3503 (MSF); Garcia-Arenas et al. (1995) *Mol. Cell. Endocrinol.* 111:29–37 (prostatic acid phosphatase); Boral et al. (1989) *J. Virol.* 63:76–84 (SL3-3); and (1990) *Science* 247:1225–1229.

The TREs listed above are provided as non-limiting examples of TREs that would function in the instant invention. Additional cell-specific TREs are known in the art, as are methods to identify and test cell specificity of suspected TREs.

Activity of a TRE can be determined as follows. A TRE polynucleotide sequence or set of such sequences can be generated using methods known in the art, such as chemical synthesis, site-directed mutagenesis, PCR, and/or recombinant methods. The sequence(s) to be tested can be inserted into a vector containing a promoter (if no promoter element is present in the TRE) and an appropriate reporter gene encoding a reporter protein, including, but not limited to, chloramphenicol acetyl transferase (CAT), β-galactosidase, (encoded by the lacZ gene), luciferase (encoded by the luc gene), alkaline phosphatase, green fluorescent protein, and horse radish peroxidase. Such vectors and assays are readily available, from; inter alia, commercial sources. Plasmids thus constructed are transfected into a suitable host cell to test for expression of the reporter gene as controlled by the putative TRE using transfection methods known in the art, such as calcium phosphate precipitation, electroporation, liposomes (lipofection), and DEAE dextran.

After introduction of the TRE-reporter gene construct into a host cell under appropriate conditions, TRE activity may be measured by detection and/or quantitation of reporter gene-derived mRNA or protein product. The reporter gene protein can be detected directly (e.g., immunochemically) or through its enzymatic activity, if any, with an appropriate substrate. Generally, to determine cell specific activity of a TRE, the TRE-reporter gene constructs are introduced into a variety of cell types. The amount of TRE activity is determined in each cell type and compared to that of a reporter gene construct without the TRE. A TRE is cell specific when it is preferentially functional in a specific type of cell over a different type of cell.

For example, the specificity of PB-TRE activity for prostate cell that express the androgen receptor (AR) was demonstrated as follows. The region of the PB 5'-flanking DNA (nt −426 to nt +28) (SEQ ID NO:9) including the endogenous promoter sequences was inserted upstream of the firefly luciferase gene to generate a chimeric PB-TRE-luc plasmid. Cationic-mediated, transient transfection of LNCaP (PSA-producing and AR-producing prostate carcinoma cells) and PC-3 (PSA-deficient and AR-deficient prostate carcinoma cells) cells was performed. The results showed that LNCaP cells transfected with PB-TRE-luc had approximately 400 times more activity than untransfected cells, indicating that the PB-TRE was intact. Further, the overall luciferase activity recovered in the cellular extracts of transfected LNCaP cells was about 30–40-fold higher than that measured in the cellular extracts of transfected PC-3 cells. Thus, the results indicate that PB-TRE expression is preferentially functional in PSA-producing, AR-producing prostate carcinoma cells as compared to PSA-deficient, AR-deficient prostate carcinoma cells and that PB-TRE is capable of mediating specific expression in cells producing the androgen receptor.

Transgenes

Use of competent adenovirus, which is competent in particular target cells, allow for proliferation of the adenovirus in the target cells resulting in the death of the host cells and proliferation of the adenovirus to other host cells.

To further ensure cytotoxicity, one may have one or more transgenes present which have cytotoxic effect. In this way one can provide high confidence that the target cells will be destroyed while providing for the appropriate level of expression of the cytotoxic agents).

Accordingly, the adenovirus vectors of this invention can further include a heterologous polynucleotide (transgene) under the control of a cell type-specific TRE. In this way, various genetic capabilities may be introduced into target cells. For example, in certain instances, it may be desirable to enhance the degree and/or rate of cytotoxic activity, due to, for example, the relatively refractory nature or particular aggressiveness of the target cell. This could be accomplished by coupling the cell-specific replicative cytotoxic activity with cell-specific expression of, one or more metabolic enzymes such as HSV-tk, nitroreductase, cytochrome P450 or cytosine deaminase (cd) which render cells capable of metabolizing 5-fluorocytosine (5-FC) to the chemotherapeutic agent 5-fluorouracil (5-FU). This type of transgenes may also be used to confer a bystander effect.

Transgenes that may be introduced into an adenovirus vector of the invention also include a factor capable of initiating apoptosis, antisense or ribozymes, which among other capabilities may be directed to mRNAs encoding proteins essential for proliferation, such as structural proteins, transcription factors, polymerases, etc., viral or other pathogenic proteins, where the pathogen proliferates intracellularly, cytotoxic proteins, e.g., the chains of diphtheria, ricin, abrin, etc., genes that encode an engineered cytoplasmic variant of a nuclease (e.g., RNase A) or protease (e.g., trypsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-α, -β, -γ, TNF-α, -β, TGF-α, -β, NGF, and the like. Further examples include, proapoptotic genes such as Fas, Bax, Caspase, Fas ligands, and the like; fusion genes which can lead to cell fusion or facilitate cell fusion such as V22, VSV and the like; tumor suppressor gene such as p53, RB, p16, p17, W9 and the like; genes associated with the cell cycle and genes which encode anti-angiogenic proteins such as endostatin, angiostatin, and the like.

Other opportunities for specific genetic modification include T cells, such as tumor infiltrating lymphocytes (TILs), where the TILs may be modified to enhance expansion, enhance cytotoxicity, reduce response to proliferation inhibitors, enhance expression of lymphokines, etc. One may also wish to enhance target cell vulnerability by providing for expression of specific surface membrane proteins, e.g., B7, SV40 T antigen mutants, etc.

In some embodiments, the adenovirus death protein (ADP), encoded within the E3 region, is maintained (i.e., contained) in the adenovirus vector. The ADP gene, under control of the major late promoter (MLP), appears to code for a protein (ADP) that is important in expediting host cell lysis. Tollefson et al. (1996) *J. Virol.* 70(4):2296; Tollefson et al. (1992) *J. Virol.* 66(6):3633. Thus, adenoviral vectors containing the ADP gene may render the adenoviral vector more potent, making possible more effective treatment and/or a lower dosage requirement.

Accordingly, the invention provides adenovirus vectors in which an adenovirus gene is under transcriptional control of a first cell type-specific TRE and a polynucleotide sequence encoding an ADP under control of a second cell type-specific TRE, and wherein preferably the adenovirus gene is essential for replication. A DNA sequence encoding an ADP and the amino acid sequence of an ADP are depicted in SEQ ID NO:10 and SEQ ID NO:11, respectively. Briefly, an ADP coding sequence is obtained preferably from Ad2 (since this is the strain in which ADP has been more fully characterized) using techniques known in the art, such as PCR. Preferably, the Y leader (which is an important sequence for correct expression of late genes) is also obtained and ligated to the ADP coding sequence. The ADP coding sequence (with or without the Y leader) can then be introduced into the adenoviral genome, for example, in the E3 region (where the ADP coding sequence will be driven by the MLP). The ADP coding sequence could also be inserted in other locations of the adenovirus genome, such as the E4 region. Alternatively, the ADP coding sequence could be operably linked to a different type of TRE, including, but not limited to, another viral TRE.

It is understood that the present invention does not exclude adenovirus vectors containing additional genes under control of cell type-specific TREs. Accordingly, the invention provides adenoviral vectors comprising a third gene under transcriptional control of a third TRE. The third TRE may or may not be substantially identical to the first and/or second cell type-specific TREs, with all three TREs functional in the same cell. Preferably, the third gene is one that contributes to cytotoxicity (whether direct and/or indirect), more preferably one that contributes to and/or enhances cell death,. Preferably the third TRE is cell type-specific. For example, an adenovirus vector may contain two PB-TREs and an hKLK2-TRE, or two PSE-TREs and an hKLK2-TRE, each prostate cell specific and each controlling the transcription of a different gene.

Accordingly, the invention provides adenoviral vectors comprising at least an additional gene (beyond the first and the second genes) under transcriptional control of a cell type-specific TRE. Preferably, the additional gene is one that contributes to cytotoxicity (whether direct and/or indirect), more preferably 6ne that enhances cell death,.

Delivery of Adenoviral Vectors to Cells

The adenoviral vectors can be used in a variety of forms, including, but not limited to, naked polynucleotide (usually DNA) constructs; polynucleotide constructs complexed with agents to facilitate entry into cells, such as cationic liposomes or other compounds such as polylysine; packaged into infectious adenovirus particles (which may render the adenoviral vector(s) more immunogenic); packaged into other particulate viral forms such as HSV or AAV; complexed with agents to enhance or dampen an immune response; complexed with agents that facilitate in vivo transfection, such as DOTMA™, DOTAP™, and polyamines.

If an adenoviral vector is packaged into an adenovirus, the adenovirus itself may be selected to further enhance targeting. For example, adenovirus fibers mediate primary contact with cellular receptor(s) aiding in tropism. See, e.g., Arnberg et al. (1997) *Virol.* 227:239–244. If a particular subgenus of an adenovirus serotype displayed tropism for a target cell type and/or reduced affinity for non-target cell types, such a subgenus (or subgenera) could be used to further increase cell-specificity of cytotoxicity and/or cytolysis.

The modified viruses may be delivered to the target cell in a variety of ways, depending upon whether the cells are in culture, ex vivo or in vivo. For the prostate for the most part, the cells will be delivered in vivo. Delivery can be achieved in a variety of ways, employing liposomes, direct injection, catheters, intravenous inhalation, topical applications, general transfection methods that are well known in the art (such as calcium phosphate precipitation and electroporation), and intravenous infusion, etc. Due to the high efficiency of transfection of adenoviruses, one can achieve a high level of modified cells. In the case of neoplasia, where toxins are produced, the toxins will be released locally, so as to affect cells which may not have been successfully transfected. In this manner, one can specifically eliminate the neoplastic cells, without significant effect on the normal cells. In addition, expression of adenovirus proteins will serve to activate the immune system against the target cells. Finally, proliferation of the adenovirus in a host cell will lead to cell death. The means of delivery will depend in large part on the particular adenoviral vector (including its form) as well as the type and location of the target cells (i.e., whether the cells are in vitro or in vivo).

If used in a packaged adenovirus, the adenovirus may be administered in an appropriate physiologically acceptable carrier at a dose of about $10^4$ to $10^{11}$. The multiplicity of infection will generally be in the range of about 0.001 to 100. The viruses may be administered one or more times, depending upon the immune response potential of the host. If necessary, the immune response may be diminished by employing a variety of immunosuppressants, so as to permit repetitive administration, without a strong immune response.

If administered as a polynucleotide construct (i.e.; not packaged as a virus) about 0.01 $\mu$g to 1000 $\mu$g of an adenoviral vector can be administered. The adenoviral vectors may be administered one or more times, depending upon the intended use and the immune response potential of the host or may be administered as multiple simultaneous injections. If an immune response is undesirable, the immune response may be diminished by employing a variety of immunosuppressants, so as to permit repetitive administration, without a strong immune response. If packaged as another viral form, such as HSV, the amount to be administered is based on standard knowledge about that particular virus (which is readily obtainable from, for example, published literature) and can be determined empirically.

In some embodiments, a packaged adenovirus vector(s) is complexed to a hydrophilic polymer to create a masked adenovirus. The hydrophilic polymer is attached (covalently or non-covalently) to the capsid proteins of the adenovirus, particularly the hexon and fiber proteins. In preferred embodiments, the adenovirus vectors of the instant invention are complexed with masking agents to create masked adenovirus vectors. Masked adenoviruses are advantageous due to (a) the masking of the adenovirus surface to adenovirus neutralizing antibodies or opsonins which are in circulation and (b) increasing systemic circulation time of adenovirus particles by reduction of non-specific clearance mechanisms in the body (i.e. macrophages, etc.). In the in vivo context, the systemic delivery of a masked adenovirus results in a longer circulation of virus particles, less immunogenicity, and increased biodistribution with a decrease in clearance by the liver and spleen. Extensive research has been done on modification of proteins and lipids with hydrophilic polymers (especially PEG) but the inventors are unaware of any other use of masking agents in conjunction with adenovirus or adenovirus vectors.

Figure 20:
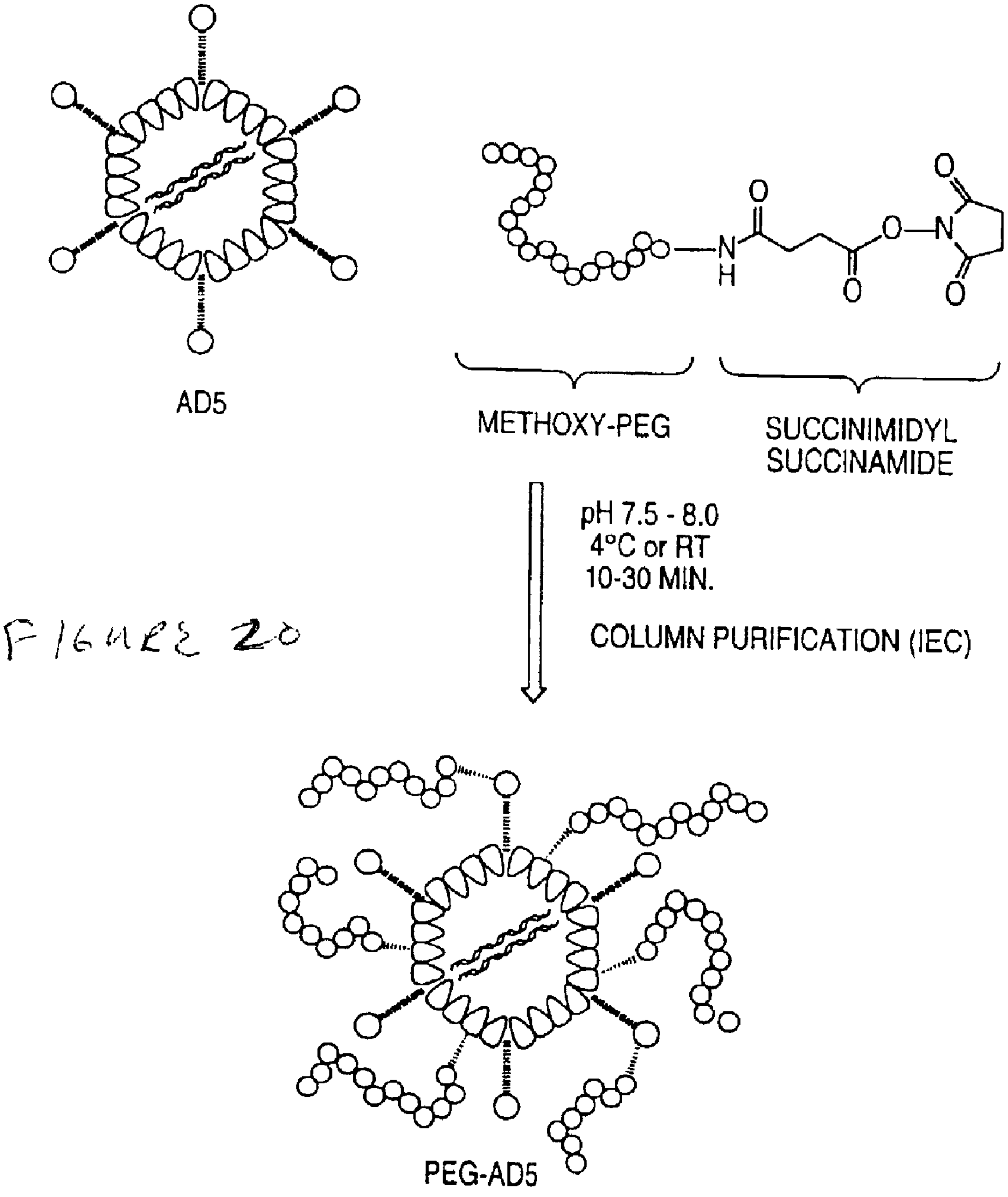
FIG. 20 is a schematic depiction of a method for covalent pegylation of an adenovirus. In this method, succinimidyl succinamide is used to covalently attach methoxy-PEG to adenovirus. The pegylated adenovirus is separated from the reaction components by ion exchange chromatography.

Accordingly, the invention provides an adenovirus complexed with a masking agent. Preferably the masking agent is PEG. A schematic of one method of making a masked adenovirus is depicted in FIG. 20 (also see Example 8). A preferred embodiment is a masked adenovirus comprising an adenovirus vector(s) described herein with a more preferred embodiment comprising a pegylated adenovirus comprising an adenovirus described herein. The invention also provides methods to make and use these masked adenoviruses, which are evident from the description herein.

The masking agents may be of various molecular weights, as long as the desired complex and requisite functionality is obtained. Most masking agents obtained from commercial sources are normally polydisperse in relation to the state molecular weight (i.e. the masking agent is supplied in a distribution of molecular weights surrounding the nominal molecular weight). Masking agents useful in masking adenoviruses according to the instant invention may have nominal weights of about 2000 to about 50,000; preferably about 2500 to about 30,000; preferably, about 3000 to about 25,00, more preferably about 5000 to about 20,000. Preferably, the nominal molecular weight is less than about 20,000, more preferably less than about 10,000, more preferably less than about 7500, more preferably less than about 5000. Preferably, the masking agents is PEG with a nominal molecular weight of less than about 5000 Da. Mixtures of different weight masking agents are also contemplated.

The masking may be covalently or non-covalently attached. In the case of non-covalent attachment, the attachment may be electrostatic, hydrophobic, or affinity interactions. The masking agents used for non-covalent attachment may be modified masking agents (i.e. the masking agent is synthesized or modified to contain particular chemical moieties not normally present in the masking agent). Masking agents useful for electrostatic attachment to adenoviral vectors will be masking agents which contain, or have been modified or synthesized to contain, charged moieties which bind to the adenovirus surface by electrostatic interaction. Negatively charged masking agents include masking agents which contain phosphate groups, sulfate groups, carboxy groups, and the like. Quaternary amine groups are useful as positively charged moieties for electrostatic, non-covalent attachment of masking agents to adenovirus. Masking agents containing or modified or synthesized to contain hydrophobic groups, such as lipids (e.g. phosphatidylethanolamine and the like) and other hydrophobic groups (such as phenyl groups or long alkyl chains) can be complexed to adenoviral vectors by hydrophobic interaction with stable hydrophobic regions on the virus. Affinity masking agents can be made using any small molecule, peptide or protein which binds to adenovirus. The affinity and hydrophobic moieties may be attached to the masking agent by any method known in the art, preferably by chemical crosslinking with a chemical crosslinker.

If the masking agent is covalently attached, a chemical crosslinker is preferably used to covalently bond the masking agent to the adenovirus. The crosslinker may be any crosslinker capable of creating a covalent linkage or bridge between the masking agent and the adenovirus. Direct crosslinking, in which the adenovirus masking agent and a separate crosslinker molecule are reacted, may be employed to create covalently masked adenovirus, using any chemical crosslinker known in the art which will create crosslinks between the masking agent and the protein. Either the masking agent or the adenovirus may be modified prior to the crosslinking reaction, so that the chemical crosslinker will react with the two molecules (e.g. the masking agent may be modified to add amine groups, allowing it to be crosslinked to the adenovirus by crosslinking agents which react with amines.)

Preferably, either the masking agent or the adenovirus is first activated by reaction with a crosslinking agent. Unreacted crosslinker is them removed from the masking agent or adenovirus. The activation preferably results in one or two molecules of crosslinking agent per molecule of masking agent, more preferably a single molecule of crosslinking agent per molecule of masking agent. The activated masking agent or adenovirus is then mixed with adenovirus, if the masking agent is activated, or masking agent, if the adenovirus is activated, under the appropriate reaction conditions to form masked adenovirus. Preferably the masking agent is activated, then reacted with adenovirus.

The preferred masking agent is PEG. Preferred activated PEGs include, but are not limited to: nucleophilic crosslinking PEGs such as N terminal amine PEG, PEG amino acid esters, PEG hydrazine hydrochloride, thiol PEGs, and the like; carboxyl PEGs including succinate PEG, carboxymethylated PEG, PEG-proprionic acid, and PEG amino acids, sulfhydryl-selective PEGs such as PEG-maleimide, PEG-orthopyridyl-disulfide and the like, heterofunctional PEGs including amines and acids PEG, NHS-maleimide PEG and NHS-vinylsulfone PEG; PEG silanes; biotin PEGs; vinyl derivatives of PEG such as allyl PEG, PEG acrylate, PEG methacrylate, and the like, and electrophilic active PEGs, including PEG succinimidyl succinate, PEG succinimidyl succinamide, PEG succinimidyl proprionate, succinimidyl ester of carboxymethylated PEG, PEG2-NHS, succinimidyl esters of amino acid PEGs, pendant modified PEG MHS esters (such as those available from Innophase, Inc.), PEG-glycidyl ether (epoxide), PEG-oxycarbonylimidazole, PEG nitrophenyl carbonates, PEG trichlorophenyl carbonates, PEG treslate, PEG aldehyde, PEG isocyanate, copolymers of PEG allyl ether and maleic anhydride, PEG vinylsulfone, and other activated PEGs as will be apparent to one of skill in the art. The activated PEG is preferably PEG-N-hydroxy succinimidyl succinamide or PEG-succinimidyl succinate, more preferably PEG-N-hydroxy succinimidyl succinamide.

Host Cells and Target Cells

The present invention also provides host cells and target cells comprising (i.e., transformed with) the adenoviral vectors described herein. Host cells include both prokaryotic and eukaryotic host cells as long as sequence requisite for maintenance in that host, such as appropriate replication origin(s), are present. For convenience, selectable markers are also provided. Prokaryotic host include bacterial cells, for example, *E. coli* and mycobacteria. Among eukaryotic host cells are yeast, insect, avian, amphibian, plant and mammalian host cells. Host systems are known in the art and need not be described in detail herein.

Suitable target cells for the adenovirus vectors of the invention include any eukaryotic cell type that allows function of the cell type-specific TREs, preferably mammalian, more preferably human, even more preferably neoplastic cells. Suitable target cells also include any cells that produce proteins and other factors necessary for expression of the gene under control of the cell type-specific TREs, such factors necessary for said expression are produced naturally or recombinantly. For example, if the cell type-specific TRE(s) used is prostate cell-specific, the cells are preferably prostate cells, for example LNCaP cells. The prostate cells used may or may not be producing an androgen receptor, depending on whether the promoter used is androgen-inducible. If an androgen-inducible promoter is used, non-androgen receptor producing cells, such as HLF, HLE, and 3T3 and the non-AR-producing prostate cancer cells PC3 and DU145 can be used, provided an androgen receptor-encoding expression vector is introduced into the cells along with the adenovirus. If the cell type-specific TRE(s) used is derived from the AFP gene, for example, suitable host cells include any cell type that produces AFP, including but not limited to, Hep3B, HepG2, HuH7, HuH1/C12. Activity of a given TRE in a given cell can be assessed by measuring the level of expression of a operably-linked reporter gene using standard assays. The comparison of expression between cells in which the TRE is suspected of being functional and the control cell indicates the presence or absence of transcriptional enhancement.

Comparisons between or among various TREs can be assessed by measuring and comparing levels of expression within a single target cell line. It is understood that absolute transcriptional activity of a TRE will depend on several factors, such as the nature of the target cell, delivery mode and form of a TRE, and the coding sequence that is to be selectively transcriptionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the CMV immediate early promoter. This analysis can also indicate negative regulatory regions, i.e., silencers.

Compositions

The present invention also includes compositions, including pharmaceutical compositions, containing the adenoviral vectors described herein. Such compositions are useful for administration in vivo, for example, when measuring the degree of transduction and/or effectiveness of cell killing in an individual. Preferably, these compositions further comprise a pharmaceutically acceptable excipient. These compositions, which can comprise an effective amount of an adenoviral vector of this invention in a pharmaceutically acceptable excipient, are suitable for systemic administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Remington's Pharmaceutical Sciences,* $18^{th}$ Edition, Mack Publishing (1990). Compositions also include lyophilized and/or reconstituted forms of the adenoviral vectors (including those packaged as a virus, such as adenovirus) of the invention.

Other compositions are used, and are useful for, detection methods described herein. For these compositions, the adenoviral vector usually is suspended in an appropriate solvent or solution, such as a buffer system. Such solvent systems are well known in the art.

Kits

The present invention also encompasses kits containing an adenoviral vector of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow one to detect the presence of target cells in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.

Preparation of the Adenovirus Vectors of the Invention

The adenovirus vectors of this invention can be prepared using recombinant techniques that are standard in the art.

Generally, cell type-specific TREs are inserted 5' to the adenoviral genes of interest, preferably one or more early genes (although late gene(s) may be used). Cell type-specific TREs can be prepared using oligonucleotide synthesis (if the sequence is known) or recombinant methods (such as PCR and/or restriction enzymes). Convenient restriction sites, either in the natural adeno-DNA sequence, or introduced by methods such as PCR or site-directed mutagenesis, provide an insertion site for the cell type-specific TREs. Accordingly, convenient restriction sites for annealing (i.e., inserting) cell type-specific TREs can be engineered onto the 5' and 3' ends of the cell type-specific TRE using standard recombinant methods, such as PCR.

Polynucleotides used for making adenoviral vectors of this invention may be obtained using standard methods in the art such as chemical synthesis recombinant methods and/or obtained from biological sources.

The vectors are conveniently prepared by employing two plasmids, one plasmid providing for the left-hand region of adenovirus and the other plasmid providing for the right hand region, where the two plasmids share at least about 500 nt of middle region for homologous recombination. In this way, each plasmid, as desired, may be independently manipulated, followed by cotransfection in a competent host, providing complementing genes as appropriate, or the appropriate transcription factors for initiation of transcription from the PSE for propagation of the adenovirus.

For convenience, plasmids are available that provide the necessary portions of the adenovirus. Plasmid pXC.1 (McKinnon (1982) *Gene* 19:33–42) contains the wild-type left-hand end of Ad5. pBHG10 provides the right-hand end of Ad5, with a deletion in E3. The deletion in E3 provides room in the virus to insert the 2 kb minimal PSE without deleting the wild-type enhancer-promoter. The gene for E3 is located on the opposite strand from E4 (r-strand).

For manipulation of the early genes, the transcription start site of Ad5 EIA is at nt 560 and the ATG start site of the EIA protein is at nt 610 in the virus genome. This region can be used for insertion of the cell specific element, e.g., PSE. Conveniently, a restriction site may be introduced by employing the polymerase chain reaction (PCR), where the primer that is employed may be limited to the Ad5 genome, or may involve a portion of the plasmid carrying the Ad5 genomic DNA. For example, where pBR322 is the backbone, the primers may use the EcoRI site in the pBR322 backbone and the XpaI site at nt 1339 of Ad5. By carrying out the PCR in two steps, where overlapping primers at the center of the region introduce a sequence change resulting in a unique restriction site, one can provide for insertion of the cell specific response element at that site.

A similar strategy may also be used for insertion of the cell specific response element to regulate EIB. The EIB promoter of Ad5 consists of a single high-affinity recognition site for SpI and a TATA box. This region extends from 1636 to 1701 nt. By insertion of the cell specific response element in this region, one can provide for cell specific transcription of the EIB gene. By employing the left-hand region modified with the cell specific response element regulating EIA, as the template for introducing the cell specific response element to regulate EIB, the resulting adenovirus will be dependent upon the cell specific transcription factors for expression of both EIA and E1B.

For example, we have introduced an AgeI site 12 bp 5' to the E1A initiation codon (Ad5 nucleotide 547) by oligo-directed mutagenesis and linked PCR. In addition, an EagI site was created upstream of the EIB start site by inserting a G residue at Ad5 nt 1682 by oligonucleotide directed mutagenesis. To simplify insertion of a TRE in the EagI site, the endogenous EagI site in CN95 was removed by digestion with EagI, treatment with mung bean nuclease, and religation to construct CN114. In this way, we generated an adenovirus vector containing unique AgeI and EagI sites in the proximal upstream region to E1A and E1B, respectively. Using these unique sites, one can insert a TRE which has engineered AgeI or EagI sites, thus simplifying construction of recombinant adenovirus vectors. Accordingly, the invention includes an adenoviral vector comprising a unique AgeI site 5' of the E1A initiation codon and a unique EagI site 5' of E1B.

For E4, one must use the right-hand portion of the adenovirus genome. The E4 transcription start site is predominantly at nt 35605, the TATA box at nt 35631 and the first AUG/CUG of ORF1 is at nt 35532 (Virtanen et al. (1984) *J. Virol.* 51:822–831). Using any of the above strategies for the other genes, the cell specific response element may be introduced in the region between the transcription start site and the initiation codon. Once again, by employing a previously manipulated adenovirus genome, one can provide for a plurality of genes being dependent upon the target cell specific transcription factor, insuring that the adenovirus will be incapable of replication in cells lacking these transcription factors.

Similarly, a cell type-specific TRE may be inserted upstream of the E2 gene to make its expression cell type-specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Microbiol. and Immunol.* (1995) 199 part 3:177–194).

The E2 late promoter overlaps with the coding sequences of a gene encoded by the counterstrand and is therefore not amenable to genetic manipulation. However, the E2 early promoter overlaps only for a few base pairs with sequences coding for a 33-kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor biding sites E2F and ATF. Therefore, insertion of a cell type-specific TRE having SpeI ends into the SpeI site in the plus-strand would disrupt the endogenous E2 early promoter of Ad5 and should allow TRE regulated expression of E2 transcripts.

For E4, one must use the right hand portion of the adenovirus genome. The E4 transcription start site is predominantly at nt 35609, the TATA box at nt 35638 and the first AUG/CUG of ORF1 is at nt 35532. Virtanen et al. (1984) *J. Virol.* 51: 822–831. Using any of the above strategies for the other genes, a heterologous TRE may be introduced upstream from the transcription start site. For the construction of mutants in the E4 region, the co-transfection and homologous recombination are performed in W162 cells (Weinberg et al. (1983) *Proc. Natl. Acad. Sci. USA* 80:5383–5386) which provide E4 proteins in trans to complement defects in synthesis of these proteins.

Methods of packaging adenovirus polynucleotides into adenovirus particles are known in the art and are described in the Examples.

Methods Using the Adenovirus Vectors of the Invention

The subject vectors can be used for a wide variety of purposes, which will vary with the desired or intended result. Accordingly, the present invention includes methods using the adenoviral vectors described above. In one embodiment, methods for using adenovirus vectors comprise introducing an adenovirus vector into a cell, preferably a eukaryotic cell, more preferably a mammalian cell.

Purposes for introducing transient expression include indications that may be treated involving undesired proliferation other than tumors, such as psoriatic lesions, restenosis, wound healing, tissue repair, enhanced immune response, resistance to infection, production of factors, enhanced proliferation, investigation of metabolic or other physiological pathways, comparison of activity of cells in the presence and absence of the adenovirus introduced transgene, by comparing the activity of the cell before, during and after the modification with the adenovirus, etc. The subject vectors can be used to free a mixture of cells of a particular group of cells, where the group of cells is the target cells. By having the adenovirus be selectively competent for propagation in the target cells, only those cells will be killed on proliferation of the adenovirus. By combining the adenovirus with the mixture of cells, for example, in culture or in vivo, the adenovirus will only be capable of proliferation in the target cells. In this way cells other than the target cells will not be affected by the adenovirus, while the target cells will be killed. The expansion of the adenovirus due to propagation in the target cells will ensure that the mixture is substantially freed of the target cells. Once the target cells are destroyed, the adenovirus will no longer be capable of propagation, but in culture may be retained so as to continually monitor the mixture for recurrence of the target cell, e.g., a mutated cell or neoplastic cell.

By identifying genes that are expressed specifically by the target host cells, based on the nature of the cells, their level of maturity or their condition, the target cell specific response element can be used to provide genetic capability to such cells, where the genetic capability will be absent in other cells, even when transfected with the adenovirus vehicle.

In one embodiment, methods for using adenovirus vectors comprise introducing an adenovirus vector into a target cell, preferably a neoplastic cell. In another embodiment, methods for using adenovirus vectors comprise introducing an adenovirus vector into a prostate cell. In another embodiment, methods for using adenovirus vectors comprise introducing an adenovirus vector into a liver cell. In another embodiment, methods for using adenovirus vectors comprise introducing an adenovirus vector into a breast cancer cell. In another embodiment, methods for using adenovirus vectors comprise introducing an adenovirus vector into a colon cancer cell.

In one embodiment, methods are provided for conferring selective cytotoxicity in cells which allow function of the cell type-specific TRE, comprising contacting cells with an adenovirus vector described herein, such that the adenovirus vector(s) enters, i.e., transduces the cell(s). Cytotoxicity can be measured using standard assays in the art, such as dye exclusion, $^3$H-thymidine incorporation, and/or lysis.

In another embodiment, methods are provided for propagating an adenovirus specific for cells which allow function of the cell type-specific TRE(s), preferably eukaryotic cells, more preferably mammalian cells. These methods entail combining an adenovirus vector with mammalian cells which allow function of the cell type-specific TREs, whereby said adenovirus is propagated.

Another embodiment provides methods of killing cells that allow a cell type-specific TRE to function (i.e., target cells) comprising combining the mixture of cells with an adenovirus vector of the present invention. The mixture of cells is generally a mixture of cancerous cells in which the cell type-specific TREs are functional and normal cells, and can be an in vivo mixture or in vitro mixture.

The invention also includes methods for detecting cells in which a cell type-specific TRE is functional in a biological sample. These methods are particularly useful for monitoring the clinical and/or physiological condition of an individual (i.e., mammal), whether in an experimental or clinical setting. For these methods, cells of a biological sample are contacted with an adenovirus vector, and replication of the adenoviral vector is detected. A suitable biological sample is one in which target cells may be or are suspected to be present. Generally, in mammals, a suitable clinical sample is one in which target cancerous cells are suspected to be present. Such cells can be obtained, for example, by needle biopsy or other surgical procedure. Cells to be contacted may be treated to promote assay conditions such as selective enrichment and/or solubilization. In these methods, target cells can be detected using in vitro assays that detect proliferation, which are standard in the art. Examples of such standard assays include, but are not limited to, burst assays (which measure virus yields) and plaque assays (which measure infectious particles per cell). Also, propagation can be detected by measuring specific adenoviral DNA replication, which are also standard assays.

The invention also provides methods of modifying the genotype of a target cell, comprising contacting the target cell with an adenovirus vector described herein, wherein the adenoviral vector enters the cell.

The invention further provides methods of suppressing tumor cell growth, comprising contacting a tumor cell with an adenoviral vector of the invention such that the adenoviral vector enters the tumor cell and exhibits selective cytotoxicity for the tumor cell. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage. "Suppressing" tumor growth indicates a growth state that is curtailed when compared to growth without contact with, i.e., transfection by, an adenoviral vector described herein. See Example 3, FIG. 6.

The invention also provides methods of lowering the levels of a tumor cell marker in an individual, comprising administering to the individual an adenoviral vector of the present invention, wherein the adenoviral vector is selectively cytotoxic in cells producing the tumor cell marker. Tumor cell markers include, but are not limited to, PSA, CEA and hK2. Methods of measuring the levels of a tumor cell marker are known to those of ordinary skill in the art and include, but are not limited to, immunological assays, such as enzyme-linked immunosorbent assay (ELISA), using antibodies specific for the tumor cell marker. In general, a biological sample is obtained from the individual to be tested, and a suitable assay, such as an ELISA, is performed on the biological sample. See Example 3, FIG. 7.

The invention also provides methods of treatment, in which an effective amount of an adenoviral vector(s) described herein is administered to an individual. For example, treatment using an adenoviral vector(s) in which at least one cell type-specific TRE is specific for prostate cells (e.g., PSE-TRE, PB-TRE, and/or hKLK2-TRE) is indicated in individuals with prostate-associated diseases as described above, such as hyperplasia and cancer. In this example, also indicated are individuals who are considered to be at risk for developing prostate-associated diseases, such as those who have had disease which has been resected and those who have had a family history of prostate-associated diseases. Determination of suitability of administering adenoviral vector(s) of the invention will depend, inter alia, on assessable clinical parameters such as serological indications and histological examination of tissue biopsies. Generally, a pharmaceutical composition comprising an adenoviral vector(s) is administered. Pharmaceutical compositions are described above.

The following examples are offered by way of illustration and not by way of limitation.

EXAMPLE 1

Replication Competent Prostate-Specific Attenuated Adenoviruses

Replication-competent adenoviral vectors were constructed in which a PSE mediates transcription of at least one adenoviral gene.

1. Ad5 with PSE Driving Expression of EIA

The cloning and characterization of a minimal prostate-specific enhancer (PSE) is described in Prostate Specific Antigen Expression is Regulated by an upstream Enhancer (Schuur et al., supra). Plasmid CN71 contains our minimal PSE (from−5322 bp to −3875bp relative to the transcription start site of the PSA gene) and −532 to +11 of the PSA promoter. CN71 was cut with XhoI/HindIII which removes the PSA promoter. A shorter promoter, from −230 to +7, amplified by PCR using primers:

```
18.119,
5'-GGACCTCGAGGTCTCCATGAGCTAC, and     (SEQ ID NO:12)

15.59B,
5'-AGCTCGAGCTTCGGGATCCTGAG.           (SEQ ID NO:13)
```

The PCR product was cut with XhoI/HindIII and ligated back into XhoI/HindIII cut CN71 creating CN105.

1A. Attenuated Ad5 with PSE Driving EIA and Retaining the Endogenous Ad5 E1A Promoter and Enhancer The EIA gene is expressed immediately after viral infection (0–2 hours) and before any other viral genes. The E1A protein acts as a trans-acting, positive-acting transcriptional regulatory factor required for the expression of the other early viral genes, EIB, E2, E3, E4, and the promoter proximal genes of the major late genes. Despite the nomenclature, the promoter proximal genes driven by the major late promoter are expressed during early times after Ad5 infection (Flint (1982) *Biochem. Biophys. Acta* 651:175–208; Flint (1986) *Advances Virus Research* 31:169–228; Grand (1987) *Biochem. J.* 241:25–38). In the absence of a functional EIA gene, viral infection does not proceed for the gene products necessary for viral DNA replication are not produced (Nevins (1989) *Adv. Virus Res.* 31:35–81). The transcription start site of Ad5 EIA is at nt 560 and the ATG start site of the E1A protein is at nt 610 in the virus genome.

pXC.1 was purchased from Microbix Biosystems Inc. (Toronto). pXC.1 contains Adenovirus 5 sequences from bp22 to 5790. We have introduced an AgeI site 12 bp 5' to the E1A initiation codon (Ad5 nucleotide 547) by oligo-directed mutagenesis and linked PCR. The plasmid pXC.1 was PCR amplified using primers:

15.133A, 5'-TCGTCTTCAAGAATTCTCA (SEQ ID NO:14), containing an EcoRI site, and 15.134B, 5'-TTTCAGTCACCGGTGTCGGA (SEQ ID NO:15), containing an extra A to introduce an AgeI site. This created a segment from the EcoRI site in the pBR322 backbone to Ad5 nt 560. A second segment of pXC.1 from Ad nucleotide 541 to the XbaI site at Ad nucleotide 1339 was amplified using primers:

15.133B, 5'-GCATTCTCTAGACACAGGTG (SEQ ID NO:16) containing an XbaI site, and 15.134A, 5'-TCCGACACCGGGTGACCTGAAA (SEQ ID NO:17), containing an extra T to introduce an AgeI site. A mixture of these two PCR amplified DNA segments was mixed and amplified with primers 3 and 4 to create a DNA segment from the EcoRI site to the XbaI site of pXC.1. This DNA segment encompasses the leftmost 1317 bases of Adenovirus sequence and contained an AgeI site at Ad nucleotide 547. This DNA segment was used to replace the corresponding segment of pXC.1 to create CN95. Similarly, a PSE with AgeI ends was PCR amplified from CN105 using primers:

15.176A, 5'-CATTAACCGGTACCTCTAGAAAATCTAGC (SEQ ID NO:18) and 15.176B, 5'-CATTAACCGGTAAGCTTGGGGCTGGGG (SEQ ID NO:19) and cloned into CN95. The virus created by homologous recombination of CN96 and BHG10 was designated CN706.

1B. Attenuated Ad5 with PSE Driving Ad5 EIA Deleted for the Ad5 Endogenous Promoter and Enhancer In order to reduce ubiquitous expression of the EIA gene we decided to delete the endogenous E1A transcription regulatory DNA sequences. The transcriptional regulatory sequences of the EIA gene are intricately embedded in DNA sequences essential for DNA packaging (see Graeble and Hearing (1992) and References cited therein). Graeble and Hearing (1990) have shown that an Adenovirus 5 with a deletion from bp 194 to bp 316 which eliminates all transcriptional regulatory elements and retains only three out of seven packaging signals reduced the yield only 3-fold compared to wild type. These observations suggested that the EIA transcription regulatory sequences are dispensable and the loss of the first three out of seven packaging signals allowed virus production in acceptable quantities.

a. In the first variant, the region of the Ad5 genome containing the EIA enhancer and promoter and the Ad5 packaging sequence were deleted and replaced with a synthetic DNA segment containing a mutated packaging sequence and a PCR amplified segment of the PSE from CN127. In this construction the EcoRI/XbaI fragment of pXC.1 containing the first 1339 bases of the Ad5 genome was cloned into pUC19 to construct CN172 as a substrate for further manipulations. The DNA sequences corresponding to Ad5 nt 123 to nt 497 were deleted from CN172 by PCR amplification using primers:

26.153.1, 5'-CCGCTCGAGATCACACTCCGCCACAC (SEQ ID NO:20) containing an XhoI site, and 26.153.2, 5'-CCGCTCGAGCACTCTTGAGTGCCA (SEQ ID NO:21), containing an XhoI site. Cleavage of the PCR product with XhoI followed by religation resulted in CN178 in which an XhoI site replaced Ad5 nt 123 to 497. The synthetic DNA segment containing the mutated Ad5 packaging sequences was composed of the following two strands:

26.160.1:
5'-TCGAGGGATGTTGTAGTAAATTTGGGCGTAACCGAGTAAGATTTGGCCATTTTCGCGGGAAAACTGAATAAGACTC (SEQ ID NO:22)

TTCGAAATCTGAATAATTTTGTGTTACTCATAGCGCGTAATATTTGTCTAGGGCCGCGGGGACTTTGACCGTTTAC

GTGG 26.160.2:
5'-GATCCCACGTAAACGGTCAAAGTCCCCGCGGCCCTAGACAAATATTACGCGCTATGAGTAACACAAAATTATTCAG (SEQ ID NO:23)

ATTTCGAAGAGTCTTATTCAGTTTTCCCGCGAAAATGGCCAAATCTTACTCGGTTACGCCCAAATTTACTACAACA

TCCC

The strands were annealed and kinased using T4 polynucleotide kinase to form the dsDNA and allow ligation to the other DNA segments in the construct.

The PSE segment used for ligation was PCR amplified from CN127 using primers:

26.160.3, 5'-GGAAGATCTGAAATCTAGCTGATATAG (SEQ ID NO:24), containing an XhoI site, and 19.16.5,5'-TTCTCGAGAAGCTTGGGGCTGGGG (SEQ ID NO:25), containing XhoI and HinDIII sites. For ligation, the PSE PCR product and CN178 were both cleaved with XhoI. The XhoI cut CN178, XhoI cut PSE PCR product, and the kinased packaging oligonucleotide were mixed in equal molar ratios and ligated with T4 DNA ligase. The resulting recombinant was designated CN201. The EcoRI/XbaI segment of CN201 containing the mutated packaging sequence and PSE driving EIA was excised from CN201 and used to replace the homologous segment of pXC.1 to generate CN202.

b. In the second variant, a different strategy was employed. In order to perform the deletion mutagenesis with a relatively small plasmid, a 2297 bp EcoRI-XhoI fragment of plasmid CN145, which contains the left end Adeno sequences including the EIA promoter region and the PSA enhancer, was subcloned into similarly cut pBluescript SKII+ yielding plasmid CN169.

The plan for the deletion mutagenesis was to delete the sequences from Ad position 194–301 and replace them with a SalI restriction site 5'-GTCGAC-3' which served as diagnostic marker to distinguish mutagenized plasmids from parental plasmids. The deletion eliminated all EIA core and E2F transcription regulatory elements as well as packaging signals AI and AII, but will preserve packaging signals AIII, AIV, AV, AVI and AVII. To this end, two oligonucleotide primers were synthesized:

28.134A, 5'-GTCGACGTGAAATCTGAATAATTTT TGTTACTCATAGC (SEQ ID NO:26). This primer matches to sequences 302–334 in Ad5.

28.134B, 5'-CACCGGCGCACACCAAAAACGTC (SEQ ID NO:27). This primer matches to sequences 171–193 in Ad5.

The PCR mutagenesis kit from Stratagene was used in the following manipulations. In a PCR tube, 15 pMol of each primer was added to 0.5 pMol CN169; 1 mM dNTP, 2.5 μl 10×PCR 11 (Stratagene), $dH_2O$ to 24 μl and 0.5 μl each of Taq Polymerase and TaqExtender (Stratagene). The mixture was overlaid with 20 μl mineral oil and programmed for PCR: 94° C. 4 minutes, 63° C. 1 minute, 72° C. 4 minutes for cycle and 94° C. 1 minute, 63° C. 1 minute, 72° C. 4 minutes for 10 cycles. 1 μl Dpn I restriction enzyme (Stratagene) was added to cut parental DNA and incubated at 37° C. for 80 minutes followed by the addition of 1 μl Pfu Polymerase (Stratagene) and incubation at 72° C. for 50 minutes to fill up protruding DNA ends generated during the former PCR process by the Taq polymerase. The PCR yielded a 5 kb linear DNA which was ligated with T4 DNA ligase to recircularize. XL-1 bacteria were transformed with the ligation reaction and mutagenized recombinants were identified by virtue of the presence of the unique SalI restriction site. One of the recombinants, CN 179, was used to rebuild the parental plasmid CN145 with the deletion by swapping the EcoRI-XhoI fragment of CN145 containing the Adeno-and PSE sequences with the one of CN179, yielding plasmid CN185. Plasmid CN185 was used in cotransfections with BHG11 into human 293 cells to generate recombinant Adenoviruses. Nine virus plaques were isolated. One virus isolate was designated CN724.

2. Attenuated Ad5 with PSE Driving Expression of EIB

The EIB protein functions in trans and is necessary for transport of late mRNA from the nucleus to the cytoplasm. Defects in EIB expression also results in poor expression of late viral proteins and an inability to shut off host-cell protein synthesis. The promoter of EIB has been implicated as the defining element of difference in the host range of Ad40 and Ad5: clinically Ad40 is an enterovirus, whereas Ad5 causes acute conjunctivitis (Bailey, Mackay et al. (1993) *Virology* 193:631; Bailey et al. (1994) *ibid* 202:695–706). The EIB promoter of Ad5 consists of a single high-affinity recognition site for SpI and a TATA box.

To insert a PSE driving expression of EIB in Ad5, an EagI site was created upstream of the EIB start site by inserting a G residue at Ad5 nt 1682 by oligonucleotide directed mutagenesis as above. To simplify insertion of the PSE in the EagI site the endogenous EagI site in CN95 was removed by digestion with EagI, treatment with mung bean nuclease, and religation to construct CN114. The primers:

15.133A, 5'-TCGTCTTCAAGAATTCTCA (SEQ ID NO:14), containing an EcoRI site, and 9.42, 5'-GCCCACGGCCGCATTATATAC (SEQ ID NO:28), containing an extra C, were used to amplify the segment between the EcoRI site and Ad5 nt 1682.

Primers:

9.39, 5'-GTATATAATGCGGCCGTGGGC (SEQ ID NO:29) containing an extra G, and 24.020, 5'-CCAGAAAATCCAGCAGGTACC (SEQ ID NO:30), containing a KpnI site, were used to amplify the segment between 1682 and the KpnI site at Ad5 nt 2048. Co-amplification the two segments with primers 9 and 12 yields a fragment with an EagI site at Ad5 nt 1682 which was used to replace the corresponding EcoRI/KpnI site in pXC.1 to construct CN124. PSE amplified from CN105 with primers:

26.1.1, 5'-TAACGGCCGTCTAGAAATCTAGCTGA (SEQ ID NO:31) and 26.1.2, 5'-TAACGGCCGAAGCTTGGGCTGGG (SEQ ID NO:32), with EagI ends, was ligated into the EagI site of CN124 to construct CN125. The resultant virus from homologous recombination of CN125 and BHG10 was designated CN711.

3. Attenuated Ad5 with PSE Driving Expression of Both EIA and EIB

A left end Ad5 plasmid with the PSE driving expression of both EIA and EIB was constructed by PCR amplifying CN95 with primers 9–12 as described for the construction of CN124. The resulting DNA segment contains the AgeI site derived from CN95 and the EagI site derived from the PCR mutagenesis. This DNA segment was cloned back into CN114 (the plasmid from which the EagI site was removed from pXC.1) to construct the plasmid CN144. CN144 contains a single AgeI site at Ad5 nt 547, and a single EagI site at Ad5 nt 1682. PSE segments were PCR-amplified with AgeI ends from CN105 or EagI ends, also by PCR from CN105, as described above and ligated into the appropriate sites of CN144 to construct CN145. CN145 is a plasmid in which the PSE drives expression of both EIA and EIB while retaining the Ad5 endogenous promoters and enhancers of both genes. Clones with the PSE in the left to right orientation were chosen. The endogenous Ad5 EIA and EIB promoter/enhancers were moved upstream by insertion of both PSE segments. The resultant virus derived by homologous recombination of CN145 and BHG10 was designated CN716.

4. Attenuated Ad5 with PSE Driving Expression of E4

E4 is located at the far right-hand end of the Ad5 genome and read right-to left from the 1-stand (Flint, supra). E4 can be deleted from the Ad5 genome and supplied in trans by W162 cells, a derivative of VERO cells (Weinberg and Ketner, supra). The transcription products of E4 are complex. Open-reading frames (ORF) 3 and ORF 6 of the E4 transcription unit increase the accumulation of major late transcription unit mRNAs by binding the 55-kDa protein from E1B (Dix and Leppard (1993) *J. Virol.* 67:3226–3231) and heterodimers of E2F-1 and DP-1 (Helin and Harlow (1994) *J. Virol.* 68:5027–5035). Mutations such that neither ORF 3 nor ORF 6 encode functional proteins, produce plaques with an efficiency less than $10^{-6}$ that of wild-type virus (Bridge and Ketner (1989) *J. Virol.* 67:5911–5921).

To facilitate insertion of the PSE driving E4 expression, the 10 kb EcoRI fragment of BHG10 containing the 3' 8 kb of Ad5 plus a portion of the pBR322 backbone was cloned into the EcoRI site of Bluescript KSII+ to construct CN108. A DraIII site at Ad nt 33906 was eliminated by partial digestion of CN108, end filling with Klenow, and relegation to construct CN113. An XhoI site was introduced at Ad nt 35577 by oligonucleotide directed mutagenesis and linked PCR as described above using primers:

10.1, 5'-TAACTCACGTTGTGCATTGT (SEQ ID NO:33), containing a DraII site, 10.4, 5'-GGTGCCGTGCTCGAGTGGTGT (SEQ ID NO:34), containing an extra C, 10.3, 5'-ACACCACTCGAGCACGGCACC (SEQ ID NO:35), containing an extra G, 19.158, 5'-GCTACTATTCGACAGTTTGTACTG (SEQ ID NO:36), containing a ClaI site.

The PCR product containing an XhoI site as well as DraIII and CIaI ends was used to replace the corresponding DraIII/ClaI fragment of CN113 to construct CN122.

Plasmid CN70 contains the minimal PSE (from−5322 bp to −4023 bp relative to the transcription start site of the PSA gene) and −532 to +11 of the PSA promoter. CN70 was cut with XhoI/HindIII which removes the PSA promoter. A shorter promoter, from −230 to +7, amplified by PCR using primers:

18.119, 5'-GGACCTCGAGGTCTCCATGAGC TAC (SEQ ID NO:12), and 15.59B, 5'-AGCTCGAGCTTCGGGATCCTGAG (SEQ ID NO:13), was ligated in it's place to construct CN104. CN127 was constructed from CN104 as follows: CN104 was cut with XhoI, end-filled with Klenow, and relegated to remove the XhoI site. The PSE from CN127 was PCR amplified using primers:

19.16.1, 5'-GGGTCGACGTACCTCTAGAAATCTAGC (SEQ ID NO:37) and 19.16.5, 5'-TTGTCGACMGCTTGGGGCTGGGG (SEQ ID NO:25), to create SalI ends. This DNA segment was then ligated to XhoI cut CN122 to insert the PSE in the correct orientation upstream of E4. The resulting plasmid was designated CN135. The kanamycin resistance gene from pABS4 (Microbix) was inserted into CN135 at the Pacl site to construct CN146; the EcoRI fragment of CN146 (containing the adenovirus sequences with the inserted PSE and kanamycin resistance gene) was then ligated to the large EcoRI fragment of BHG10, replacing the homologous wild type Ad sequences in BHG10. Recombinants were identified by resistance to both ampicillin and kanamycin, then the kanamycin gene was excised by PacI digestion and relegation to yield CN190 which is BHG10 with the PSE inserted upstream of the E4 coding region.

5. Attenuated Ad5 with PSE Driving Ad5 EIA containing Cytosine Deaminase in ΔE3

A prostate specific adenovirus vector that contains the cytosine deaminase ("cd") gene incorporated into its genome could deliver this gene to targeted tissue (i.e. prostate tumors). Consequently, infected cancer cells would metabolize 5-FC and release the chemotherapeutic agent 5-FU into the surrounding tissue suppressing cell division, and exhibit the so-called "bystander effect" (Hirshowitz et al. (1995) *Human Gene Ther.* 6:1055–1063; Griffith and Jarvis (1993) *J. Biol. Chem.* 268:20085–20090). In contrast, noninfected, nonproximal cells would not be affected. This suggests two uses for the cd gene in an attenuated adenovirus vector. First, cd can serve as an additional therapeutic agent to provide a bystander killing ability and expedite local tumor reduction without systemic toxicity (Moolten and Wells (1990) *J. Nat'l Cancer Inst.* 82:297–300). Second, the gene can serve as a recall mechanism to halt a runaway infection by preventing viral DNA and RNA synthesis in infected and noninfected, local cells.

The enzyme cytosine deaminase, which deaminates cytosine to uracil, is found in many bacteria and fungi. These microorganisms can convert 5-fluorocytosine (5-FC), a harmless prodrug, to 5-fluorouracil (5-FU), a highly toxic compound that inhibits both DNA and RNA synthesis (Calibrisi and Chabner *Goodman and Gilman's The Pharmacological Basis of Therapeutics* (Eds. A. G. Gilman, T. Rall, A. S. Nies, and P. Taylor, Pergamon, N.Y.) (1990) 8 ed., pp 1209–1263); Damon et al. (1989). Because mammalian cells do not express significant amounts of the cd gene, they are not sensitive to 5-FU. Mammalian cells modified by gene transfer to express the gene can metabolize 5-FC, however. In this application, cd acts as a "suicide gene" selectively conferring sensitivity to those cells that contain the gene.

Adenovirus Vector Construction. The plasmid pCMV-cd, which contains cd coding region downstream of the CMV promoter, was obtained from David Crooks (Stanford). A SpeI restriction endonuclease site located in a multiple cloning region between the promoter and the cd ATG was removed by digesting the plasmid with enzymes which recognize sequences flanking the SpeI site, BamHI and EcoRI, filling the ends with Klenow, and relegating (CN130). With this site removed, the CMV-cd cassette was cloned by digesting CN130 with SpeI and ligating the appropriate fragment into the XbaI site in pABS4 (Microbix, Toronto), a shuttle plasmid containing the kanamycin-resistance gene (CN131). By digesting CN131 with PacI, a fragment containing the $Kan^R$ gene and the cd gene was isolated and ligated into similarly cut BHG11 (Microbix), which contains a unique PacI site engineered in the E3 region of Ad5 (CN141). The $kan^R$ gene was removed by digesting CN141 with SwaI and religating the vector (CN148).

Two Ad5 recombinant viruses containing the cd gene in the E3 region were constructed. The first contains only the CMV-cd cassette in the E3 region (CN719). The second has the CMV-cd cassette in E3 and the prostate specific enhancer (PSE) minimal element modulating expression of EIA proteins (CN720). Viruses were generated by homologous recombination in low passage 293 cells, a human kidney cell line that expresses Ad EIA and EIB proteins, accomplished by cotransfecting them with pXCI/CN148 and CN145(PSE-E1A)/CN148.

In vitro Characterization. In this first functional assay, CN720, an attenuated, prostate-specific adenovirus containing the cd gene in the E3 region, was studied to test its ability to confer 5-FC sensitivity on infected cells and neighboring cells. Wild type Ad5 (CN702) was also tested. CV1 cells, a semipermissive monkey kidney cell line, seeded in four, 96 well microtitre plates in DMEM, 5% FBS, were infected in a series of 1:2 dilutions from wells 1–11 with either CN702 or CN720. The multiplicity of infection of well one was approximately twenty-five for CN702 and two for CN720. Row 12 in each plate was left as an noninfected control. One day post infection the media was changed. Two plates of cells, one infected with CN720 and one infected with CN702, were treated with 5 mM 5-FC. The media on the remaining two plates was changed with complete DMEM only. These infected, untreated cells illustrate the lytic ability of the virus and were used to differentiate between the two causes of cell death in this experiment, virus cell lysis and 5-FU toxicity. The cells were fixed with 50% methanol-50% acetone and stained with Giemsa stain 6 days after the prodrug was administered. Plates were assayed by measuring absorbance at 530 nm in a SpectraMAX 340 microtitre plate reader (Molecular Devices). Cell survival was calculated by relating the absorbance of the cells in the noninfected wells to the absorbance in infected wells. The results were graphed as cell survival versus virus dilution.

Several conclusions can be made from this experiment. Most important, the graph suggests that the recombinant adenoviruses are expressing the cd gene. While the cell killing ability of both viruses appears to increase in the presence of 5-FC, perhaps due to a generalized toxicity to high concentrations of the prodrug, the change in cell killing is dramatic for CN720. The graph of CN720 shows a clear cell survival difference between 5-FC treated cells and untreated cells indicative of a 5-FU bystander effect. This result illustrates the potential to exploit cd function to either enhance the killing potential of Ad5 or to harness a runaway infection by generating an intracellular pool of toxic drug in noninfected cells that prevents DNA replication, a recall mechanism.

As an in vitro model, six 96 well plates were seeded with a human intestine epithelia cell line, DLD-1, that is permissive to human Ad in DMEM, 10% FBS. They were infected as described above with Ad5-cd virus (CN719). Prodrug (1 mM) was added to one plate at each time point, 0 hrs, 24 hrs, and 48 hrs post infection. The remaining three plates were untreated and served as infected controls. One set of two plates, one with prodrug, one without, was harvested on day 7, 8, and 9 post infection.

These results corroborate the previous data and extend it. Increased cell death is seen at all time points in infected pro-drug treated cells relative to infected but untreated cells. These data also reveal that the bystander effect is more pronounced as the infection becomes more advanced. When 5-FC is added at 24 hours and at 48 hours post infection, cell death is greater than when the prodrug is added immediately after initial infection. These data demonstrate that a tissue specific adenovirus harboring the cd gene has superior killing ability to wild type adenovirus.

6. Attenuated Ad5 with PSE Driving E1A and SV40 T Antigen in ΔE3 to Increase Host Range to Include Monkey and Human Cells Human adenovirus does not efficiently replicate in monkey cells. Associated with decreased levels of fiber mRNA in the cytoplasm, the abortive infection is caused by defects in the late gene expression regulated by E4 proteins (Ross and Ziff (1992) *J. Virology* 66:3110–3117). Adenovirus-SV40 hybrids—shown to contain a small portion of the SV40 genome coding for the large T antigen integrated into the E3 region of the adenovirus 2 genome, overcome this defect and lyse monkey cells (Lewis and Rowe (1970) ibid 5:413–420; Lewis et al, (1973) ibid 11:655–664). The large T antigen (Tag) is believed to confer this host-range capability on these hybrids (Tijan et al., (1979) *PNAS* 75:1279–1283). Several Ad2-SV40 hybrids have been isolated from SV40 and Ad2 infected cultures, each containing a conserved amount of the Tag carboxy terminal coding region and varying lengths of amino terminal coding region.

We have adopted this paradigm to develop Ad5 tissue specific, host-range mutants for use in monkey studies. Two strategies were undertaken. The first used the host-range mutant Ad2+ ND1, which harbors SV40 Tag coding sequence from map units 0.28–0.11, as a model (Zain & Roberts (1978) *J. Mol. Biol* 120:13). A 666 base pair PstI/BamHI restriction fragment in the plasmid pDIS (obtained from Edgar Schrieber), a plasmid which contains the entire Tag coding sequence, the endogenous SV40 early promoter, and an inverted SV40 enhancer, contains the appropriate 3' sequence and was cloned via the shuttle plasmid pABS4 (Microbix) into the unique PacI restriction site in the E3 region of BHG11 (Microbix). Upstream of the coding sequence was cloned an oligo (+) strand:

26.99.1, 5'-GTTIGTGTATITTTAGATCAAAGATGCTGCA (SEQ ID NO:38), and (−) strand:

26.99.2, 5'-GCATCTTTGATCTAAAATACACAAAC (SEQ ID NO:39), that contains a splicing acceptor sequence, ribosome recognition sequences, and an ATG to achieve expression of the appropriate peptide (CN170). Expression of this construct is dependent on a transcript originating from the major late promoter.

The second strategy involved creating an internal deletion in the Tag sequence in the plasmid pDIS between the EcoNI site in the amino terminal region and the PstI site in the carboxy terminal coding sequence by using an adapter oligo (+) strand:

27.183.1, 5'-TAAAGGAGGAGATCTGCCTAAAACACTGCA (SEQ ID NO:40), and (−) strand:

27.183.2, 5'-GTGTTTTAGGCAGATCTCCTCCTTT (SEQ ID NO:41).

The entire transcription unit, including the enhancer, promoter, and the coding sequence was excised by HpaII/

BamHI digestion and cloned via shuttle plasmid into the unique PacI site of BHG11 (CN183). This method generates a discrete transcription unit in Ad5 sequence whose expression is not dependent on the major late promoter.

Two host-range Ad5-SV40 viruses were produced. Both contain the carboxy termini of the Tag but lack the promoter. One is a tissue-specific, attenuated virus with the prostate specific enhancer (PSE) modulating expression of the EIA proteins (CN725). The other is wild type Ad5 with a Tag insertion (CN726). Both were generated by homologous recombination by cotransfecting 293 cells, a human kidney cell line that expresses Ad EIA and EIB proteins, with CN145(PSE-EIA) or pXCI (wild type Ad5 left hand end) and CN170.

Host-Range Mutant Characterization. Wild type Ad5 (CN702) and CN726 were plaqued on both 293 cells and CV1 cells, an African Green Monkey kidney cell line. Plaques were counted in both cell monolayers and a ratio between the plaques in the two cell lines was determined. The ratio for CN726 and CN702 was 0.01 and 0.0007, respectively. The capability of replication of adenovirus in monkey cells allows preclinical evaluation of recombinant attenuated adenoviruses in monkeys, yielding valuable information for dosage and formulation of these viruses as therapeutic agents in humans.

7. Construction of Recombinant DNA to Introduce Mutations in E2, the DNA Binding Protein (DBP), for the Generation of Recombinant Ad5 with Extended Host Range Allowing Replication in Human and Monkey Cells Wild type adenovirus type 5 is only replication competent in human cells. For preclinical evaluation of therapeutic attenuated adenoviruses it would be desirable to test efficacy and toxicity in large human-like animals such as monkeys. A host range mutant hr404 has been described that confers a replication phenotype of human Ad5 in monkey cells (Klessig & Grodzicker (1979) *Cell* 17:957–966). The nature of the hr404 mutation was shown to be a single point mutation C-->T at adeno position 32657 in the DBP gene resulting in a change of Histidine to Tyrosine amino acid at codon 130 (HI30Y) in the 72K DNA binding protein (Kruijer et al. (1981) *Nucleic Acids Res.* 9:4439–4457).

We constructed a recombinant DNA molecule with the 5.8 kb EcoRI-BamHI fragment from plasmid BHG10 (Bett et al., supra) containing the right end sequences of Adenovirus type 5 and introduced by site-directed mutagenesis the H130Y mutation in the DBP gene. This plasmid should allow the construction of recombinant adenoviruses which are capable to replicate in human and monkey cells.

The 5769 bp EcoRI-BamHI fragment of BHG10 (Bett et al., supra) was cloned into similarly cut pBluescript KSII+ resulting in plasmid CN184. In order to eliminate disturbing restriction sites, a 2568 bp XhoI fragment was deleted yielding plasmid CN 186. The mutagenesis upper PCR primer reads:

```
                                        (SEQ ID NO:42)
28.180U,
5'-GCAACCCACCGGTGCTAATCAAGTATGGCAAAGGAGTAAGCGC-3
```

The mutated T residue causing the H130Y mutation is shown in bold underlined style. Shown in italics is the unique SgrAI site in pCN186. The lower PCR primer reads:

28.180L, 5'-TGGCCTTGCTAGACTGCTCCTTCAGC-3' (SEQ ID NO:43)

PCR amplification was done with 100 pMol of each of these primers, 200 ng CN186 as emplate, 1 mM dNTP, 1× Pfu buffer (Stratagene), dH2O to 100 ⊠l, and 5U cloned Pfu polymerase (Stratagene) at 94° C. 1 minute, 60° C. 1 minute, 72° C. 2 minutes for 30 cycles. The PCR yielded the expected DNA fragment of 588 bp. The DNA fragment was purified with a Wizard DNA clean-up column (Promega) and digested with restriction enzymes SgrAI and AflII. The 473 bp fragment of interest containing the H130Y mutation was gel purified and isolated. For reinsertion into the DBP gene, the mutated DNA fragment was ligated with the 1639 bp AscI-SgrAl fragment from CN184 and the 6609 bp AflII-AscI fragment from CN184 resulting in plasmid CN188.

Recombinant adenovirus genomes were constructed by in vitro ligation of the 5.8 kb EcoRI-BamHI fragment of CN188 with a 21562 bp EcoRI-Bst1107 center DNA fragment of BHG10 and Bst1107-cut plasmid CN144. The resultant virus was designated CN723.

The capability of replication of adenovirus in monkey cells allows preclinical evaluation of recombinant attenuated adenoviruses in monkeys, yielding valuable information for dosage and formulation of these viruses as therapeutic agents in humans. Further, with the use of the hr404 mutation in CN723, the same virus used for monkey studies can be used as the human clinical trial virus.

8. Deletion of ORF 1,2,3 and Part of ORF 4 from the E4 Region of Adenovirus Type 5

The E4 region codes for two polypeptides which are responsible for stimulating the replication of viral genomic DNA and for stimulating late gene expression. The protein products of open reading frames (ORFS) 3 and 6 can both perform these functions, however the ORF 6 protein requires interaction with the EIB 55K protein for activity while the ORF 3 protein does not. To further restrict viral replication to prostate epithelial cells E4 orfs 1–3 can be deleted, making viral DNA replication and late gene synthesis dependent on E4 ORF 6 protein. By combining such a mutant with sequences in which the EIB region is regulated by the PSE, a virus can be obtained in which both the EIB function and E4 function are dependent on the PSE driving EIB.

A virus of this type was constructed by combining sequences from the plasmid d11006 which contains an E4 deletion of ORFS 1–3 (Bridge & Ketner, *J. Virol.* (1989) 63:631–638) with BHG10, followed by co-transfection with CN144 to construct a recombinant virus. The plasmid pd11006 is cleaved with AvrII and AgeI to isolate sequences containing the mutated E4 region. This DNA segment is used to replace the homologous segment of CN108 cleaved with the same enzymes.

CN108 contains the 6 kb EcoRI fragment from BHG10 cloned into BSKSII+. Due to the E3 deletion in BHG10, the AvrII site at Ad5 nt 28752 had been deleted. AvrII still cut CN108 at Ad5 nt 35463; AgeI cut CN108 at Ad5 nt 31102. The 4.4 kb AvrII/AgeI fragment from CN108 was replaced with the 3.8 kb AvrII/AgeI fragment from d11006 producing CN203 containing the E4 deletion. The EcoRI fragment from CN203 was cloned into BHG10 to construct CN204. Homologous recombination of CN204 and CN144 yielded the virus CN726.

A similar virus of this type was constructed in the following manner. As previously described AvrII cut CN108 at Ad5 nt 35463. SapI cut CN108 twice, with one of the sites at Ad5 nt 34319. A complete AvrII cut and a partial SapI cut of CN108 and religation removed 1144 bp from E4 yielded CN205. The 5.3 kb EcoRI/BamHI fragment from CN205 was cloned into similarly cut CN188 yielding CN206. The 14 kb BamHI fragment of CN206 containing both the E4 deletion and the hr404 mutation was cloned in BamHI cut BHG10 producing CN207. Homologous recombination of CN144 and CN207 in 293 cells yielded CN727.

9. PSE Controlling the E2 Region of Ad5

The E2 region of Adenovirus 5 codes for proteins related to replication of the adenoviral genome, including the 72 kDa DNA-binding protein, the 80 kDa precursor terminal protein and the viral DNA polymerase. The objective is to control expression of the E2 genes by the prostate-specific PSA enhancer/promoter in a recombinant adenovirus.

The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the EIA transactivator protein, the E2 early promoter is crucial during the early phases of viral replication.

The E2 early promoter, mapping in Ad5 from nt 27053–27121 consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan & Thimmapaya, Current Topics in Microbiology and Immunology (1995) 199 part 3:177–194.

The E2 late promoter overlaps with the coding sequences of the L4 gene encoded by the counterstrand and is therefore not amenable for genetic manipulation. However, the E2 early promoter overlaps only for a few base pairs with sequences coding for a 33 k protein on the counterstrand. Notably, the SpeI restriction site (Ad5 position 27082) is part of the stop codon for the above mentioned 33 kDa protein and conveniently separates the major E2 early transcription initiation site and TATA-binding protein site from the upstream transcription factor biding sites E2F and ATF. Therefore, an insertion of the PSA enhancer/promoter into the SpeI site would disrupt the endogenous E2 early promoter of Ad5 and should allow prostate-restricted expression of E2 transcripts.

Construction of recombinant Ad5 with the PSA enhancer/promoter in the E2 early promoter region. The BamHI-EcoRI fragment of Ad5 (positions 21562–27331) encompassing the E2 region was previously subcloned into pBluescript KSII+ resulting in plasmid CN184. A variant of this plasmid, CN188, carrying a mutation in the DBP gene (HI30Y) allowing extended host range applications has been constructed and described above.

Plasmid CN188 was used for insertion of the PSA enhancer/promoter into the E2 region. The plasmid was linearized with SpeI and the 540 protruding ends were dephosphorylated with calf intestine alkaline phosphatase and then end-filled with Klenow polymerase and dNTP. The blunt ended PSE enhancer/promoter was ligated to SpeI linearized, blunt ended vector CN188. Recombinant DNAs with the PSE enhancer/promoterin the appropriate orientation for directing transcription initiation into the E2 region were identified. Plasmid CN196 contains the PSE enhancer/promoter in the backbone of CN188. The 5.3 kb EcoRI fragment of plasmid CN205, containing a deletion of the orf 1, 2, 3 and 4 of the E4 gene, was inserted in the appropriate orientation into EcoRI cut CN196, yielding plasmid CN197.

A recombinant viral genome with the PSE enhancer/promoter controlling expression of the EIA, EIB and the E2 early genes and the hr404 mutation H130Y in the DBP gene and deletion of open reading frames 1, 2, 3, and 4 of the E4 gene was obtained by in vitro ligation of the 9152 bp BamHI-Bst11071 fragment of CN144 with the 15802 bp Bst11071-BamHI fragment of BHG10 and the 12425 bp BamHI fragment of CN197.

Virus Preparation

Viruses were prepared as described previously (above). Table 1, below, lists the combinations of right end and left end Ad5 plasmids used to generate recombinant Ad5 with the desired features:

TABLE 1

| Virus | Name | Left End Plasmid | Right End Plasmid |
|---|---|---|---|
| PSE-E1A | CN704-708 | CN96 | BHG10 |
| PSE-E1A | CN718 | CN145 | BHG10 |
| PSE-E1B | CN711 | CN125 | BHG111 |
| PSE-E1A/EIB | CN716 | CN144 | BHG10 |
| PSE-E1A/EIB | CN717 | CN144 | BHG10 |
| PSE-E4 | | pXC.1 | CN135-BHG10 |
| ΔEnh/PSE-E1A | CN724 | | BHG10 |
| PSE-E1A, ΔE3 CMV-SV40 T Ag | CN725 | CN96 | CN183 |
| PSE-E1A/EIB, with HR404 with ΔE3 CMV-CD | CN723 | CN144 | CN188, CN108, BHG10 |
| PSE-EIA/EIB. ΔE4 (d11006) | CN726 | CN144 | CN207 |
| PSE-E1A/E1B, hr404, ΔE4 | CN727 | CN144 | CN207 |

Results:

Virus Construction and Genomic Structure.

In the initial round of construction three replication competent, prostate-specific adenoviruses were produced. CN706 which contains the PSE driving the expression of the EIA gene, CN711 which contains the PSE driving the expression of the EIB gene, and CN716 which contains the PSE driving EIA expression and the PSE driving EIB expression. The viruses were generated by homologous recombination in 293 cells and cloned twice by plaque purification. The structure of the genomic DNA was analyzed by PCR and sequencing of the junctions between the inserted sequences and the Ad genomic sequences. All viruses contained the desired structures.

Virus Growth in Vitro.

The growth of the viruses in vitro was characterized by two assays: a burst size assay to measure the amount of infectious particles produced in one round of infection and plaque assays to assess the growth of the viruses in various types of cells.

For the burst size assays either LNCaP cells (a CaP cell line which produces PSA) or HBL100 cells (a non-malignant breast epithelial cell line) were infected with virus at a multiplicity of infection (MOI) of 1 (5×105 PFU per sample). At various time points samples were harvested and the amount of infectious virus present measured by plaque assays on 293 cells. Table 2 shows that CN706 produced $6.3\times10^6$ pfU from an input of $5\times10^5$ pfu in LNCaP cells after 48 hours. In HBL100 cells the increase from the same amount of input virus was to $2.0\times10^6$ pfu. CN706 then yielded 13 pfu per input infectious particle in LNCaP cells which was 3 fold greater than that produced in HBL100 cells over the same time period.

Burst size assays on CN711 also revealed preferential growth in LNCaP cells versus HBL100 cells (Table 2). In LNCaP cells $5\times10^5$ Y pfu input virus produced $4\times10^7$ pfu at 48 hours while in HBL100 cells $8\times10^6$ pfu were obtained at 48 hours. This represented a 40 fold increase in virus in LNCaP cells or a 5 fold greater yield than in HBL100 cells.

The differential in virus production for CN716 showed a wider disparity between the two cell lines. In LNCaP cells $1.7 \times 10^7$ pfu were obtained after 48 hours while in HBL100 cells $8 \times 10^5$ pfu were obtained at the same time point. Therefore in LNCaP cells 34 infectious particles were produced for each input particle at 48 hours while for HBL100 1.6 infectious particles was produced.

These results indicate that the expression of the-early genes EIA and EIB can be controlled by the inserted PSE. To further characterize this regulation, production of CN706 virus was assayed by the burst assay in LNCaP cells in the presence or absence of the testosterone analog R1881. Since the PSE is highly active in the presence of androgens but essentially inactive in the absence of androgens, the production of early proteins controlled by the PSE and therefore the production of virus should be sensitive to androgen levels. As shown in Table 3 in the absence of R1881, $3 \times 10^6$ pfu were obtained at 48 hours for a three fold increase over input virus. In the presence of 1 nM or 10 nM R1881 two to three fold more pfu were obtained at 48 hours. In contrast, with wild type adenovirus assayed in parallel, no difference was evident in pfu obtained in the presence or absence of R1881.

TABLE 2

| | Burst Assays | |
|---|---|---|
| | LNCaP | HBL100 |
| CN706 | $6.3 \times 10_6$ | $2.0 \times 10^6$ |
| CN711 | $4 \times 10_7$ | $8 \times 10^6$ |
| CN716 | $1.7 \times 10_7$ | $8 \times 10^5$ |

TABLE 3

| | R1881 induction | | |
|---|---|---|---|
| | 0 nM R1881 | 1 nM R1881 | 10 nM R1881 |
| CN706 | $3 \times 10_6$ | $8 \times 10_6$ | 5 × 106 |

To further assess the growth selectivity of CN706, CN711, and CN716, the viruses were analyzed in plaque assays in which a single infectious viral particle produces a visible plaque by multiple rounds of infection and replication. The results of a representative assay are shown in Table 4.

TABLE 4

| | Plaque assay Cell line | | | | |
|---|---|---|---|---|---|
| | 293 | LNCaP | HBL100 | TSU | A549 |
| CN702 | $2.3 \times 10_5$ | $4.1 \times 10_5$ | $4.3 \times 10_5$ | $1.1 \times 10_6$ | $5.1 \times 10_5$ |
| CN706 | $2.3 \times 10_5$ | $4.4 \times 10_4$ | $1.7 \times 10_3$ | $5.4 \times 10_4$ | $2.9 \times 10_4$ |
| CN711 | $2.3 \times 10_5$ | $5.5 \times 10_5$ | $2.7 \times 10_5$ | $1.6 \times 10_5$ | $2.6 \times 10_5$ |
| CN716 | $2.3 \times 10_5$ | $6.9 \times 10_5$ | $2.7 \times 10_3$ | $4.4 \times 10_3$ | 4.1 × 104 |

Virus stocks were diluted to equal pfu/ml, then used to infect monolayers of cells for 1 hour. The inoculum was then removed and the cells were overlayed with semisolid agar containing medium and incubated at 37° C. for one week. Plaques in the monolayer were then counted and titers of infectious virus on the various cells were calculated. The data were normalized to the titer of CN702 on 293 cells.

The wild type virus CN702 showed approximately equal titers on each of the five cell lines. In contrast, each of the PSE modified viruses displayed a variable pattern of growth on the different cell types. CN706 grew to a 10 fold lower titer on LNCaP cells as on 293 cells, however, its titer on HBL100 cells was 260 fold lower than on 293 cells. On the non-PSA secreting CaP cell line TSU the titer of CN706 was approximately the same as on LNCaP cells which do secrete PSA. Similarly, the titer on the lung cell line A549 was also close to that on LNCaP cells. The virus CN711 displayed no significant difference in titer on the cell lines tested.

The data for the CN716 virus revealed a marked selectivity for growth in the LNCaP cell line. This virus grew well in LNCaP cells, reaching an even higher titer than on 293 cells. Growth of the virus on other cell lines was significantly lower, 18 fold lower on the next highest titer line, A549. The greatest differential was on HBL100 cells, where the titer was 225 fold lower relative to that on LNCaP cells. The data from the burst size assay and the plaque assay demonstrate that human adenovirus can be modified using the PSE to develop viruses with selective growth properties for PSA secreting CaP cells.

EXAMPLE 2

Treatment of LNCaP Tumor Xenografts

The ultimate objective in the development of prostate-specific viruses is to treat patients with prostate disease. The feasibility of this objective was tested using LNCaP tumor xenografts grown subcutaneously in Balb/c nu/nu mice. The test viruses were inoculated into the mice either by direct intratumoral injection of approximately $10^8$ pfu of virus in 0.1 ml PBS+10% glycerol or intravenously via the tail vein. Tumor sizes were measured and, in some experiments, blood samples were taken weekly.

The effect of intratumoral injection of CN706 on tumor size and serum PSA levels was compared to sham treatment. The sizes of the CN706 treated tumors continued to increase for two weeks, then progressively decreased for the duration of the experiment. At the end of the experiment all of the CN706 treated tumors (10 total) had diminished in size and five mice were cured of their tumor. In contrast, the buffer treated tumors continued to grow for the duration of the experiment, reaching approximately twice their original size by 42 days.

Previously published results have shown that serum PSA levels correlate with tumor size in the LNCaP tumor xenograft model. Measurement of PSA levels in the mice with tumors treated with CN706 indicated a rise in PSA levels one week after treatment, followed by a steady decline in PSA levels out to 35 days. Serum PSA levels increased during the course of the experiment, averaging over 250 ng/ml at 35 days.

While it is likely that a therapeutic based on the viruses described here would be given intralesionally, it would also be desirable to determine if the virus can affect tumor growth following intravenous administration. If so, then it is conceivable that the virus could be used to treat metastatic tumor deposits inaccessible to direct injection. Groups of five mice bearing LNCaP tumors were inoculated with $10^8$ pfu of CN706 by tail vein injection, or $10^8$ pfu of a replication-defective adenovirus (CMV-LacZ) to control for non-specific toxic effects of the virus, or with buffer used to carry the virus. Tumors in mice treated with buffer or CMV-LacZ continued to grow for the duration of the experiment, ultimately reaching approximately five times their original size on average. Tumors in mice treated with CN706 grew slightly between the time of inoculation and the first measurement at 7 days, then the average tumor size diminished to approximately 75% of the original tumor volume by day 42.

Treatment of LNCaP tumors in nude mice with CN711 resulted in a similar outcome to treatment with CN706. In the CN711 treated animals (5 total) the tumors continued to grow between inoculation and day 8. Thereafter the average tumor size diminished, reaching 65% by day 49. The average tumor size of the buffer treated mice (4 total) increased through the duration of the experiment, reaching 300% of the original tumor volume by 49 days.

The same experimental protocol was used to test the CN716 virus in LNCaP tumors. Mice were inoculated with PBS+10% glycerol, CN716, or CN702. The tumors in the buffer mice grew rapidly and the mice were sacrificed due to large tumor sizes after three weeks. Tumors treated with CN702 continued to grow for two weeks, then diminished in size to 80% of their original volume by day 42. Tumors treated with CN716 remained at their original size for one week, then diminished in size to 40% of their original size by day 42. At the end of the experiment 2 of the 4 mice treated were cured of their tumors.

EXAMPLE 3

Construction of Replication-Competent Adenoviral Vectors in which Adenoviral Genes are Under Transcriptional Control of Alpha-Fetoprotein TRE A replication-competent adenoviral vector, CN733, was constructed in which multiple copies of the Alpha Fetoprotein Transcriptional Response Element (AFP-TRE) were placed upstream of adenovirus genes E1A and E1B, as shown schematically in FIG. 1. AFP-TRE is depicted in SEQ ID NO:44. An alternative AFP-TRE is depicted in SEQ ID NO:45.

Cloning Strategy for Vector Construction

A human embryonic kidney cell line, 293, efficiently expresses E1A and E1B genes of Ad5 and exhibits a high transfection efficiency with adenovirus DNA. For these experiments, 293 cells were co-transfected with one left end Ad5 plasmid and one right end Ad5 plasmid. Homologous recombination generates adenoviruses with the required genetic elements for replication in 293 cells which provide E1A and E1B proteins in trans to complement defects in synthesis of these proteins.

The plasmids to be combined were co-transfected into 293 cells using cationic liposomes such as Lipofectin (DOTMA:DOPE™, Life Technologies) by combining the two plasmids, then mixing the plasmid DNA solution (10 ⊠g of each plasmid in 500 ⊠l of minimum essential medium (MEM) without serum or other additives) with a four-fold molar excess of liposomes in 200 ⊠1of the same buffer. The DNA-lipid complexes were then placed on the cells and incubated at 37° C., 5% $CO_2$ for 16 hours. After incubation the medium was changed to MEM with 10% fetal bovine serum and the cells are further incubated at 37° C., 5% $CO_2$, for 10 days with two changes of medium. At the end of this time the cells and medium were transferred to tubes, freeze-thawed three times, and the lysate was used to infect 293 cells at the proper dilution to detect individual viruses as plaques.

Plaques obtained were plaque purified twice, and viruses were characterized for presence of desired sequences by PCR and occasionally by DNA sequencing. For further experimentation, the viruses were purified on a large scale by cesium chloride gradient centrifugation.

Using the above procedure, three replication competent, hepatocarcinoma cell-specific adenoviruses were produced: CN732, which contains an AFP-TRE driving the expression of the EIA gene; CN733, which contains two AFP-TREs driving expression of the E1A and EIB genes; and CN734, which contains an AFP-TRE driving E1B expression. The viruses were generated by homologous recombination in 293 cells and cloned twice by plaque purification. The structure of the genomic DNA was analyzed by PCR and sequencing of the junctions between the inserted sequences and the Ad genomic sequences to confirm that the viruses contained the desired structures. The structure of the viruses was also confirmed by Southern blot.

Table 5 lists the combinations of right end and left end Ad5 plasmids used to generate recombinant Ad5 with the desired features.

TABLE 5

Adenovirus vectors containing AFP-TRE

| Virus | Name | Left End Plasmid | Right End Plasmid |
|---|---|---|---|
| E1A-AFP | CN732 | CN219 | BHG10 |
| EIA/EIB-AFP | CN733 | CN224 | BHG10 |
| E1B-AFP | CN734 | CN234 | BHG10 |

Adenoviral Vector Construction

Plasmid pXC.1 was purchased from Microbix Biosystems Inc. (Toronto). pXC.1 contains Ad5 sequences from (nucleotide) 22 to 5790. We introduced an AgeI site 12 bp 5' to the E1A initiation codon (Ad5 547) by oligo-directed mutagenesis and linked PCR. To achieve this, pXC.1 was PCR amplified using primers:

5'-TCGTCTTCAAGAATTCTCA (15.133A) (SEQ ID NO:14), containing an EcoRI site, and 5'-TTTCAGTCACCGGTGTCGGA (15.134B) (SEQ ID NO:15), containing an extra A to introduce an AgeI site. This created a segment from the EcoRI site in the pBR322 backbone to Ad5 560. A second segment of pXC.1 from Ad 541 to the XbaI site at Ad nucleotide 1339 was amplified using primers:

5'-GCATTCTCTAGACACAGGTG (15.133B) (SEQ ID NO:16) containing an XbaI site, and 5'-TCCGACACCGGTGACTGAAA (15.134A) (SEQ ID NO:17), containing an extra T to introduce an AgeI site. A mixture of these two PCR-amplified DNA segments was mixed and amplified with primers 15.133A and 15.133B to create a DNA segment from the EcoRI site to the XbaI site of pXC.1. This DNA segment encompasses the leftmost 1317 bases of Ad sequence and contains an AgeI site at Ad 547. This DNA segment was used to replace the corresponding segment of pXC.1 to create CN95.

An EagI site was created upstream of the E1B start site by inserting a G residue at Ad5 1682 by oligonucleotide directed mutagenesis as above. To simplify insertion of an AFP-TRE in the EagI site the endogenous EagI site in CN95 was removed by digestion with EagI, treatment with mung bean nuclease, and re-ligation to construct CN114. The primers:

5'-TCGTCTTCAAGAATTCTCA (15.133A) (SEQ ID NO:14), containing an EcoRI site, and 5'-GCCCACGGCCGCATTATATAC (9.4) (SEQ ID NO:46), containing an EagI site, and 5'-GTATATAATGCGGCCGTGGGC (9.3) (SEQ ID NO:47) containing an extra G and an EagI site, and 5'-CCAGAAAATCCAGCAGGTACC (24.020) (SEQ ID-NO:30), containing a KpnI site, were used to amplify the segment between 1682 and the KpnI site at Ad5,2048:

Co-amplification of the two segments with primers 15.133A and 24.020 yielded a fragment with an EagI site at Ad5 1682 which was used to replace the corresponding EcoRI/KpnI site in pXC.1 to construct CN124.

For construction of CN732, human AFP enhancer domains A and B (included in the region −3954 bp to −3335 bp relative to the AFP cap site) were PCR amplified from human genomic DNA (Clontec, Palo Alto, Calif.) using the following primers:

```
5' GTGACCGGTGCATTGCTGTGAACTCTGTA 3'  (SEQ ID NO:48)
(39.055B)

5' ATAAGTGGCCTGGATAAAGCTGAGTGG 3'    (SEQ ID NO:49)
(39.044D)
```

The AFP promoter was amplified from −163 to +34 using the following primers:

```
5' GTCACCGGTCTTTGTTATTGGCAGTGGT 3'   (SEQ ID NO:50)
(39.055J)

5' ATCCAGGCCACTTATGAGCTCTGTGTCCTT 3' (SEQ ID NO:51)
(29.055M)
```

The enhancer and promoter segments were annealed, and a fusion construct was generated using overlap PCR with primers 39.055B and 39.055J. This minimal enhancer/promoter fragment was digested with PinA1 and ligated with CN124 using the engineered AgeI site 5' of the E1A cap site to produce CN219. The liver specific viral vector CN732 was generated by homologous recombination by cotransfecting 293 cells with CN219 and BHG10.

CN733 was constructed by using the following two PCR primers to amplify the enhancer/promoter element described above (−3954 to −3335 and −174 to +29):

```
5' TATCGGCCGGCATTGCTGTGAACTCT 3'    (SEQ ID NO:52)
(39.077A)

5' TTACGGCCGCTTTGTTATTGGCAGTG 3'    (SEQ ID NO:53)
(39.0770)
```

The PCR product was digested with EagI and ligated into similarly cut CN219. The resulting plasmid, CN244, contains two identical AFP regulatory elements, one each modulating expression of the E1A gene and the E1B gene. CN733 was generated by homologous recombination in 293 cells by cotransfecting CN224 and BHG10.

To make CN734, the AFP-TRE regulating the expression of the E1A gene was excised from CN224 by the plasmid with PinA1 and religating the vector. The resulting plasmid, CN234, was co-transfected with BHG10 in 293 cells to generate CN734.

Adenovirus Growth In Vitro

Growth selectivity of CN732, CN733, and CN734 was analyzed in plaque assays in which is single infectious particle produces a visible plaque by multiple rounds of infection and replication. Virus stocks were diluted to equal pfu/ml, then used to infect monolayers of cells for 1 hour. The inoculum was then removed and the cells were overlayed with semisolid agar containing medium and incubated at 37° C. for 10 days (12 days for Table 8). Plaques in the monolayer were the counted and titers of infectious virus on the various cells were calculated. The data were normalized to the titer of CN702 (wild type) on 293 cells. The results of four representative assays are shown in Tables 6–9.

TABLE 6

Plaque assay for 733 (E1A/E1B)

| Cell line | Virus | Titer | Avg. titer | Titre/293 | 702/733 |
|---|---|---|---|---|---|
| 293 | 733 | $2.70 \times 10^6$ | $2.65 \times 10^6$ | 1 | N/A |
| (control) | 733 | $2.60 \times 10^6$ | | | |
| | 702 | $1.30 \times 10^6$ | $1.70 \times 10^6$ | 1 | |
| | 702 | $2.10 \times 10^6$ | | | |
| Hep3B | 733 | $1.01 \times 10^7$ | $1.02 \times 10^7$ | 3.7 | .37 |
| ($AFP^+$) | 733 | $1.03 \times 10^7$ | | | |
| | 702 | $1.00 \times 10^6$ | $7.02 \times 10^5$ | 1.36 | |
| | 702 | $5.00 \times 10^5$ | | | |
| HepG2 | 733 | $9.70 \times 10^6$ | $1.04 \times 10^7$ | 3.92 | 0.292 |
| ($AFP^+$) | 733 | $1.10 \times 10^7$ | | | |
| | 702 | $1.60 \times 10^6$ | $1.95 \times 10^6$ | 1.14 | |
| | 702 | $2.30 \times 10^6$ | | | |
| LNCaP | 733 | $4.00 \times 10^3$ | $3.00 \times 10^3$ | 0.0011 | 290 |
| ($AEP^-$) | 733 | $2.00 \times 10^3$ | | | |
| | 702 | $4.00 \times 10^5$ | $5.05 \times 10^5$ | 0.32 | |
| | 702 | $7.00 \times 10^5$ | | | |
| HBL100 | 733 | 0 | 0 | 0 | 100–1000 |
| ($AFP^-$) | 733 | 0 | | | |
| | 702 | $1.00 \times 10^2$ | $3.07 \times 10^2$ | 0.00022 | |
| | 702 | $6.40 \times 10^2$ | | | |

TABLE 7

CN732, CN733, CN734 Plaque Assay Data

| Cell line | Virus | Ave Titer | Titre/293 | 7XX/702 |
|---|---|---|---|---|
| 293 | 702 | $1.2 \times 10^6$ | 1 | |
| (control) | 732 | $6.15 \times 10^5$ | 1 | |
| | 733 | $2.20 \times 10^6$ | 1 | |
| | 734 | $2.50 \times 10^5$ | 1 | |
| Huh-7 | 702 | $1.10 \times 10^4$ | 0.01375 | |
| | 732 | $1.10 \times 10^5$ | 0.1788 | 13 |
| | 733 | $8.50 \times 10^4$ | 0.0386 | 3 |
| | 734 | $1.90 \times 10^4$ | 0.076 | 6 |
| Sk-Hep-1 | 702 | $9.00 \times 10^2$ | 0.00113 | |
| | 732 | 0 | 0 | 0 |
| | 733 | 0 | 0 | 0 |
| | 734 | $1.00 \times 10^3$ | 0.004 | 4 |
| HeLa | 702 | $2.45 \times 10^2$ | 0.00030625 | |
| | 732 | 0 | 0 | 0 |
| | 733 | 1.5 | $6.81 \times 10^{-7}$ | 0.0022 |
| | 734 | $2.50 \times 10^3$ | 0.01 | 32 |
| MCF-7 | 702 | $3.10 \times 10^3$ | 0.003875 | |
| | 732 | 7.5 | $1.22 \times 10^{-5}$ | 0.0031 |
| | 733 | $2.30 \times 10^1$ | $1.05 \times 10^{-5}$ | 0.0027 |
| | 734 | $1.70 \times 10^3$ | 0.0068 | 2 |
| DLD-1 | 702 | $1.70 \times 10^3$ | 0.00213 | |
| | 732 | $1.40 \times 10^1$ | $2.28 \times 10^{-5}$ | 0.011 |
| | 733 | 1 | $4.54 \times 10^{-7}$ | 0.00021 |
| | 734 | $1.55 \times 10^3$ | 0.0062 | 3 |

TABLE 8

CN732, CN733, CN734 Plaquing Efficiency

| Cell line | Virus | Titer |
|---|---|---|
| 293 | 702 | $1 \times 10^7$ |
| | 732 | $1 \times 10^7$ |
| | 733 | $1 \times 10^7$ |
| | 734 | $1 \times 10^7$ |
| HepG2 | 702 | $5 \times 10^6$ |
| ($AFP^+$) | 732 | $3 \times 10^6$ |
| | 733 | $3 \times 10^6$ |
| | 734 | $1 \times 10^7$ |
| Sk-Hep-1 | 702 | $6 \times 10^4$ |
| ($AFP^-$) | 732 | 0 |
| | 733 | 0 |
| | 734 | $3 \times 10^4$ |

TABLE 8-continued

CN732, CN733, CN734 Plaquing Efficiency

| Cell line | Virus | Titer |
|---|---|---|
| OVCAR-3 | 702 | $8 \times 10^5$ |
| ($AFP^-$) | 732 | 0 |
| | 733 | 0 |
| | 734 | $3 \times 10^4$ |
| HBL-100 | 702 | $2 \times 10^6$ |
| ($AFP^-$) | 732 | 0 |
| | 733 | 0 |
| | 734 | $1 \times 10^4$ |

TABLE 9

Plaque assay for CN732, CN733, and CN734

| Cell line | Virus | Ave Titer | Titer (cell line)/ Titer 293 | CN7XX/CN702 |
|---|---|---|---|---|
| 293 | 702 | $5.0 \times 10^6$ | 1 | |
| (control) | 732 | $4.8 \times 10^6$ | 1 | |
| | 733 | $3.2 \times 10^6$ | 1 | |
| | 734 | $3.0 \times 10^8$ | 1 | |
| HepG2 | 702 | $2.3 \times 10^7$ | 4.6 | — |
| ($AFP^+$) | 732 | $3.2 \times 10^7$ | 6.7 | 1.5 |
| | 733 | $6.0 \times 10^6$ | 1.9 | 0.41 |
| | 734 | $4.2 \times 10^8$ | 1.4 | 0.30 |
| DU145 | 702 | $2.2 \times 10^6$ | 0.44 | — |
| ($AFP^-$) | 732 | $3.0 \times 10^4$ | 0.0063 | 0.0143 |
| | 733 | $3.1 \times 10^3$ | 0.00097 | 0.002 |
| | 734 | $1.0 \times 10^7$ | 0.033 | 0.075 |
| HBL-100 | 702 | $4.0 \times 10^5$ | 0.8 | — |
| ($AFP^-$) | 732 | 0 | — | 0 |
| | 733 | 0 | — | 0 |
| | 734 | $6.0 \times 10^6$ | 0.02 | 0.025 |
| OVCAR-3 | 702 | $3.3 \times 10^5$ | 0.066 | — |
| ($AFP^-$) | 732 | 0 | — | 0 |
| | 733 | 0 | — | 0 |
| | 734 | $3.1 \times 10^5$ | 0.001 | 0.015 |

The wild type virus CN702 produced plaques on each of the cell lines tested. The number of plaques produced by CN702 was used as a base line against which to compare plaque formation by CN733.

In 293 cells growth of the viruses should be independent of the alterations to the E1 region due to the trans complementation in this cell line. As expected, both CN702 and CN733 produced similar numbers of plaques on 293 cells.

Regarding the data from Table 6, in the AFP positive cell lines Hep3B and HepG2 CN702 produced similar numbers of plaques relative to 293 cells. In contrast, CN733 produced approximately four fold more plaques in the AFP positive cell lines than in 293 cells. The super normal level of plaque formation by CN733 in the AFP positive lines indicates that the AFP enhancer is active in these cells.

In the AFP negative cell lines LNCaP and HBL100 growth of both viruses was curtailed but to different extents. Wild type CN702 virus produced plaques in LNCaP cells at approximately 30% of the level seen in 293 cells. In HBL-100 cells CN702 formed plaques at 0.02% of the level formed in 293 cells. CN733 plaque formation was diminished even further in these AFP negative cell lines relative to CN702. In LNCaP cells CN733 produced plaques at a level 0.1% of that seen in 293 cells. In HBL100 cells CN733 did not produce plaques at all. In comparison to CN702, the growth of CN733 on AFP negative cell lines was reduced by at least 100 fold. This compares favorably with previous results where the E1B promoter of Ad40 was shown to specify a differential of approximately 100 fold between gut and conjunctival epithelial tissues (Bailey et al., 1994) and with deletion mutants of the E1B gene which were shown to specify a 100 fold differential in Ad growth between p53+ and p53− cells (Bischoff et al., 1996). Lastly, comparison of the titer of an AFP+ cell type to the titer of an AFP− cell type provides a key indication that the overall replication preference is enhanced due to depressed replication in AFP− cells as well as the replication in AFP+ cells.

Regarding the data from Table 7, several observations can be made. First, CN732, CN733, and CN734 all plaque as efficiently in Huh-7 cells as CN702. In contrast, the plaquing efficiency for two of the adenoviruses (CN732 and CN733) decreases dramatically in the non-AFP producing cell lines included in the experiment. In the non AFP producing hepatocellular carcinoma cell line Sk-Hep-1, CN732 and CN733 produced no plaques at the dilutions tested. The results are similar for these two viruses in HeLa, MCF-7, and DLD-1. CN702's efficiency in DLD-1 cells exceeds CN733's by over 4000 fold.

With respect to the data in Table 8 (in which titers are normalized to $1\times10^7$ in 293 cells), CN732, CN733, and CN734 plaqued similarly to wild type (CN702) in HepG2 cells. However, these viruses plaqued poorly compared to CN702 in cell lines that do not express AFP. CN732 and CN733 produced no plaques at the dilutions tested in SK-Hep-1, OVCAR-3 and HBL-100, thus displaying significant titer differential. This corresponds to at least a 10,000 fold difference with wild type in HBL-100 and OVCAR-3 and a 1,000 fold difference in SK-Hep-1. CN734 also plaqued less efficiently than CN702 in OVCAR-3 (25 fold) and HBL-100 (200 fold) cells.

The data of Table 9 suggest that CN732, CN733, and CN734 plaque as efficiently as CN702 in cells that express AFP. However, they do not plaque as efficiently as CN702 in cell lines that do not express AFP. For example, neither CN732 nor CN733 produced any plaques at the dilutions tested in HBL100 cells or OVCAR-3 cells. CN734's plaquing differential was not as striking as CN732's or CN733's in the cell lines tested. It plaqued 13-fold, 40-fold, and 67-fold less efficiently than wild type in DU145, HBL100, and OVCAR-3, respectively.

The plaque assay data demonstrate that human adenovirus can be modified using an AFP-TRE to develop viruses with selective growth properties for AFP producing cells, particularly AFP-producing tumor cells such as hepatic carcinoma cells.

Western Analysis of E1A Expression from CN733

In the next experiment, we examined the effect of an AFP-TRE on the accumulation of E1A protein in CN733 infected cells. We reasoned that if one of the AFP regulatory regions installed in CN733 was modulating the E1A gene, the level of E1A protein in infected cells should also be affected. A western blot was conducted to test our hypothesis.

Figure 2A:
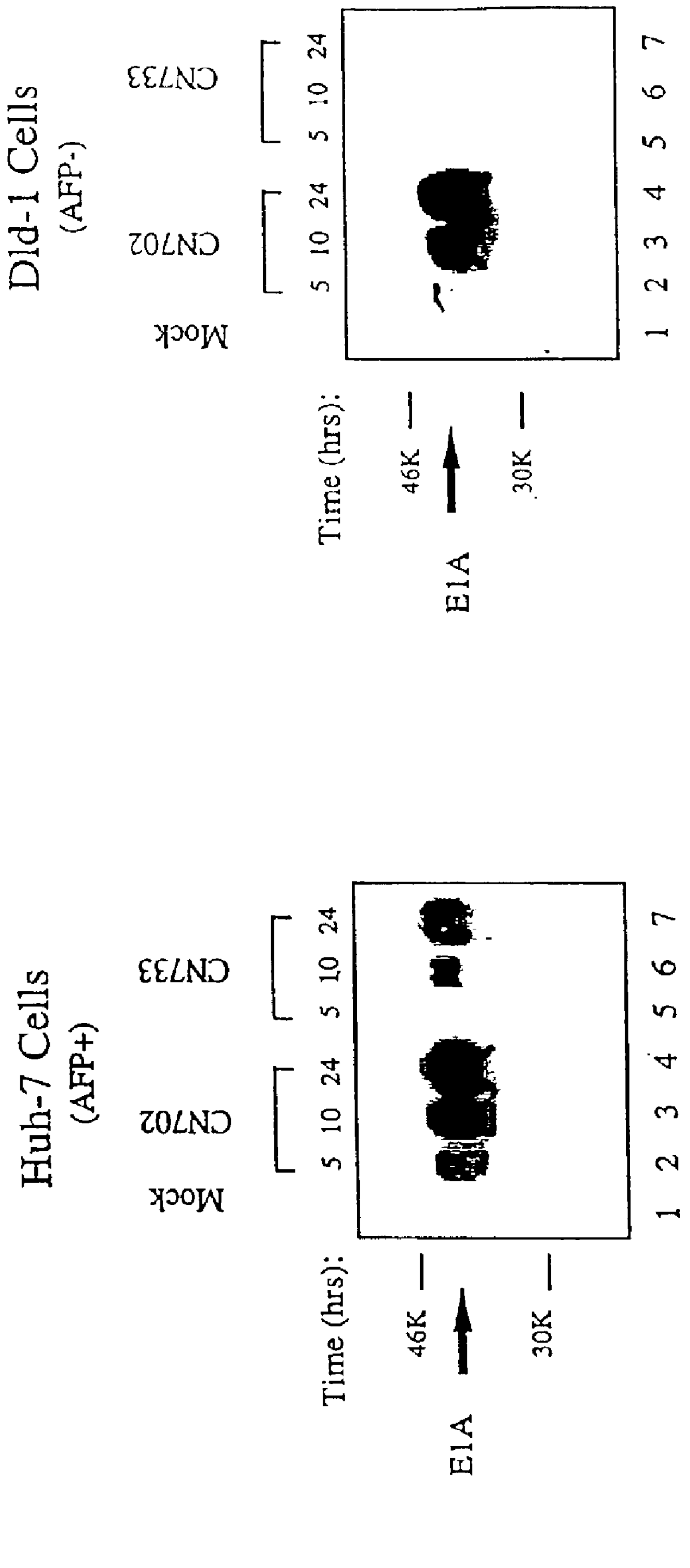
FIGS. 2(A) and (B) are half tone reproductions depicting western analysis of E1A levels in CN733 (containing two AFP-TREs) and CN702 (control) infected cells.

CN733's E1A accumulation was evaluated in Huh-7, SK-Hep-1 and DLD-1 cells. Monolayers were infected with either CN702 or CN733 at an MOI of ten and the harvested at various time points after infection. Samples were electrophoresed through a 10% acrylimide gel and transferred by electrophoresis to a nitrocellulose membrane. E1A protein was detected by using the ECL Western Detection system (Amersham, Arlington Heights, Ill.) using the suggested protocol. The primary antibody used was rabbit anti-Ad2 E1A antibody (Santa Cruz Biotechnology, Santa Cruz, Calif.). The results are shown in FIG. 2(A).

E1A accumulated rapidly in CN702 and CN733 infected Huh-7 cells. A high level of E1A was also detected in CN702 infected DId-1 cells. However, little E1A protein was detected in CN733 infected DId-1 cells. This result is intriguing because it suggests that CN733's poor plaquing efficiency in non AFP producing cell lines could be attributed to its restricted E1A expression. These data are consistent with the hypothesis that the AFP-TRE affects CN733's compromised replication in non-permissive cell types.

Figure 2B:
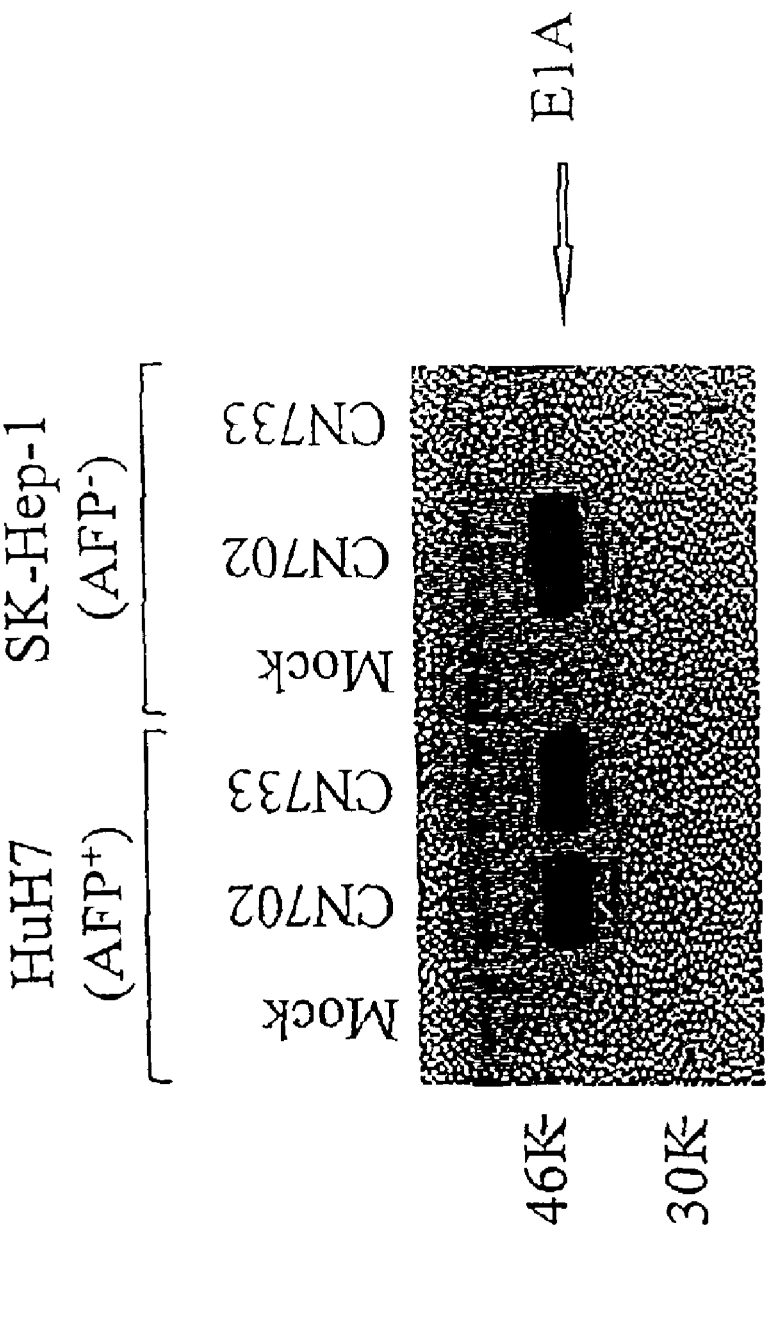
In FIG. 2(B), Sk-Hep-1 were the AFP− cells used.

The experiment was repeated using Sk-Hep-1 cells as non AFP producing cells. Data were obtained after 24 hours post-infection. The results are shown in FIG. 2(B). The conclusion of this experiment is the same as the previous experiment: E1A expression is tightly regulated by the AFP-TRE.

Growth of CN733

Figure 3A:
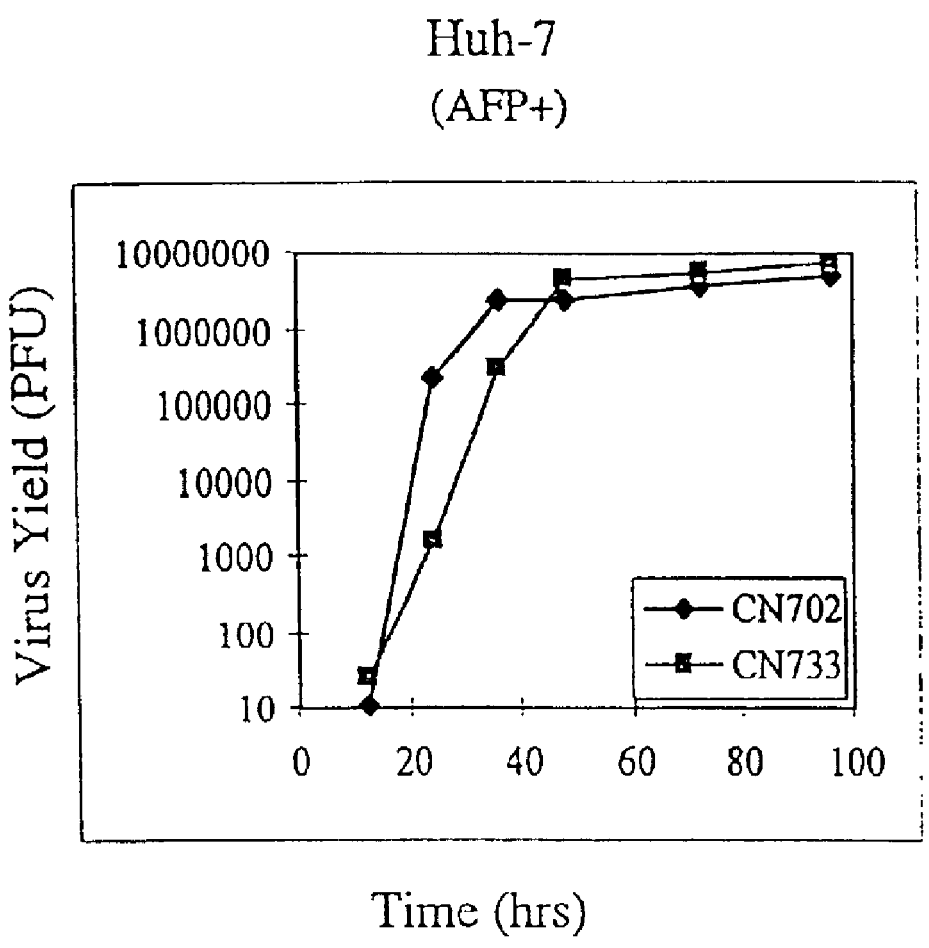
FIGS. 3(A)–(C) are graphs depicting growth of CN733 in AFP producing (Huh-7.
Figure 3B:
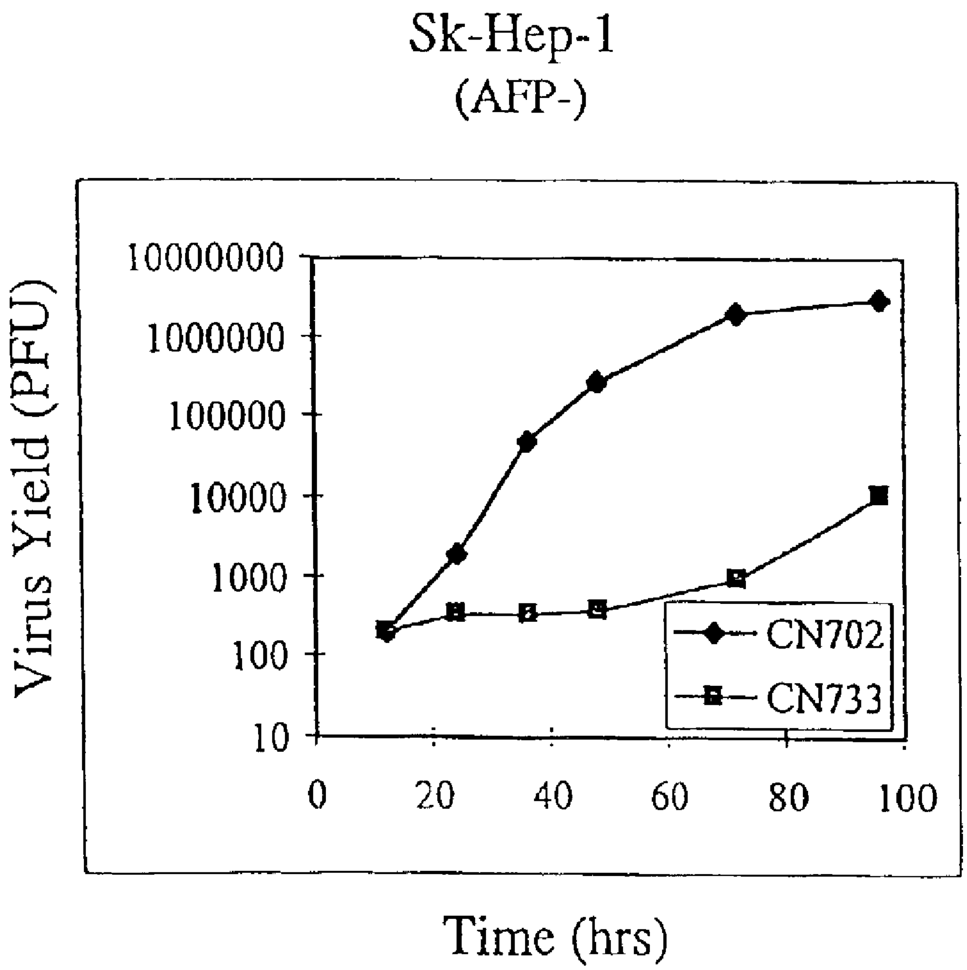
Figure 3C:
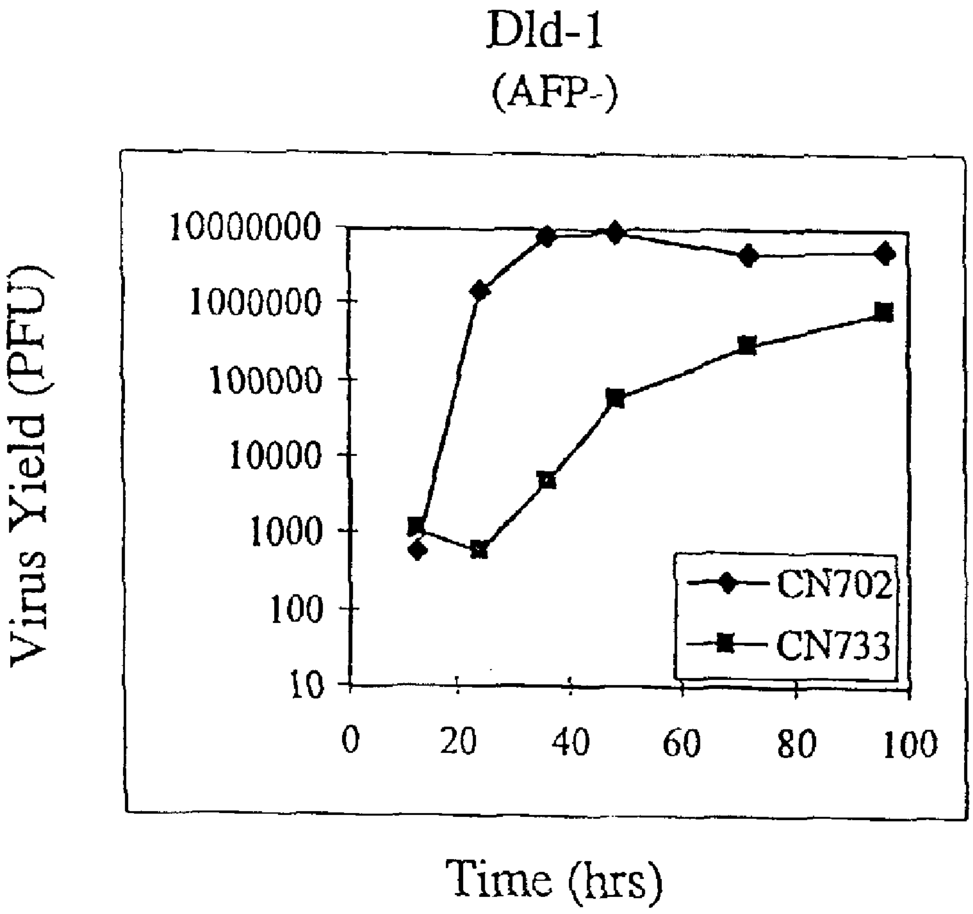

CN733's growth in AFP- and non-AFP-producing cells was evaluated. Monolayers of Huh-7, Sk-Hep-1, and DId-1 cells were infected at an MOI of ten with either CN702 or CN733. At various times after infection, duplicate samples were harvested, freeze-thawed three times, and titered on 293 cells to determine the total virus yield. Virus yield curves for CN702 and CN733 are plotted in FIGS. 3(A)–(C).

CN702 and CN733 grew efficiently in Huh-7 cells. Huh-7 cells produced similar amounts of infectious CN702 and CN733. In contrast, CN733's growth was severely restricted in SK-Hep-1 cells. CN702's titer at the conclusion of the experiment is about 1000 times greater than CN733's titer. The results were similar in DId-1 cells.

Figure 4A:
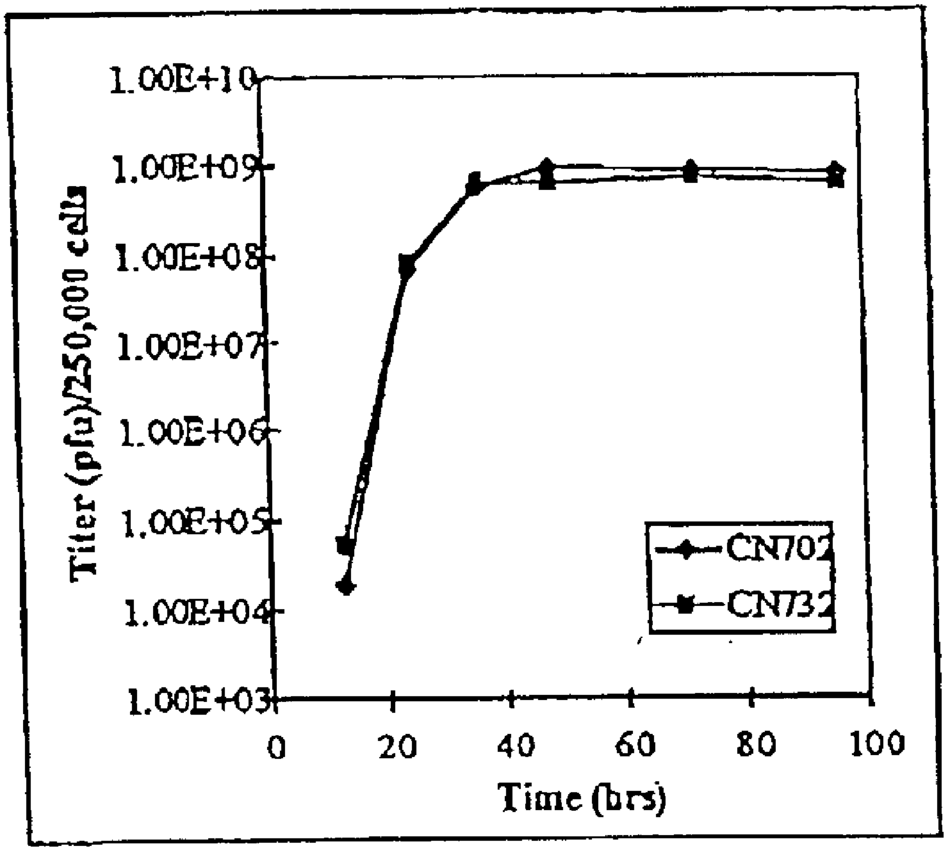
FIGS. 4(A)–(C) are graphs depicting growth of CN732 (FIG. 4(A); solid diamonds), CN733 (FIG. 4(B); solid diamonds), and CN734 (FIG. 4(C); solid diamonds) in HepG2 cells, as compared to control CN702 (solid squares).
Figure 4B:
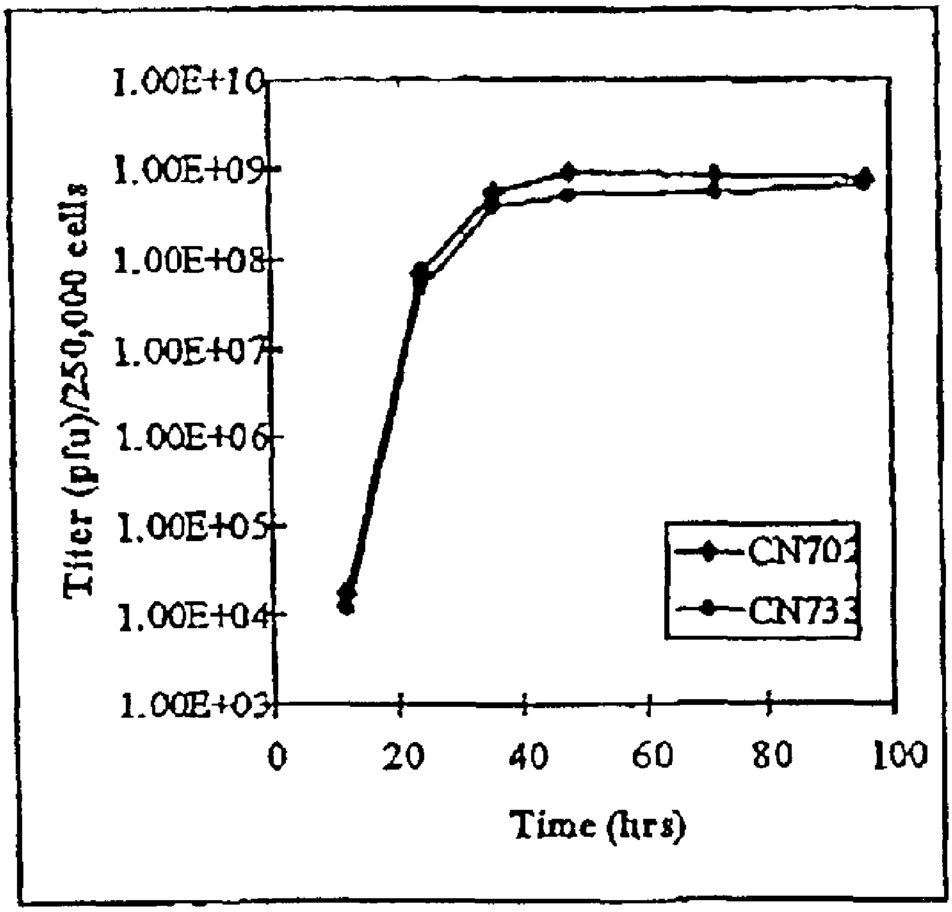
Figure 4C:
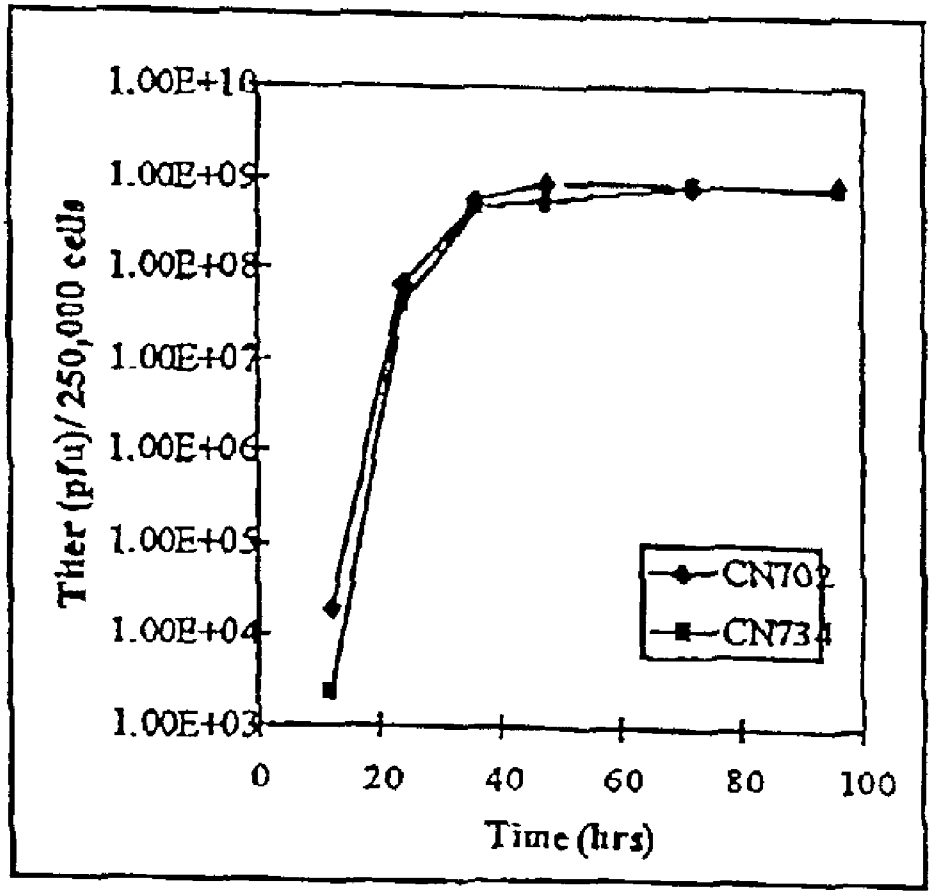

The growth experiment was also performed to compare growth of CN732, CN733, and CN734 in HepG2 cells. Monolayers of HepG2 cells were infected at a multiplicity of infection (MOI) of two and harvested at various times after infection. Samples were titered on 293 cells to determine the final virus yield. The results are shown in FIGS. 4(A)–(C). The data demonstrate that the adenovirus containing AFP-TREs grow efficiently in this cancer cell line. CN732, CN733, and CN734 each reach a high final titer at 36 hours post infection that is similar to that of CN702.

Figure 5A:
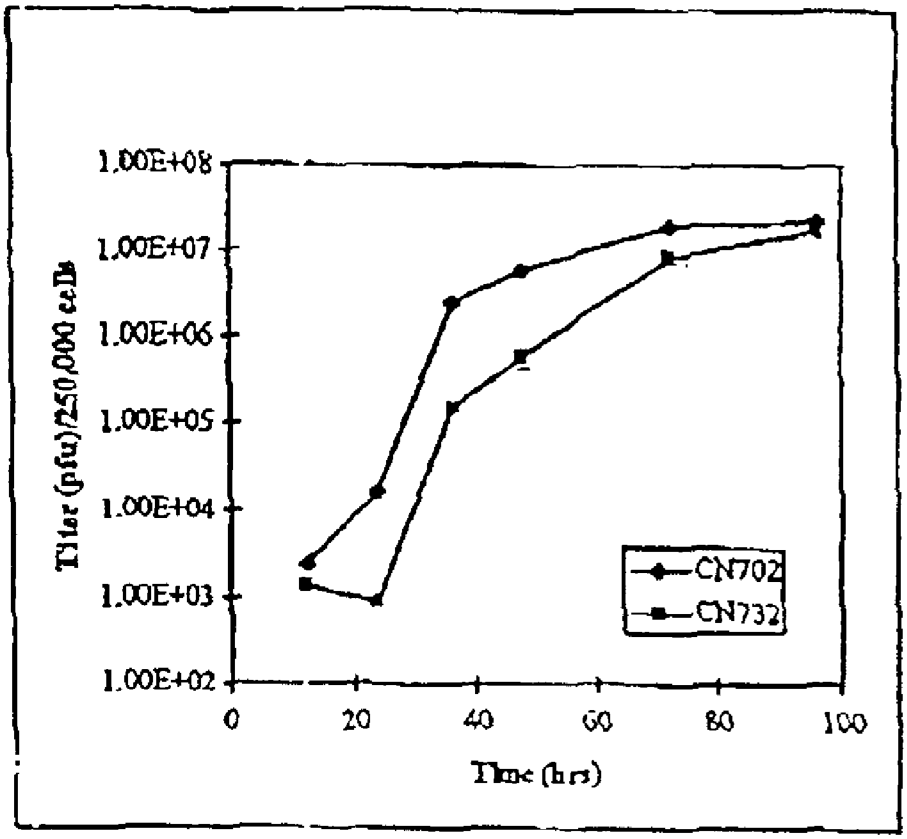
FIGS. 5(A)–(B) are graphs depicting growth of CN732 (FIG. 5(A); solid squares), and CN733 (FIG. 5(B); solid circles) in primary hepatocytes, compared to control CN702 (solid diamonds).
Figure 5B:
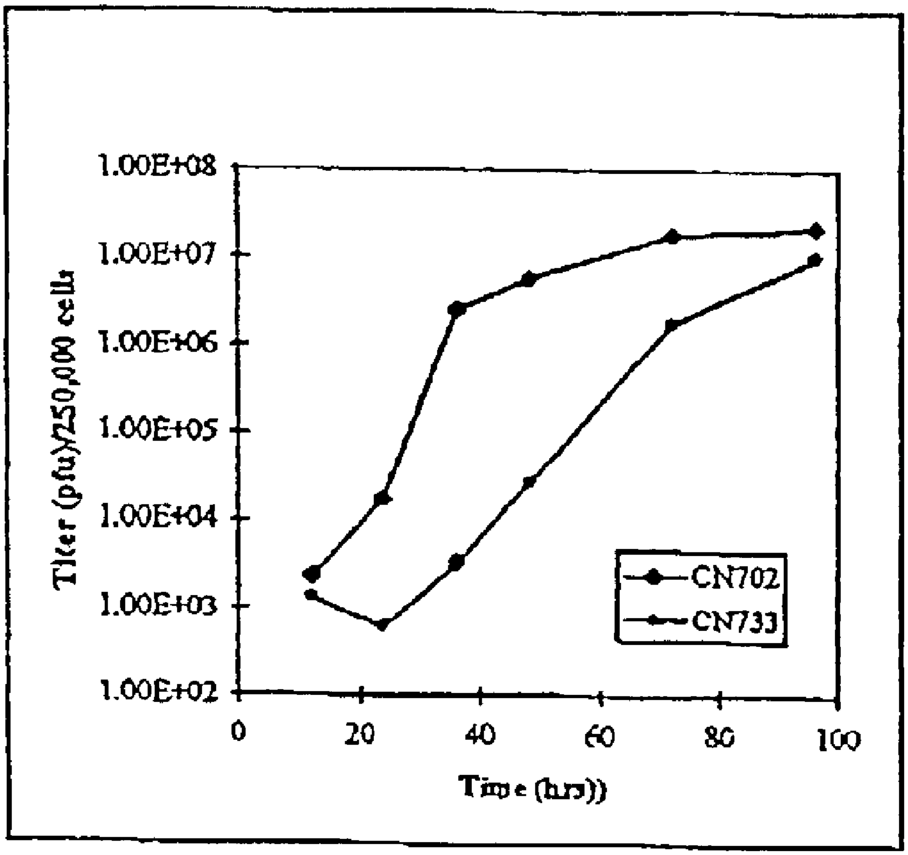

In another experiment, propagation was evaluated in primary hepatocytes (hNheps) isolated from a donor (32 year old black male) three days before the start of the experiment. Monolayers of cells were infected with virus at an MOI of two, harvested at various times after infection and titered on 293 monolayers. The results are shown in FIGS. 5(A)–(C). The data suggest that CN732 and CN733 grow less efficiently in hNheps than CN702. CN732's growth is delayed by twenty-four hours compared to CN702's. At thirty-six hours post infection, there is over ten fold more infectious CN702 than CN733. CN733's growth is delayed by thirty-six hours. At thirty-six hours post infection, there is nearly 1000 times more infections CN702 than CN733. CN734 grows similarly to CN702. The data also suggest that CN733 has the most restrictive phenotype, followed by CN732 and CN734. Taken together, these results also indicate that an AFP-TRE inserted upstream of the E1A gene may be more effective in restricting host-range than an AFP-TRE engineered upstream of the E1B region. The presence of two AFP-TREs is even more effective.

In conclusion, the experiments described above indicate that it is possible to restrict an adenoviral vector's host range to AFP producing cells. As demonstrated by plaque assay and growth assay, the adenovirus vectors containing an AFP-TRE propagate efficiently in HepG2 and Huh-7 cells but poorly in non AFP producing cells.

Testing Cytotoxic Ability of Adenovirus Vector CN733 on HepG2 Tumor Xenographs

Figure 6A:
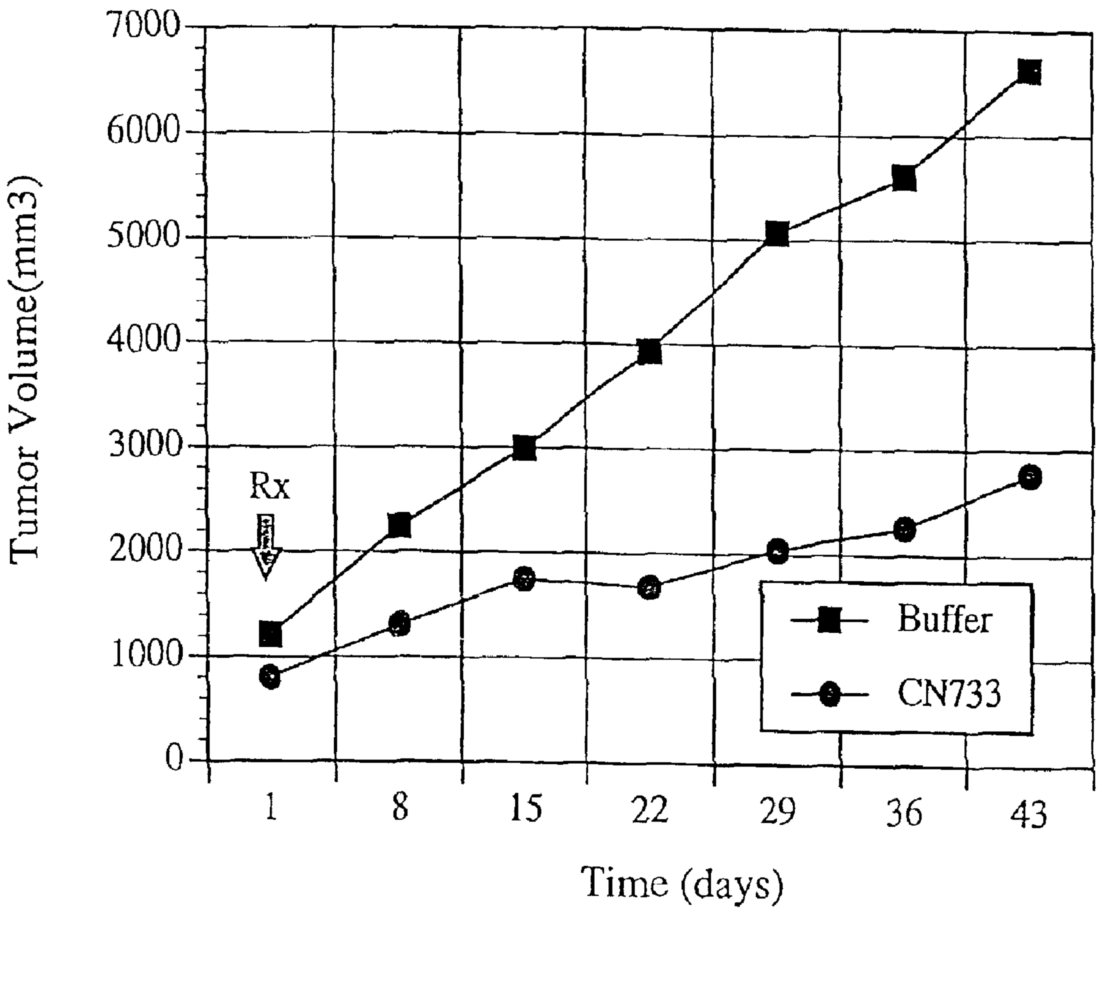
FIGS. 6(A)–(B) are graphs comparing tumor volume in mice harboring hepatocarcinoma cell line HepG2 and treated with CN733 (FIG. 5(A); squares) or with control buffer (circles).

An HCC mouse xenograft model was used to evaluate CN733's potential as a therapeutic adenovirus for liver cancer. The AFP producing HCC cell line HepG2 was injected subcutaneously on the right flanks of Balb/c nu/nu mice. After allowing several weeks for the tumors to take, each was treated with an intratumoral injection of either $1.5\times10^{11}$ particles of CN733 in PBS, glycerol or buffer alone. Eleven mice bearing HepG2 tumors were treated, six with CN733 and five with buffer. Tumors were measured weekly until the conclusion of the experiment. Tumor volume was calculated by multiplying the tumor's length by the square of its width and dividing the product by two. FIG. 6(A) is a graph of average tumor volume for each treatment group vs. time.

In six weeks, HepG2 tumors challenged with buffer grew to over five times their original size. In contrast, tumor growth in CN733 treated mice was attenuated. One tumor even regressed to 3% of its maximum volume. These data suggest that CN733 invaded the tumors and delivered cytotoxicity.

Figure 7:
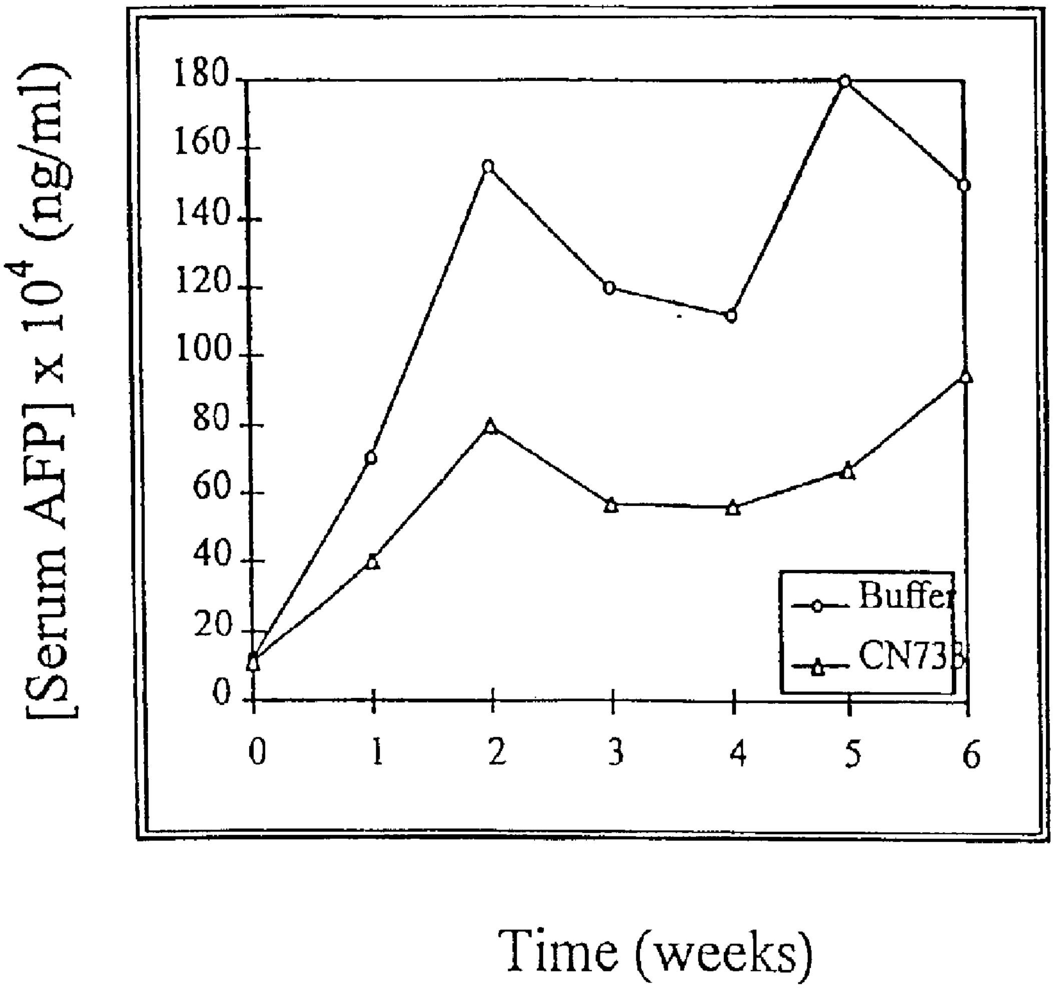
FIG. 7 is a graph depicting serum AFP levels in tumor-bearing mice receiving CN733 (triangles) or receiving buffer (circles).

In addition to monitoring tumor growth, we harvested serum samples and assayed AFP levels. The results are shown in FIG. 7. The data suggest that serum AFP levels rises more slowly in mice receiving CN733 than in control mice receiving buffer.

Figure 6B:
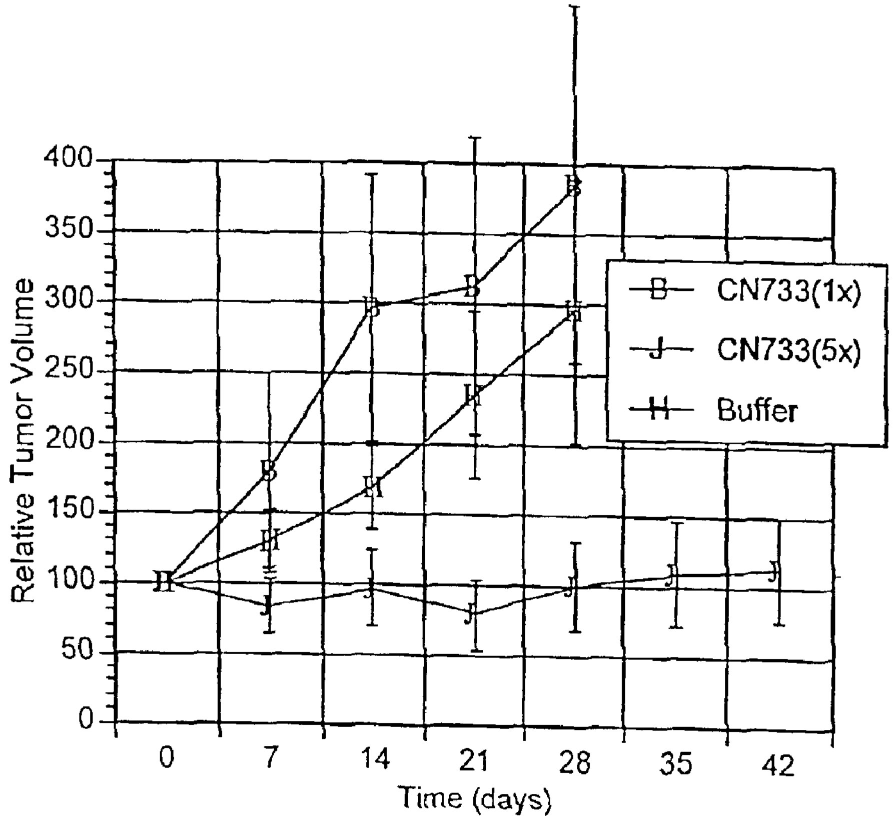

In another experiment, antitumor activity of different administrative regimens was compared for CN733. Animals were treated with a single intramuoral administration of either buffer (n=8; volume=919 $mm^3$) or $1.5\times10^{11}$ particles of CN733 (n=8, volume=944 $mm^3$). A third group of animals was treated with five consecutive daily doses of $1.5\times10^{11}$ particles of CN733 (n=8, volume=867 $mm^3$). Despite the large systemic virus burden, the mice displayed no obvious signs of toxicity. Tumors were measured weekly by external caliper for four weeks after injection. Animals from groups treated with a single dose of CN733 and buffer were sacrificed four weeks after treatment because of excessive tumor burden. All animals from the group treated with five doses of CN733 survived until the conclusion of the study. Despite the large systemic virus burden, these animals showed no obvious signs of treatment related toxicity. The results are shown in FIG. 6(B). On average, buffer treated tumors increased to three times their initial volume by four weeks after treatment. Tumors treated with a single dose of CN733 increased to nearly four times their initial volume. In contrast, tumors treated with five doses of CN733 remained the same volume. Five out of eight tumors (63%) responded to treatment. One animal had no palpable tumor at the end of the study.

Statistical analysis using the Students T-test suggests that there was no significant difference at any time point between buffer treated animals and those treated with one dose of CN733 ($p>0.5$). However, there was a significant difference between buffer treated animals and those treated with five doses of CN733 beginning at two weeks post injection ($p=0.045$) and continuing through four weeks ($p=0.034$).

The data suggest that CN733 exhibits significant antitumor activity in HepG2 nude mouse xenografts. CN733 administered daily for five consecutive days at a dose of $1.5\times10^{11}$ particles can cause tumor regression in some animals. A single dose, however, is not sufficient to cause tumor killing.

In the first experiment, the tumors responded to a single dose of CN733 but did not appear to respond in the second. The inventors note that there is often a variation in tumor phenotype (including growth characteristics and AFP expression) from experiment to experiment.

In conclusion, the in vivo experiments suggest that CN733 causes significant tumor killing in large hepatoma xenografts. Five doses of intratumorally administered virus induced regression in four out of eight animals and cured one animal twenty-eight days after injection. On average, buffer treated tumors tripled while CN733 treated tumors remained the same.

EXAMPLE 4

Figure 8:
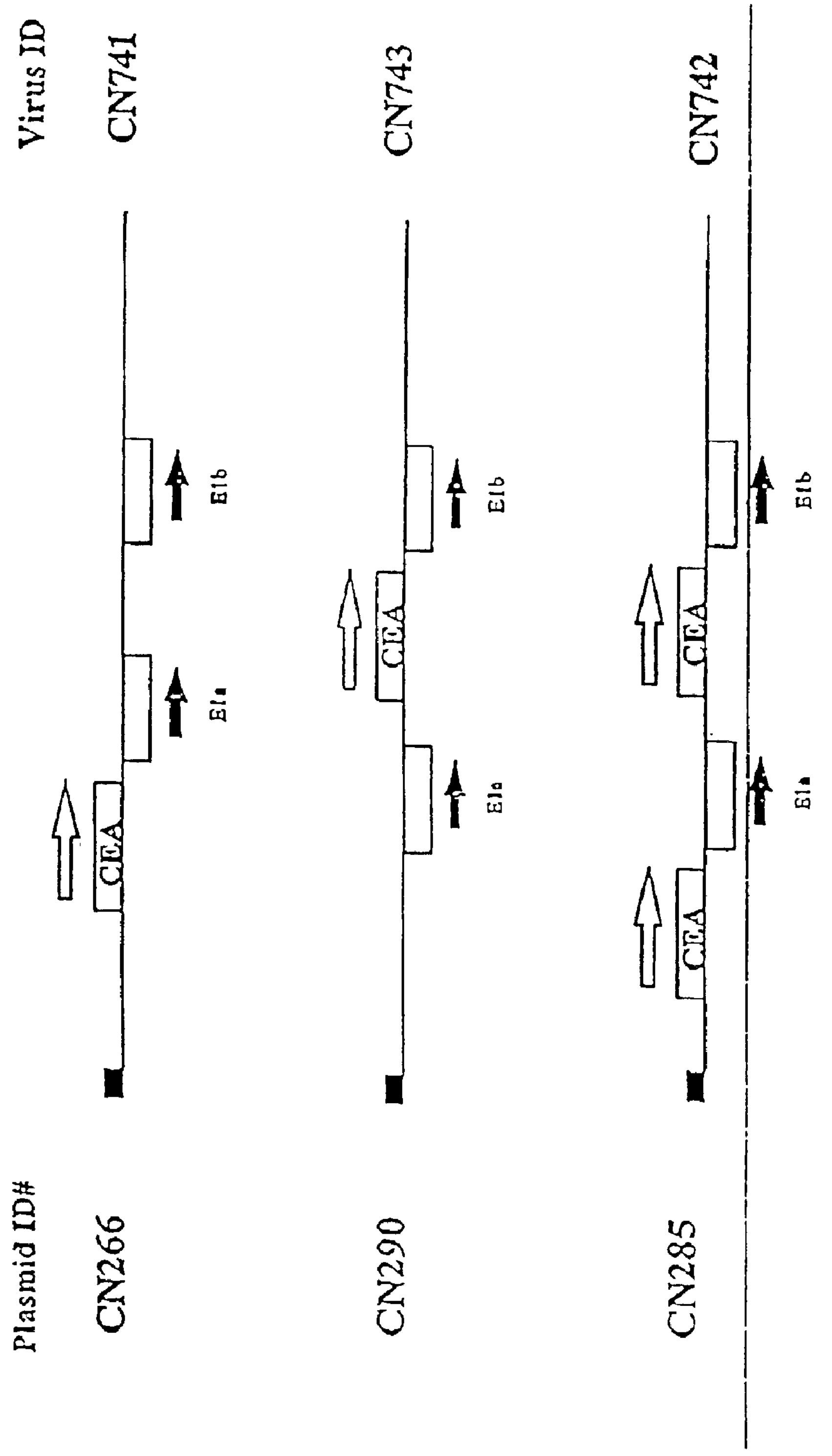
FIG. 8 is a schematic representation of various adenoviral vector constructs comprising CEA-TRE controlling expression of E1A, E1B or both, as described in Example 4.

Construction of Replication-Competent Adenoviral Vectors in which Adenoviral Genes are Under Transcriptional Control of Carcinoembrvonic Antigen (CEA) TRE Using the procedure described above in Example 3, three replication competent, CEA cell-specific adenoviruses were produced: CN741, which contains an CEA-TRE driving the expression of the EIA gene; CN742, which contains two CEA-TREs driving expression, of the E1A and EIB genes; and CN743, which contains an CEA-TRE driving E1B expression. These constructs are shown schematically in FIG. 8. The viruses were generated by homologous recombination in 293 cells and cloned twice by plaque purification. The structure of the genomic DNA was analyzed by PCR and sequencing of the junctions between the inserted sequences and the Ad genomic sequences to confirm that the viruses contained the desired structures.

Table 10 lists the combinations of right end and left end Ad5 plasmids used to generate recombinant Ad5 with the desired features.

TABLE 10

Adenovirus vectors containing CEA-TRE

| Virus | Name | Left End Plasmid | Right End Plasmid |
|---|---|---|---|
| E1A-CEA | CN741 | CN266 | BHG11 |
| EIA/EIB-CEA | CN742 | CN285 | BHG11 |
| EIB-CEA | CN743 | CN290 | BHG11 |

A replication-competent adenoviral vector, CN742, was constructed in which copies of the Carcinoembryonic Antigen Transcriptional Response Element (CEA-TRE) were placed upstream of adenoviral genes E1A and E1B.

The Carcinoembryonic Antigen Transcriptional Response Element (CEA-TRE)

The transcriptional response element of the carcinoembryonic antigen (CEA-TRE), about −402 to about +69 bp relative to the transcriptional start (SEQ ID NO:54), was amplified by polymerase chain reaction (PCR) from human genomic DNA using primers:

5' ATT ACC GGT AGC CAC CAC CCA GTG AG 3' (39.174B, upper primer) (SEQ ID NO:55) and 5' TAG ACC GGT GCT TGA GTT CCA GGA AC 3' (39.174D) (SEQ ID NO:56).

A unique restriction site, AgeI, was introduced by the primer pair at the ends of the PCR-amplified product.

The CEA-TRE PCR fragment was ligated into pGEM-T vector (Promega) which had been linearized with EcoRV. The ligation mixture was transformed into *E. coli* DH5α cells. The desired clone, carrying a CEA-TRE fragment, was obtained and designated CN265.

Construction of CEA-TRE Adenoviruses Comprising One or Two Adenovirus Genes Under Transcriptional Control of CEA-TRE Three replication-competent, CEA cell-specific adenoviruses were produced:

CN741, which contains a CEA-TRE driving the expression of the E1A gene;

CN742, which contains two CEA-TREs driving expression of both the E1A and EIB genes; and CN743, which contains a CEA-TRE driving E1B expression.

The viruses were generated by homologous recombination in 293 cells and cloned by plaque purification. The structure of the genomic DNA was analyzed by PCR and sequencing of the junctions between the inserted sequences and the Ad genomic sequences to confirm that the viruses contained the desired structures.

CEA-TRE-Driven E1A Adenovirus Plasmid (CN741)

Briefly, a CEA-TRE fragment was inserted into CN124 (a left-hand adenovirus plasmid, described below) to generate CN266, which comprises the left-hand end of adenovirus with a CEA-TRE controlling expressing of the adenovirus E1A gene. CN266 was recombined with a plasmid carrying the right-hand portion of adenovirus to generate CN741, which is a full-length adenovirus in which CEA-TRE controls expression of adenovirus gene E1A.

In more detail, the CEA-TRE sequence was excised from CN265 (described in Example 1) by digestion with PinAI.

CN124 is a derivative of construct pXC.1, which contains the wild-type (wt) left-hand end of Ad5, from nt (nucleotide) 22 to 5790, including both E1A and E1B [McKinnon (1982) *Gene* 19:33–42]. Plasmid pXC.1 was purchased from Microbix Biosystems Inc. (Toronto). An AgeI site was introduced 12 bp 5' to the E1A initiation codon (Ad5 nt 547) by oligo-directed mutagenesis and linked PCR. To achieve this, pXC.1 was PCR-amplified using primers: 15.133A, 5'-TCGTCTTCAAGAATTCTCA (SEQ ID NO:14), containing an EcoRI site, and 15.134B, 5'-TTTCAGTCACCGGTGTCGGA (SEQ ID NO:15), containing an extra A to introduce an AgeI site. This created a segment-from the EcoRI site in the pBR322 backbone to Ad5 nt 560. A second segment of pXC.1 from Ad nt 541 to the XbaI site at Ad nucleotide 1339 was amplified using primers:

15.133B, 5'-GCATTCTCTAGACACAGGTG (SEQ ID NO:16) containing an XbaI site, and 15.134A, 5'-TCCGACACCGGTGACTGAAA (SEQ ID NO:17), containing an extra T to introduce an AgeI site.

These two PCR-amplified DNA segments were mixed and amplified with primers 15.133A and 15.133B to create a DNA segment from the EcoRI site to the XbaI site of pXC.1. This DNA segment encompasses the leftmost 1317 bases of Ad sequence and contains an AgeI site at Ad nt 547. This DNA segment was used to replace the corresponding segment of pXC.1 to create CN95.

An EagI site was created upstream of the E1B start site by inserting a G residue at Ad5 nt 1682 by oligonucleotide directed mutagenesis as above. To simplify insertion of a CEA-TRE in the EagI site, the endogenous EagI site in CN95 was removed by digestion with EagI, treatment with mung bean nuclease, and re-ligation to construct CN114. The following primers were used to amplify the segment between 1682 and the KpnI site at Ad5 nt 2048: 15.133A, 5'-TCGTCTTCAAGAATTCTCA (SEQ ID NO:14), containing an EcoRI site, and 9.4, 5'-GCCCACGGCCGCATTATATAC (SEQ ID NO:46), containing an EagI site 9.3, 5'-GTATATAATGCGGCCGTGGGC (SEQ ID NO:47), containing an extra G as well as an EagI site, and 24.020, 5'-CCAGAAAATCCAGCAGGTACC (SEQ ID NO:30), containing a KpnI site. Co-amplification of the two segments with primers 15.133A and 24.020 yielded a fragment with an EagI site at Ad5 nt 1682, which was used to replace the corresponding EcoRI/KpnI site in pXC.1 to construct CN124.

A CEA-TRE fragment excised from CN265 (see above) by digestion with PinA1 was ligated into similarly digested CN124 (which contains the left hand end of the adenovirus) to generate CN266. CN266 is a vector comprising the left-hand portion of adenovirus, in which a CEA-TRE is inserted upstream of and controls expression of E1A.

The full-length CEA-E1A virus, designated CN741, was constructed by homologous recombination of CN266 and BHG11, which contains the right hand side of Adenovirus 5. Briefly, the plasmid CN266 was digested with PvuI; BHG11, with ClaI. Equivalent amounts (5 ⊠g) of each linearly cut plasmid were transfected into 293 cells with a 4-fold excess of cationic liposomes such as Lipofectin DOTAP/DOPE (1:1). 293 is a human embryonic kidney cell line which efficiently expresses the E1A and E1B genes of Ad5 and exhibits a high transfection efficiency with adenovirus DNA. 8 days after infection, viral plaques were observed on the cell monolayer; cells/viruses were harvested, freeze-thawed 3×,centrifuged to pellet the cellular debris, and the supernatant collected. CN741, the full-length adenovirus in which a CEA-TRE controls E1A expression, was plaque-purified three times.

In an alternative protocol for transfection of right- and left-hand adenovirus plasmids into 293 cells, the plasmids are first combined, then the plasmid DNA solution (10 $\mu$g of each plasmid in 200 ⊠l of minimum essential medium without serum or other additives) is mixed with an 4-molar excess of liposomes (e.g., DOTAP/DOPE) in 200 ⊠1of the same buffer. The DNA-lipid complexes are then placed on the cells and incubated at 37° C., 5% $CO_2$ for 16 hours. After incubation, the medium is changed to MEM with 10% fetal bovine serum and the cells are further incubated at 37° C., 5% $CO_2$, for two weeks with two changes of medium. At the end of this time the cells and medium are transferred to tubes, freeze-thawed three times, and the lysate is used to infect 293 cells at the proper dilution to detect individual viruses as plaques. Plaques obtained were plaque-purified twice, and viruses were characterized for presence of desired sequences by PCR and occasionally by DNA sequencing. For further experimentation the viruses are prepared on a larger scale by cesium chloride gradient centrifugation.

Several clones of CN741, the full-length adenovirus in which a CEA-TRE controls E1A expression, were characterized by PCR, Southern Blot, and the plaque assay for specificity.

1. PCR: Primers were used to amplify the region of clones of CN741 starting upstream of the CEA insert in the E1A region (primer 39.141C: 5' ATT TGT CTA GGG CCG GGA CTT 3' (SEQ ID NO:57)) and downstream at the 3' end of the EIB region (primer 39.141H : 5' CGC GCG CAA AAC CCC TAA ATA AAG 3' (SEQ ID NO:58)) of adenovirus. The amplified fragment is 4249 bp. The following clones tested positive by PCR: 46.130.7.4., 46.130.8.3, 46.130.9.1.1, 46.130.9.2.1, 46.130.9.3.1, and 46.130.9.4.1.

2. Southern blot: Positive clones of CN741 were further characterized by Southern blot. Viral DNA of CN741 clones was digested by the following enzymes: ScaI, AflII, and AflII/XbaI. The viral DNA was probed with a randomly primed fragment of E1A. The correct fragments were as follows: ScaI digest, 926 and 5645 bp; AflII digest, 4011 bp; and AflII/XbaI digest, 1817 bp. Each positive clone displayed the correct fragment pattern.

3. Plaque assay: The plaque assay is described in Example 2.

These assays confirmed the identity of CN741, the full-length adenovirus in which a CEA-TRE controls E1A expression.

CEA-TRE-Driven E1B Adenovirus Plasmid (CN743)

Briefly, a CEA-TRE fragment was inserted into CN124 (a left-hand Ad vector, described above) to generate CN290, which comprises the left-hand end-of adenovirus with a CEA-TRE controlling expressing of the adenovirus E1B gene. CN290 was recombined with a plasmid carrying the right-hand portion of adenovirus to generate CN743, which is a full-length adenovirus in which CEA-TRE controls expression of adenovirus gene E1B.

In more detail, the CEA-TRE was obtained as an EagI fragment from CN284 (described below). This fragment was isolated by gel electrophoresis and inserted into CN124, similarly cut with EagI. CN124, also described above, contains the left-hand portion of Adenovirus 5, with an artificial EagI site upstream of the E1B start site. The resulting clone, designated CN290, has a CEA-TRE inserted upstream of the E1B in a left-hand portion of adenovirus. The identity of CN290 was confirmed by restriction digest (ScaI: 2937 and 7406 bp; SmaI: 180, 783, 2628, and 6752 bp).

CN743 was generated by homologous recombination by co-transfecting 293 cells, which produces E1B, with CN290 and BHG11, which contains the wt right hand portion of Ad5. Thus, CN743 is a full-length adenoviral genome in which gene E1B is under control of a CEA-TRE.

Construction of Adenovirus Vectors in which Expression of Two Adenovirus Genes are Each Controlled by a CEA-TRE (CN742)

Briefly, a CEA-TRE fragment was inserted upstream of the E1B gene in construct CN266, which already had a CEA-TRE fragment inserted upstream of E1A. The resulting plasmid was designated CN285 and contained a left-hand portion of adenovirus with separate copies of a CEA-TRE driving expression of E1A and E1B. CN285 was recombined with a right-hand portion of adenovirus to generate CN742, which is a full-length adenovirus in which expression of both E1A and E1B is controlled by CEA-TRE.

In more detail, CN285 was constructed by amplifying the CEA-TRE inserted into the E1A region (e.g., CN266) by PCR using primers: 5' TM CGG CCG AGC CAC CAC CCA 3' (39.180A, upper primer) (SEQ ID NO:59) and 5' TAT CGG CCG GCT TGA GTT CCA GG 3' (39.180B, lower primer) (SEQ ID NO:60). The unique restriction site EagI was introduced by the primer pair at the ends of the PCR-amplified product. The PCR product was ligated into pGEM-T Vector (Promega), and the resultant plasmid designated CN284.

The EagI CEA-TRE fragment was excised from CN284 and isolated by gel electrophoresis. The CEA-TRE fragment was ligated into CN266 which had been cut with EagI. CN266 (described above) is a left-hand portion of adenovirus in which a CEA-TRE controls expression of E1A. The resulting clone was confirmed by restriction digest (ScaI: 1682, 1732, and 7406 bp; SmaI: 783, 899 2628, and 6330 bp). The clone was designated CN285, which represents a left-hand portion of adenovirus in which both E1A and E1B are under control of separate CEA-TREs.

CN742 was generated by homologous recombination by co-transfecting 293 cells with CN285 and BHG11, which has the wt right hand portion of adenovirus. Thus, construct CN742 is a full-length adenoviral genome with genes E1A and E1B both under control of a CEA-TRE.

In short, full-length adenoviruses were constructed in which one or two adenoviral early genes were under transcriptional control of a CEA-TRE.

Comparative Testing of Virus Growth in Vitro

Growth selectivity of CN741, CN742 and/or CN743 (full-length adenoviruses in which one or two early genes is under control of a CEA-TRE) is analyzed in plaque assays in which a single infectious particle produces a visible plaque by multiple rounds of infection and replication. Virus stocks are diluted to equal pfu/ml, then used to infect monolayers of cells for 1 hour. Comparison of. normalized titres in cells that allow a CEA-TRE to function and cells that do not allow a CEA-TRE to function indicates replication preference. Cells chosen for this study are cells that allow a CEA-TRE to function, such as NCIH508, LoVo, SW1463, MKN1, MKN28, MKN45 and cells that do not allow such function, such as HuH7 or HeLa. The inoculum is then removed and the cells are overlayed with semisolid agar containing medium and incubated at 37° C. for one week. Plaques in the monolayer are then counted and titers of infectious virus on the various cells are calculated. The data are normalized to the titer of CN702 (wild type) on 293 cells.

Full-length adenovirus CN741, in which transcription of E1A is under control of CEA-TRE, was tested in this way. Clone 46.130.8.3 was used, and CN702 (wt adenovirus) was a control. Plaques observed on cell lines were normalized to infectivity on control 293 Cells. The ratio of normalized plaques of CN741 and CN702 were compared to evaluate plaque preference in cell types. Table 2 depicts the plaque assay results. Cells examined were 293 (CEA-deficient), LoVo (CEA-producing), OVCAR (CEA-deficient), HBL100 (CEA-deficient), and HepG2 (CEA-producing). We have found that OVCAR and HBL100 cells do not express levels of CEA detectable by ELISA, using a standard protocol with a kit purchased from Genzyme. However, while we also found that HepG2 cell do not produce CEA detectable in the ELISA test, Zhai et al. [(1990) *Gastroenter.* 98:470–7] showed that HepG2 cells do produce CEA, as detectable by the PAP and avidin-biotin technique.

TABLE 11

Plaque assay results of CN741 (CEA-E1A) on human cell lines

| Cell Line | Normalized Plaques CN702 (wt) | Normalized Plaques CN741 (CEA-E1A) | Ratio of CN741/CN702 |
|---|---|---|---|
| 293 | 1.0 | 1.0 | 1.0 |
| LoVo | 1.5 | 0.579 | 0.39 |
| OVCAR | 1.2 | 0.372 | 0.31 |
| HBL100 | 0.75 | 0.085 | 0.11 |
| HepG2 | 1.75 | 0.69 | 0.39 |

The plaque assay results in Table 11 indicate that the growth pattern of CN741 has been altered by the introduction of a CEA-TRE. In each cell line, the growth of the CN741 virus is reduced in comparison to wild-type adenovirus CN702. The ratio of CN741/CN702 in the CEA-proficient cell lines LoVo and HepG2 were similar. Importantly, there was a 4-fold reduction in the ability of CN741 to replicate in the CEA-deficient cell line HBL100 cells. These data seem to indicate that CN741 has a greater ability (i.e., more specificity for replication) in CEA-proficient cells (LoVo and HepG2) than in CEA-deficient cells (HBL100).

Curiously, the CN741/CN702 ratio was similar in OVCAR (CEA-deficient) to that in CEA-producing cells. This suggests that replication of the CEA-E1A adenovirus relative to wt virus in OVCAR (CEA-deficient) was similar to that in CEA-producing cells. There are several possible explanations for this finding. Note that HepG2, as stated above, was determined to be CEA-deficient a CEA ELISA assay, but revealed to be CEA-proficient by the PAP and avidin-biotin technique. The ELISA method may be similarly insufficient to detect low levels of CEA present in OVCAR. Alternatively, it is possible that OVCAR cells also produce CEA, but the protein is expressed too transiently or too quickly degraded to be detectable by ELISA, yet is somehow able to allow activation of transcription of a CEA-TRE and replication of CN741.

EXAMPLE 5

Construction of Replication-Competent Adenoviral Vectors in which Adenoviral Genes are Under Transcriptional Control of Mucin TRE Adenoviral vectors in which a MUC1-TRE controls expression of E1A and/or E1B were constructed. A construct (CN226) was built in which MUC1-TRE controls E1A. In another vector, a MUC1-TRE was inserted upstream of the E1B gene in CN226. A third vector CN237 was constructed, in which MUC1-TRE mediates E1A and E1B expression.

Construction of CN226 (MUC1-TRE E1A)

Briefly, CN226, in which MUC1-TRE controls E1A expression, was constructed as follows. The MUC1-TRE region of SEQ ID NO:61 was amplified from human genomic DNA (Clonetech) by PCR (Perkin Elmer 2400) with the following primer pairs: 5' TAA TCC GGA CGG TGA CCA CTA GAG GG 3' (39.088A, upper primer-SEQ ID NO:62) and 5' TAT TCC GGA TCA CTT AGG CAG CGC TG 3' (39.088B, lower primer-SEQ ID NO:63). The primers were constructed with BspEI ends, which are compatible with the AgeI site in CN124. CN124 is a derivative of construct pXC.1, which contains the wild-type left-hand portion of Adenovirus 5 (Ad5), from nt 22 to 5790, including both E1A and E1B (McKinnon (1982) *Gene* 19:33–42). CN124 also has, among other alterations, an artificial AgeI site at Ad5 nt 547 (just upstream of the E1A transcriptional start at nt 498 and the E1A coding segment beginning with ATG at 610). CN124 also contains an artificial EagI site at Ad5 nt 1682, or just upstream of the E1B coding segment. To construct CN124 from pXC.1, we introduced an AgeI site 12 bp 5' to the E1A initiation codon (Ad5 547) by oligonucleotide-directed mutagenesis and linked PCR. To achieve this, pXC.1 was PCR amplified using primers: 5'-TCGTCTTCAAGAATTCTCA (15.133A) (SEQ ID NO:14), containing an EcoRI site, and 5'-TTTCAGTCACCGGTGTCGGA (15.134B) (SEQ ID NO:15), containing an extra A to introduce an AgeI site. This created a segment from the EcoRI site in the pBR322 backbone to Ad5 560. A second segment of pXC.1 from Ad 541 to the XbaI site at Ad nucleotide 1339 was amplified using primers: 5'-GCATTCTCTAGACACAGGTG (15.133B) (SEQ ID NO:16) containing an XbaI site, and 5'-TCCGACACCGGTGACTGAAA (15.134A).(SEQ ID NO:17), containing an extra T to introduce an AgeI site. A mixture of these two PCR-amplified DNA segments was mixed and amplified with primers 15.133A and 15.133B to create a DNA segment from the EcoRI site to the XbaI site of pXC.1. This DNA segment encompasses the leftmost 1317 bases of Ad sequence and contains an AgeI site at Ad 547. This DNA segment was used to replace the corresponding segment of pXC.1 to create CN95. An EagI site was created upstream of the E1B start site by inserting a G residue at Ad5 1682 by oligonucleotide directed mutagenesis as above. To simplify insertion of an AFP-TRE in the EagI site the endogenous EagI site in CN95 was removed by digestion with EagI, treatment with mung bean nuclease, and re-ligation to construct CN114. The primers: 5'-TCGTCTTCAAGAATTCTCA (15.133A) (SEQ ID NO:14), containing an EcoRI site, and 5'-GCCCACGGCCGCATTATATAC (9.4) (SEQ ID NO:46), containing an EagI site, and 5'-GTATATAATGCGGCCGTGGGC (9.3) (SEQ ID NO:47) containing an extra G and an EagI site, and 5'-CCAGAAAATCCAGCAGGTACC (24.020) (SEQ ID NO:30), containing a KpnI site, were used to amplify the segment between 1682 and the KpnI site at Ad5 2048. Co-amplification of the two segments with primers 15.133A and 24.020 yielded a fragment with an EagI site at Ad5 1682 which was used to replace the corresponding EcoRI/KpnI site in pXC.1 to construct CN124.

Amplification of the MUC1-TRE utilized an annealing temperature of 55° C. (30 cycles) with an extension temperature and time of 72° C. for 60 seconds. PCR products were purified with the QIAQuick Spin PCR Purification Kit (Qiagen). The MUC1-TRE PCR product was digested with BspI and ligated in front of the E1A region of CN124, which had been linearized with PinAI to AgeI ends. Ligation of the insert into the vector destroyed the AgeI restriction site. The resulting clone was confirmed by restriction digest : HindIII/PinA1, 1278, 1524, 6730 bp. The MUC1-E1A adenoviral clone was designated CN226 (ref. 39.112).

MUC1 E1B Ad5 Plasmid (CN292)

An adenovirus vector in which the expression of the E1B gene is under control of the MUC1-TRE was constructed as follows.

The plasmid CN237 (MUC1 E1A/E1B, described above) was digested with EagI to excise the MUC1-TRE EagI fragment. The MUC1-TRE fragment was isolated by gel electrophoresis (1.2% SeaKem Agarose) onto DEAE filter paper and ligated into CN124 (described above) which had been linearized with EagI. The resulting clone was confirmed by restriction digest: PinA1, 1924 and 7826-bp; HindIII/PinAI 807, 1199, 1924, 6730 bp. The MUC1 E1B clone has been designated CN292 (ref. 46.050).

Construction of MUC1-TRE E1A/E1B Construct CN237

To construct adenoviral vector CN237, in which a MUC1-TRE controls expression of both E1A and E1B, a second MUC1-TRE was inserted upstream of the E1B gene in construct CN226, which already contained a MUC1-TRE controlling expression of E1A.

In more detail, a fragment containing the MUC1-TRE with EagI ends was obtained by PCR of CN226 with the following primer pairs: 5' TAA CGG CCG CGG TGA CCA CTA GAG 3' (39.120A, upper primer-SEQ ID NO:64) and 5' TAT CGG CCG GCA GAA CAG ATT CAG 3' (39.120B, lower primer-SEQ ID NO:65). Amplification of the MUC1-TRE containing EagI ends utilized an annealing temperature of 55° C. (30 cycles) with an extension temperature and time of 72° C. for 60 seconds. PCR products were purified with the QIAQuick Spin PCR Purification Kit (Qiagen). The MUC1-TRE PCR product was digested with EagI and ligated in front of the E1B region of CN226, which had been linearized with EagI, which cuts just upstream of the E1B coding segment. The resulting clone was confirmed by restriction digest: PinAI, 1997 and 9453 bp; SmaI, 179, 980, 1917, 2711, 6562 bp. The MUC1 E1A/E1B clone has been designated CN237 (ref. 39.143).

Homologous Recombination of CN226, CN237, and CN292 with BHG10 or BHG11

Adenovirus containing the MUC1-TRE regulating expression of E1A, E1B, and E1A/E1B, in the context of the otherwise intact genome have been obtained through homologous recombination with the right hand end plasmids BHG10 and/or BHG11 [Bett. et al. (1994); Microbix Biosystems Inc., Toronto] in 293 cells (human embryonic kidney cell line). The plasmids (e.g. CN226 and BHG10; or CN237 and BHG10, etc.) have been co-transfected into 293 cells via cationic lipids (DOTAP:DOPE™ 1/1 mole ratio) by a standard transfection protocol, including, but not limited to, that detailed below.

Figure 9:
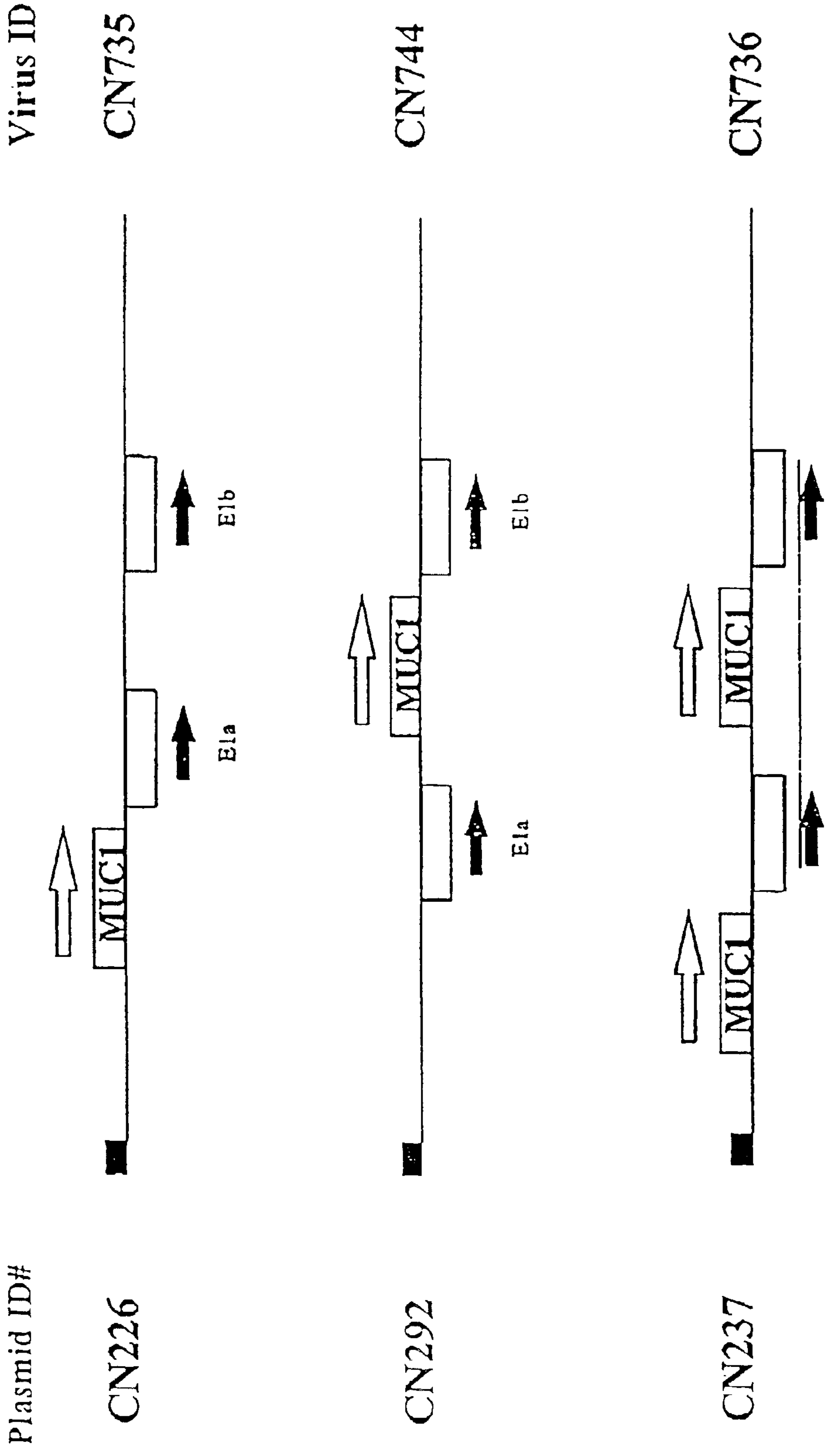
FIG. 9 is a schematic representation of various adenoviral vector constructs comprising MUC-TRE controlling expression of E1A, E1B or both, as described in Example 5.

Adenoviral vector CN735, in which E1A is under control of MUC1-TRE, was obtained by homologous recombination of CN226 and BHG10. An adenoviral vector, to be designated CN744, comprising E1B under control of MUC1-TRE, can be obtained by homologous recombination of CN292 and BHG11. Adenoviral vector CN736, in which both E1A and E1B are under control of MUC1-TRE, was obtained by homologous recombination of CN237 and BHG10. These plasmids and adenoviral vectors are diagrammed in FIG. 9.

EXAMPLE 6

Construction of Replication-Competent Adenoviral Vectors in which Adenoviral Genes are Under Transcriptional Control of Probasin TRE Adenoviral vectors in which a PB-TRE was placed upstream of E1A and/or E1B were constructed.

The Probasin Transcriptional Response Element (PB-TRE)

The 454 nucleotide fragment (nt about −426 to about +28) of the rat PB-TRE, which contains two androgen response elements (ARE sites), a CAAT box and a TATAA box (FIG. 10, SEQ ID NO:9), was amplified by polymerase chain reaction (PCR) using rat genomic DNA as template and the synthetic oligonucleotides:

42.2.1 (SEQ ID NO:66):
5'-GATCACCGGTAAGCTTCCACAAGTGCATTTACC-3',
PinAI site underlined,
and
42.2.2 (SEQ ID NO:67):
5'-GATCACCGGTCTGTAGGTATCTGGACCTCACTG-3'
or oligonucleotides
42.2.3 (SEQ ID NO:68):
5'-GATC <u>CGGCCG</u>AAGCTTCCACAAGTGCATTTAGCC-3',
EagI site underlined,
and
42.2.4 (SEQ ID NO:69):
5'-GATCCGGCCGCTGTAGGTATCTGGACCTCACTG-3'.

The oligonucleotides created a unique PinAI (AgeI) site (A/CCGGT) or EagI site (C/GGCCG) at both ends of the PCR fragments. The PCR fragments were ligated into the pGEM-T vector (Promega) to generate plasmids CN249 and CN250. Similarly, CN256 was created using the same strategy but the PB-TRE fragment was ligated into the pCRT vector (Invitrogen); CN271 is identical to CN250 but with a HindIII site at the 5'-end. These plasmids provide the PB-TRE DNA fragments for the constructs reported below. In some of the adenovirus vectors described below, the endogenous (adenoviral) TREs were not deleted; rather, in each construct, the PB-TRE was inserted between the endogenous TRE (e.g., the E1A TRE) and its respective coding segment (e.g., the E1A coding segment). In other vectors, the endogenous (Ad5) promoter-enhancer has been deleted, and the prostate-specific promoter-enhancer placed immediately upstream of an early gene.

PB-TRE-driven E1A Ad5 Plasmid (CN251)

An adenovirus vector in which expression of an early gene, E1A, is under control of PB-TRE was constructed as follows.

CN124 is a derivative of construct pXC.1, which contains the wild-type left-hand end of Ad5, from nt 22 to 5790, including both E1A and E1B (McKinnon (1982) *Gene* 19:33–42). CN124 also has, among other alterations, an artificial PinA1 site at Ad5 nt 547 (between the E1A transcriptional start at nt 498 and the E1A coding segment beginning with ATG at 560).

To construct CN124 from pXC.1, we introduced an AgeI site 12 bp 5' to the E1A initiation codon (Ad5 547) by oligonucleotide-directed mutagenesis and linked PCR. To achieve this, pXC.1 was PCR-amplified using primers:

5'-TCGTCTTCAAGAATTCTCA (15.133A) (SEQ ID NO:14), containing an EcoRI site, and

5'-TTTCAGTCACCGGTGTCGGA (15.134B) (SEQ ID NO:15), containing an extra A to introduce an AgeI site. This created a segment from the EcoRI site in the pBR322 backbone to Ad5 560. A second segment of pXC.1 from Ad 541 to the XbaI site at Ad nucleotide 1339 was amplified using primers:

5'-GCATTCTCTAGACACAGGTG (15.133B) (SEQ ID NO:16) containing an XbaI site, and

5'-TCCGACACCGGTGACTGAAA (15.134A) (SEQ ID NO:17), containing an extra T to introduce an AgeI site. These two PCR-amplified DNA segments were mixed and amplified with primers 15.133A and 15.133B to create a DNA segment from the EcoRI site to the XbaI site of pXC.1. This DNA segment encompasses the leftmost 1317 bases of Ad sequence and contains an AgeI site at Ad 547. This DNA segment was used to replace the corresponding segment of pXC.1 to create CN95.

An EagI site was created upstream of the El B start site by inserting a G residue at Ad5 1682 by oligonucleotide directed mutagenesis as above. To simplify insertion of an PB-TRE in the EagI site, the endogenous EagI site in CN95 was removed by digestion with EagI, treatment with mung bean nuclease, and re-ligation to construct CN114. The primers:

5'-TCGTCTTCAAGMTTCTCA (15.133A) (SEQ ID NO:14), containing an EcoRI site, and

5'-GCCCACGGCCGCATTATATAC (9.4) (SEQ ID NO:46), containing an EagI site, and

5'-GTATATMTGCGGCCGTGGGC (9.3) (SEQ ID NO:47) containing an extra G and an EagI site, and 5'-CCAGAAAATCCAGCAGGTACC (24.020) (SEQ ID NO:30), containing a KpnI site, were used to amplify the segment between 1682 and the KpnI site at Ad5 2048. -Co-amplification of the two segments with primers-15.133A and 24.020 yielded a fragment with an EagI site at Ad5 1682 which was used to replace the corresponding EcoRI/KpnI site in pXC.1 to construct CN124.

CN124 was linearized with PinA1 and dephosphorylated with calf intestinal alkaline phosphatase (New England Biolabs). CN249 was digested with PinA1 to free the PB-TRE fragment. The PB-TRE fragment was then ligated into the PinA1-linearized CN124, producing CN251. CN253 is similar to CN251 except for the PB-TRE fragment is in the reverse orientation.

Thus, construct CN251 contains the PB-TRE inserted upstream of and operably linked to the E1A coding segment in the Adenovirus 5 genome.

PB-TRE-driven E1B Ad5 Plasmid (CN254)

An adenovirus derivative in which the expression of the E1B gene is under control of the PB-TRE was constructed as follows.

CN124, described above, also contains an artificial EagI site at Ad5 nt 1682, or just upstream of the E1B coding segment. The PB-TRE fragment was excised from CN250 with EagI and inserted into CN124 digested with EagI. This produced CN254, which contains the PB-TRE immediately upstream of and operably linked to the E1B coding segment.

CN255 is identical to CN254, but the orientation of the PB-TRE insert is reversed.

CN275 is the same as CN254, but with a HindIII site at the 5'-end.

PB-TRE-driven E1A and PB-TRE-driven E1B Ad5 Plasmid (CN268)

An adenovirus vector in which expression of both E1A and E1B are driven by PB-TRE was constructed as follows.

CN251, described above, comprises a PB-TRE fragment inserted just upstream of the E1A coding segment.

Figure 11:
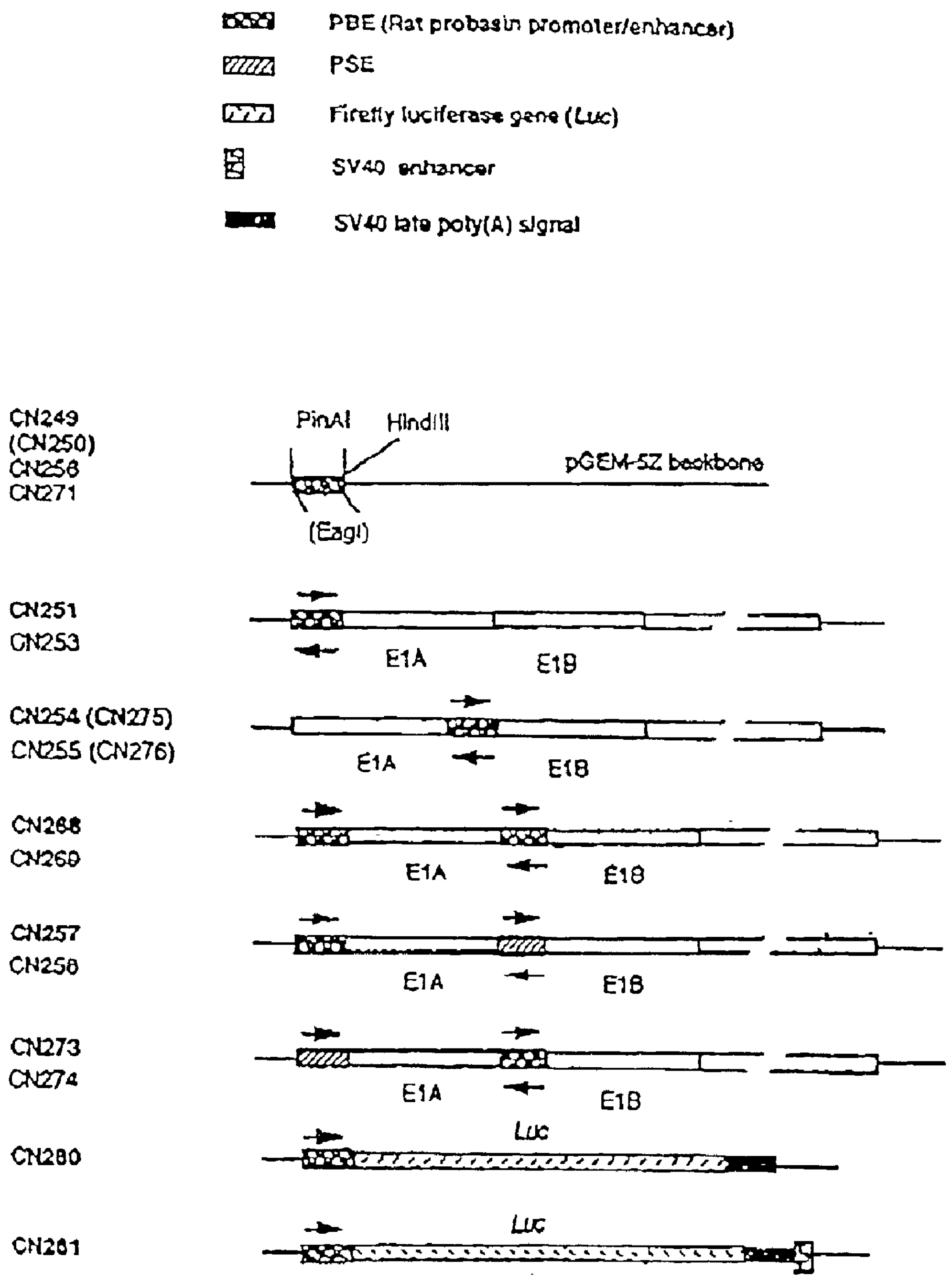
FIG. 11 depicts schematic diagrams of various adenovirus vectors in which various genes are under control of a PB-TRE.
Figure 12:
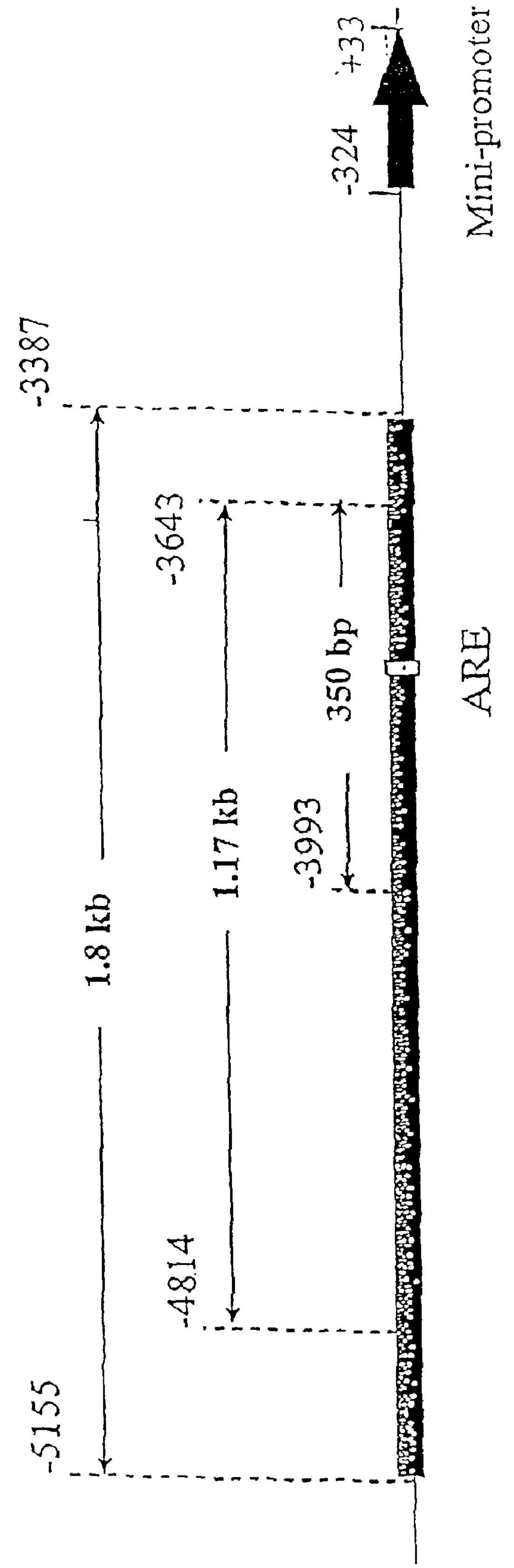
FIG. 12 is a schematic representation of the hKLK2-TREs used to-generate the adenoviral constructs described in Example 7.
Figure 13:
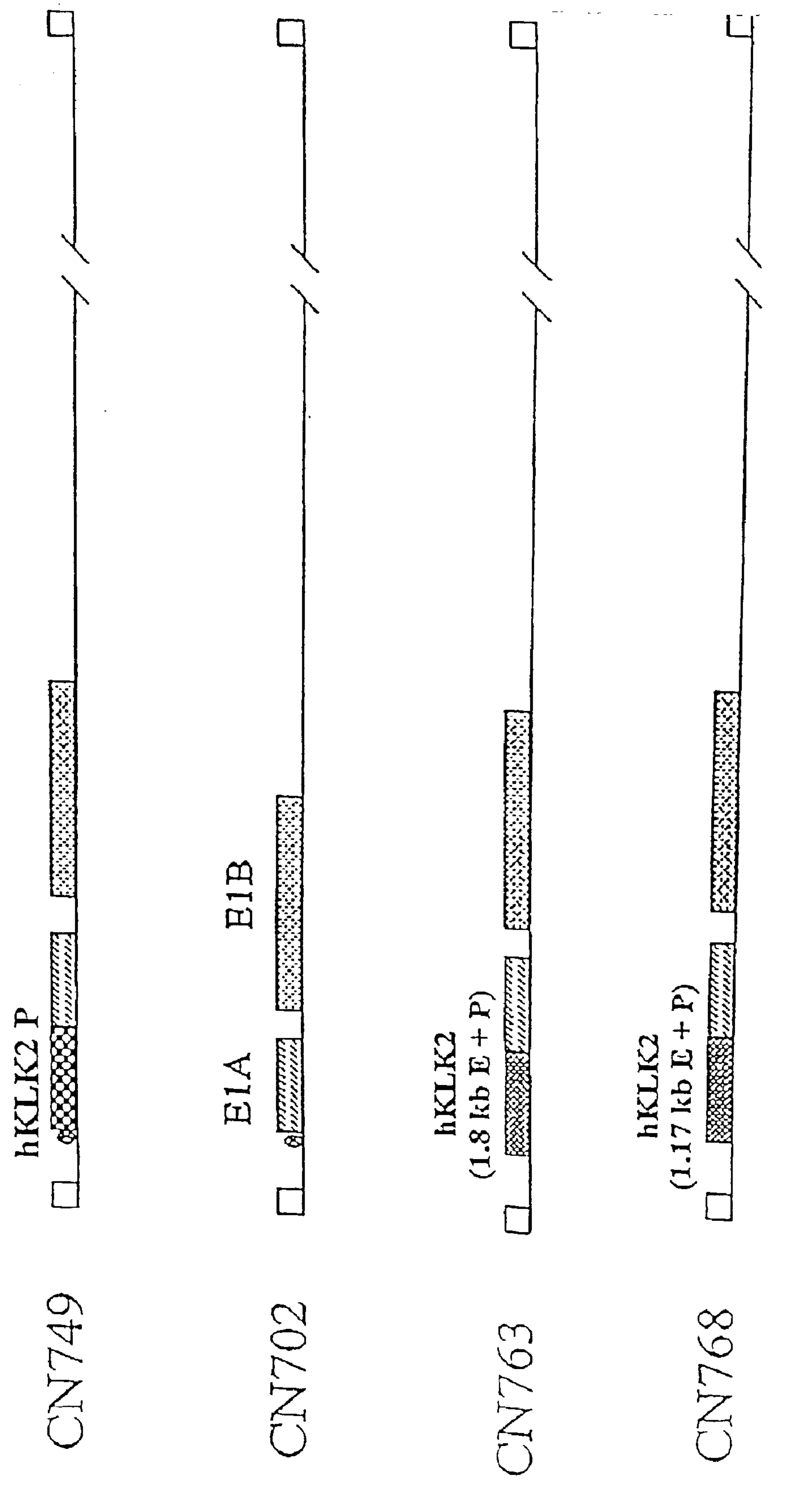
FIG. 13 is a schematic representation of the adenoviral constructs described in Example 7, in which adenoviral genes E1A and E1B are under transcriptional control of hKLK2-TREs. The ovals indicate that the endogenous E1A is present. The triangles indicate that the endogenous E1B promoter was removed. Abbreviations for TREs are as follows: hKLK2 P: hKLK2 promoter; hKLK2 (1.8 E+P): 1.8 kb hKLK2 enhancer and minimal hKLK2 promoter, as depicted in FIG. 12; hKLK2 (1.17 kb E+P): 1.17 kb hKLK2 enhancer and minimal hKLK2 promoter, as depicted in FIG. 12.

CN268 was generated by inserting a second PB-TRE in front of the E1B gene in CN251. A PB-TRE fragment was excised from CN250 by EagI-digestion and ligated into EagI-digested CN251 to create CN268. The final construct is a plasmid with PB-TRE driving E1A and a second PB-TRE driving E1B. CN269 is the same as CN268 but the orientation of the second PB-TRE is reversed. Constructs CN251, CN254, and CN268 are shown schematically in FIG. 11.

EXAMPLE 7

Construction of Replication-Competent Adenoviral Vectors in which Adenoviral Genes are Under Transcriptional Control of a Kallikrein TRE hKLK2 Promoter-driven E1A Ad5 Plasmid CN303

CN303 was produced by inserting the minimal hKLK2 promoter (−324 to +33) just upstream of the E1A coding segment in a derivative of pXC-1, a plasmid containing the left hand end of the Ad5 genome.

CN124 is a derivative of construct pXC-1 which contains the wild-type left hand end of Ad5, including both E1A and E1B (McKinnon (1982) *Gene* 19:33–42). CN124 also has among other alterations, an artificial PinAI site at Ad5 nt 547 (just upstream of the E1A transcriptional start at nt 560 and the E1A coding segment beginning with ATG at 610). CN124 was linearized with PinAI and dephosphorylated with calf intestinal alkaline phosphatase (New England Biolab).

CN294 was digested with PinA1 to free the hKLK2 promoter. The hKLK2 promoter was then ligated into the PinAI linearized CN124, producing CN303. CN304 is similar to CN303 except for the hKLK2 promoter fragment is in the reverse orientation.

CN421 was constructed by inserting an hKLK2-TRE (comprising an hKLK2 enhancer from nucleotides −5155 to −3387 relative to the hKLK2 gene transcription start site (nucleotides 6859 to 8627 of SEQ ID NO:1) and an hKLK2 minimal promoter as in CN379; see Table 1 and FIG. 16) into CN306. The hKLK2-TRE fragment was amplified by PCR from CN379, digested with PinAI and ligated into similarly cut CN306, to produce CN421.

CN438 was constructed by inserting an hKLK2-TRE (comprising an hKLK2 enhancer from nucleotides −4814 to −3643 relative to the hKLK2 gene transcription start site (nucleotides 7200 to 8371 of SEQ ID NO:1) and a minimal hKLK2 promoter as in CN390; see Table 1 and FIG. 16) into CN306. The enhancer fragment was amplified by PCR from CN390, digested with PinAI and ligated into similarly cut CN306, to produce CN438.

CN306 was derived from CN124 by removing the endogenous 64-nucleotide E1A promoter. CN124 is a derivative of construct pXC-1 which contains the wild-type left hand end of Ad5, including both E1A and E1B (McKinnon (1982) *Gene* 19:33–42). CN124 also has among other alterations, an artificial PinA1 site at Ad5 nt 547 Oust upstream of the E1A transcriptional start at nt 560 and the E1A coding segment beginning with ATG at 610). CN124 was linearized with PinAI and dephosphorylated with calf intestinal alkaline phosphatase (New England Biolabs).

CN390 was constructed as follows. A fragment with KpnI and XhoI sites at the ends was amplified from CN379 with synthetic oligonucleotides 51.96.3 (5'-GAT CGG TAC CAA AAG CTT AGA GAT GAC CTC CC-3'; SEQ ID NO:70) and 51.96.4 (5'-GAT CCT CGA GGC AAT AAT ACC GTT TTC TTT TCT GG-3; SEQ ID NO:71). The resulting fragment was digested with XhoI and KpnI, then cloned into similarly cut CN325, to generate CN390. CN390 has a 1.17-kb hKLK2 enhancer (nucleotides 7200 to 8371 of SEQ ID NO:74) and a minimal hKLK2 promoter (−324 to +33 relative to the transcription start site).

CN379 has, in addition to the minimal hKLK2 promoter, the hKLK2 5' flanking region from −5155 to −3387 (nucleotides 6859 to 8627 of SEQ ID NO:1) driving expression of the luciferase gene.

Construction of Adenovirus Vectors Comprising hKLK2-TRE Controlling Expression of Adenovirus E1A CN749, comprising an hKLK2 promoter (−324 to +33) driving adenovirus E1A gene expression, was generated by co-transfecting CN303 and pBHG10 into 293 cells.

CN763, comprising an hKLK2-TRE promoter/enhancer from CN379 controlling transcription of E1A, was generated from CN421 and pBHG10. To produce plasmid CN421, the hKLK2-TRE was amplified from CN379 and cloned into CN306. Therefore, CN763 is an adenoviral vector in which an hKLK2-TRE comprising a minimal hKLK2 promoter and the hKLK2 5' flanking region from −5155 to −3387 (nucleotides 6859 to 8627 of SEQ ID NO:1) controls expression of E1A.

CN768, comprising an hKLK2-TRE controlling transcription of E1A, was constructed from CN438 and pBHG10. Thus, CN768 is an adenoviral vector in which an hKLK2-TRE (comprising an hKLK2 enhancer from nucleotides −4814 to −3643 relative to the hKLK2 gene transcription start site (nucleotides 7200 to 8371 of SEQ ID NO:1) and a minimal hKLK2 promoter controls expression of E1A.

In Vitro Characterization of Adenoviral Constructs Comprising an Adenoviral Gene Under Transcriptional Control of an hKLK2-TRE Plaque Assays To determine whether the adenoviral constructs described above replicate preferentially in prostate cells, plaque assays were performed. Plaquing efficiency was evaluated in the following cell types: prostate tumor cell lines (LNCaP), breast normal cell line (HBL-100), ovarian tumor cell line (OVCAR-3, SK-OV-3), and human -embryonic kidney cells (293). LNCaP cells express both androgen receptor and PSA, while the other cell lines tested do not. 293 cells serve as a positive control for plaquing efficiency, since this cell line expresses Ad5 EIA and EIB proteins. The plaque assay was performed as follows: Confluent cell monolayers were seeded in 6-well dishes eighteen hours before infection. The monolayers were infected with 10-fold serial dilutions of each virus. After infecting monolayers for four hours in serum-free media (MEM), the media was removed and replaced with a solution of 0.75% low melting point agarose and tissue culture media. Plaques were scored two weeks after infection. CN702 has no modifications in its EI region and is used as a wild type control. CN706 demonstrates selective cytotoxicity toward PSA-expressing cells in vitro and in vivo. Rodriguez et al. (1997) *Cancer Res.* 57:2559–2563.

TABLE 12

| Viruses | 293 | LNCaP | HBL-100 | OVCAR-3 |
|---|---|---|---|---|
| CN702 | 100 | 100 | 100 | 100 |
| CN706 | 100 | 23 | 2.4 | 5.5 |
| CN763 | 100 | 35 | 1.2 | 1.9 |
| CN768 | 100 | 29 | 1.3 | 3.9 |

Table 12 shows the results of plaque assays performed with the adenoviral vectors described above. The results are expressed as percent of wild-type adenovirus plaque-forming units (PFU) per ml. The average titer of duplicate samples for the viruses tested. The titer for a particular virus in all cell lines was normalized to its titer on 293 cells. Once the titers on a cell type were normalized to 293 cells, the normalized numbers of the recombinant viruses were compared to CN702. A ratio of less than 100 suggests that the virus tested plaques less efficiently than CN702. Conversely, a ratio greater than 100 suggests that the virus plaques more efficiently than CN702.

The following observations were made. First, hKLK2-TRE engineered adenoviruses demonstrate preferential replication in prostate tumor cells. Since this carcinoma expresses androgen receptors, the hKLK-TRE contained in the adenoviral vectors should be active in promoting the transcription of the adenovirus early genes. The data presented in Table 12 suggest that the hKLK2-TRE containing adenoviral vectors induce cytopathic effects with a lower efficiency than wild type adenovirus in prostate tumor cells. Second, hKLK2-TRE controlled adenoviruses show a dramatically lower plaquing efficiency in non-prostate tumor cells when compared to wild type. For example, in the ovarian carcinoma cell line OVCAR-3, CN763 and CN768 produced about 25 to 50-fold less plaques than wild type Ad5. The results are similar for these two viruses in HBL-100 cells, where virus replication is also severely compromised. Third, PSA-TRE adenoviral vectors and hKLK2-TRE adenoviral vectors give similar plaques in HBL-100 and OVCAR-3 cells. Thus, like PSA-TRE adenoviral vector CN706, hKLK2-TRE adenoviral vectors were significantly attenuated relative to wild-type adenovirus in non-prostate cells, but these vectors grew comparably in prostate tumor cells.

EXAMPLE 8

Preparation of Covalently Pegylated Adenovirus

A series of experiments were carried out to alter the surface capsids of adenovirus by complexing adenovirus with PEG. The objective of PEG complexation masking of the adenovirus surface is the following: 1) adenovirus neutralizing antibodies or opsonins which are in circulation and 2) increase systemic circulation time of adenovirus particles by reduction of non-specific clearance mechanisms in the body (i.e., macrophages, etc.)

Surface capsids of wild type adenovirus CN706 were modified through covalent attachment of PEG to hexon and fiber proteins using N-hydroxysuccinimidyl (NHS). The PEGs (Shearwater polymers, Inc.) had nominal molecular weight of 5000 Da. The activated PEG (approximately 2 mM) was reacted with $5 \times 10^9$ particles/ml adenovirus in a tris-HCl buffer (the approximate molar ratio of virus particle to PEG was 1:4×$10^6$). Various combinations of pH, temperature, and reaction time were used. After the reaction, unreacted activated PEG, unreacted adenovirus, and pegylated adenovirus were separated by anionic ion exchange chromatography on Q Sepharose XL (Pharmacia), running a 0 to 1.5 M NaCl gradient in 50 mM tris, pH 8.0. The gradient was run over 10 column volumes.

Figure 21:
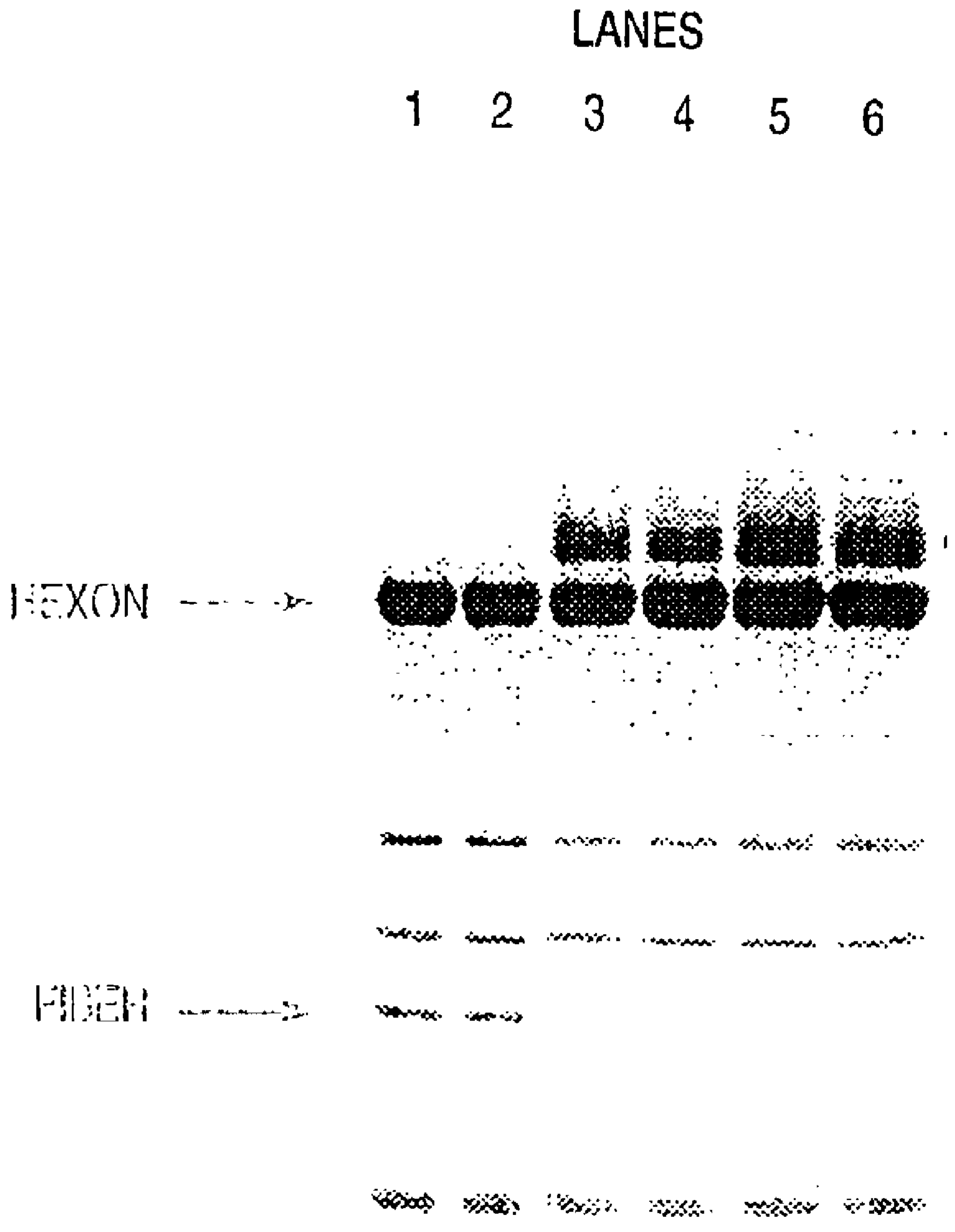
FIG. 21 shows a half-tone reproduction depicting a sodium dodecyl sulfate polyacrylamide gel electrophoresis (SDS-PAGE) gel (mobility shift) of pegylated adenovirus proteins. Lanes 1 and 2 are non-pegylated CN706 (control), lanes 3 through 6 are CN706 pegylated under various pH and temperature conditions (lane 3, pH 7.6, room temperature (RT); lane 4, pH 7.6, 4° C.; lane 5, pH 8.2, RT, lane 6, pH 8.2, 4° C.).

Characterization of PEG-CN706. Pegylation of CN706 was verified by SDS-page. FIG. 21 depicts the pegylation of CN706 and the mobility shift of pegylated proteins. Lanes 1 and 2 are non-pegylated CN706 (control), lanes 3 through 6 show the appearance of a second band above the hexon proteins of CN706, most likely pegylated hexon, and the loss of the fiber protein band. Since no additional bands associated with the virus except that corresponding to the PEG-hexon protein, the pegylated fiber protein is assumed to be under one of the unpegylated proteins on the SDS gel.

Figure 22:
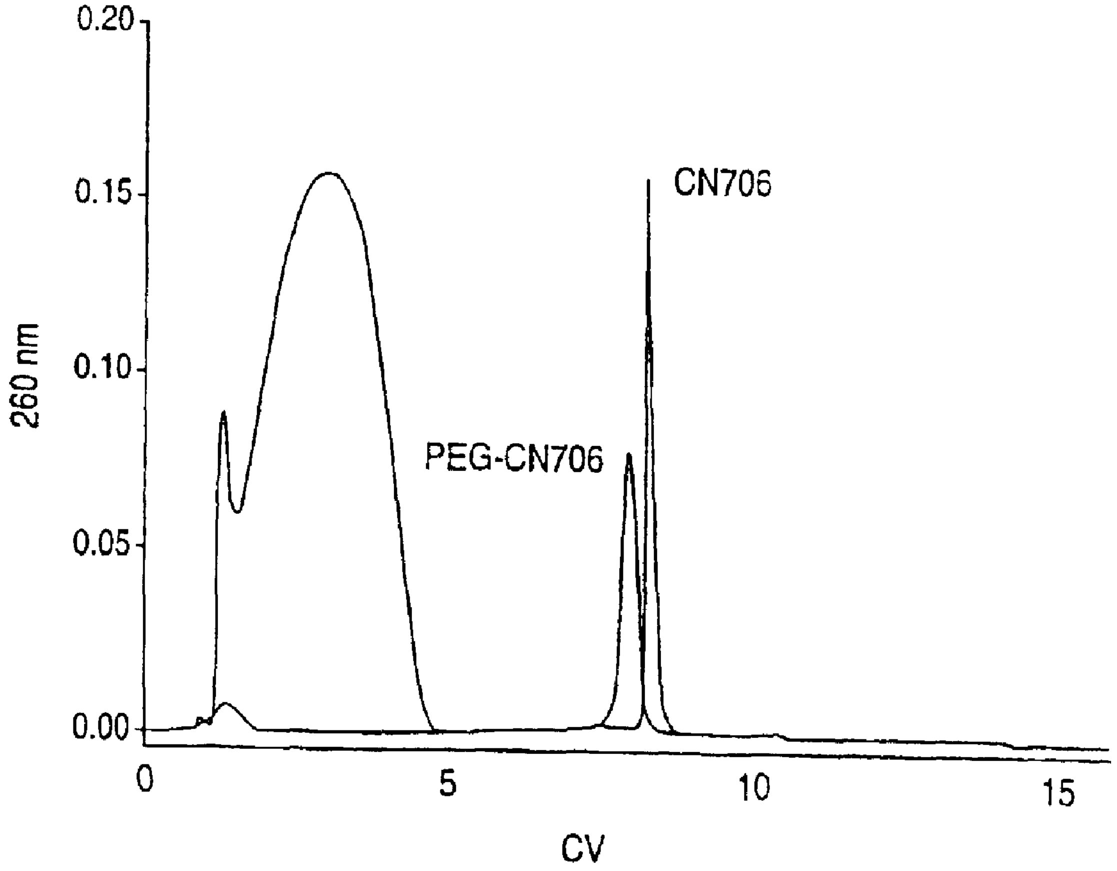
FIG. 22 is a chromatogram of ion exchange chromatography analysis of pegylated adenovirus (PEG-706) mixed with control adenovirus CN706.

FIG. 22 is an ion exchange chromatogram showing the change in surface properties of CN706. Pegylation of CN706 results from its earlier elution from the Q sepharose resin used to capture the virus. This result is most likely due to PEG rendering the virus more charge neutral in appearance and hence decreasing its binding-potential to the ion exchange matrix. A broadening of the virus chromatogram is expected since the pegylation of CN706 occurs to different percentages.

The infectivity of pegylated CN706 was evaluated in an in vitro plaque assay on 293 cells. Table 13 depicts a 5 to 10-fold reduction in plaquing efficiency of PEG-CN706 and compared to CN706. This is most likely due to pegylation masking the virus cells, decreasing the recognition and endocytosis of the viral particles.

TABLE 13

Comparison of Plaquing Efficiency of CN706 and PEG-CN706

| Sample Description | Number of Plaques (arbitrary units) |
|---|---|
| CN706 | 15 ± 5 |
| PEG-CN706 | 4 ± 1 |

It is evident from the above results that adenoviruses can be provided as vehicles specific for particular host cells, where the viruses are replication-competent. The viruses may be vehicles for a wide variety of genes for introduction in the target host cells. Particularly, employing the prostate specific element, the early genes essential for replication may be modified so as to be under the control of prostate cell responsive elements. All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A composition comprising:

a replication competent adenovirus having an adenovirus gene essential for replication under transcriptional control of a cell type specific transcriptional response element (TRE); and a masking agent, wherein the masking agent is polyethylene glycol (PEG).

2. The composition according to claim 1, wherein said adenovirus gene is an early gene.

3. The composition according to claim 2, wherein said early gene is selected from the group consisting of E1A, E1B and E4.

4. The composition according to claim 1, wherein said adenovirus further comprises a transgene.

5. The composition according to claim 1, wherein said cell type specific TRE is prostate cell specific.

6. The composition according to claim 5, wherein said adenovirus is replication competent only in mammalian cells expressing prostate specific antigen.

7. The composition according to claim 5, wherein said cell type specific TRE comprises nucleotides −540 to +8 relative to the transcription start site of the prostate specific antigen gene.

8. The composition according to claim 5, wherein said prostate cell specific response element comprises the enhancer sequence in the region −5322 to −3739 relative to the transcription start site of the prostate specific antigen gene.

9. The composition according to claim 5, wherein said prostate cell specific response element is a probasin TRE.

10. The composition according to claim 5, wherein said prostate cell specific response element is a hKLK2-TRE.

11. The composition according to claim 1, wherein said adenovirus gene essential for replication is under transcriptional control of an α-fetoprotein transcriptional regulatory element (AFP-TRE).

12. The composition according to claim 1, wherein said adenovirus gene essential for replication is under transcriptional control of a MUC1-TRE.

13. The composition according to claim 1, wherein said adenovirus gene essential for replication is under transcriptional control of a CEA-TRE.

14. The composition according to claim 1, further comprising a physiologically acceptable carrier.

15. The composition according to claim 1, wherein said PEG is of a molecular weight between about 2500 to about 30,000 Da.

16. The composition according to claim 15, wherein said PEG is of a molecular weight between about 3000 to about 20,000 Da.

17. The composition of claim 16, wherein said PEG is of a molecular weight between about 5000 to about 10,000 Da.

18. The composition according to claim 1, wherein said PEG is covalently attached to said adenovirus.

19. The composition according to claim 18, wherein the PEG is covalently attached to the adenovirus by using N-hydroxysuccinimidyl (NHS) active ester.

20. The composition according to claim 19, wherein said N-hydroxysuccinimidyl (NHS) active ester is selected from the group consisting of succinimidyl succinate, succinimidyl succinamide, and succinimidyl propionate.

21. The composition according to claim 20, wherein said N-hydroxysuccinimidyl (NHS) active ester is succinimidyl succinate.

* * * * *